United States Patent
Fujio et al.

(10) Patent No.: US 7,501,412 B2
(45) Date of Patent: Mar. 10, 2009

(54) ISOQUINOLINE COMPOUNDS AND MEDICINAL USE THEREOF

(75) Inventors: Masakazu Fujio, Tokyo (JP); Hiroyuki Satoh, Tokyo (JP); Shinya Inoue, Tokyo (JP); Toshifumi Matsumoto, Tokyo (JP); Yasuhiro Egi, Tokyo (JP); Taichi Takahashi, Tokyo (JP)

(73) Assignee: Mitsubishi Tanabe Pharma Corporation, Osaka (JP)

( * ) Notice: Subject to any disclaimer, the term of this patent is extended or adjusted under 35 U.S.C. 154(b) by 608 days.

(21) Appl. No.: 10/536,173

(22) PCT Filed: Nov. 21, 2003

(86) PCT No.: PCT/JP03/14904

§ 371 (c)(1),
(2), (4) Date: Jul. 5, 2005

(87) PCT Pub. No.: WO2004/048339

PCT Pub. Date: Jun. 10, 2004

(65) Prior Publication Data

US 2006/0094743 A1 May 4, 2006

(30) Foreign Application Priority Data

Nov. 22, 2002 (JP) .............................. 2002-340174

(51) Int. Cl.
*C07D 403/02* (2006.01)
*A61K 31/47* (2006.01)

(52) U.S. Cl. ........................... 514/235.02; 514/253.05; 514/309; 544/128; 544/363; 546/141

(58) Field of Classification Search ........................ None
See application file for complete search history.

(56) References Cited

U.S. PATENT DOCUMENTS

| | | | |
|---|---|---|---|
| 4,113,731 A | 9/1978 | Winters et al. | |
| 4,808,595 A | 2/1989 | Hoffman, Jr. | |
| 7,220,759 B2 | 5/2007 | Fujio et al. | |
| 2004/0176361 A1 | 9/2004 | Fujio et al. | |

FOREIGN PATENT DOCUMENTS

| | | |
|---|---|---|
| CA | 2 371 174 A1 | 11/2000 |
| CA | 2 371 645 A1 | 11/2000 |
| CA | 2 372 704 A1 | 11/2000 |
| DE | 2 121 031 A | 11/1972 |
| EP | 0 005 745 A1 | 12/1979 |
| EP | 0 355 750 A1 | 2/1990 |
| EP | 1 142 881 A1 | 10/2001 |
| EP | 1 148 053 A1 | 10/2001 |
| EP | 1 396 488 A1 | 3/2004 |
| GB | 1062357 | 3/1967 |
| GB | 1174272 | 12/1969 |
| JP | 46-12454 B | 3/1971 |
| JP | 52-156875 | 12/1977 |
| JP | 52-156876 A1 | 12/1977 |
| JP | 54-84597 A | 7/1979 |
| JP | 64-42472 A | 2/1989 |
| JP | 02-124874 A | 5/1990 |
| WO | WO 99/08680 A1 | 2/1999 |
| WO | WO 99/11624 A1 | 3/1999 |
| WO | WO 99/11628 A1 | 3/1999 |
| WO | WO 99/11645 A1 | 3/1999 |
| WO | WO 99/11649 A2 | 3/1999 |
| WO | WO 99/59973 A1 | 11/1999 |
| WO | WO 00/42025 A1 | 7/2000 |
| WO | WO 00/44726 A1 | 8/2000 |
| WO | WO 00/64878 A1 | 11/2000 |
| WO | WO 00/67734 A2 | 11/2000 |
| WO | WO 00/68206 A1 | 11/2000 |
| WO | WO 01/79184 A1 | 10/2001 |
| WO | WO 02/44157 A2 | 6/2002 |
| WO | WO 02/48117 A1 | 6/2002 |
| WO | WO 02/090334 A1 | 11/2002 |
| WO | WO 02/094790 A1 | 11/2002 |
| WO | WO 03/063874 A1 | 8/2003 |

OTHER PUBLICATIONS

Winters et al., *Tetrahedron Letters*, 44: 3877-3878 (1975).
Eliasson et al., *Nature Medicine*, 3(10); 1089-1095 (1997).
Kimoto et al., Yakugaku Zasshi, 91(12): 1279-1285 (1971).
Ohta et al. *Chem. Pharm Bull*, 41(6): 1188-1190 (1993).
Tomisawa et al., *Chem. Pharm. Bull*, 19(11): 2414-2417 (1971).

*Primary Examiner*—Zinna N Davis
(74) *Attorney, Agent, or Firm*—Leydig, Voit & Mayer, Ltd.

(57) ABSTRACT

The present invention relates to an isoquinoline compound represented by the following formula (I) or (II), an optically active form thereof, a pharmaceutically acceptable salt thereof, a water adduct thereof, a hydrate thereof and a solvate thereof, as well as an agent for the prophylaxis and/or treatment of a disease caused by hyperreactivity of poly(ADP-ribose)polymerase, containing the compound, and a poly (ADP-ribose)polymerase inhibitor containing the compound. In addition, this compound is useful as an agent for the prophylaxis and/or treatment of cerebral infarction, particularly as an agent for the prophylaxis and/or treatment of acute cerebral infarction.

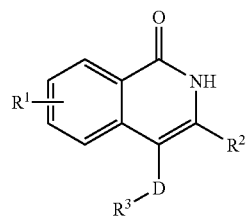

(I)

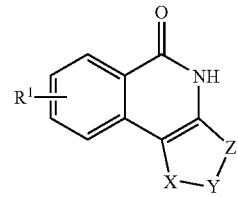

(II)

24 Claims, No Drawings

ISOQUINOLINE COMPOUNDS AND MEDICINAL USE THEREOF

This application is a 371 of PCT/JP03/14904 filed Nov. 21, 2003.

TECHNICAL FIELD

The present invention relates to a novel isoquinoline compound and a pharmaceutical agent containing same as an active ingredient.

BACKGROUND ART

Poly(ADP-ribose)polymerase, hereinafter to be abbreviated as "PARP", is an intranuclear enzyme that utilizes nicotinamide nucleotide (NAD) as a substrate, cleaves the bond between nicotinamide and ribose, transfers ADP-ribose residue into a protein, and causes addition polymerization of plural ADP-ribose residues. This enzyme is attractive as an apoptosis-related enzyme, which is considered to be activated by recognizing the nick of DNA damaged by a free radical, such as nitrogen monoxide, active oxygen and the like, which is produced in the lesion during ischemia, and have a primary role to aid DNA repair.

It is considered in recent years that the activation of PARP decreases intracellular NAD, a large amount of ATP is consumed to compensate for the decrease, as a result of which intracellular energy is depleted, and the cell is driven to death. In an experiment using a PARP knockout mouse, it has been clarified that a cultured neuronal cells show resistance to disorders due to nitrogen monoxide, excitatory amino acids such as NMDA (N-methyl-D-aspartate) and the like, and that it shows a tremendous protective effect by inhibiting cerebral infarction by not less than 80% in cerebral ischemia model (Eliasson M J L. et al., Nature Med., 3, 1089-95 (1997)).

However, none of the reported PARP inhibitors to date has subjected to a clinical trial as a therapeutic agent for cerebral infarction. As the reported PARP inhibitors to date, for example, 5-substituted-3,4-dihydro-2H-isoquinoline derivatives (EP 355750 A), 1,11b-dihydrobenzopyrano[4.3.2-de]isoquinolin-3-one derivatives (WO99/11645), 3,4-dihydro-5-[4-(1-piperidinyl)-butoxy]-1(2H)-isoquinoline (each of WO99/08680 and WO99/11649), pyrimidine derivatives (WO00/42025), benzimidazole derivatives (each of WO00/64878 and WO00/68206), phthalazine derivatives (each of WO00/67734, WO00/44726 and WO 01/79184), quinazolinone derivatives (each of WO02/48117 and WO02/44157) and the like are known, but the PARP inhibitory activity thereof is not very strong.

Moreover, JP-B-S46-12454 discloses isoquinoline derivatives having an analgesic action and a hypoglycemic action, U.S. Pat. No. 4,113,731 discloses a production method of 3H-pyrazolo[3,4-c]isoquinolin-5(4H)one derivatives, Chemical & Pharmaceutical Bulletin (Chem. Pharm. Bull., Vol. 19 (No. 11), 1971, p. 2414) discloses 2-methyl-4-dimethylaminomethylisoquinolin-1-one, YAKUGAKU ZASSHI (Vol. 91 (No. 12), p. 1279, 1971) discloses 3-amino-4-acetyl-2H-isoquinolin-1-one, JP-B-S52-156875 discloses a production method of 4-dialkylaminomethyl-2H-isoquinolin-1-one derivatives, and JP-B-S54-84597 discloses condensed isoquinolin-1-one derivatives. However, none of these compounds takes note of the PARP inhibitory activity.

[patent reference 1] EP 355750 A
[patent reference 2] WO99/11645
[patent reference 3] WO99/08680
[patent reference 4] WO99/11649
[patent reference 5] WO00/42025
[patent reference 6] WO00/64878
[patent reference 7] WO00/68206
[patent reference 8] WO00/67734
[patent reference 9] WO00/44726
[patent reference 10] WO01/79184
[patent reference 11] WO02/48117
[patent reference 12] WO02/44157
[patent reference 13] JP-B-S46-12454
[patent reference 14] U.S. Pat. No. 4,113,731
[patent reference 15] JP-B-S52-156875
[patent reference 16] JP-B-S54-84597
[non-patent reference 1] Eliasson M J L. et al., Nature Med., 3, 1089-95 (1997)
[non-patent reference 2] Chemical & Pharmaceutical Bulletin (Chem. Pharm. Bull., Vol. 19 (No. 11), 1971, p. 2414)
[non-patent reference 3] YAKUGAKU ZASSHI (Vol. 91 (No. 12), p. 1279, 1971)

DISCLOSURE OF THE INVENTION

An object of the present invention is to provide a compound having a PARP inhibitory activity and useful as a therapeutic agent for cerebral infarction, particularly a therapeutic agent for acute cerebral infarction. The present inventors have conducted intensive studies and found that an isoquinoline compound represented by the following formula (I) and (II), an optically active form thereof, a pharmaceutically acceptable salt thereof, a hydrate thereof, a water adduct thereof and a solvate thereof have potent PARP inhibitory activity, which resulted in the completion of the present invention. Accordingly, the present invention provides the following:

(1) an isoquinoline compound represented by the following formula (I) or (II)

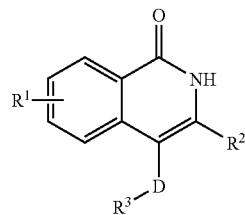

(I)

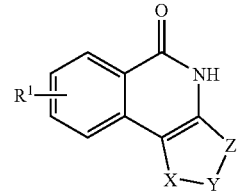

(II)

wherein $R^1$ is a hydrogen atom, a halogen atom, alkyl, alkoxy, haloalkyl, a hydroxyl group, amino, alkylamino, dialkylamino, nitro, cyano, acyl, carboxyl, alkoxycarbonyl, carbamoyl, N-alkylcarbamoyl, N,N-dialkylcarbamoyl, acylamino, diacylamino, thiol, alkylthio, alkoxycarbonylamino, sulfamoyl, N-alkylsulfamoyl, N,N-dialkylsulfamoyl or alkoxyalkyloxy;

$R^2$ is a hydrogen atom, alkyl or amino;

D is void, —C(O)—$(CH_2)_n$— wherein n is an integer of 0 to 7, or straight chain or branched chain alkylene having 1 to 8 carbon atoms, provided that when D is methylene, then $R^2$ is alkyl and when D is void, then $R^2$ is a hydrogen atom;

R³ is amino, monoalkylamino, dialkylamino, or a group selected from the following formulas (a), (b), (c) and (d), provided that when D is void, then R³ is (a) or (d) and when n is 0, then R³ is (a),

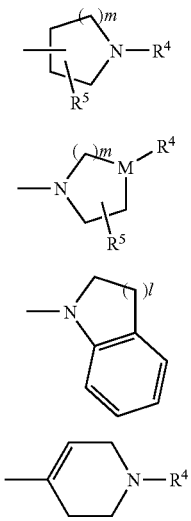

(a)

(b)

(c)

(d)

wherein
m is an integer of 1 to 3,
l is an integer of 1 to 3,
R⁴ is a hydrogen atom, alkyl, hydroxyalkyl, amino, monoalkylamino, dialkylamino, alkoxycarbonyl, alkylsulfonyl, acyl, acylamino, aryl optionally having substituent(s), heteroaryl optionally having substituent(s), arylalkyl optionally having substituent(s) heteroarylalkyl optionally having substituent(s), sulfamoyl or alkylsulfonylamino,
R⁵ is a hydrogen atom, a hydroxyl group, alkyl, hydroxyalkyl or ketone, and
M is —CH—, —C=C—, a nitrogen atom, an oxygen atom or a sulfur atom; and -X-Y-Z- is a group selected from the following formulas (e) to (g)

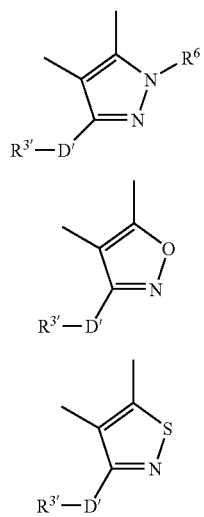

(e)

(f)

(g)

wherein, in the formulas (e) to (g),

R³' is a hydrogen atom, amino, monoalkylamino, dialkylamino, or (a), (b) or (c) for R³, provided that when -X-Y-Z- is the formula (f) or (g), then R³' is (a) or (b) for R³ (R⁴, R⁵, M, m or l for R³' is as defined for R⁴, R⁵, M, m or l for R³ in this claim),
D' is void or straight chain or branched chain alkylene having 1 to 8 carbon atoms, and
R⁶ is a hydrogen atom, methyl, aryl optionally having substituent(s), heteroaryl optionally having substituent(s), arylalkyl optionally having substituent(s), heteroarylalkyl optionally having substituent(s) or -D"-R³", provided that when R³' is a hydrogen atom, then R⁶ is -D"-R³",
wherein D" is phenylene or straight chain or branched chain alkylene having 1 to 8 carbon atoms, and R³" is (b) for R³;

an optically active form thereof, a pharmaceutically acceptable salt thereof, a hydrate thereof, a water adduct thereof and a solvate thereof.

(2) The isoquinoline compound of the above-mentioned (1), wherein, in the formula (I) or (II),
R¹ is a hydrogen atom, a halogen atom, alkyl having 1 to 4 carbon atoms, alkoxy having 1 to 4 carbon atoms, haloalkyl having 1 to 4 carbon atoms, a hydroxyl group, amino, dialkylamino having 1 to 4 carbon atoms, nitro, cyano, acyl having 1 to 4 total carbon atoms, carboxyl, alkoxycarbonyl having 1 to 4 carbon atoms, carbamoyl, N-alkylcarbamoyl, N,N-dialkylcarbamoyl, acylamino, diacylamino, thiol, alkylthio, alkoxycarbonylamino, sulfamoyl, N-alkylsulfamoyl, N,N-dialkylsulfamoyl or alkoxyalkyloxy;
R² is a hydrogen atom, alkyl having 1 to 4 carbon atoms or amino;
D is void, —C(O)—(CH₂)$_n$— wherein n is an integer of 0 to 7, or straight chain or branched chain alkylene having 1 to 8 carbon atoms, provided that when D is methylene, then R² is alkyl having 1 to 4 carbon atoms and when D is void, then R² is a hydrogen atom;
R³ is amino, monoalkylamino having 1 to 4 carbon atoms, dialkylamino having 1 to 4 carbon atoms, or a group selected from the formulas (a), (b), (c) and (d), provided that when D is void, then R³ is (a) or (d) and when n is 0, then R³ is (a),
wherein
m is an integer of 1 to 3,
l is an integer of 1 to 3,
R⁴ is a hydrogen atom, alkyl having 1 to 4 carbon atoms, hydroxyalkyl having 1 to 4 carbon atoms, amino, monoalkylamino having 1 to 4 carbon atoms, dialkylamino having 1 to 4 carbon atoms, alkoxycarbonyl having 1 to 4 carbon atoms, alkylsulfonyl having 1 to 4 carbon atoms, acyl, acylamino, aryl optionally having substituent(s), heteroaryl optionally having substituent(s), arylalkyl optionally having substituent(s), heteroarylalkyl optionally having substituent(s), sulfamoyl or alkylsulfonylamino,
R⁵ is a hydrogen atom, a hydroxyl group, alkyl having 1 to 4 carbon atoms, hydroxyalkyl or ketone, and
M is —CH—, —C=C—, a nitrogen atom, an oxygen atom or a sulfur atom; and
-X-Y-Z- is a group selected from the formulas (e) to (g),
wherein, in the formulas (e) to (g),
R³' is a hydrogen atom, or (a) or (b) for R³, provided that when -X-Y-Z- is the formula (f) or (g), then R³' is (a) or (b) for R³ (R⁴, R⁵, M, or m for R³' is as defined for R⁴, R⁵, M or m for R³ in this claim),
D' is void or straight chain or branched chain alkylene having 1 to 4 carbon atoms, and $R^6$ is a hydrogen atom, methyl, aryl optionally having substituent(s), heteroaryl optionally having substituent(s), arylalkyl optionally having substituent(s), heteroarylalkyl optionally having substituent(s) or -D"-$R^{3"}$, provided that when $R^{3'}$ is a hydrogen atom, then $R^6$ is -D"-$R^{3"}$, wherein D" is phenylene or straight chain or branched chain alkylene having 2 to 4 carbon atoms, and $R^{3"}$ is (b) for $R^3$ ($R^4$, $R^5$, M or m for $R^{3"}$ is as defined for $R^4$, $R^5$, M or m for $R^3$ in this claim);

an optically active form thereof, a pharmaceutically acceptable salt thereof, a hydrate thereof, a water adduct thereof and a solvate thereof.

(3) The isoquinoline compound of the above-mentioned (1) or (2), wherein, in the formula (I) or (II), $R^1$ is a hydrogen atom, a halogen atom, alkyl having 1 to 4 carbon atoms or alkoxy having 1 to 4 carbon atoms;

$R^2$ is a hydrogen atom or alkyl having 1 to 4 carbon atoms;

D is void or straight chain or branched chain alkylene having 1 to 5 carbon atoms, provided that when D is methylene, then $R^2$ is alkyl having 1 to 4 carbon atoms and when D is void, then $R^2$ is a hydrogen atom;

$R^3$ is dialkylamino having 1 to 4 carbon atoms or a group selected from the formulas (a), (b) and (d), provided that when D is void, then $R^3$ is (a) or (d), wherein m is an integer of 1 to 3, $R^4$ is a hydrogen atom, alkyl having 1 to 4 carbon atoms, hydroxyalkyl having 1 to 4 carbon atoms, aryl optionally having substituent(s), heteroaryl optionally having substituent(s), arylalkyl optionally having substituent(s), heteroarylalkyl optionally having substituent(s), $R^5$ is a hydrogen atom, a hydroxyl group, alkyl having 1 to 4 carbon atoms or hydroxyalkyl, and M is —CH—, a nitrogen atom or oxygen atom; and -X-Y-Z- is a group selected from the formulas (e) to (g), wherein, in the formulas (e) to (g), $R^{3'}$ is a hydrogen atom, or (a) or (b) for $R^3$, provided that when -X-Y-Z- is the formula (f) or (g), then $R^{3'}$ is (a) or (b) for $R^3$ ($R^4$, $R^5$, M, or m for $R^{3'}$ is as defined for $R^4$, $R^5$, M or m for $R^3$ in this claim), D' is void or straight chain or branched chain alkylene having 1 to 4 carbon atoms, and $R^6$ is a hydrogen atom, methyl, aryl optionally having substituent(s), heteroaryl optionally having substituent(s), arylalkyl optionally having substituent(s), heteroarylalkyl optionally having substituent(s) or -D"-$R^{3"}$, provided that when $R^{3'}$ is a hydrogen atom, then $R^6$ is -D"-$R^{3"}$, wherein D" is phenylene or straight chain or branched chain alkylene having 2 to 4 carbon atoms, and $R^{3"}$ is (b) for $R^3$ ($R^4$, $R^5$, M or m for $R^{3"}$ is as defined for $R^4$, $R^5$, M or m for $R^3$ in this claim);

an optically active form thereof, a pharmaceutically acceptable salt thereof, a hydrate thereof, a water adduct thereof or a solvate thereof.

(4) The isoquinoline compound of any of the above-mentioned (1) to (3), wherein, in the formula (I) or (II), $R^1$ is a hydrogen atom, a halogen atom, alkyl having 1 to 4 carbon atoms or alkoxy having 1 to 4 carbon atoms;

$R^2$ is a hydrogen atom;

D is void;

$R^3$ is the formula (a) or (d), wherein m is an integer of 1 to 3, l is an integer of 1 to 3, $R^4$ is a hydrogen atom, alkyl having 1 to 4 carbon atoms, hydroxyalkyl having 1 to 4 carbon atoms, aryl optionally having substituent(s), heteroaryl optionally having substituent(s), arylalkyl optionally having substituent(s), heteroarylalkyl optionally having substituent(s), and $R^5$ is a hydrogen atom, a hydroxyl group, alkyl having 1 to 4 carbon atoms or hydroxyalkyl having 1 to 4 carbon atoms;

and

-X-Y-Z- is a group selected from the formulas (e) to (g), wherein, in the formulas (e) to (g), $R^{3'}$ is (a) or (b) for $R^3$ ($R^4$, $R^5$ or m for $R^{3'}$ is as defined for $R^4$, $R^5$ or m for $R^3$ in this claim), D' is void or straight chain or branched chain alkylene having 1 to 4 carbon atoms, and $R^6$ is a hydrogen atom or methyl;

an optically active form thereof, a pharmaceutically acceptable salt thereof, a hydrate thereof, a water adduct thereof or a solvate thereof.

(5) The isoquinoline compound of any of the above-mentioned (1) to (4), wherein, in the formula (I) or (II), $R^1$ is a hydrogen atom, a halogen atom, alkyl having 1 to 4 carbon atoms or alkoxy having 1 to 4 carbon atoms;

$R^2$ is a hydrogen atom;

D is void;

$R^3$ is a group represented by the formula (a), wherein m is an integer of 1 to 3, $R^4$ is a hydrogen atom, alkyl having 1 to 4 carbon atoms or hydroxyalkyl having 1 to 4 carbon atoms, and $R^5$ is a hydrogen atom, a hydroxyl group, alkyl having 1 to 4 carbon atoms or hydroxyalkyl having 1 to 4 carbon atoms;

and

-X-Y-Z- is a group selected from the formulas (e) and (f), wherein, in the formulas (e) and (f), $R^{3'}$ is (a) for $R^3$ ($R^4$, $R^5$ or m for $R^{3'}$ is as defined for $R^4$, $R^5$ or m for $R^3$ in this claim), D' is void, and $R^6$ is a hydrogen atom or methyl;

an optically active form thereof, a pharmaceutically acceptable salt thereof, a hydrate thereof, a water adduct thereof or a solvate thereof.

(6) The isoquinoline compound of any of the above-mentioned (1) to (5), wherein, in the formula (I) or (II), $R^1$ is a hydrogen atom, a fluorine atom, a chlorine atom, methyl or methoxy;

$R^2$ is a hydrogen atom;

D is void;

$R^3$ is a group represented by the formula (a), wherein m is 2, $R^4$ is a hydrogen atom, methyl, ethyl or 2-hydroxyethyl, and $R^5$ is a hydrogen atom; and -X-Y-Z- is a group selected from the formulas (e) and (f), wherein, in the formulas (e) and (f), $R^{3'}$ is (a) for $R^3$ ($R^4$, $R^5$ or m for $R^{3'}$ is as defined for $R^4$, $R^5$ or m for $R^3$ in this claim), D' is void, and $R^6$ is a hydrogen atom or methyl;

an optically active form thereof, a pharmaceutically acceptable salt thereof, a hydrate thereof, a water adduct thereof or a solvate thereof.

(7) The isoquinoline compound of any of the above-mentioned (1) to (6), which is selected from
(193) 1-methyl-3-[2-(pyrrolidin-1-yl)ethyl]pyrazolo[3,4-c]isoquinolin-5(4H)-one,
(194) 1-methyl-3-[2-(4-methylpiperazin-1-yl)ethyl]pyrazolo[3,4-c]isoquinolin-5(4H)-one,
(195) 1-methyl-3-[2-(morpholin-4-yl)ethyl]pyrazolo[3,4-c]isoquinolin-5(4H)-one,
(196) 8-fluoro-4-(1-methylpiperidin-4-yl)-2H-isoquinolin-1-one,
(197) 6-fluoro-4-(1-methylpiperidin-4-yl)-2H-isoquinolin-1-one,
(198) 4-(1-methylpiperidin-4-yl)-7-trifluoromethyl-2H-isoquinolin-1-one,
(199) (R)-7-fluoro-3-methyl-1-[(3-hydroxypyrrolidin-1-yl)methyl]-3H-pyrazolo[3,4-c]isoquinolin-5(4H)-one,
(200) (S)-7-fluoro-3-methyl-1-[(3-hydroxypyrrolidin-1-yl)methyl]-3H-pyrazolo[3,4-c]isoquinolin-5(4H)-one,
(201) 7-methoxy-4-(1-methylpiperidin-4-yl)-2H-isoquinolin-1-one,
(202) 4-(1-methyl-1,2,3,6-tetrahydropyridin-4-yl)-2H-isoquinolin-1-one,
(203) 7-methyl-4-(1-methylpiperidin-4-yl)-2H-isoquinolin-1-one,
(204) 7-dimethylamino-4-(1-methylpiperidin-4-yl)-2H-isoquinolin-1-one,
(205) 4-(1,2,3,6-tetrahydropyridin-4-yl)-2H-isoquinolin-1-one,
(206) 4-(1-benzyl-1,2,3,6-tetrahydropyridin-4-yl)-2H-isoquinolin-1-one,
(207) 4-(1-isopropyl-1,2,3,6-tetrahydropyridin-4-yl)-2H-isoquinolin-1-one,
(208) 4-(1-ethyl-1,2,3,6-tetrahydropyridin-4-yl)-2H-isoquinolin-1-one,
(209) 1-(1-methylpiperidin-4-yl)-3-methyl-pyrazolo[3,4-c]isoquinolin-5(4H)-one,
(210) 1-(1-ethylpiperidin-4-yl)-3-methyl-pyrazolo[3,4-c]isoquinolin-5(4H)-one,
(211) 1-(1-isopropylpiperidin-4-yl)-3-methyl-pyrazolo[3,4-c]isoquinolin-5(4H)-one,
(212) 7-fluoro-4-(1-ethylpiperidin-4-yl)-2H-isoquinolin-1-one,
(213) 7-fluoro-4-(1-isopropylpiperidin-4-yl)-2H-isoquinolin-1-one,
(214) 1-methyl-3-[4-(pyrrolidin-1-yl)phenyl]-3,4-dihydropyrazolo[3,4-c]isoquinolin-5-one hydrochloride,
(215) 1-methyl-3-[4-(piperidin-1-yl)phenyl]-3,4-dihydropyrazolo[3,4-c]isoquinolin-5-one hydrochloride,
(216) 1-methyl-3-[4-(morpholin-4-yl)phenyl]-3,4-dihydropyrazolo[3,4-c]isoquinolin-5-one hydrochloride,
(217) 1-methyl-3-[4-(4-methylpiperazin-1-yl)phenyl]-3,4-dihydropyrazolo[3,4-c]isoquinolin-5-one dihydrochloride,
(218) 1-methyl-3-[4-(4-phenylpiperazin-1-yl)phenyl]-3,4-dihydropyrazolo[3,4-c]isoquinolin-5-one hydrochloride,
(219) 1-methyl-3-[4-(3-dimethylaminopyrrolidin-1-yl)phenyl]-3,4-dihydropyrazolo[3,4-c]isoquinolin-5-one dihydrochloride,
(220) 1-methyl-3-[4-(4-dimethylaminopiperidin-1-yl)phenyl]-3,4-dihydropyrazolo[3,4-c]isoquinolin-5-one dihydrochloride,
(221) 7-fluoro-1-(piperidin-4-yl)-3-methyl-pyrazolo[3,4-c]isoquinolin-5(4H)-one hydrochloride,
(222) 7-fluoro-1-(1-methylpiperidin-4-yl)-3-methyl-pyrazolo[3,4-c]isoquinolin-5(4H)-one,
(223) 1-(1-ethylpiperidin-4-yl)-7-fluoro-3-methyl-pyrazolo[3,4-c]isoquinolin-5(4H)-one,
(224) 7-fluoro-1-(1-isopropylpiperidin-4-yl)-3-methyl-pyrazolo[3,4-c]isoquinolin-5(4H)-one,
(225) 7-fluoro-1-(1-propylpiperidin-4-yl)-3-methyl-pyrazolo[3,4-c]isoquinolin-5(4H)-one,
(226) 1-(1-propylpiperidin-4-yl)-3-methyl-pyrazolo[3,4-c]isoquinolin-5(4H)-one,
(227) 1-(piperidin-4-yl)-3-methyl-pyrazolo[3,4-c]isoquinolin-5(4H)-one hydrochloride,
(228) 7-fluoro-3-methyl-1-[(piperidin-4-yl)methyl]-3,4-dihydropyrazolo[3,4-c]isoquinolin-5-one hydrochloride,
(229) 7-fluoro-3-methyl-1-[(1-methylpiperidin-4-yl)methyl]-3,4-dihydropyrazolo[3,4-c]isoquinolin-5-one,
(230) 3-methyl-1-(1-methylpyrrolidin-3-yl)-3,4-dihydropyrazolo[3,4-c]isoquinolin-5-one,
(231) 1-(piperidin-4-yl)-isoxazolo[5,4-c]isoquinolin-5(4H)-one hydrochloride,
(232) 1-(1-methylpiperidin-4-yl)-isoxazolo[5,4-c]isoquinolin-5(4H)-one, and
(233) 1-(1-ethylpiperidin-4-yl)-isoxazolo[5,4-c]isoquinolin-5(4H)-one, an optically active form thereof, a pharmaceutically acceptable salt thereof, a hydrate thereof, a water adduct thereof and a solvate thereof.

(8) The isoquinoline compound of any of the above-mentioned (1) to (7), wherein, in the formula (I) or (II),
$R^1$ is a hydrogen atom, a fluorine atom or a chlorine atom;
$R^2$ is a hydrogen atom;
D is void;
$R^3$ is a group represented by the formula (a),
    wherein
    m is 2,
    $R^4$ is a hydrogen atom, methyl, ethyl or 2-hydroxyethyl, and
    $R^5$ is a hydrogen atom; and
-X-Y-Z- is a group represented by the formula (e),
    wherein, in the formula (e),
    $R^{3'}$ is (a) for $R^3$ ($R^4$, $R^5$ or m for $R^{3'}$ is as defined for $R^4$, $R^5$ or m for $R^3$ in this claim),
    D' is void, and
    $R^6$ is a hydrogen atom or methyl;

an optically active form thereof, a pharmaceutically acceptable salt thereof, a hydrate thereof, a water adduct thereof or a solvate thereof.

(9) The isoquinoline compound of any of the above-mentioned (1) to (8), which is selected from
(31) 4-(piperidin-4-yl)-2H-isoquinolin-1-one,
(32) 4-(1-(2-hydroxyethyl)piperidin-4-yl)-2H-isoquinolin-1-one,
(33) 4-(l-methylpiperidin-4-yl)-2H-isoquinolin-1-one,
(44) 7-chloro-4-(piperidin-4-yl)-2H-isoquinolin-1-one,
(45) 7-fluoro-4-(piperidin-4-yl)-2H-isoquinolin-1-one,
(46) 7-chloro-4-(l-methylpiperidin-4-yl)-2H-isoquinolin-1-one,
(47) 7-fluoro-4-(1-methylpiperidin-4-yl)-2H-isoquinolin-1-one,
(48) 7-fluoro-4-(1-(2-hydroxyethyl)piperidin-4-yl)-2H-isoquinolin-1-one,
(74) 4-(1-ethylpiperidin-4-yl)-2H-isoquinolin-1-one,
(192) 7-chloro-4-(1-(2-hydroxyethyl)piperidin-4-yl)-2H-isoquinolin-1-one,
(209) 1-(1-methylpiperidin-4-yl)-3-methyl-pyrazolo[3,4-c]isoquinolin-5(4H)-one,
(210) 1-(1-ethylpiperidin-4-yl)-3-methyl-pyrazolo[3,4-c]isoquinolin-5(4H)-one,
(212) 7-fluoro-4-(1-ethylpiperidin-4-yl)-2H-isoquinolin-1-one, (221) 7-fluoro-1-(piperidin-4-yl)-3-methyl-pyrazolo[3,4-c]isoquinolin-5(4H)-one hydrochloride,
(222) 7-fluoro-1-(1-methylpiperidin-4-yl)-3-methyl-pyrazolo[3,4-c]isoquinolin-5(4H)-one,
(223) 1-(1-ethylpiperidin-4-yl)-7-fluoro-3-methyl-pyrazolo[3,4-c]isoquinolin-5(4H)-one,
(225) 7-fluoro-1-(1-propylpiperidin-4-yl)-3-methyl-pyrazolo[3,4-c]isoquinolin-5(4H)-one,
(226) 1-(1-propylpiperidin-4-yl)-3-methyl-pyrazolo[3,4-c]isoquinolin-5(4H)-one, and
(227) 1-(piperidin-4-yl)-3-methyl-pyrazolo[3,4-c]isoquinolin-5(4H)-one hydrochloride, an optically active form thereof, a pharmaceutically acceptable salt thereof, a hydrate thereof, a water adduct thereof and a solvate thereof.

(10) The isoquinoline compound of the above-mentioned (1), wherein, in the formula (I) or (II), $R^1$ is a hydrogen atom, a halogen atom, alkyl, alkoxy, haloalkyl, a hydroxyl group, amino, dialkylamino, nitro, cyano, acyl, carboxyl, alkoxycarbonyl, carbamoyl, N-alkylcarbamoyl, N,N-dialkylcarbamoyl, acylamino, diacylamino, thiol, alkylthio, alkoxycarbonylamino, sulfamoyl, N-alkylsulfamoyl, N,N-dialkylsulfamoyl or alkoxyalkyloxy;

$R^2$ is a hydrogen atom, alkyl or amino;

D is void, —C(O)—$(CH_2)_n$— wherein n is an integer of 0 to 7, or straight chain or branched chain alkylene chain having 1 to 8 carbon atoms, provided that when D is methylene, then $R^2$ is alkyl and when D is void, then $R^2$ is a hydrogen atom;

$R^3$ is amino, monoalkylamino, dialkylamino, or a group selected from the above-mentioned formulas (a), (b) and (c), provided that when D is void, then $R^3$ is (a) and when n is 0, then $R^3$ is (a), wherein m is an integer of 1 to 3, l is an integer of 1 to 3, $R^4$ is a hydrogen atom, alkyl, hydroxyalkyl, amino, monoalkylamino, dialkylamino, alkoxycarbonyl, alkylsulfonyl, acyl, acylamino, aryl optionally having substituent(s), heteroaryl optionally having substituent(s), arylalkyl optionally having substituent(s), heteroarylalkyl optionally having substituent(s), sulfamoyl or alkylsulfonylamino, $R^5$ is a hydrogen atom, a hydroxyl group, alkyl, hydroxyalkyl or ketone, and M is —CH—, —C=C—, a nitrogen atom, an oxygen atom or a sulfur atom; and -X-Y-Z- is a group selected from the formulas (e) to (g), wherein in the formulas (e) to (g), $R^{3'}$ is amino, monoalkylamino, dialkylamino, or a group selected from the formulas (a), (b) and (c) ($R^4$, $R^5$ M, m or l for $R^{3'}$ is as defined for $R^4$, $R^5$ M, m or l for $R^3$ in this claim), D' is void or straight chain or branched chain alkylene chain having 1 to 8 carbon atoms, and $R^6$ is a hydrogen atom, methyl, aryl optionally having substituent(s), heteroaryl optionally having substituent(s), arylalkyl optionally having substituent(s) or heteroarylalkyl optionally having substituent(s);

an optically active form thereof, a pharmaceutically acceptable salt thereof, a hydrate thereof, a water adduct thereof or a solvate thereof.

(11) The isoquinoline compound of the above-mentioned (10), wherein, in the formula (I) or (II), $R^1$ is a hydrogen atom, a halogen atom, alkyl having 1 to 4 carbon atoms, alkoxy having 1 to 4 carbon atoms, haloalkyl having 1 to 4 carbon atoms, a hydroxyl group, amino, dialkylamino having 1 to 4 carbon atoms, nitro, cyano, acyl having 1 to 4 carbon atoms, carboxyl, alkoxycarbonyl having 1 to 4 carbon atoms, carbamoyl, N-alkylcarbamoyl having 1 to 4 carbon atoms, N,N-dialkylcarbamoyl having 1 to 4 carbon atoms, acylamino having 1 to 4 carbon atoms, diacylamino having 1 to 4 carbon atoms, thiol, alkylthio having 1 to 4 carbon atoms, alkoxycarbonylamino having 1 to 4 carbon atoms, sulfamoyl, N-alkylsulfamoyl having 1 to 4 carbon atoms, N,N-dialkylsulfamoyl having 1 to 4 carbon atoms or alkoxyalkyloxy having 1 to 4 carbon atoms;

$R^2$ is a hydrogen atom, alkyl having 1 to 4 carbon atoms or amino;

D is void, —C(O)—$(CH_2)_n$— wherein n is an integer of 0 to 7, or alkylene chain having 1 to 5 carbon atoms, provided that when D is methylene, then $R^2$ is alkyl having 1 to 4 carbon atoms and when D is void, then $R^2$ is a hydrogen atom;

$R^3$ is amino, monoalkylamino having 1 to 4 carbon atoms, dialkylamino having 1 to 4 carbon atoms, or a group selected from the formulas (a), (b) and (c), provided that when D is void, then $R^3$ is a group represented by the formula (a) and when n is 0, then $R^3$ is a group represented by the formula (a), wherein m is an integer of 1 to 3, l is an integer of 1 to 3, $R^4$ is a hydrogen atom, alkyl having 1 to 4 carbon atoms, hydroxyalkyl having 1 to 4 carbon atoms, arylalkyl optionally having substituent(s) or aryl optionally having substituent(s), $R^5$ is a hydrogen atom, a hydroxyl group, alkyl having 1 to 4 carbon atoms, hydroxyalkyl having 1 to 4 carbon atoms, and M is —CH—, —C=C—, a nitrogen atom or oxygen atom; and -X-Y-Z- is a group selected from the formulas (e) to (g), wherein in the formulas (e) to (g), $R^{3'}$ is amino, monoalkylamino having 1 to 4 carbon atoms, dialkylamino having 1 to 4 carbon atoms, or a group selected from the formulas (a), (b) and (c) ($R^4$, $R^5$ M, m or l for $R^{3'}$ is as defined for $R^4$, $R^5$ M, m or l for $R^3$ in this claim), D' is void or straight chain or branched chain alkylene chain having 1 to 8 carbon atoms, and $R^6$ is a hydrogen atom, methyl, aryl optionally having substituent(s), heteroaryl optionally having substituent(s), arylalkyl optionally having substituent(s) or heteroarylalkyl optionally having substituent(s);

an optically active form thereof, a pharmaceutically acceptable salt thereof, a hydrate thereof, a water adduct thereof and a solvate thereof.

(12) The isoquinoline compound of the above-mentioned (10) or (11), wherein, in the formula (I) or (II), $R^1$ is a hydrogen atom, a halogen atom, alkyl having 1 to 4 carbon atoms or alkoxy having 1 to 4 carbon atoms;

$R^2$ is a hydrogen atom, alkyl having 1 to 4 carbon atoms or amino;

D is void, —C(O)—$(CH_2)_n$— wherein n is an integer of 0 to 5, or alkylene chain having 1 to 5 carbon atoms, provided that when D is methylene, then $R^2$ is alkyl having 1 to 4 carbon atoms and when D is void, then $R^2$ is a hydrogen atom;

R³ is amino, monoalkylamino having 1 to 4 carbon atoms, dialkylamino having 1 to 4 carbon atoms, or a group selected from the formulas (a), (b) and (c), provided that when D is void, then R³ is a group represented by the formula (a) and when n is 0, then R³ is a group represented by the formula (a), wherein m is an integer of 1 to 3, l is an integer of 1 to 3, R⁴ is a hydrogen atom, alkyl having 1 to 4 carbon atoms, hydroxyalkyl having 1 to 4 carbon atoms, arylalkyl optionally having substituent(s) or aryl optionally having substituent(s), R⁵ is a hydrogen atom, a hydroxyl group, alkyl having 1 to 4 carbon atoms or hydroxyalkyl having 1 to 4 carbon atoms, and M is —CH—, —C=C— or a nitrogen atom or an oxygen atom;

-X-Y-Z- is a group selected from the formulas (e) to (g), wherein in the formulas (e) to (g), R³' is dialkylamino having 1 to 4 carbon atoms or (a) or (b) for R³ (R⁴, R⁵ M, m or l for R³' is as defined for R⁴, R⁵ M, m or l for R³ in this claim), D' is void or straight chain or branched chain alkylene having 1 to 4 carbon atoms, and R⁶ is a hydrogen atom or methyl;

an optically active form thereof, a pharmaceutically acceptable salt thereof, a hydrate thereof, a water adduct thereof or a solvate thereof.

(13) The isoquinoline compound of any of the above-mentioned (10) to (12), wherein, in the formula (I) or (II), R¹ is a hydrogen atom, a fluorine atom, a chlorine atom, methyl, or methoxy;

R² is a hydrogen atom, methyl, ethyl, isopropyl or amino;

D is void, —C(O)—(CH₂)ₙ— wherein n is an integer of 0 to 3, or methylene, provided that when D is methylene, then R² is methyl, ethyl or isopropyl and when D is void, then R² is a hydrogen atom, R³ is dimethylamino, diethylamino, diisopropylamino or a group selected from the following formulas (a), (b) and (c), provided that when D is void, then R³ is (a) and when n is 0, then R³ is (a), wherein m is an integer of 1 to 2, l is an integer of 1 to 2, R⁴ is a hydrogen atom, methyl, ethyl, 2-hydroxyethyl, phenyl or benzyl, R⁵ is a hydrogen atom, a hydroxyl group or hydroxymethyl, and M is —CH—, —C=C—, a nitrogen atom or an oxygen atom;

-X-Y-Z- is a group selected from the formulas (e) to (g), wherein, in the formulas (e) to (g), R³' is dimethylamino, pyrrolidin-1-yl, 4-methylpiperazin-1-yl, 4-phenylpiperazin-1-yl, morpholin-4-yl, piperidin-1-yl, 4-phenylpiperidin-1-yl, 3-hydroxypyrrolidin-1-yl or 2-hydroxymethylpyrrolidin-1-yl, and D' is methylene or ethylene;

an optically active form thereof, a pharmaceutically acceptable salt thereof, a hydrate thereof, a water adduct thereof or a solvate thereof.

(14) The isoquinoline compound of any of the above-mentioned (10) to (13), which is selected from (1) 3-amino-4-(2-(dimethylamino)acetyl)-2H-isoquinolin-1-one,
(2) 3-amino-4-(2-(piperidin-1-yl)acetyl)-2H-isoquinolin-1-one,
(3) 3-amino-4-(2-(dimethylamino)acetyl)-5-methyl-2H-isoquinolin-1-one,
(4) 3-amino-4-(3-(dimethylamino)propionyl)-2H-isoquinolin-1-one,
(5) 3-amino-4-(4-(dimethylamino)butyryl)-2H-isoquinolin-1-one,
(6) (R)-3-amino-4-((1-methylpyrrolidin-2-yl)carbonyl)-2H-isoquinolin-1-one,
(7) 3-methyl-1-(pyrrolidin-1-yl)methyl-3H-pyrazolo[3,4-c]isoquinolin-5(4H)-one,
(8) (S)-3-amino-4-((1-methylpyrrolidin-2-yl)carbonyl)-2H-isoquinolin-1-one,
(9) 3-amino-4-(3-(pyrrolidin-1-yl)propionyl)-2H-isoquinolin-1-one,
(10) 3-amino-7-methyl-4-((dimethylamino)acetyl)-2H-isoquinolin-1-one,
(11) 3-amino-7-methyl-4-((pyrrolidin-1-yl)acetyl)-2H-isoquinolin-1-one,
(12) 3-amino-4-(3-(dimethylamino)propionyl)-7-methyl-2H-isoquinolin-1-one,
(13) 3-amino-4-((pyrrolidin-1-yl)acetyl)-2H-isoquinolin-1-one,
(14) 3-amino-4-(2-(dimethylamino)acetyl)-7-fluoro-2H-isoquinolin-1-one,
(15) 3-amino-7-fluoro-4-((pyrrolidin-1-yl)acetyl)-2H-isoquinolin-1-one,
(16) 3-amino-4-(3-(dimethylamino)propionyl)-7-fluoro-2H-isoquinolin-1-one,
(17) 3-methyl-1-dimethylaminomethyl-3H-pyrazolo[3,4-c]isoquinolin-5(4H)-one,
(18) 3-amino-4-(2-(dimethylamino)acetyl)-7-chloro-2H-isoquinolin-1-one,
(19) 3-amino-4-(3-(dimethylamino)propionyl)-7-chloro-2H-isoquinolin-1-one,
(20) 3-amino-4-(2-(pyrrolidin-1-yl)acetyl)-7-chloro-2H-isoquinolin-1-one,
(21) 3-methyl-1-((4-methylpiperazin-1-yl)methyl)-3H-pyrazolo[3,4-c]isoquinolin-5(4H)-one,
(22) 3-methyl-1-((morpholin-4-yl)methyl)-3H-pyrazolo[3,4-c]isoquinolin-5(4H)-one,
(23) 3-methyl-1-((piperidin-1-yl)methyl)-3H-pyrazolo[3,4-c]isoquinolin-5(4H)-one,
(24) 1-(2-(pyrrolidin-1-yl)ethyl)-3-methyl-3H-pyrazolo[3,4-c]isoquinolin-5(4H)-one,
(25) 3-methyl-4-(pyrrolidin-1-yl)methyl-2H-isoquinolin-1-one,
(26) 3-amino-6-chloro-4-(2-(dimethylamino)acetyl)-2H-isoquinolin-1-one,
(27) 7-chloro-3-methyl-4-((pyrrolidin-1-yl)methyl)-2H-isoquinolin-1-one,
(28) 7-fluoro-3-methyl-4-((pyrrolidin-1-yl)methyl)-2H-isoquinolin-1-one,
(29) 4-((pyrrolidin-1-yl)methyl)-2H-isoquinolin-1-one,
(30) 3-methyl-4-(dimethylaminomethyl)-2H-isoquinolin-1-one,
(31) 4-(piperidin-4-yl)-2H-isoquinolin-1-one,
(32) 4-(1-(2-hydroxyethyl)piperidin-4-yl)-2H-isoquinolin-1-one,
(33) 4-(1-methylpiperidin-4-yl)-2H-isoquinolin-1-one,
(34) 3-methyl-4-(piperidin-1-yl)methyl-2H-isoquinolin-1-one,
(35) 4-dimethylaminomethyl-3-isopropyl-2H-isoquinolin-1-one,

(36) 4-(pyrrolidin-1-yl)methyl-3-isopropyl-2H-isoquinolin-1-one,
(37) 3-methyl-4-((4-phenylpiperidin-1-yl)methyl)-2H-isoquinolin-1-one,
(38) (S)-3-methyl-1-((3-hydroxypyrrolidin-1-yl)methyl)-3H-pyrazolo[3,4-c]isoquinolin-5(4H)-one,
(39) (R)-3-methyl-1-((3-hydroxypyrrolidin-1-yl)methyl)-3H-pyrazolo[3,4-c]isoquinolin-5(4H)-one,
(40) 3-methyl-4-((4-phenylpiperazin-1-yl)methyl)-2H-isoquinolin-1-one,
(41) 3-methyl-4-diethylaminomethyl-2H-isoquinolin-1-one,
(42) 3-methyl-4-(morpholin-4-yl)methyl-2H-isoquinolin-1-one,
(43) 4-(4-phenylpiperazin-1-yl)methyl-3-isopropyl-2H-isoquinolin-1-one,
(44) 7-chloro-4-(piperidin-4-yl)-2H-isoquinolin-1-one,
(45) 7-fluoro-4-(piperidin-4-yl)-2H-isoquinolin-1-one,
(46) 7-chloro-4-(1-methylpiperidin-4-yl)-2H-isoquinolin-1-one,
(47) 7-fluoro-4-(1-methylpiperidin-4-yl)-2H-isoquinolin-1-one,
(48) 7-fluoro-4-(1-(2-hydroxyethyl)piperidin-4-yl)-2H-isoquinolin-1-one,
(49) 4-dimethylaminomethyl-3-ethyl-2H-isoquinolin-1-one,
(50) 4-(pyrrolidin-1-yl)methyl-3-ethyl-2H-isoquinolin-1-one,
(51) 7-chloro-3-methyl-1-(pyrrolidin-1-yl)methyl-3H-pyrazolo[3,4-c]isoquinolin-5(4H)-one,
(52) 7-chloro-3-methyl-1-dimethylaminomethyl-3H-pyrazolo[3,4-c]isoquinolin-5(4H)-one,
(53) 7-fluoro-3-methyl-1-(pyrrolidin-1-yl)methyl-3H-pyrazolo[3,4-c]isoquinolin-5(4H)-one,
(54) 7-fluoro-3-methyl-1-dimethylaminomethyl-3H-pyrazolo[3,4-c]isoquinolin-5(4H)-one,
(55) 7-methoxy-3-methyl-1-(pyrrolidin-1-yl)methyl-3H-pyrazolo[3,4-c]isoquinolin-5(4H)-one,
(56) 7-methoxy-3-methyl-1-dimethylaminomethyl-3H-pyrazolo[3,4-c]isoquinolin-5(4H)-one,
(57) 3-methyl-1-(4-phenylpiperidin-1-yl)methyl-3H-pyrazolo[3,4-c]isoquinolin-5(4H)-one,
(58) 3-methyl-1-(4-phenylpiperazin-1-yl)methyl-3H-pyrazolo[3,4-c]isoquinolin-5(4H)-one,
(59) 3-methyl-1-(4-phenyl-1,2,3,6-tetrahydropyridin-1-yl)methyl-3H-pyrazolo[3,4-c]isoquinolin-5(4H)-one,
(60) (R)-3-methyl-1-(2-hydroxymethylpyrrolidin-1-yl)methyl-3H-pyrazolo[3,4-c]isoquinolin-5(4H)-one,
(61) (S)-3-methyl-1-(2-hydroxymethylpyrrolidin-1-yl)methyl-3H-pyrazolo[3,4-c]isoquinolin-5(4H)-one,
(62) 1-(pyrrolidin-1-yl)methylisoxazolo[5,4-c]isoquinolin-5(4H)-one,
(63) 1-dimethylaminomethylisoxazolo[5,4-c]isoquinolin-5(4H)-one,
(64) 7-chloro-1-dimethylaminomethylisoxazolo[5,4-c]isoquinolin-5(4H)-one,
(65) 7-chloro-1-(pyrrolidin-1-yl)methylisoxazolo[5,4-c]isoquinolin-5(4H)-one,
(66) 7-fluoro-1-dimethylaminomethylisoxazolo[5,4-c]isoquinolin-5(4H)-one,
(67) 7-fluoro-1-(pyrrolidin-1-yl)methylisoxazolo[5,4-c]isoquinolin-5(4H)-one,
(68) 1-(pyrrolidin-1-yl)methylisothiazolo[5,4-c]isoquinolin-5(4H)-one,
(69) 1-dimethylaminomethylisothiazolo[5,4-c]isoquinolin-5(4H)-one,
(70) 7-chloro-1-dimethylaminomethylisothiazolo[5,4-c]isoquinolin-5(4H)-one,
(71) 7-chloro-1-(pyrrolidin-1-yl)methylisothiazolo[5,4-c]isoquinolin-5(4H)-one,
(72) 7-fluoro-1-dimethylaminomethylisothiazolo[5,4-c]isoquinolin-5(4H)-one,
(73) 7-fluoro-1-(pyrrolidin-1-yl)methylisothiazolo[5,4-c]isoquinolin-5(4H)-one,
(74) 4-(1-ethylpiperidin-4-yl)-2H-isoquinolin-1-one,
(75) 4-(piperidin-4-yl)-3-methyl-2H-isoquinolin-1-one,
(76) 4-(1-methylpiperidin-4-yl)-3-methyl-2H-isoquinolin-1-one,
(77) 4-(1-(2-hydroxyethyl)piperidin-4-yl)-3-methyl-2H-isoquinolin-1-one,
(78) 4-(1-ethylpiperidin-4-yl)-3-methyl-2H-isoquinolin-1-one,
(79) 4-(piperidin-4-yl)-7-chloro-3-methyl-2H-isoquinolin-1-one,
(80) 4-(1-methylpiperidin-4-yl)-7-chloro-3-methyl-2H-isoquinolin-1-one,
(81) 4-(1-(2-hydroxyethyl)piperidin-4-yl)-7-chloro-3-methyl-2H-isoquinolin-1-one,
(82) 4-(1-ethylpiperidin-4-yl)-7-chloro-3-methyl-2H-isoquinolin-1-one,
(83) 4-(piperidin-4-yl)-7-fluoro-3-methyl-2H-isoquinolin-1-one,
(84) 4-(1-methylpiperidin-4-yl)-7-fluoro-3-methyl-2H-isoquinolin-1-one,
(85) 4-(1-(2-hydroxyethyl)piperidin-4-yl)-7-fluoro-3-methyl-2H-isoquinolin-1-one,
(86) 4-(1-ethylpiperidin-4-yl)-7-fluoro-3-methyl-2H-isoquinolin-1-one,
(87) 4-(piperidin-4-yl)-3,7-dimethyl-2H-isoquinolin-1-one,
(88) 4-(1-methylpiperidin-4-yl)-3,7-dimethyl-2H-isoquinolin-1-one,
(89) 4-(1-(2-hydroxyethyl)piperidin-4-yl)-3,7-dimethyl-2H-isoquinolin-1-one,
(90) 4-(1-ethylpiperidin-4-yl)-3,7-dimethyl-2H-isoquinolin-1-one,
(91) 4-(pyrrolidin-3-yl)-2H-isoquinolin-1-one,
(92) 4-(1-methylpyrrolidin-3-yl)-2H-isoquinolin-1-one,
(93) 4-(1-ethylpyrrolidin-3-yl)-2H-isoquinolin-1-one,
(94) 4-(1-(2-hydroxyethyl)pyrrolidin-3-yl)-2H-isoquinolin-1-one,
(95) 4-(pyrrolidin-3-yl)-7-chloro-2H-isoquinolin-1-one,
(96) 4-(1-methylpyrrolidin-3-yl)-7-chloro-2H-isoquinolin-1-one,
(97) 4-(1-ethylpyrrolidin-3-yl)-7-chloro-2H-isoquinolin-1-one,
(98) 4-(1-(2-hydroxyethyl)pyrrolidin-3-yl)-7-chloro-2H-isoquinolin-1-one,
(99) 4-(pyrrolidin-3-yl)-7-fluoro-2H-isoquinolin-1-one,
(100) 4-(1-methylpyrrolidin-3-yl)-7-fluoro-2H-isoquinolin-1-one,
(101) 4-(1-ethylpyrrolidin-3-yl)-7-fluoro-2H-isoquinolin-1-one,
(102) 4-(1-(2-hydroxyethyl)pyrrolidin-3-yl)-7-fluoro-2H-isoquinolin-1-one,
(103) 4-(pyrrolidin-3-yl)-3-methyl-2H-isoquinolin-1-one,
(104) 4-(1-methylpyrrolidin-3-yl)-3-methyl-2H-isoquinolin-1-one,
(105) 4-(1-ethylpyrrolidin-3-yl)-3-methyl-2H-isoquinolin-1-one,
(106) 4-(1-(2-hydroxyethyl)pyrrolidin-3-yl)-3-methyl-2H-isoquinolin-1-one,
(107) 4-(pyrrolidin-3-yl)-7-chloro-3-methyl-2H-isoquinolin-1-one,
(108) 4-(1-methylpyrrolidin-3-yl)-7-chloro-3-methyl-2H-isoquinolin-1-one, (109) 4-(1-ethylpyrrolidin-3-yl)-7-chloro-3-methyl-2H-isoquinolin-1-one,
(110) 4-(1-(2-hydroxyethyl)pyrrolidin-3-yl)-7-chloro-3-methyl-2H-isoquinolin-1-one,
(111) 4-(pyrrolidin-3-yl)-7-fluoro-3-methyl-2H-isoquinolin-1-one,
(112) 4-(1-methylpyrrolidin-3-yl)-7-fluoro-3-methyl-2H-isoquinolin-1-one,
(113) 4-(1-ethylpyrrolidin-3-yl)-7-fluoro-3-methyl-2H-isoquinolin-1-one,
(114) 4-(1-(2-hydroxyethyl)pyrrolidin-3-yl)-7-fluoro-3-methyl-2H-isoquinolin-1-one,
(115) 4-(pyrrolidin-2-yl)-3-methyl-2H-isoquinolin-1-one,
(116) 4-(1-methylpyrrolidin-2-yl)-3-methyl-2H-isoquinolin-1-one,
(117) 4-(1-(2-hydroxyethyl)pyrrolidin-2-yl)-3-methyl-2H-isoquinolin-1-one,
(118) 4-(pyrrolidin-2-yl)-7-chloro-3-methyl-2H-isoquinolin-1-one,
(119) 4-(1-methylpyrrolidin-2-yl)-7-chloro-3-methyl-2H-isoquinolin-1-one,
(120) 4-(pyrrolidin-2-yl)-7-fluoro-3-methyl-2H-isoquinolin-1-one,
(121) 4-(1-methylpyrrolidin-2-yl)-7-fluoro-3-methyl-2H-isoquinolin-1-one,
(122) 3-methyl-4-[(4-methylpiperazin-1-yl)methyl]-2H-isoquinolin-1-one,
(123) 3-methyl-4-[4-(2-hydroxyethyl)piperazin-1-yl]methyl-2H-isoquinolin-1-one,
(124) 3-methyl-4-(4-benzylpiperidin-1-yl)methyl-2H-isoquinolin-1-one,
(125) 3-methyl-4-(1,2,3,4-tetrahydroisoquinolin-2-yl)methyl-2H-isoquinolin-1-one,
(126) 3-methyl-4-(indolin-1-yl)methyl-2H-isoquinolin-1-one,
(127) 3-methyl-4-(diisopropylamino)methyl-2H-isoquinolin-1-one,
(128) (S)-3-methyl-4-(3-hydroxypyrrolidin-1-yl)methyl-2H-isoquinolin-1-one,
(129) (R)-3-methyl-4-(3-hydroxypyrrolidin-1-yl)methyl-2H-isoquinolin-1-one,
(130) (R)-3-methyl-4-(2-hydroxymethylpyrrolidin-1-yl)methyl-2H-isoquinolin-1-one,
(131) (S)-3-methyl-4-(2-hydroxymethylpyrrolidin-1-yl)methyl-2H-isoquinolin-1-one,
(132) 3-methyl-4-(4-hydroxypiperidin-1-yl)methyl-2H-isoquinolin-1-one,
(133) 3-methyl-4-(4-phenyl-1,2,3,6-tetrahydropyridin-1-yl)methyl-2H-isoquinolin-1-one,
(134) 7-chloro-4-dimethylaminomethyl-3-methyl-2H-isoquinolin-1-one,
(135) 7-chloro-4-diethylaminomethyl-3-methyl-2H-isoquinolin-1-one,
(136) 7-chloro-4-(4-phenylpiperidin-1-yl)methyl-3-methyl-2H-isoquinolin-1-one,
(137) 7-chloro-4-(4-phenylpiperazin-1-yl)methyl-3-methyl-2H-isoquinolin-1-one,
(138) 7-chloro-4-(morpholin-4-yl)methyl-3-methyl-2H-isoquinolin-1-one,
(139) 7-chloro-4-(4-methylpiperazin-1-yl)methyl-3-methyl-2H-isoquinolin-1-one,
(140) 7-chloro-4-(4-(2-hydroxyethyl)piperazin-1-yl)methyl-3-methyl-2H-isoquinolin-1-one,
(141) 7-chloro-4-(4-benzylpiperidin-1-yl)methyl-3-methyl-2H-isoquinolin-1-one,
(142) 7-chloro-4-(1,2,3,4-tetrahydroisoquinolin-2-yl)methyl-3-methyl-2H-isoquinolin-1-one,
(143) 7-chloro-4-(indolin-1-yl)methyl-3-methyl-2H-isoquinolin-1-one,
(144) 7-chloro-4-diisopropylaminomethyl-3-methyl-2H-isoquinolin-1-one,
(145) (S)-7-chloro-4-(3-hydroxypyrrolidin-1-yl)methyl-3-methyl-2H-isoquinolin-1-one,
(146) (R)-7-chloro-4-(3-hydroxypyrrolidin-1-yl)methyl-3-methyl-2H-isoquinolin-1-one,
(147) (R)-7-chloro-4-(2-hydroxymethylpyrrolidin-1-yl)methyl-3-methyl-2H-isoquinolin-1-one,
(148) (S)-7-chloro-4-(2-hydroxymethylpyrrolidin-1-yl)methyl-3-methyl-2H-isoquinolin-1-one,
(149) 7-chloro-4-(4-hydroxypiperidin-1-yl)methyl-3-methyl-2H-isoquinolin-1-one,
(150) 7-chloro-4-(4-phenyl-1,2,3,6-tetrahydropyridin-1-yl)methyl-3-methyl-2H-isoquinolin-1-one,
(151) 7-fluoro-4-dimethylaminomethyl-3-methyl-2H-isoquinolin-1-one,
(152) 7-fluoro-4-diethylaminomethyl-3-methyl-2H-isoquinolin-1-one,
(153) 7-fluoro-4-(4-phenylpiperidin-1-yl)methyl-3-methyl-2H-isoquinolin-1-one,
(154) 7-fluoro-4-(4-phenylpiperazin-1-yl)methyl-3-methyl-2H-isoquinolin-1-one,
(155) 7-fluoro-4-(morpholin-4-yl)methyl-3-methyl-2H-isoquinolin-1-one,
(156) 7-fluoro-4-(4-methylpiperazin-1-yl)methyl-3-methyl-2H-isoquinolin-1-one,
(157) 7-fluoro-4-(4-(2-hydroxyethyl)piperazin-1-yl)methyl-3-methyl-2H-isoquinolin-1-one,
(158) 7-fluoro-4-(4-benzylpiperidin-1-yl)methyl-3-methyl-2H-isoquinolin-1-one,
(159) 7-fluoro-4-(1,2,3,4-tetrahydroisoquinolin-2-yl)methyl-3-methyl-2H-isoquinolin-1-one,
(160) 7-fluoro-4-(indolin-1-yl)methyl-3-methyl-2H-isoquinolin-1-one,
(161) 7-fluoro-4-diisopropylaminomethyl-3-methyl-2H-isoquinolin-1-one,
(162) (S)-7-fluoro-4-(3-hydroxypyrrolidin-1-yl)methyl-3-methyl-2H-isoquinolin-1-one,
(163) (R)-7-fluoro-4-(3-hydroxypyrrolidin-1-yl)methyl-3-methyl-2H-isoquinolin-1-one,
(164) (R)-7-fluoro-4-(2-hydroxymethylpyrrolidin-1-yl)methyl-3-methyl-2H-isoquinolin-1-one, (165) (S)-7-fluoro-4-(2-hydroxymethylpyrrolidin-1-yl)methyl-3-methyl-2H-isoquinolin-1-one,
(166) 7-fluoro-4-(4-hydroxypiperidin-1-yl)methyl-3-methyl-2H-isoquinolin-1-one,
(167) 7-fluoro-4-(4-phenyl-1,2,3,6-tetrahydropyridin-1-yl)methyl-3-methyl-2H-isoquinolin-1-one,
(168) (S)-4-(3-hydroxypyrrolidin-1-yl)methyl-3-ethyl-2H-isoquinolin-1-one,
(169) (R)-4-(3-hydroxypyrrolidin-1-yl)methyl-3-ethyl-2H-isoquinolin-1-one,
(170) (R)-4-(2-hydroxymethylpyrrolidin-1-yl)methyl-3-ethyl-2H-isoquinolin-1-one,
(171) (S)-4-(2-hydroxymethylpyrrolidin-1-yl)methyl-3-ethyl-2H-isoquinolin-1-one,
(172) 4-(4-hydroxypiperidin-1-yl)methyl-3-ethyl-2H-isoquinolin-1-one,
(173) (S)-4-(3-hydroxypyrrolidin-1-yl)methyl-3-isopropyl-2H-isoquinolin-1-one,
(174) (R)-4-(3-hydroxypyrrolidin-1-yl)methyl-3-isopropyl-2H-isoquinolin-1-one,
(175) (R)-4-(2-hydroxymethylpyrrolidin-1-yl)methyl-3-isopropyl-2H-isoquinolin-1-one, (176) (S)-4-(2-hydroxymethylpyrrolidin-1-yl)methyl-3-isopropyl-2H-isoquinolin-1-one,
(177) 4-(4-hydroxypiperidin-1-yl)methyl-3-isopropyl-2H-isoquinolin-1-one,
(178) 7-chloro-4-dimethylaminomethyl-3-ethyl-2H-isoquinolin-1-one,
(179) 7-chloro-4-(pyrrolidin-1-yl)methyl-3-ethyl-2H-isoquinolin-1-one,
(180) (S)-7-chloro-4-(3-hydroxypyrrolidin-1-yl)methyl-3-ethyl-2H-isoquinolin-1-one,
(181) (R)-7-chloro-4-(3-hydroxypyrrolidin-1-yl)methyl-3-ethyl-2H-isoquinolin-1-one,
(182) (R)-7-chloro-4-(2-hydroxymethylpyrrolidin-1-yl)methyl-3-ethyl-2H-isoquinolin-1-one,
(183) (S)-7-chloro-4-(2-hydroxymethylpyrrolidin-1-yl)methyl-3-ethyl-2H-isoquinolin-1-one,
(184) 7-chloro-3-ethyl-4-(4-hydroxypiperidin-1-yl)methyl-2H-isoquinolin-1-one,
(185) 7-fluoro-4-dimethylaminomethyl-3-ethyl-2H-isoquinolin-1-one,
(186) 7-fluoro-4-(pyrrolidin-1-yl)methyl-3-ethyl-2H-isoquinolin-1-one,
(187) (S)-7-fluoro-4-(3-hydroxypyrrolidin-1-yl)methyl-3-ethyl-2H-isoquinolin-1-one,
(188) (R)-7-fluoro-4-(3-hydroxypyrrolidin-1-yl)methyl-3-ethyl-2H-isoquinolin-1-one,
(189) (R)-7-fluoro-4-(2-hydroxymethylpyrrolidin-1-yl)methyl-3-ethyl-2H-isoquinolin-1-one,
(190) (S)-7-fluoro-4-(2-hydroxymethylpyrrolidin-1-yl)methyl-3-ethyl-2H-isoquinolin-1-one,
(191) 7-fluoro-3-ethyl-4-(4-hydroxypiperidin-1-yl)methyl-2H-isoquinolin-1-one, and
(192) 7-chloro-4-(1-(2-hydroxyethyl)piperidin-4-yl)-2H-isoquinolin-1-one, an optically active form thereof, a pharmaceutically acceptable salt thereof, a hydrate thereof, a water adduct thereof and a solvate thereof.

(15) The isoquinoline compound of any of the above-mentioned (10) to (14), which is selected from (1) 3-amino-4-(2-(dimethylamino)acetyl)-2H-isoquinolin-1-one,
(2) 3-amino-4-(2-(piperidin-1-yl)acetyl)-2H-isoquinolin-1-one,
(3) 3-amino-4-(2-(dimethylamino)acetyl)-5-methyl-2H-isoquinolin-1-one,
(4) 3-amino-4-(3-(dimethylamino)propionyl)-2H-isoquinolin-1-one,
(5) 3-amino-4-(4-(dimethylamino)butyryl)-2H-isoquinolin-1-one,
(6) (R)-3-amino-4-((1-methylpyrrolidin-2-yl)carbonyl)-2H-isoquinolin-1-one,
(7) 3-methyl-1-(pyrrolidin-1-yl)methyl-3H-pyrazolo[3,4-c]isoquinolin-5(4H)-one,
(8) (S)-3-amino-4-((1-methylpyrrolidin-2-yl)carbonyl)-2H-isoquinolin-1-one,
(9) 3-amino-4-(3-(pyrrolidin-1-yl)propionyl)-2H-isoquinolin-1-one,
(10) 3-amino-7-methyl-4-((dimethylamino)acetyl)-2H-isoquinolin-1-one,
(11) 3-amino-7-methyl-4-((pyrrolidin-1-yl)acetyl)-2H-isoquinolin-1-one,
(12) 3-amino-4-(3-(dimethylamino)propionyl)-7-methyl-2H-isoquinolin-1-one,
(13) 3-amino-4-((pyrrolidin-1-yl)acetyl)-2H-isoquinolin-1-one,
(14) 3-amino-4-(2-(dimethylamino)acetyl)-7-fluoro-2H-isoquinolin-1-one,
(15) 3-amino-7-fluoro-4-((pyrrolidin-1-yl)acetyl)-2H-isoquinolin-1-one,
(16) 3-amino-4-(3-(dimethylamino)propionyl)-7-fluoro-2H-isoquinolin-1-one,
(17) 3-methyl-1-dimethylaminomethyl-3H-pyrazolo[3,4-c]isoquinolin-5(4H)-one,
(18) 3-amino-4-(2-(dimethylamino)acetyl)-7-chloro-2H-isoquinolin-1-one,
(19) 3-amino-4-(3-(dimethylamino)propionyl)-7-chloro-2H-isoquinolin-1-one,
(20) 3-amino-4-(2-(pyrrolidin-1-yl)acetyl)-7-chloro-2H-isoquinolin-1-one,
(21) 3-methyl-1-((4-methylpiperazin-1-yl)methyl)-3H-pyrazolo[3,4-c]isoquinolin-5(4H)-one,
(22) 3-methyl-1-((morpholin-4-yl)methyl)-3H-pyrazolo[3,4-c]isoquinolin-5(4H)-one,
(23) 3-methyl-1-((piperidin-1-yl)methyl)-3H-pyrazolo[3,4-c]isoquinolin-5(4H)-one,
(24) 1-(2-(pyrrolidin-1-yl)ethyl)-3-methyl-3H-pyrazolo[3,4-c]isoquinolin-5(4H)-one,
(25) 3-methyl-4-(pyrrolidin-1-yl)methyl-2H-isoquinolin-1-one,
(26) 3-amino-6-chloro-4-(2-(dimethylamino)acetyl)-2H-isoquinolin-1-one,
(27) 7-chloro-3-methyl-4-((pyrrolidin-1-yl)methyl)-2H-isoquinolin-1-one,
(28) 7-fluoro-3-methyl-4-((pyrrolidin-1-yl)methyl)-2H-isoquinolin-1-one,
(29) 4-((pyrrolidin-1-yl)methyl)-2H-isoquinolin-1-one,
(30) 3-methyl-4-(dimethylaminomethyl)-2H-isoquinolin-1-one,
(31) 4-(piperidin-4-yl)-2H-isoquinolin-1-one,
(32) 4-(1-(2-hydroxyethyl)piperidin-4-yl)-2H-isoquinolin-1-one,
(33) 4-(1-methylpiperidin-4-yl)-2H-isoquinolin-1-one,
(34) 3-methyl-4-(piperidin-1-yl)methyl-2H-isoquinolin-1-one,
(35) 4-dimethylaminomethyl-3-isopropyl-2H-isoquinolin-1-one,
(36) 4-(pyrrolidin-1-yl)methyl-3-isopropyl-2H-isoquinolin-1-one,
(37) 3-methyl-4-((4-phenylpiperidin-1-yl)methyl)-2H-isoquinolin-1-one,
(38) (S)-3-methyl-1-((3-hydroxypyrrolidin-1-yl)methyl)-3H-pyrazolo[3,4-c]isoquinolin-5(4H)-one,
(39) (R)-3-methyl-1-((3-hydroxypyrrolidin-1-yl)methyl)-3H-pyrazolo[3,4-c]isoquinolin-5(4H)-one,
(40) 3-methyl-4-((4-phenylpiperazin-1-yl)methyl)-2H-isoquinolin-1-one,
(41) 3-methyl-4-diethylaminomethyl-2H-isoquinolin-1-one,
(42) 3-methyl-4-(morpholin-4-yl)methyl-2H-isoquinolin-1-one,
(43) 4-(4-phenylpiperazin-1-yl)methyl-3-isopropyl-2H-isoquinolin-1-one,
(44) 7-chloro-4-(piperidin-4-yl)-2H-isoquinolin-1-one,
(45) 7-fluoro-4-(piperidin-4-yl)-2H-isoquinolin-1-one,
(46) 7-chloro-4-(1-methylpiperidin-4-yl)-2H-isoquinolin-1-one,
(47) 7-fluoro-4-(1-methylpiperidin-4-yl)-2H-isoquinolin-1-one,
(48) 7-fluoro-4-(1-(2-hydroxyethyl)piperidin-4-yl)-2H-isoquinolin-1-one,
(49) 4-dimethylaminomethyl-3-ethyl-2H-isoquinolin-1-one,
(50) 4-(pyrrolidin-1-yl)methyl-3-ethyl-2H-isoquinolin-1-one, (122) 3-methyl-4-[(4-methylpiperazin-1-yl)methyl]-2H-isoquinolin-1-one,
(123) 3-methyl-4-[4-(2-hydroxyethyl)piperazin-1-yl]methyl-2H-isoquinolin-1-one,
(124) 3-methyl-4-(4-benzylpiperidin-1-yl)methyl-2H-isoquinolin-1-one,
(125) 3-methyl-4-(1,2,3,4-tetrahydroisoquinolin-2-yl)methyl-2H-isoquinolin-1-one
(126) 3-methyl-4-(indolin-1-yl)methyl-2H-isoquinolin-1-one, and
(127) 3-methyl-4-(diisopropylamino)methyl-2H-isoquinolin-1-one, an optically active form thereof, a pharmaceutically acceptable salt thereof, a hydrate thereof, a water adduct thereof or a solvate thereof.

(16) The isoquinoline compound of any of the above-mentioned (10) to (15), wherein, in the formula (I),
$R^1$ is a hydrogen atom, a fluorine atom or a chlorine atom;
$R^2$ is a hydrogen atom;
D is void; and
$R^3$ is a group selected from the formula (a),
  wherein m is 2,
  $R^4$ is a hydrogen atom, methyl or hydroxyethyl, and
  $R^5$ is hydrogen;

an optically active form thereof, a pharmaceutically acceptable salt thereof, a hydrate thereof, a water adduct thereof or a solvate thereof.

(17) The isoquinoline compound of any of the above-mentioned (10) to (16), which is selected from
(31) 4-(piperidin-4-yl)-2H-isoquinolin-1-one,
(32) 4-(1-(2-hydroxyethyl)piperidin-4-yl)-2H-isoquinolin-1-one,
(33) 4-(1-methylpiperidin-4-yl)-2H-isoquinolin-1-one,
(44) 7-chloro-4-(piperidin-4-yl)-2H-isoquinolin-1-one,
(45) 7-fluoro-4-(piperidin-4-yl)-2H-isoquinolin-1-one,
(46) 7-chloro-4-(1-methylpiperidin-4-yl)-2H-isoquinolin-1-one,
(47) 7-fluoro-4-(1-methylpiperidin-4-yl)-2H-isoquinolin-1-one,
(48) 7-fluoro-4-(1-(2-hydroxyethyl)piperidin-4-yl)-2H-isoquinolin-1-one,
(74) 4-(1-ethylpiperidin-4-yl)-2H-isoquinolin-1-one, and
(192) 7-chloro-4-(1-(2-hydroxyethyl)piperidin-4-yl)-2H-isoquinolin-1-one, an optically active form thereof, a pharmaceutically acceptable salt thereof, a hydrate thereof, a water adduct thereof or a solvate thereof.

(18) An agent for the prophylaxis and/or treatment of a disease caused by hyperactivity of poly(ADP-ribose)polymerase, which comprises the isoquinoline compound of any of the above-mentioned (1) to (17), an optically active form thereof, a pharmaceutically acceptable salt thereof, a hydrate thereof, a water adduct thereof or a solvate thereof.

(19) The agent for the prophylaxis and/or treatment of the above-mentioned (18), wherein the disease caused by hyperactivity of poly(ADP-ribose)polymerase is cerebral infarction.

(20) The agent for the prophylaxis and/or treatment of the above-mentioned (19), wherein the disease caused by hyperactivity of poly(ADP-ribose)polymerase is acute cerebral infarction.

(21) A poly(ADP-ribose)polymerase inhibitor comprising the isoquinoline compound of any of the above-mentioned (1) to (17), an optically active form thereof, a pharmaceutically acceptable salt thereof, a hydrate thereof, a water adduct thereof or a solvate thereof.

BEST MODE FOR EMBODYING THE INVENTION

The present invention is explained in detail in the following.

Each substituent in the formula (I) or (II) is now explained. Specific examples of the substituent for $R^1$ are as follows, and these substituents may be on any carbon atom in a ring.

halogen atom: fluorine atom, chlorine atom, bromine atom and iodine atom, with preference given to fluorine atom, chlorine atom and bromine atom, particularly preferably fluorine atom and chlorine atom.

alkyl: linear or branched chain alkyl having 1 to 4 carbon atoms, such as methyl, ethyl, propyl, isopropyl, butyl, isobutyl, tert-butyl and the like, with preference given to methyl and ethyl, particularly preferably methyl.

alkoxy: alkoxyl consisting of alkyl (as defined for alkyl for $R^1$) and oxygen atom, such as methoxy, ethoxy, propoxy, isopropoxy, butoxy, tert-butoxy and the like, with preference given to methoxy.

haloalkyl: alkyl (as defined for alkyl for $R^1$) substituted by one or more halogen atoms (as defined for halogen for $R^1$), such as fluoromethyl, difluoromethyl, trifluoromethyl, 2-fluoroethyl, 2,2-difluoroethyl, 2,2,2-trifluoroethyl and the like, with preference given to trifluoromethyl.

monoalkylamino: monoalkylamino having alkyl (as defined for alkyl for $R^1$), such as methylamino, ethylamino, n-propylamino, isopropylamino, n-butylamino and the like.

dialkylamino: dialkylamino wherein the alkyl moieties are the same or different and each is independently alkyl (as defined for alkyl for $R^1$) and the alkyl moieties may form a ring. For example, dimethylamino, diethylamino, N-methyl-N-ethylamino, pyrrolidin-1-yl, piperidin-1-yl and the like can be mentioned.

acyl: acyl having 1 to 4 carbon atoms in total, which consists of alkyl and carbonyl, such as formyl, acetyl, propionyl, 2-methylpropionyl, butyryl and the like.

alkoxycarbonyl: alkoxycarbonyl consisting of alkoxy (as defined for alkoxy for $R^1$) and carbonyl, such as methoxycarbonyl, ethoxycarbonyl, propoxycarbonyl, isopropoxycarbonyl, butoxycarbonyl, tert-butoxycarbonyl and the like.

N-alkylcarbamoyl: N-alkylcarbamoyl consisting of monoalkylamino having 1 to 4 carbon atoms and carbonyl, such as N-methylcarbamoyl, N-ethylcarbamoyl, N-propylcarbamoyl, N-butylcarbamoyl and the like.

N,N-dialkylcarbamoyl: N,N-dialkylcarbamoyl consisting of dialkylamino (as defined for dialkylamino for $R^1$) and carbonyl, such as N,N-dimethylcarbamoyl, N,N-diethylcarbamoyl, N,N-dipropylcarbamoyl, N,N-dibutylcarbamoyl and the like.

acylamino: acylamino consisting of acyl (as defined for acyl for $R^1$) and amino, such as formylamino, acetylamino, propionylamino, butyrylamino and the like.

diacylamino: diacylamino consisting of two acyls (as defined for acyl for $R^1$) and amino, wherein the acyl moieties are independent and may be the same or different, such as N,N-diacetylamino, N,N-dipropionylamino, N,N-dibutyrylamino and the like.

alkylthio: alkylthio consisting of alkyl (as defined for alkyl for $R^1$) and a sulfur atom, such as methylthio, ethylthio, propylthio, butylthio and the like, with preference given to methylthio.

alkoxycarbonylamino: alkoxycarbonylamino consisting of alkoxycarbonyl (as defined for alkoxycarbonyl for $R^1$) and amino, such as methoxycarbonylamino, ethoxycarbonylamino, propoxycarbonylamino, butoxycarbonylamino and the like.

N-alkylsulfamoyl: N-alkylsulfamoyl consisting of monoalkylamino (as defined for monoalkylamino for $R^1$) and sulfone, such as N-methylsulfamoyl, N-ethylsulfamoyl, N-propylsulfamoyl, N-butylsulfamoyl and the like.

N,N-dialkylsulfamoyl: N,N-dialkylsulfamoyl consisting of dialkylamino (as defined for dialkylamino for $R^1$) and sulfone, such as N,N-dimethylsulfamoyl, N,N-diethylsulfamoyl, N,N-dipropylsulfamoyl, N,N-dibutylsulfamoyl and the like.

alkoxyalkyloxy: alkoxyalkyloxy consisting of alkoxy (as defined for alkoxy for $R^1$), alkyl (as defined for alkyl for $R^1$) and oxygen, such as methoxymethyloxy, ethoxymethyloxy and the like, with preference given to methoxymethyloxy.

$R^1$ is preferably a hydrogen atom, halogen, alkyl or alkoxy, particularly preferably fluorine atom or chlorine atom.

The positions of substitution of $R^1$ are preferably the following positions.

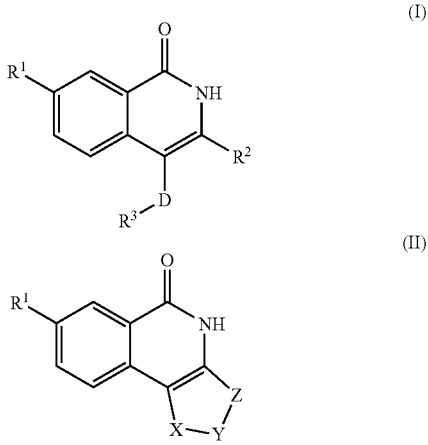

Specific examples of the substituent for $R^2$ are as follows.
alkyl: as defined for alkyl for $R^1$.

As the straight chain or branched chain alkylene having 1 to 8 carbon atoms for D, for example,
(1) —$CH_2$—
(2) —$CH_2CH_2$—,
(3) —$CH_2CH_2CH_2$—,
(4) —$CH_2CH_2CH_2CH_2$—,
(5) —$CH_2CH_2CH_2CH_2CH_2$—,
(6) —$CH_2CH_2CH_2CH_2CH_2CH_2$—,
(7) —$CH_2CH_2CH_2CH_2CH_2CH_2CH_2$—,
(8) —$CH_2CH_2CH_2CH_2CH_2CH_2CH_2CH_2$—,
(9) —$CH(CH_3)$—,
(10) —$C(CH_3)_2$—,
(11) —$CH(CH_3)CH_2$—,
(12) —$C(CH_3)_2CH_2$—,
(13) —$CH(CH_3)CH_2CH_2$—,
(14) —$C(CH_3)_2CH_2CH_2$—, and the like can be mentioned. Of these, (1), (2) and (3) are preferable, and (1) and (2) are particularly preferable.

n is an integer of 0 to 7, and 0 to 3 are preferable, 0 to 2 are more preferable, and 1 is particularly preferable.

D is preferably void or methylene or ethylene, and particularly preferably void.

Specific examples of the substituent for $R^3$ are as follows.
monoalkylamino: as defined for a monoalkylamino for $R^1$.
dialkylamino: as defined for dialkylamino for $R^1$.
As the substituent for $R^3$, dialkylamino, the formulas (a) and (b) are preferable, and the formula (a) is particularly preferable.

m is an integer of 1 to 3, and 1 or 2 is particularly preferable.
l is an integer of 1 to 3, and 1 or 2 is particularly preferable.
Specific examples of the substituent for $R^4$ are as follows.
alkyl: as defined for alkyl for $R^1$, with preference given to methyl, ethyl, propyl and isobutyl, particularly preferably methyl.

hydroxyalkyl: hydroxyalkyl consisting of alkyl (as defined for alkyl for $R^1$) and hydroxyl group, such as hydroxyethyl, hydroxypropyl, 2-hydroxy-2-methylpropyl, 4-hydroxybutyl and the like, with preference given to hydroxyethyl.

monoalkylamino: as defined for monoalkylamino for $R^1$.
dialkylamino: as defined for dialkylamino for $R^1$, with preference given to dimethylamino.

alkoxycarbonyl: as defined for alkoxycarbonyl for $R^1$, with preference given to ethoxycarbonyl.

alkylsulfonyl: alkylsulfonyl consisting of alkyl (as defined for alkyl for $R^1$) and sulfonyl, with preference given to methanesulfonyl.

acylamino: as defined for acylamino for $R^1$, such as formylamino, acetylamino, propionylamino, 2-methylpropionylamino, butyrylamino and the like. The acyl moiety may have a substituent and as the substituent, a halogen atom is preferable, a fluorine atom is particularly preferable and, for example, trifluoroacetylamino can be mentioned.

aryl optionally having substituent(s): as the aryl, phenyl and naphthyl can be mentioned, and phenyl is particularly preferable. As the substituent, those similar to the substituents for $R^1$ can be mentioned.

heteroaryl optionally having substituent(s): as the heteroaryl, furan, thiophene, oxazole, isoxazole, thiazole, isothiazole, pyridine, pyrimidine and the like can be mentioned. As the substituent, those similar to the substituents for $R^1$ can be mentioned.

arylalkyl optionally having substituent(s): a group consisting of aryl (as defined for aryl for $R^4$) and alkyl (as defined for alkyl for $R^1$) and, for example, benzyl and phenethyl can be mentioned, and benzyl is particularly preferable. As the substituent, those similar to the substituents for $R^1$ can be mentioned.

heteroarylalkyl optionally having substituent(s): a group consisting of heteroaryl (as defined for heteroaryl for $R^4$) and alkyl (as defined for alkyl for $R^1$). As the substituent, those similar to the substituents for $R^1$ can be mentioned.

alkylsulfonylamino: alkylsulfonylamino consisting of alkoxysulfonyl (as defined for alkoxysulfonyl for $R^1$) and amino, such as methanesulfonylamino, ethanesulfonylamino and the like, with preference given to methanesulfonylamino.

As the substituent for $R^4$, a hydrogen atom, alkyl and hydroxyalkyl are preferable, and hydrogen atom, methyl and ethyl are particularly preferable.

Specific examples of the substituent for $R^5$ are as follows.
alkyl: as defined for alkyl for $R^1$.
hydroxyalkyl: hydroxyalkyl consisting of alkyl (as defined for alkyl for $R^1$) and hydroxyl group, with preference given to hydroxymethyl.

-X-Y-Z- is preferably the formula (e).

As the straight chain or branched chain alkylene for D', those similar to the straight chain or branched chain alkylene for D can be mentioned, and methylene and ethylene are preferable, and methylene is more preferable. D' is most preferably void.

Specific examples of the substituent for $R^6$ are as follows.

aryl optionally having substituent(s): as defined for aryl optionally having substituent(s) for $R^4$.

heteroaryl optionally having substituent(s): as defined for heteroaryl optionally having substituent(s) for $R^4$.

arylalkyl optionally having substituent(s): as defined for arylalkyl optionally having substituent(s) for $R^4$.

heteroarylalkyl optionally having substituent(s): as defined for heteroarylalkyl optionally having substituent(s) for $R^4$.

As phenylene for D", 1,4-phenylene, 1,3-phenylene and 1,2-phenylene can be mentioned. As the linear or branched chain alkylene, those similar to the straight chain or branched chain alkylene for D can be mentioned.

As a compound of the formula (I) or (II), and a pharmaceutically acceptable salt thereof, acid addition salts thereof with inorganic acids or organic acids can be mentioned.

The compound of the formula (I) or (II), and a pharmaceutically acceptable salt thereof may be in the form of a hydrate, a water adduct or a solvate thereof, and these hydrate, water adduct and solvate are also encompassed in the present invention. When a compound of the formula (I) or (II) has an asymmetric atom, at least two optical isomers are present. These optical isomers and mixtures thereof (including racemate) are encompassed in the present invention.

The compounds encompassed in the formulas (I) and (II) of the present invention can be synthesized according to the following methods. In the following reaction schemes, each symbol is as defined above unless otherwise specified.

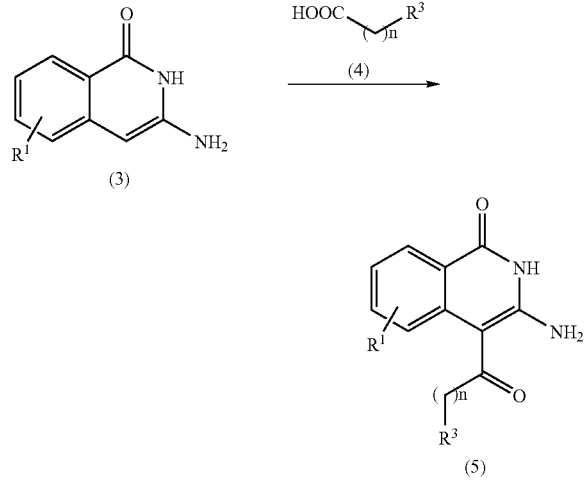

A compound of the formula (5) can be obtained by reacting a compound of the formula (3), obtained by the method shown in Starting Material Synthetic Examples below, with a compound of the formula (4) in a solvent that does not inhibit progress of the reaction (dimethylformamide, dimethylsulfoxide, acetonitrile, tetrahydrofuran, acetone, methyl ethyl ketone, toluene, benzene, water, dichloromethane, dichloroethane, chloroform, carbon tetrachloride or a mixed solvent of any of these) in the presence of a suitable base used in the organic synthesis chemistry (sodium hydrogen carbonate, potassium hydrogen carbonate, sodium carbonate, potassium carbonate, triethylamine, diisopropylethylamine, pyridine, N-methylmorpholine and the like) and a suitable condensing agent used in the organic synthesis chemistry (1,3-dimethyl-2-chloroimidazolinium chloride, diethyl cyanophosphate, benzotriazol-1-yl-oxy-tris(dimethylamino)phosphonium hexafluorophosphate, 1-ethyl-3-(3'-dimethylaminopropyl) carbodiimide and the like), under ice-cooling to the refluxing temperature of the solvent. A compound of the formula (5) can be also obtained by once converting a compound of the formula (4) to a reactive intermediate using an activating agent generally used in organic synthesis chemistry, such as thionyl chloride, phosphorus oxychloride, phosphorus pentachloride, 1,1'-carbonylbis-1H-imidazole and the like, and then reacting the intermediate with a compound of the formula (3) in a solvent that does not inhibit progress of the reaction (dimethylformamide, dimethylsulfoxide, acetonitrile, tetrahydrofuran, acetone, methyl ethyl ketone, toluene, benzene, water, dichloromethane, dichloroethane, chloroform, carbon tetrachloride or a mixed solvent of any of these) in the presence of a suitable base used in the organic synthesis chemistry (sodium hydrogen carbonate, potassium hydrogen carbonate, sodium carbonate, potassium carbonate, triethylamine, diisopropylethylamine, pyridine, N-methylmorpholine and the like).

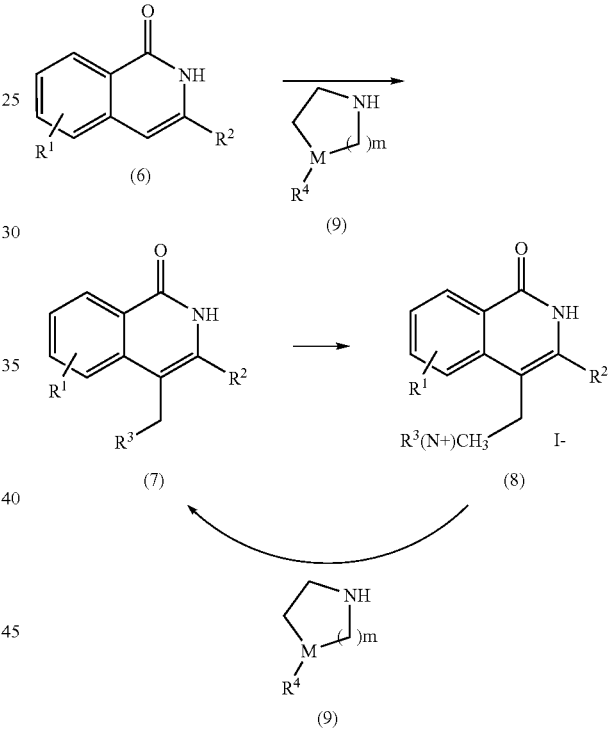

A compound of the formula (7) wherein $R^3$ is dialkylamino or a group of the formula (b) can be obtained by reacting a compound of the formula (9) or dialkylamine with formaldehyde or paraformaldehyde in a solvent that does not interfere with the reaction such as acetic acid, acetic anhydride, chloroform, dichloromethane, dichloroethane, carbon tetrachloride, tetrahydrofuran, toluene, benzene, dimethylformamide, dimethylsulfoxide, acetonitrile, a mixed solvent of any of these and the like, under ice-cooling to the refluxing temperature of the solvent to once form a Mannich base, and then reacting the base with a compound of the formula (6) obtained by a method such as the methods shown in Starting Material Synthetic Examples below. A compound of the formula (7) can be also obtained by reacting a compound of the formula (6) with Eschenmoser's salt (N,N-dimethylmethyleneammonium iodide) in a solvent that does not interfere with the reaction such as acetic acid, acetic anhydride, chloroform, dichloromethane, dichloroethane, carbon tetrachloride, tetrahydrofuran, toluene, benzene, dimethylformamide, dimethylsulfoxide, acetonitrile, a mixed solvent of any of these and the like, under ice-cooling to the refluxing temperature of the solvent.

Alternatively, a compound of the formula (7) is reacted with methyl iodide in a solvent that does not interfere with the reaction such as chloroform, dichloromethane, dichloroethane, carbon tetrachloride, tetrahydrofuran, toluene, benzene, dimethylformamide, dimethylsulfoxide, acetonitrile, methanol, ethanol, isopropanol, n-propanol, butanol, a mixed solvent of any of these and the like, under ice-cooling to the refluxing temperature of the solvent to give a compound of the formula (8), which is then reacted with a compound of the formula (9) or dialkylamine in a solvent that does not interfere with the reaction such as chloroform, dichloromethane, dichloroethane, carbon tetrachloride, tetrahydrofuran, toluene, benzene, dimethylformamide, dimethylsulfoxide, acetonitrile, methanol, ethanol, isopropanol, n-propanol, butanol, a mixed solvent of any of these and the like, under ice-cooling to the refluxing temperature of the solvent to give a compound of the formula (7).

General Synthetic Method 3

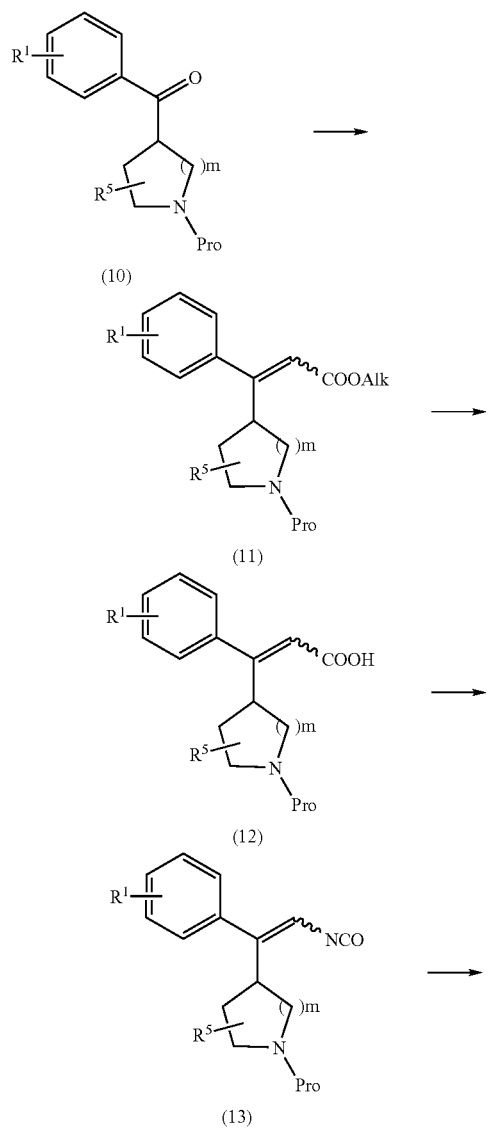

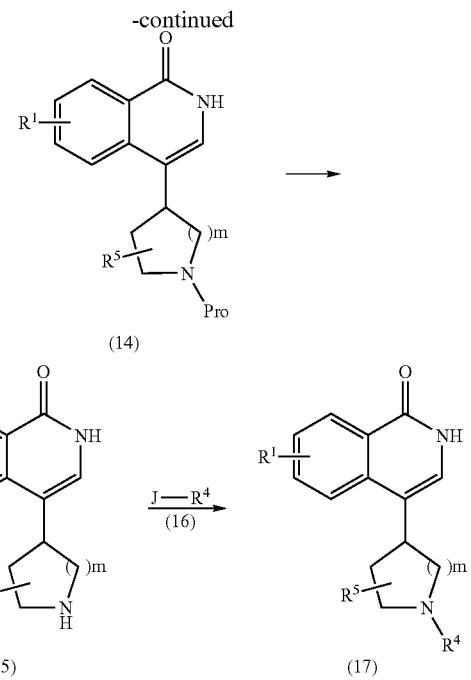

A compound of the formula (11) wherein Alk is alkyl can be obtained by reacting a compound of the formula (10), wherein Pro is a protecting group generally used in the organic synthesis chemistry such as acyl, alkoxycarbonyl, benzoyl and the like, with a compound generally used for the HORNER-EMMONS reaction in the organic synthesis chemistry, such as ethyl diethylphosphonoacetate, methyl diethylphosphonoacetate, tert-butyl diethylphosphonoacetate, (methoxycarbonylmethyl)triphenylphosphonium chloride, (methoxycarbonylmethyl)triphenylphosphonium bromide, (ethoxycarbonylmethyl)triphenylphosphonium chloride, (ethoxycarbonylmethyl)triphenylphosphonium bromide, (tertiary butoxy carbonylmethyl)triphenylphosphonium chloride, (tertiary butoxy carbonylmethyl)triphenylphosphonium bromide and the like, in a solvent that does not interfere with the progress of the reaction, such as tetrahydrofuran, diethyl ether, 1,4-dioxane, methanol, ethanol and the like, in the presence of a base generally used in the organic synthesis chemistry such as sodium methoxide, sodium ethoxide, sodium hydride, potassium tert-butoxide and the like at room temperature to the refluxing temperature of the solvent.

A compound of the formula (12) can be obtained by reacting a compound of the formula (11) in a solvent that does not interfere with the reaction such as tetrahydrofuran, 1,4-dioxane, methanol, ethanol, propanol, isopropanol, butanol, dimethylformamide, water, a mixed solvent of any of these and the like, in the presence of a base generally used in the organic synthesis chemistry such as sodium hydroxide, potassium hydroxide, lithium hydroxide and the like, under ice-cooling to the refluxing temperature of the solvent.

A compound of the formula (13) can be obtained by reacting a compound of the formula (12) with diphenylphosphoryl azide in a solvent that does not interfere with the progress of the reaction such as tetrahydrofuran, diethyl ether, 1,4-dioxane, benzene, toluene, xylene and the like, in the presence of a base generally used in the organic synthesis chemistry such as sodium hydrogen carbonate, potassium hydrogen carbonate, sodium carbonate, potassium carbonate, triethylamine, diisopropylethylamine, pyridine, N-methylmorpholine and the like, under ice-cooling to the refluxing temperature of the solvent.

A compound of the formula (13) can be also obtained by once converting a compound of the formula (12) using an activating agent generally used in the organic synthesis chemistry such as thionyl chloride, phosphorus oxychloride, phosphorus pentachloride, 1,1'-carbonylbis-1H-imidazole and the like to a reactive intermediate, which is then reacted with sodium azide to give an acid azide, and subjecting the acid azide to a rearrangement reaction in a solvent that does not interfere with the progress of the reaction such as tetrahydrofuran, diethyl ether, 1,4-dioxane, benzene, toluene, xylene and the like from room temperature to the refluxing temperature of the solvent.

A compound of the formula (14) can be obtained by reacting a compound of the formula (13) in a suitable solvent such as dichlorobenzene, diphenyl ether and the like or without solvent from room temperature to the refluxing temperature of the solvent or from room temperature to 300° C.

A compound of the formula (15) can be obtained by deprotection of a compound of the formula (14) under deprotection conditions generally employed in the organic synthesis chemistry, which are suitable for the protecting group represented by Pro (acetic acid-hydrochloric acid, hydrogen bromide-acetic acid, potassium hydroxide and the like).

A compound of the formula (17) can be obtained by reacting a compound of the formula (15) with a compound of the formula (16) wherein J is a leaving group generally used in the organic synthesis chemistry such as chlorine atom, bromine atom, iodine atom, p-toluenesulfonyloxy, methanesulfonyloxy and the like, in a solvent that does not inhibit progress of the reaction (dimethylformamide, dimethylsulfoxide, acetonitrile, tetrahydrofuran, acetone, methylethylketone, toluene, benzene, water or a mixed solvent of any of these), in the presence of a suitable base used in the organic synthesis chemistry (sodium hydrogen carbonate, potassium hydrogen carbonate, sodium carbonate, potassium carbonate, sodium hydroxide, potassium hydroxide, lithium hydroxide, sodium hydride and the like), under ice-cooling to the refluxing temperature of the solvent.

General Synthetic Method 4

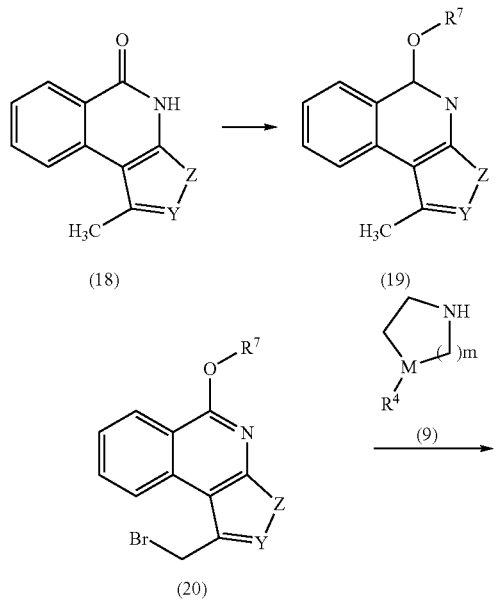

-continued

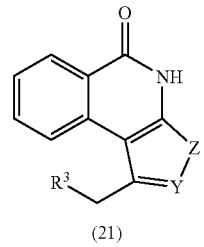

A compound of the formula (19) wherein $R^7$ is a phenolic hydroxyl-protecting group generally used in the organic synthesis chemistry such as methoxymethyl, methoxyethyl, benzyl, p-methoxybenzyl and the like can be obtained by reacting a compound of the formula (18) with a phenolic hydroxyl-protecting agent generally used in the organic synthesis chemistry such as chloromethyl methyl ether, methoxyethyl chloride, benzyl bromide, benzyl chloride, p-methoxybenzyl chloride and the like, in a solvent that does not interfere with the progress of the reaction such as tetrahydrofuran, diethyl ether, 1,4-dioxane, tetrahydrofuran, dimethylformamide, dimethylsulfoxide, 1,3-dimethyl-2-imidazolone and the like, in the presence of a base generally used in the organic synthesis chemistry such as sodium methoxide, sodium ethoxide, sodium hydride, potassium tert-butoxide and the like, from room temperature to the refluxing temperature of the solvent.

A compound of the formula (20) can be obtained by reacting a compound of the formula (19) with N-bromosuccinimide in carbon tetrachloride, in the presence of a radical initiator such as benzoyl peroxide and the like, under ice-cooling to the refluxing temperature of the solvent.

A compound of the formula (21) can be obtained by reacting a compound of the formula (20) with a compound of the formula (9) or dialkylamine in a solvent that does not interfere with the reaction such as chloroform, dichloromethane, dichloroethane, carbon tetrachloride, tetrahydrofuran, toluene, benzene, dimethylformamide, dimethylsulfoxide, acetonitrile, methanol, ethanol, isopropanol, n-propanol, butanol, a mixed solvent of any of these and the like, under ice-cooling—refluxing temperature of the solvent and treating the resultant compound under deprotection conditions suitable for $R^7$, such as hydrochloric acid, sulfuric acid, trifluoroacetic acid, 10% palladium carbon-hydrogen and the like.

General Synthetic Method 5

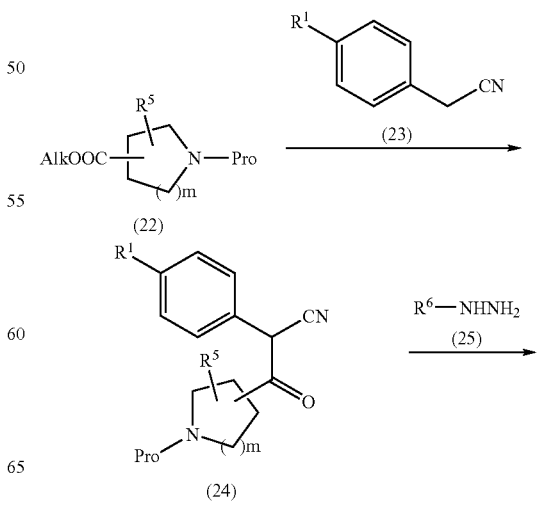

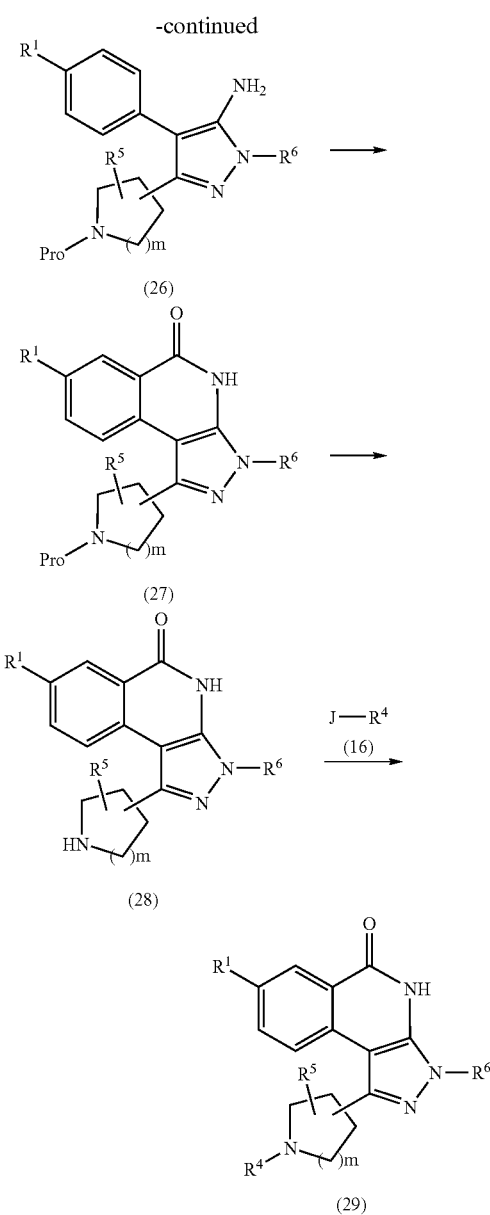

A compound of the formula (27) can be obtained by reacting a compound of the formula (26) with triphosgene in a suitable solvent that does not inhibit progress of the reaction (methylene chloride, chloroform, 1,2-dichloroethane, carbon tetrachloride, a mixed solvent of any of these and the like), in the presence of a base such as pyridine and the like to once give an isocyanate, and reacting the isocyanate with a Lewis acid such as aluminum chloride, zinc chloride, iron(II) chloride and the like at room temperature—refluxing temperature of the solvent for 0.1-24 hr to allow cyclization.

A compound of the formula (28) can be obtained by reacting a compound of the formula (27) under suitable deprotection conditions for the protecting group to allow deprotection, which includes, for example, reaction using potassium hydroxide or sodium hydroxide in methanol, ethanol, n-propanol, isopropanol, n-butanol, tetrahydrofuran, 1,4-dioxane, water or a mixed solvent of any of these at room temperature—refluxing temperature of the solvent for 0.1-24 hr, or reaction in hydrochloric acid, sulfuric acid, acetic acid or a mixed solvent of any of these at room temperature—refluxing temperature of the solvent for 0.1-24 hr and the like.

In addition, the compounds of the formula (I) or (II) of the present invention can be synthesized according to the aforementioned synthetic method or a general organic synthesis method.

A compound of the formula (29) can be obtained by reacting a compound of the formula (28) with a compound of the formula (16) wherein J is a leaving group generally used in the organic synthesis chemistry such as chlorine atom, bromine atom, iodine atom, p-toluenesulfonyloxy, methanesulfonyloxy and the like, in a solvent that does not inhibit progress of the reaction (dimethylformamide, dimethyl sulfoxide, acetonitrile, tetrahydrofuran, acetone, methylethylketone, toluene, benzene, water or a mixed solvent of any of these), in the presence of a suitable base used in the organic synthesis chemistry (sodium hydrogen carbonate, potassium hydrogen carbonate, sodium carbonate, potassium carbonate, sodium hydroxide, potassium hydroxide, lithium hydroxide, sodium hydride and the like), under ice-cooling to the refluxing temperature of the solvent.

In addition, a compound of the formula (29) can be also obtained by reacting a compound of the formula (28) with sodium cyanoborohydride or sodium triacetoxyborohydride in the presence of aldehydes such as formalin, acetaldehyde, propionaldehyde and the like, in a suitable solvent that does not inhibit progress of the reaction (acetonitrile, tetrahydrofuran, dimethylformamide, dimethyl sulfoxide and the like), under ice-cooling to the refluxing temperature of the solvent.

The compounds of the present invention thus obtained can be isolated or purified according to a conventional method.

The compounds of the formulas (I) and (II), an optically active form thereof, a pharmaceutically acceptable salt thereof, a hydrate thereof, a water adduct thereof and a solvate thereof obtained by the above-mentioned methods have a potent PARP inhibitory activity, and are useful as agents for the treatment of cerebral infarction, particularly agents for the treatment of acute cerebral infarction.

According to the method described in U.S. Pat. No. 3,262,937, a compound of the formula (24) can be obtained by reacting a compound of the formula (22) wherein Pro is a protecting group generally used in the organic synthesis chemistry such as acyl, alkoxycarbonyl, benzoyl and the like, Alk is alkyl, and m and R5 are as defined above, with a compound of the formula (23) wherein $R^1$ is as defined above in the presence of sodium hydride, sodium amide or metal sodium in toluene or xylene at room temperature—refluxing temperature of the solvent for 0.1-24 hr.

A compound of the formula (26) can be obtained by reacting a compound of the formula (24) with a compound of the formula (25) wherein $R^6$ is as defined above, in a suitable solvent that does not inhibit progress of the reaction (methanol, ethanol, n-propanol, isopropanol, n-butanol, tetrahydrofuran, 1,4-dioxane, toluene, xylene, dimethylformamide, dimethylsulfoxide, a mixed solvent of any of these and the like) at room temperature—refluxing temperature of the solvent for 0.1-24 hr.

When the isoquinoline compound, an optical isomer thereof, a pharmaceutically acceptable salt thereof, a hydrate thereof, a water adduct thereof or a solvate thereof according to the present invention is used as a pharmaceutical agent, the compound of the present invention can be orally or parenterally administered in the form of a pharmaceutical composition or a preparation (tablet, pill, capsule, granule, powder, syrup, emulsion, elixir, suspension, solution, injection, infusion, suppository and the like) obtained by admixing with a pharmaceutically acceptable carrier (excipient, binder, disintegrant, corrigent, flavor, emulsifier, diluent, dissolution aids and the like).

The pharmaceutical composition can be formulated according to a conventional method.

In the present specification, parenteral administration includes subcutaneous injection, intravenous injection, intramuscular injection, intraperitoneal injection, dripping and the like. A preparation for injection can be prepared according to a method known in this field. The suppository for rectal administration can be produced by admixing the drug with a suitable excipient and the like. As the dosage form of a solid preparation for oral administration, those mentioned above such as powder, granule, tablet, pill, capsule and the like can be mentioned. As the liquid for oral administration, emulsion, syrup, elixir, suspension, solution and the like acceptable as a pharmaceutical agent can be mentioned.

The dose is determined in consideration of age, body weight, general health condition, sex, diet, administration time, administration method, clearance rate, combination of drugs, the disease state of the patient then under treatment, and other factors.

The compound of the present invention, an optical isomer thereof, a pharmaceutically acceptable salt thereof, a hydrate hereof, a water adduct thereof and a solvate thereof are low toxic and can be used safely. While the daily dose varies depending on the condition and body weight of patient, the kind of the compound, administration route and the like, for example, it is desirably administered parenterally (subcutaneously, intravenously, intramuscularly or rectally) at about 0.01-50 mg/individual/day, preferably 0.01-20 mg/individual/day, and orally at about 0.01-150 mg/individual/day, preferably 0.1-100 mg/individual/day.

EXAMPLES

The present invention is explained in more detail in the following by referring to Examples, which are not to be construed as limitative as long as the spirit of the invention is not deviated. The unit of J is Hz.

Starting Material Synthetic Example 1

1,3-Dimethyl-3H-pyrazolo[3,4-c]isoquinolin-5(4H)-one (10 g) was suspended in dimethylsulfoxide (100 mL), and sodium hydride (60%, 2.1 g) was added at room temperature. The mixture was stirred with heating at 70° C. for 2 hrs, and cooled to room temperature. Chloromethyl methyl ether (4.6 mL) was added, and the mixture was stirred at room temperature for 30 min. After the completion of the reaction, the reaction mixture was poured into ice-water, and the mixture was extracted with ethyl acetate. The organic layer was washed with saturated brine and dried over magnesium sulfate, and the solvent was evaporated. The obtained residue was purified by silica gel column chromatography (chloroform:methanol=50:1) to give 1,3-dimethyl-5-methoxymethoxy-3H-pyrazolo[3,4-c]isoquinoline (10.6 g).

$^1$H-NMR (CDCl$_3$) δ: 2.77(3H, s), 3.65 (3H, s), 4.03 (3H, s), 5.84 (2H, s), 7.47 (1H, t, J=8 Hz), 7.77 (1H, t, J=8 Hz), 8.13 (1H, d, J=8 Hz), 8.38 (1H, d, J=8 Hz).

1,3-Dimethyl-5-methoxymethoxy-3H-pyrazolo[3,4-c]isoquinoline (1.03 g), N-bromosuccinimide (0.72 g) and benzoyl peroxide (0.05 g) were dissolved in carbon tetrachloride (20 mL), and the mixture was heated under reflux for 4 hrs. After the completion of the reaction, the reaction mixture was cooled to room temperature, washed with saturated aqueous sodium hydrogen carbonate and dried over magnesium sulfate. The solvent was evaporated. The obtained solid was collected by filtration and washed with ether to give 1-bromomethyl-3-methyl-5-methoxymethoxy-3H-pyrazolo[3,4-c]isoquinoline (1.0 g).

$^1$H-NMR (CDCl$_3$) δ: 3.66 (3H, s), 4.08 (3H, s), 4.97 (2H, s), 5.85 (2H, s), 7.55 (1H, t, J=8 Hz), 7.87 (1H, t, J=8 Hz), 8.24 (1H, d, J=8 Hz), 8.42 (1H, d, J=8 Hz).

Starting Material Synthetic Example 2

6-Methyl-1-indanone (40.4 g) and isoamyl nitrite (40.6 mL) were dissolved in ethanol (300 mL), and 4N hydrogen chloride-dioxane (10 mL) was added dropwise under ice-cooling. After the completion of the reaction, the precipitated crystals were collected by filtration and washed with ether to give 6-methyl-2-hydroxyimino-1-indanone (37 g).

$^1$H-NMR (DMSO-d$_6$) δ: 2.39 (3H, s), 3.72 (2H, s), 7.49-7.58 (3H, m), 12.61 (1H, s).

6-Methyl-2-hydroxyimino-1-indanone (37 g) and sodium hydroxide (19.7 g) were dissolved in water (287 mL), and p-toluenesulfonyl chloride (44.3 g) was added with stirring at 50° C. After the completion of the reaction, aqueous citric acid solution was added to acidify the reaction mixture, and the mixture was extracted with ethyl acetate. The organic layer was washed with saturated brine and dried over magnesium sulfate. The solvent was evaporated. Ether was added to the precipitated crystals, and the crystals were collected by filtration to give 2-cyanomethyl-5-methylbenzoic acid (16.3 g).

$^1$H-NMR (DMSO-d$_6$) δ: 2.35 (3H, s), 4.22 (2H, s), 7.43 (2H, s), 7.80 (1H, s), 13.21 (1H, brs).

2-Cyanomethyl-5-methylbenzoic acid (16.3 g) and dimethylformamide (0.1 mL) were suspended in tetrahydrofuran (160 mL), and oxalyl dichloride (12.2 mL) was added dropwise under ice-cooling. After cease of foaming, the solvent was evaporated. The obtained residue was dissolved in tetrahydrofuran, and the solution was added dropwise to 28% aqueous ammonia solution under ice-cooling. After the completion of the reaction, the solvent was evaporated, and the precipitated crystals were collected by filtration to give 2-cyanomethyl-5-methylbenzamide (10.9 g).

$^1$H-NMR (DMSO-d$_6$) δ: 2.33 (3H, s), 4.10 (2H, s), 7.29-7.37 (2H, m), 7.41 (1H, s), 7.51 (1H, brs), 7.94 (1H, brs).

2-Cyanomethyl-5-methylbenzamide (10.9 g) was suspended in methanol (100 mL), and 10% aqueous potassium carbonate solution (100 mL) was added. The mixture was heated under reflux for 1 hr. The precipitated crystals were collected by filtration to give 3-amino-7-methyl-2H-isoquinolin-1-one (9.6 g).

$^1$H-NMR (DMSO-d$_6$) δ: 2.30 (3H, s), 5.41 (1H, s), 5.43 (2H, brs), 7.13 (1H, d, J=8 Hz), 7.24 (1H, dd, J=2 Hz, 8 Hz), 7.70 (1H, s), 10.52 (1H, brs).

Starting Material Synthetic Example 3

Sodium hydride (60%, 1.4 g) was suspended in tetrahydrofuran (30 mL), and a solution (30 mL) of ethyl diethylphosphonoacetate (7.2 g) in tetrahydrofuran was added dropwise. The mixture was stirred at room temperature for 1 hr, and a solution (30 mL) of 1,4-dibenzoylpiperidine (7.9 g) in tetrahydrofuran was added dropwise. After the completion of the dropwise addition, the reaction mixture was heated under reflux. After the completion of the reaction, the solvent was evaporated. Water was added to the obtained residue, and the mixture was extracted with ethyl acetate. The organic layer was washed with saturated brine and dried over magnesium sulfate. The solvent was evaporated, and the obtained-residue was dissolved in methanol (80 mL). An aqueous solution (10 mL) of lithium hydroxide monohydrate (1.13 g) was added, and the mixture was stirred with heating for 3 hrs. After the completion of the reaction, the solvent was evaporated. Water was added to the obtained residue, and the mixture was extracted with chloroform. The organic layer was dried over magnesium sulfate, and the solvent was evaporated to quantitatively give (E)- and (Z)-β-(1-benzoylpiperidin-4-yl)cinnamic acid.

$^1$H-NMR (CDCl$_3$) δ: 1.22-1.90 (4H, m), 2.44-3.18 (3H, m), 3.71-4.10 (1H, m), 4.72-4.88 (1H, m), 5.77 (0.5H, s), 5.86 (1H, d, J=1 Hz), 7.06-7.16 (2H, m), 7.32-7.42 (8H, m).

The total amount of (E)- and (Z)-β-(1-benzoylpiperidin-4-yl) cinnamic acid and triethylamine (4.1 mL) were dissolved in toluene (70 mL), and diphenylphosphoryl azide (8.1 g) was added at room temperature. The reaction mixture was stirred with heating at 80° C. for 1 hr, and then at 100° C. for 1 hr. After cease of foaming, the solvent was evaporated. The obtained residue was suspended in diphenyl ether, and the mixture was added dropwise to diphenyl ether (10 mL) heated at 250° C. After the completion of the reaction, the reaction mixture was cooled to room temperature, dissolved in chloroform and washed with water. The organic layer was purified by silica gel column chromatography (chloroform:methanol=20:1) to give 4-(1-benzoylpiperidin-4-yl)-2H-isoquinolin-1-one (2.5 g).

$^1$H-NMR (CDCl$_3$) δ: 1.58-1.80 (2H, m), 1.92-2.22 (2H, m), 2.92-3.30 (3H, m), 3.90-4.05 (1H, m), 4.90-5.02 (1H, m), 7.02 (1H, d, J=4 Hz), 7.38-7.47 (5H, m), 7.53-7.60 (1H, m), 7.76 (1H, d, J=4 Hz), 8.52 (1H, d, J=8 Hz), 11.10 (1H, brs).

Starting Material Synthetic Example 4

(E)- and (Z)-β-(1-Benzoylpiperidin-4-yl)-4-chlorocinnamic acid was obtained quantitatively by the reaction in the same manner as in Starting Material Synthetic Example 3 using 1-benzoyl-4-(4-chlorobenzoyl)piperidine (14.4 g).

$^1$H-NMR (CDCl$_3$) δ: 1.22-1.90 (4H, m), 2.44-3.18 (3H, m), 3.71-4.10 (1H, m), 4.72-4.88 (1H, m), 5.76 (0.5H, s), 5.87 (1H, d, J=1 Hz), 7.02-7.10 (2H, m), 7.31-7.42 (7H, m).

4-(1-Benzoylpiperidin-4-yl)-7-chloro-2H-isoquinolin-1-one (0.67 g) was obtained by the reaction in the same manner as in Starting Material Synthetic Example 3 using total amount of (E)- and (Z)-β-(1-benzoylpiperidin-4-yl)-4-chlorocinnamic acid.

H-NMR (CDCl$_3$) δ: 1.59-1.76 (2H, m), 1.88-2.14 (2H, m), 2.90-3.32 (3H, m), 3.88-4.04 (1H, m), 4.86-5.02 (1H, m), 6.97 (1H, d, J=5 Hz), 7.44 (5H, s), 7.69 (2H, s), 8.48 (1H, s), 10.51 (1H, brs).

Starting Material Synthetic Example 5

(E)- and (Z)-β-(1-Benzoylpiperidin-4-yl)-4-fluorocinnamic acid was obtained quantitatively by the reaction in the same manner as in Starting Material Synthetic Example 3 using 1-benzoyl-4-(4-fluorobenzoyl)piperidine (25.4 g).

4-(1-Benzoylpiperidin-4-yl)-7-fluoro-2H-isoquinolin-1-one (1.9 g) was obtained by the reaction in the same manner as in Starting Material Synthetic Example 3 using total amount of (E)- and (Z)-β-(1-benzoylpiperidin-4-yl)-4-fluorocinnamic acid.

$^1$H-NMR (CDCl$_3$) δ: 1.63-1.79 (2H, m), 1.88-2.21 (2H, m), 2.90-3.34 (3H, m), 3.90-4.09 (1H, m), 4.83-5.05 (1H, m), 6.98 (1H, d, J=3 Hz), 7.41-7.52 (6H, m), 7.74-7.79 (1H, m), 8.15 (1H, dd, 3 Hz, 9 Hz), 11.25 (1H, brs).

Starting Material Synthetic Example 6

4-Dimethylaminomethyl-3-isopropyl-2H-isoquinolin-1-one (1.6 g) was dissolved in chloroform (20 mL) and methanol (2 mL), and methyl iodide (0.41 mL) was added, and the mixture was heated under reflux. After the completion of the reaction, the precipitated crystals were collected by filtration to give N-(3-isopropyl-2H-1-oxoisoquinolin-4-yl)methyl-trimethylammonium iodide (1.1 g).

$^1$H-NMR(DMSO-d$_6$) δ: 1.29 (6H, d, J=5 Hz), 3.11 (9H, s), 3.42-3.51 (1H, m), 4.57 (2H, brs), 7.56 (1H, t, J=8 Hz), 7.82 (1H, t, J=8 Hz), 7.92 (1H, d, J=8 Hz), 8.26 (1H, d, J=8 Hz), 9.03 (1H, brs), 11.23 (1H, brs).

Starting Material Synthetic Example 7

N-(3-Ethyl-2H-1-oxoisoquinolin-4-yl)methyl-trimethylammonium iodide was obtained quantitatively by the reaction in the same manner as in Starting Material Synthetic Example 6 using 4-dimethylaminomethyl-3-ethyl-2H-isoquinolin-1-one (2.5 g).

$^1$H-NMR(DMSO-d$_6$) δ: 1.18 (6H, d, J=7 Hz), 2.55-2.68 (1H, m), 2.92-3.11 (1H, m), 3.05 (9H, s), 4.62 (1H, d, J=15 Hz), 4.91 (1H, d, J=15 Hz), 7.52 (1H, t, J=8 Hz), 7.63 (1H, t, J=8 Hz), 8.17 (1H, d, J=8 Hz), 8.24 (1H, d, J=8 Hz), 11.22 (1H, brs).

Starting Material Synthetic Example 8

7-Chloro-1,3-dimethyl-5-methoxymethoxy-3H-pyrazolo[3,4-c]isoquinoline is obtained by the reaction in the same manner as in Starting Material Synthetic Example 1 using 7-chloro-1,3-dimethyl-3H-pyrazolo[3,4-c]isoquinolin-5(4H)-one.

1-Bromomethyl-7-chloro-3-methyl-5-methoxymethoxy-3H-pyrazolo[3,4-c]isoquinoline is obtained by the reaction in the same manner as in Starting Material Synthetic Example 1 using 7-chloro-1,3-dimethyl-5-methoxymethoxy-3H-pyrazolo[3,4-c]isoquinoline.

Starting Material Synthetic Example 9

α-Acetyl-4-fluorophenylacetonitrile (65.1 g) and methylhydrazine (30.9 mL) were dissolved in ethanol (320 mL), and the mixture was heated under reflux for 3 hrs. After the completion of the reaction, the reaction mixture was cooled to room temperature, and the solvent was evaporated. The obtained solid was collected by filtration and washed with hexane to give 5-amino-4-(4-fluorophenyl)-1,3-dimethylpyrazole (69.5 g).

$^1$H-NMR(DMSO-d$_6$) δ: 2.04 (3H, s), 3.51 (3H, s), 5.01 (2H, s), 7.15-7.21 (2H, m), 7.26-7.30 (2H, m).

A solution of 5-amino-4-(4-fluorophenyl)-1,3-dimethylpyrazole (20.0 g) and pyridine (23.6 mL) in dichloromethane (150 mL) was added dropwise over 30 min to a solution of triphosgene (11.6 g) in dichloromethane (100 mL) under ice-cooling, and the mixture was stirred at room temperature for 2 hrs. The reaction solution was added dropwise to a solution of aluminum chloride (97.5 g) in dichloromethane under ice-cooling, and the mixture was stirred at room temperature for 2 days. After the completion of the reaction, the reaction solution was poured into ice-water. The precipitated crystals were collected by filtration and washed with water to give 7-fluoro-1,3-dimethyl-3H-pyrazolo[3,4-c]isoquinolin-5(4H)-one (13.2 g).

$^1$H-NMR(DMSO-d$_6$) δ: 2.46 (3H, s), 3.69 (3H, s), 7.38-7.45 (1H, m), 7.77-7.82 (1H, m), 7.85-7.89 (1H, m).

1,3-Dimethyl-7-fluoro-5-methoxymethoxy-3H-pyrazolo[3,4-c]isoquinoline (8.1 g) was obtained by the reaction in the same manner as in Starting Material Synthetic Example 1 using 7-fluoro-1,3-dimethyl-3H-pyrazolo[3,4-c]isoquinolin-5(4H)-one (12.7 g).

$^1$H-NMR(CDCl$_3$) δ: 2.75 (3H, s), 3.65 (3H, s), 4.09 (3H, s), 5.82 (2H, s), 7.50-7.57 (1H, m), 7.98-8.02 (1H, m), 8.08-8.13 (1, m).

Starting Material Synthetic Example 10

7-Methoxy-1,3-dimethyl-5-methoxymethoxy-3H-pyrazolo[3,4-c]isoquinoline is obtained by the reaction in the same manner as in Starting Material Synthetic Example 1 using 7-methoxy-1,3-dimethyl-3H-pyrazolo[3,4-c]isoquinolin-5(4H)-one.

1-Bromomethyl-7-methoxy-3-methyl-5-methoxymethoxy-3H-pyrazolo[3,4-c]isoquinoline is obtained by the reaction in the same manner as in Starting Material Synthetic Example 1 using 7-methoxy-1,3-dimethyl-5-methoxymethoxy-3H-pyrazolo[3,4-c]isoquinoline.

Starting Material Synthetic Example 11

1-Methyl-5-methoxymethoxyisoxazolo[5,4-c]isoquinoline is obtained by the reaction in the same manner as in Starting Material Synthetic Example 1 using 1-methylisoxazolo[5,4-c]isoquinolin-5(4H)-one.

1-Bromomethyl-5-methoxymethoxyisoxazolo[5,4-c]isoquinoline is obtained by the reaction in the same manner as in Starting Material Synthetic Example 1 using 1-methyl-5-methoxymethoxyisoxazolo[5,4-c]isoquinoline.

Starting Material Synthetic Example 12

7-Chloro-1-methyl-5-methoxymethoxyisoxazolo[5,4-c]isoquinoline is obtained by the reaction in the same manner as in Starting Material Synthetic Example 1 using 7-chloro-1-methylisoxazolo[5,4-c]isoquinolin-5(4H)-one.

7-Chloro-1-bromomethyl-5-methoxymethoxyisoxazolo[5,4-c]isoquinoline is obtained by the reaction in the same manner as in Starting Material Synthetic Example 1 using 7-chloro-1-methyl-5-methoxymethoxyisoxazolo[5,4-c]isoquinoline.

Starting Material Synthetic Example 13

7-Fluoro-1-methyl-5-methoxymethoxyisoxazolo[5,4-c]isoquinoline is obtained by the reaction in the same manner as in Starting Material Synthetic Example 1 using 7-fluoro-1-methylisoxazolo[5,4-c]isoquinolin-5(4H)-one.

7-Fluoro-1-bromomethyl-5-methoxymethoxyisoxazolo[5,4-c]isoquinoline is obtained by the reaction in the same manner as in Starting Material Synthetic Example 1 using 7-fluoro-1-methyl-5-methoxymethoxyisoxazolo[5,4-c]isoquinoline.

Starting Material Synthetic Example 14

1-Methyl-5-methoxymethoxyisothiazolo[5,4-c]isoquinoline is obtained by the reaction in the same manner as in Starting Material Synthetic Example 1 using 1-methylisothiazolo[5,4-c]isoquinolin-5(4H)-one.

1-Bromomethyl-5-methoxymethoxyisothiazolo[5,4-c]isoquinoline is obtained by the reaction in the same manner as in Starting Material Synthetic Example 1 using 1-methyl-5-methoxymethoxyisothiazolo[5,4-c]isoquinoline.

Starting Material Synthetic Example 15

7-Chloro-1-methyl-5-methoxymethoxyisothiazolo[5,4-c]isoquinoline is obtained by the reaction in the same manner as in Starting Material Synthetic Example 1 using 7-chloro-1-methylisothiazolo[5,4-c]isoquinolin-5(4H)-one.

7-Chloro-1-bromomethyl-5-methoxymethoxyisothiazolo[5,4-c]isoquinoline is obtained by the reaction in the same manner as in Starting Material Synthetic Example 1 using 7-chloro-1-methyl-5-methoxymethoxyisothiazolo[5,4-c]isoquinoline.

Starting Material Synthetic Example 16

7-Fluoro-1-methyl-5-methoxymethoxyisothiazolo[5,4-c]isoquinoline is obtained by the reaction in the same manner as in Starting Material Synthetic Example 1 using 7-fluoro-1-methylisothiazolo[5,4-c]isoquinolin-5(4H)-one.

7-Fluoro-1-bromomethyl-5-methoxymethoxyisothiazolo[5,4-c]isoquinoline is obtained by the reaction in the same manner as in Starting Material Synthetic Example 1 using 7-fluoro-1-methyl-5-methoxymethoxyisothiazolo[5,4-c]isoquinoline.

Starting Material Synthetic Example 21

(E)- and (Z)-β-(1-Benzoylpyrrolidin-3-yl) cinnamic acid is obtained by the reaction in the same manner as in Starting Material Synthetic Example 3 using 1,3-dibenzoylpyrrolidine. 4-(1-Benzoylpyrrolidin-3-yl)-2H-isoquinolin-1-one is obtained by the reaction in the same manner as in Starting Material Synthetic Example 3 using (E)- and (Z)-β-(1-benzoylpyrrolidin-3-yl)cinnamic acid.

Starting Material Synthetic Example 22

(E)- and (Z)-β-(1-Benzoylpyrrolidin-3-yl)-4-chlorocinnamic acid is obtained by the reaction in the same manner as in Starting Material Synthetic Example 3 using 1-benzoyl-3-(4-chlorobenzoyl)pyrrolidine.

4-(1-Benzoylpyrrolidin-3-yl)-7-chloro-2H-isoquinolin-1-one is obtained by the reaction in the same manner as in Starting Material Synthetic Example 3 using (E)- and (Z)-β-(1-benzoylpyrrolidin-3-yl)-4-chlorocinnamic acid.

Starting Material Synthetic Example 23

(E)- and (Z)-β-(1-Benzoylpyrrolidin-3-yl)-4-fluorocinnamic acid is obtained by the reaction in the same manner as in Starting Material Synthetic Example 3 using 1-benzoyl-3-(4-fluorobenzoyl)pyrrolidine.

4-(1-Benzoylpyrrolidin-3-yl)-7-fluoro-2H-isoquinolin-1-one is obtained by the reaction in the same manner as in Starting Material Synthetic Example 3 using (E)- and (Z)-β-(1-benzoylpyrrolidin-3-yl)-4-fluorocinnamic acid.

Starting Material Synthetic Example 29

To 7-chloro-3-methyl-4-dimethylaminomethyl-2H-isoquinolin-1-one (1.40 g) was added methanol (110 mL), and the mixture was heated to dissolve. 2,6-Lutidine (1.23 mL) and methyl iodide (3.60 mL) were added, and the mixture was stirred overnight at room temperature. After the completion of the reaction, the solvent was evaporated under reduced pressure, and the obtained crystals were washed with ethyl acetate and collected by filtration to give N-(7-chloro-3-methyl-2H-1-oxoisoquinolin-4-yl)methyl-trimethylammonium iodide (2.20 g).

$^1$H-NMR(DMSO-d$_6$) δ: 2.41 (3H, s), 3.04 (6H, s), 3.11 (3H, s), 4.61 (1H, d, J=14 Hz), 4.90 (1H, d, J=14 Hz), 7.77-7.80 (1H, m), 8.15-8.24 (2H, m), 11.8 (1H, brs).

Starting Material Synthetic Example 30

N-(7-Fluoro-3-methyl-2H-1-oxoisoquinolin-4-yl)methyl-trimethylammonium iodide (860 mg) was obtained by the reaction in the same manner as in Starting Material Synthetic Example 29 using 7-fluoro-4-dimethylaminomethyl-3-methyl-2H-isoquinolin-1-one (536 mg).

$^1$H-NMR(DMSO-d$_6$) δ: 2.40 (3H, s), 3.04 (6H, s), 3.11 (3H, s), 4.66 (1H, d, J=15 Hz), 4.91 (1H, d, J=15 Hz), 7.64-7.70 (1H, m), 7.80-7.91 (1H, m), 8.24-8.29 (1H, m), 11.8 (1H, brs).

Starting Material Synthetic Example 31

N-(7-Chloro-3-ethyl-2H-1-oxoisoquinolin-4-yl)methyl-trimethylammonium iodide is obtained by the reaction in the same manner as in Starting Material Synthetic Example 6 using 7-chloro-4-dimethylaminomethyl-3-ethyl-2H-isoquinolin-1-one.

Starting Material Synthetic Example 32

N-(7-Fluoro-3-ethyl-2H-1-oxoisoquinolin-4-yl)methyl-trimethylammonium iodide is obtained by the reaction in the same manner as in Starting Material Synthetic Example 6 using 7-fluoro-4-dimethylaminomethyl-3-ethyl-2H-isoquinolin-1-one.

Starting Material Synthetic Example 33

3-Methyl-4-(pyrrolidin-1-yl)methyl-2H-isoquinolin-1-one (3.92 g) was dissolved in chloroform (60 mL), and methyl iodide (1.04 mL) was added, and the mixture was heated under reflux for 7 hrs. After the completion of the reaction, the solvent was evaporated under reduced pressure, and the obtained crystals were washed with diethyl ether and collected by filtration to give (3-methyl-2H-1-oxoisoquinolin-4-yl)methylpyrrolidinium iodide (5.28 g).

$^1$H-NMR(DMSO-d$_6$) δ: 1.90-2.10 (4H, m), 2.38 (3H, s), 3.07 (3H, s), 3.40-3.60 (4H, m), 4.72 (1H, d, J=14.7 Hz), 5.01 (1H, d, J=14.7 Hz), 7.52 (1H, t, J=7.5 Hz), 7.78 (1H, t, J=7.5 Hz), 8.12 (1H, d, J=7.5 Hz), 8.23 (1H, d, J=7.5 Hz), 11.7 (1H, brs).

Starting Material Synthetic Example 34

3-Amino-7-fluoro-2H-isoquinolin-1-one was synthesized by the reaction in the same manner as in Starting Material Synthetic Example 2 using 6-fluoro-2-hydroxyimino-1-indanone.

$^1$H-NMR(DMSO-d$_6$) δ: 5.49 (1H, s), 5.54 (2H, brs), 7.27-7.34 (2H, m), 7.55 (1H, dd, J=2 Hz, J=9 Hz), 10.76 (1H, brs).

Starting Material Synthetic Example 35

5-Chloro-2-cyanomethylbenzoic acid (16.8 g) was obtained by the reaction in the same manner as in Starting Material Synthetic Example 2 using 6-chloro-2-hydroxyimino-1-indanone (22.0 g).

$^1$H-NMR(DMSO-d$_6$) δ: 4.25 (2H, s), 7.32-7.72 (3H, m), 12.75 (1H, brs).

5-Chloro-2-cyanomethylbenzamide (11.2 g) was obtained by the reaction in the same manner as in Starting Material Synthetic Example 2 using 5-chloro-2-cyanomethylbenzoic acid (13.6 g).

$^1$H-NMR(DMSO-d$_6$) δ: 4.15 (2H, s), 7.32-7.68 (3H, m), 7.98 (1H, brs), 8.10 (1H, brs).

3-Amino-7-chloro-2H-isoquinolin-1-one (11.2 g) was obtained by the reaction in the same manner as in Starting Material Synthetic Example 2 using 5-chloro-2-cyanomethylbenzamide (14.0 g).

$^1$H-NMR(DMSO-d$_6$) δ: 5.46 (1H, s), 5.71 (2H, brs), 7.25 (1H, d, J=8.4 Hz), 7.39 (1H, d, J=8.4 Hz), 7.81 (1H, s), 10.85 (1H, brs).

Starting Material Synthetic Example 36

4-Chloro-2-cyanomethylbenzoic acid (4.4 g) was obtained by the reaction in the same manner as in Starting Material Synthetic Example 2 using 5-chloro-2-hydroxyimino-1-indanone (6.3 g).

$^1$H-NMR(DMSO-d$_6$) δ: 4.27 (2H, s), 7.58 (1H, d, J=8.4 Hz), 7.66 (1H, s), 7.98 (1H, d, J=8.4 Hz), 13.50 (1H, brs).

4-Chloro-2-cyanomethylbenzamide (3.9 g) was obtained by the reaction in the same manner as in Starting Material Synthetic Example 2 using 4-chloro-2-cyanomethylbenzoic acid (4.4 g).

$^1$H-NMR(DMSO-d$_6$) δ: 4.17 (2H, s), 7.50-7.63 (4H, m), 8.05 (1H, brs).

3-Amino-6-chloro-2H-isoquinolin-1-one (2.9 g) was obtained by the reaction in the same manner as in Starting Material Synthetic Example 2 using 4-chloro-2-cyanomethylbenzamide (3.9 g).

$^1$H-NMR(DMSO-d$_6$) δ: 5.42 (1H, s), 5.76 (2H, brs), 6.93 (1H, d, J=8.6 Hz), 7.29 (1H, s), 7.84 (1H, d, J=8.6 Hz), 10.71 (1H, brs).

Starting Material Synthetic Example 37

α-Acetylphenylacetonitrile (10 g) was dissolved in methanol (100 mL), and hydrazinoethanol (5.3 g) was added, and the mixture was heated under reflux for 4 hrs. After the completion of the reaction, the solvent was evaporated. The obtained residue was subjected to silica gel column chromatography, and the fraction eluted with chloroform:methanol=40:1 was concentrated to give 5-amino-1-(2-hydroxyethyl)-3-methyl-4-phenylpyrazole (11.4 g) as white crystals.

$^1$H-NMR(CDCl$_3$) δ: 2.24 (3H, s), 3.92-4.92 (4H, m), 4.10 (2H, t, J=6 Hz), 7.24-7.31 (3H, m), 7.40-7.45 (2H, m).

Starting Material Synthetic Example 38

Benzoic acid (16.1 g) and triethylamine (18.4 mL) were dissolved in toluene (100 mL), and diphenylphosphoryl azide (36.3 g) was added, and the mixture was heated under reflux for 1 hr. 5-Amino-1-(2-hydroxyethyl)-3-methyl-4-phenylpyrazole (12 g) obtained in Starting Material Synthetic Example 37 was added to the reaction mixture, and the mixture was further heated under reflux for 3 hrs. After the completion of the reaction, the reaction mixture was cooled to room temperature, and ethyl acetate was added. The mixture was washed with successively aqueous potassium carbonate solution and saturated brine, and dried over magnesium sulfate. The solvent was evaporated, and a small amount of ethanol was added to the obtained residue. The precipitated crystals were collected by filtration to give 2-[3-methyl-5-(3-phenyl-1-ureido)-4-phenylpyrazol-2-yl]ethyl phenylcarbamate (13 g).

$^1$H-NMR(DMSO-$d_6$) δ: 2.22 (3H, s), 4.24 (2H, t, J=6 Hz), 4.46 (2H, t, J=6 Hz), 6.88-7.00 (2H, m), 7.20-7.28 (5H, m), 7.34-7.45 (8H, m), 8.20 (1H, brs), 8.92 (1H, brs), 9.67 (1H, brs).

Starting Material Synthetic Example 39

2-[3-Methyl-5-(3-phenyl-1-ureido)-4-phenylpyrazol-2-yl]ethyl phenylcarbamate (12 g) obtained in Starting Material Synthetic Example 38 was heated at 250° C. for 10 min. The reaction vessel was cooled to 100° C., and methanol, potassium hydroxide (5 g) and water (20 mL) were added, and the mixture was. heated under reflux for 3 hrs. After the completion of the reaction, the reaction mixture was cooled to room temperature, and methanol was evaporated. The precipitated insoluble material was filtered off, and ammonium chloride was added to the filtrate. The precipitated crystals were collected by filtration to give 3-(2-hydroxyethyl)-1-methylpyrazolo[3,4-c]isoquinolin-5(4H)-one (3.8 g).

$^1$H-NMR(DMSO-$d_6$) δ: 2.53 (3H, s), 3.72 (2H, t, J=6 Hz) 4.26 (2H, t, J=6 Hz), 4.83 (1H, t, J=5 Hz), 7.40 (1H, t, J=8 Hz), 7.75 (1H, t, J=8 Hz), 7.88 (1H, d, J=8 Hz), 8.23 (1H, d, J=8 Hz), 12.08 (1H, brs).

Starting Material Synthetic Example 40

3-(2-Hydroxyethyl)-1-methylpyrazolo[3,4-c]isoquinolin-5(4H)-one (3.0 g) obtained in Starting Material Synthetic Example 39 was dissolved in thionyl chloride (20 mL), and the mixture was stirred with heating at 70° C. After the completion of the reaction, thionyl chloride was evaporated. The obtained crystals were washed with water and chloroform to give 3-(2-chloroethyl)-1-methylpyrazolo[3,4-c]isoquinolin-5(4H)-one (2.9 g).

$^1$H-NMR(DMSO-$d_6$) δ: 2.62 (3H, s), 3.98 (2H, t, J=6 Hz), 4.57 (2H, t, J=6 Hz), 7.42 (1H, t, J=8 Hz), 7.77 (1H, t, J=8 Hz), 7.90 (1H, d, J=8 Hz), 8.24 (1H, d, J=8 Hz), 12.39 (1H, brs).

Starting Material Synthetic Example 41

Sodium hydride (purity 60%, 2.0 g) was suspended in dimethylformamide (100 mL), and trimethylsulfoxonium iodide (11 g) was added, and the mixture was stirred at room temperature for 1 hr. Then, methyl 2-isonicotinoylbenzoate (11 g) was added, and the mixture was further stirred at room temperature for 1 hr. Water was added to the reaction mixture, and the precipitated crystals were collected by filtration to give 4-(pyridin-4-yl)isocoumarin (4.9 g).

$^1$H-NMR(DMSO-$d_6$) δ: 7.44 (1H, d, J=8 Hz), 7.52 (2H, dd, J=2 Hz, 5 Hz), 7.71 (1H, t, J=8 Hz), 7.74 (1H, s), 7.89 (1H, t, J=8 Hz), 8.29 (1H, d, J=8 Hz), 8.73 (2H, dd, J=2 Hz,5 Hz).

4-(Pyridin-4-yl)isocoumarin (4.9 g) was suspended in ethanol and 28% aqueous ammonia, and the mixture was heated under reflux for 1 hr. Concentrated hydrochloric acid was added to acidify the reaction mixture, and the mixture was further stirred at room temperature for 1 hr. After the completion of the reaction, aqueous potassium carbonate solution was added to the reaction mixture, and the mixture was extracted with a mixed solvent (chloroform:methanol=10:1). The organic layer was dried over magnesium sulfate. The solvent was evaporated, and the obtained residue was collected by filtration to give 4-(pyridin-4-yl)-2H-isoquinolin-1-one (2.9 g).

$^1$H-NMR(DMSO-$d_6$) δ: 7.26 (1H, s), 7.50 (2H, d, J=5 Hz), 7.55-7.60 (2H, m), 7.41 (1H, t, J=8 Hz), 8.32 (1H, d, J=8 Hz), 8.67 (2H, d, J=5 Hz), 11.65 (1H, brs).

Starting Material Synthetic Example 42

Phenylacetonitrile (5.8 g), ethyl 1-ethoxycarbonylisonipecotate (11.5 g), sodium hydride (purity 60%, 2.0 g) and toluene (25 mL) were mixed, and the mixture was stirred at 80° C. for 3 hrs. After the completion of the reaction, the reaction mixture was cooled to room temperature, and the insoluble material was washed by decantation. The insoluble material was dissolved in water, and acetic acid was added to acidify the mixture, and the mixture was extracted with chloroform. The organic layer was dried over magnesium sulfate, and the solvent was evaporated. The obtained residue was subjected to silica gel column chromatography, and the fraction eluted with hexane:ethyl acetate=2:1 was concentrated to give α-(1-ethoxycarbonylpiperidin-4-yl)carbonylphenylacetonitrile (9.2 g) as an oil.

$^1$H-NMR(CDCl$_3$) δ: 1.25 (3H, t, J=7 Hz), 1.45-2.92 (7H, m), 4.00-4.18 (4H, m), 4.79-4.90 (1H, m), 7.32-7.48 (5H, m).

Starting Material Synthetic Example 43

α-(1-Ethoxycarbonylpiperidin-4-yl)carbonylphenylacetonitrile (9.2 g) obtained in Starting Material Synthetic Example 42 was dissolved in ethanol (100 mL), and methylhydrazine (1.7 g) was added, and the mixture was heated under reflux for 2 hrs. After the completion of the reaction, the solvent was evaporated. The obtained residue was subjected to silica gel column chromatography, and the fraction eluted with chloroform:methanol=40:1 was concentrated to give 5-amino-1-methyl-3-(1-ethoxycarbonylpiperidin-4-yl)-4-phenylpyrazole (4.2 g) as an oil.

$^1$H-NMR(CDCl$_3$) δ: 1.23 (3H, t, J=7 Hz), 1.65-1.78 (4H, m), 2.65-2.84 (3H, m), 3.48 (2H, brs), 3.68 (3H, s), 4.06-4.22 (4H, m), 7.24-7.33 (3H, m), 7.40-7.45 (2H, m).

Starting Material Synthetic Example 44

A mixture (1:1, 31 g) of α-(1-ethoxycarbonylpiperidin-4-yl) carbonyl-4-fluorophenylacetonitrile and α-(1-methoxycarbonylpiperidin-4-yl)carbonyl-4-fluorophenylacetonitrile was obtained as an oil by the reaction in the same manner as in Starting Material Synthetic Example 42 using 4-fluorophenylacetonitrile (22.2 g) and methyl 1-ethoxycarbonylisonipecotate (38.8 g). Further purification was not performed and the mixture was used in the next reaction.

Starting Material Synthetic Example 45

A mixture (1:1, 21.6 g) of 5-amino-1-methyl-3-(1-ethoxycarbonylpiperidin-4-yl)-4-(4-fluorophenyl)pyrazole and 5-amino-1-methyl-3-(1-methoxycarbonylpiperidin-4-yl)-4-(4-fluorophenyl)pyrazole was obtained as an oil by the reaction in the same manner as in Starting Material Synthetic Example 43 using the mixture (31 g) obtained in Starting Material Synthetic Example 44 of α-(1-ethoxycarbonylpiperidin-4-yl)carbonyl-4-fluorophenylacetonitrile and α-(1-methoxycarbonylpiperidin-4-yl)carbonyl-4-fluorophenylacetonitrile. Further purification was not performed and the mixture was used in the next reaction.

$^1$H-NMR(CDCl$_3$) δ: 1.23 (1.5H, t, J=7 Hz), 1.67-1.80 (4H, m), 2.65-2.80 (3H, m), 3.43 (2H, brs), 3.66 (1.5H, s), 3.68 (3H, s), 4.06-4.22 (3H, m), 7.08-7.15 (2H, m), 7.17-7.22 (2H, m).

Starting Material Synthetic Example 46

5-Amino-1-(4-bromophenyl)-3-methyl-4-phenylpyrazole was obtained by the reaction in the same manner as in Starting Material Synthetic Example 9 using α-acetylphenylacetonitrile and (4-bromophenyl)hydrazine.

$^1$H-NMR(DMSO-d$_6$) δ: 2.15 (3H, s), 5.14 (2H, s), 7.24-7.68 (9H, m).

3-(4-Bromophenyl)-5-methoxymethoxy-1-methyl-3H-pyrazolo[3,4-c]isoquinoline was obtained by the reaction in the same manner as in Starting Material Synthetic Example 1 using 5-amino-1-(4-bromophenyl)-3-methyl-4-phenylpyrazole.

$^1$H-NMR(CDCl$_3$) δ: 2.86 (3H, s), 3.64 (3H, s), 5.82 (2H, s), 7.52-8.43 (8H, m).

Starting Material Synthetic Example 47

Sodium ethoxide was prepared using sodium (1.3 g) and ethanol (200 mL), and a solution of ethyl (1-ethoxycarbonylpiperidin-4-yl)acetate (9.0 g) and (4-fluorophenyl)acetonitrile (5.0 g) in ethanol (20 mL) was added dropwise with heating under reflux, and the mixture was heated under reflux for 5 hrs. After the completion of the reaction, the solvent was evaporated. The obtained residue was dissolved in water, and acetic acid was added to acidify the mixture. The mixture was extracted with ethyl acetate, and the organic layer was dried over magnesium sulfate. The solvent was evaporated, and the obtained residue was purified by silica gel column chromatography, and the fraction eluted with hexane:ethyl acetate=2:1-1:1 was concentrated to give 4-(1-ethoxycarbonylpiperidin-4-yl)-2-(4-fluorophenyl)-3-oxobutyronitrile (5.3 g) as an oil.

$^1$H-NMR(CDCl$_3$) δ: 0.90-1.02 (2H, m), 1.23 (3H, t, J=7 Hz), 1.55 (2H, brd), 1.98 (1H, m), 2.52 (2H, m), 2.72 (2H, m), 4.06-4.19 (4H, m), 4.66 (1H, s), 7.03-7.39 (4H, m).

Starting Material Synthetic Example 48

5-Amino-3-[(1-ethoxycarbonylpiperidin-4-yl)methyl]-4-(4-fluorophenyl)-1-methylpyrazole (12.4 g) was obtained by the reaction in the same manner as in Starting Material Synthetic Example 43 using 4-(1-ethoxycarbonylpiperidin-4-yl)-3-oxo-2-(4-fluorophenyl)butyronitrile (16.7 g) obtained in Starting Material Synthetic Example 47 and methylhydrazine (4.6 g).

$^1$H-NMR(CDCl$_3$) δ: 1.03-1.28 (5H, m), 1.62-1.68 (2H, m), 1.99-2.05 (3H, m), 2.63 (3H, s), 2.76 (2H, m), 4.05-4.15 (6H, m), 7.07-7.22 (4H, m).

Starting Material Synthetic Example 49

3-Methyl-4-dimethylaminomethyl-2H-isoquinolin-1-one (1.25 g) was dissolved in chloroform (25 mL), and methyl iodide (373 μL) was added, and the mixture was heated under reflux for 4 hrs. After the completion of the reaction, the solvent was evaporated under reduced pressure. The obtained crystals were washed with diethyl ether and collected by filtration to give N-(3-methyl-2H-1-oxoisoquinolin-4-yl)methyl-trimethylammonium iodide (1.72 g).

$^1$H-NMR(DMSO-d$_6$) δ: 2.40 (3H, s), 3.05 (6H, s), 3.11 (3H, s), 4.60 (1H, d, J=14 Hz), 4.92 (1H, d, J=14 Hz), 7.49-7.54 (1H, m), 7.74-7.82 (1H, m), 8.15-8.29 (2H, m), 11.7 (1H, brs).

The structural formulas of the compounds of the respective Starting Material Synthetic Examples are shown below. The following numbers correspond to the numbers of the above-mentioned Starting Material Synthetic Examples.

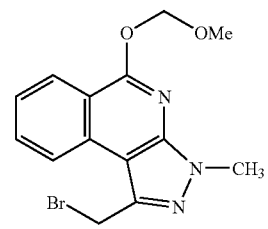

1

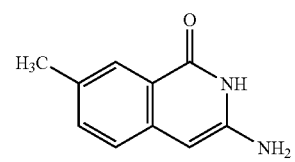

2

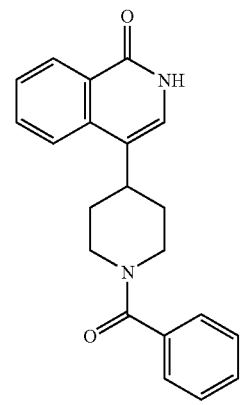

3

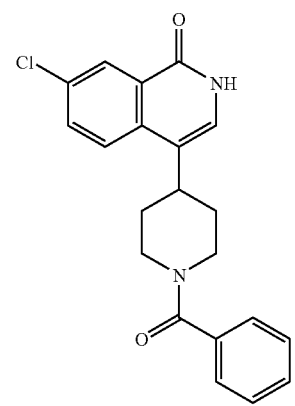

4

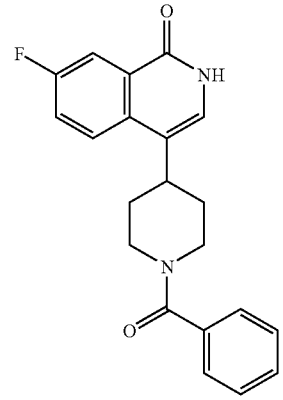

5

-continued
6
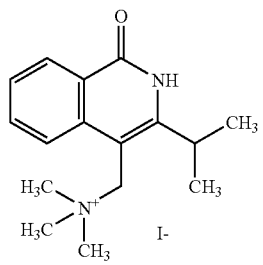
7
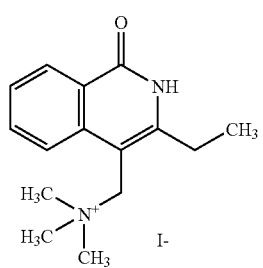
8
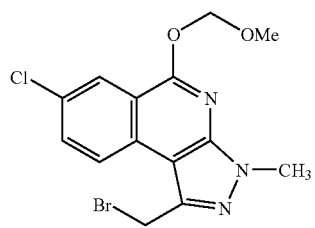
9
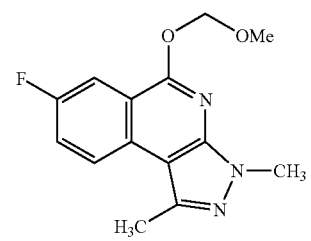
10
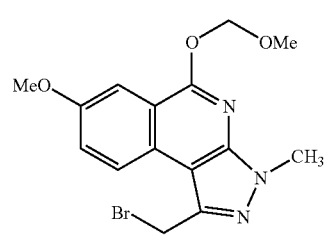
11
-continued
12
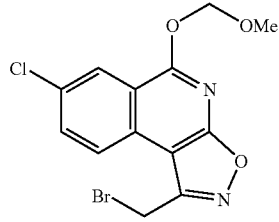
13
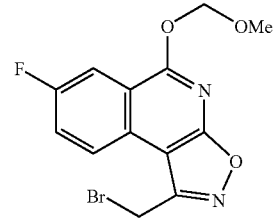
14
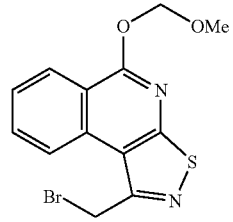
15
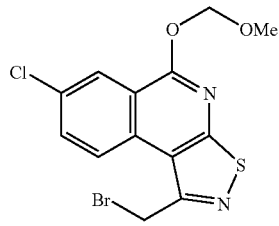
16
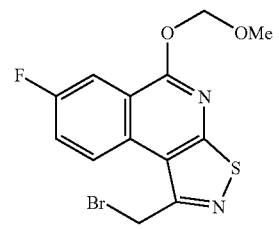
Starting Material Synthetic Examples 17-20 are missing numbers.
21
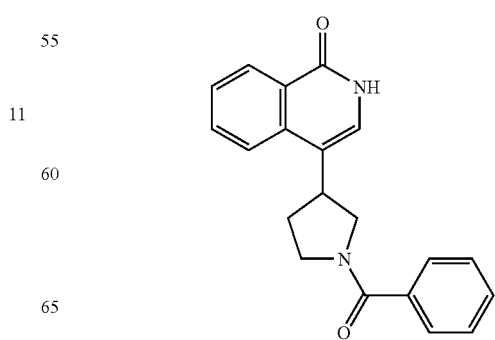

22
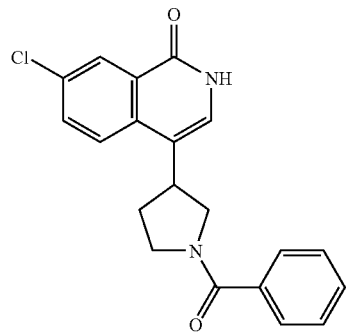
23
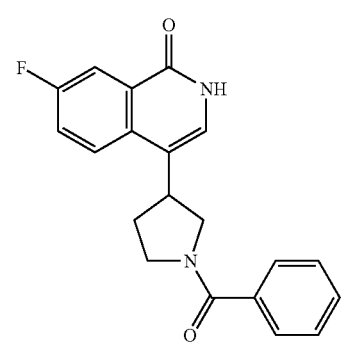
24 missing number
25 missing number
26 missing number
27 missing number
28 missing number
29
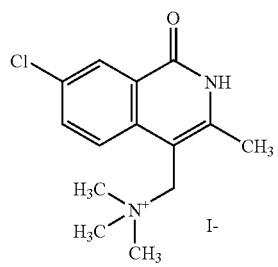
30
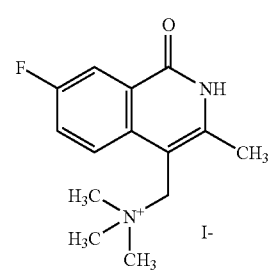
31
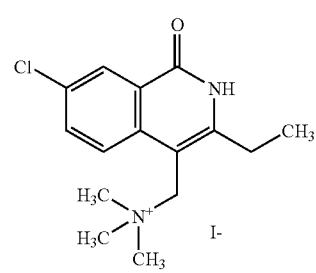
32
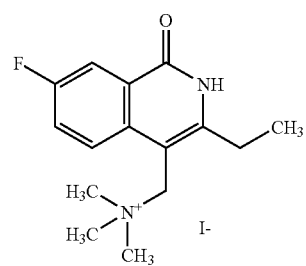
33
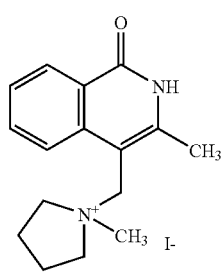
34
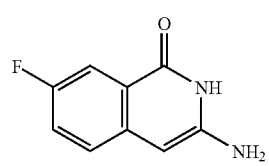
35
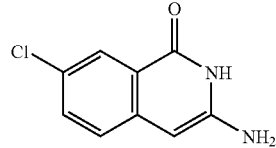
36
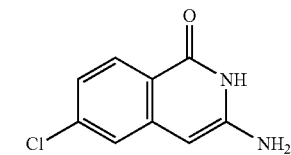
37
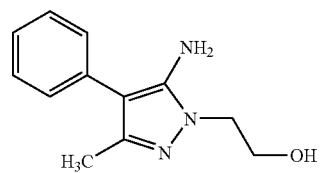

-continued
38 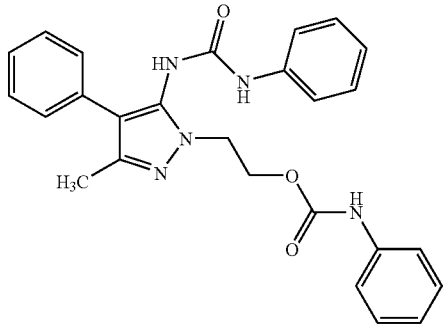
39 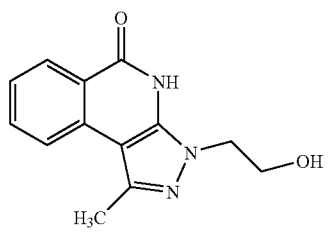
40 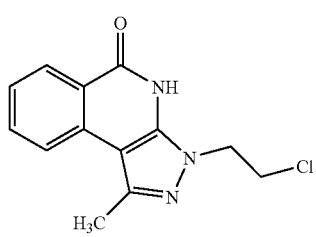
41 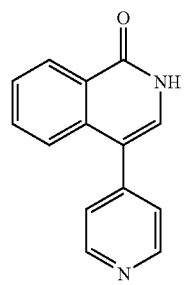
42 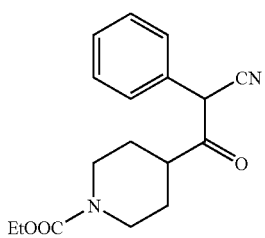
43 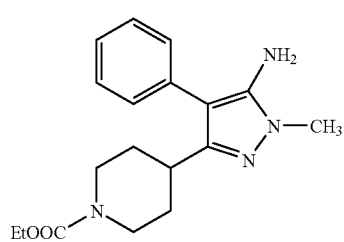
-continued
44 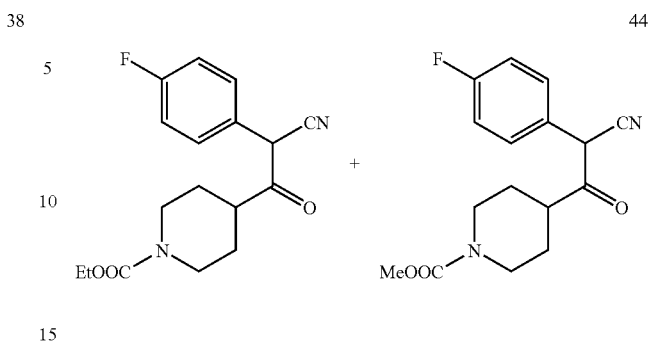
45 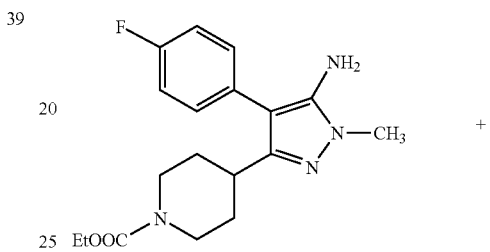
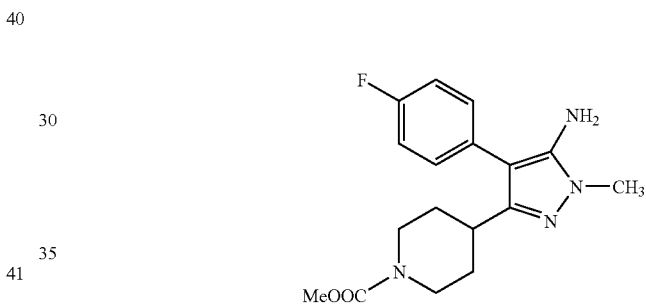
46 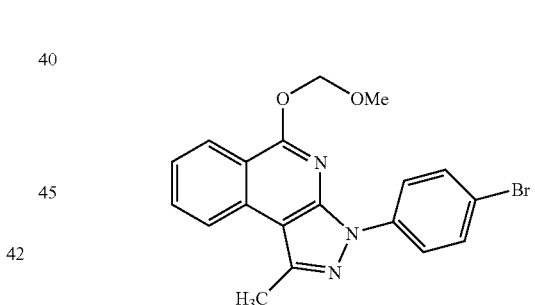
47 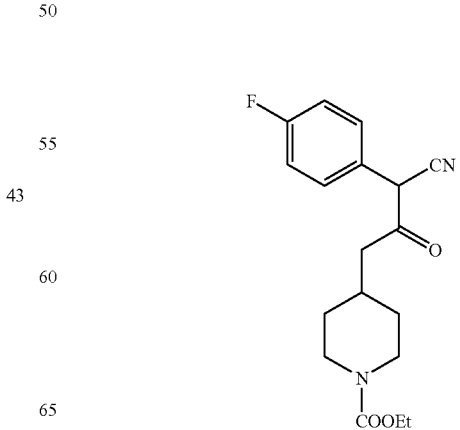

-continued

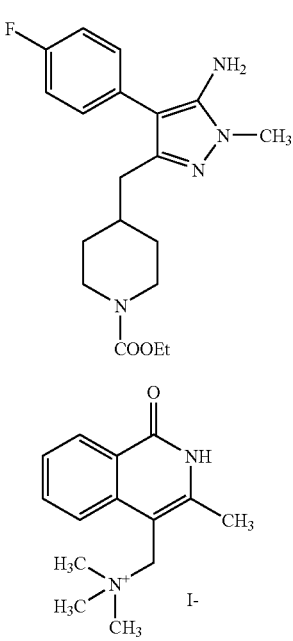

48

49

Example 1

3-Amino-2H-isoquinolin-1-one (9.0 g), dimethylglycine hydrochloride (10.2 g) and pyridine (22.7 mL) were suspended in methylene chloride (100 mL), and 2-chloro-1,3-dimethylimidazolinium chloride (12.4 g) was added under ice-cooling. Then the mixture was stirred at room temperature for 2 hrs. After the completion of the reaction, the reaction mixture was dissolved in a mixed solvent (chloroform and lo methanol 10:1), washed with aqueous potassium carbonate solution and the organic layer was dried over magnesium sulfate. The solvent was evaporated, and the obtained residue was purified by silica gel column chromatography. The fraction eluted with chloroform:methanol was concentrated, and the precipitated crystals were collected by filtration to give 3-amino-4-(2-(dimethylamino) acetyl)-2H-isoquinolin-1-one (5.5 g). This compound was dissolved in chloroform-methanol mixed solvent, and 4N hydrogen chloride-dioxane was added. The precipitated crystals were collected by filtration, and recrystallized from ethanol-water mixed solvent to give 3-amino-4-(2-(dimethylamino)acetyl)-2H-isoquinolin-1-one hydrochloride monohydrate (4.5 g).

$^1$H-NMR (DMSO-$d_6$) δ: 2.80 (6H, s), 4.72 (2H, s), 7.31 (1H, t, J=7 Hz), 7.55 (1H, d, J=8 Hz), 7.68 (1H, d, J=8 Hz), 8.11 (1H, d, J=8 Hz), 8.74 (2H, brs), 9.77 (1H, brs), 11.71 (1H, brs). MS(EI): 245(M+).

Example 2

3-Amino-4-(2-(piperidin-1-yl)acetyl)-2H-isoquinolin-1-one (0.3 g) was obtained by the reaction in the same manner as in Example 1 using 3-amino-2H-isoquinolin-1-one (0.8 g) and (piperidin-1-yl)acetic acid hydrochloride (0.79 g).

$^1$H-NMR (DMSO-$d_6$) δ: 1.31-1.54 (6H, m), 2.41-2.53 (4H, m), 3.34 (2H, s), 7.18 (1H, t, J=7 Hz), 7.54 (1H, t, J=7 Hz), 7.99-8.03 (3H, m), 8.28 (1H, d, J=8 Hz), 10.97 (1H, brs). MS(EI): 285(M+).

Example 3

3-Amino-4-(2-(dimethylamino)acetyl)-5-methyl-2H-isoquinolin-1-one (0.2 g) was obtained by the reaction in the same manner as in Example 1 using 3-amino-5-methyl-2H-isoquinolin-1-one (0.87 g) and dimethylglycine hydrochloride (0.91 g).

$^1$H-NMR (DMSO-$d_6$) δ: 2.12 (6H, s), 2.23 (3H, s), 3.15 (2H, s), 7.16 (1H, t, J=8 Hz), 7.24 (2H, brs), 7.44 (1H, d, J=7 Hz), 7.88 (1H, d, J=8 Hz), 10.86 (1H, brs). MS(EI): 259(M+).

Example 4

3-Amino-4-(3-(dimethylamino)propionyl)-2H-isoquinolin-1-one oxalate (0.4 g) was obtained by the reaction in the same manner as in Example 1 using 3-amino-2H-isoquinolin-1-one (0.8 g) and 3-(dimethylamino)propionic acid hydrochloride (1.0 g).

$^1$H-NMR (DMSO-$d_6$) δ: 2.77 (6H, s), 3.26-3.40 (4H, m), 7.25 (1H, t, J=7 Hz), 7.62 (1H, t, J=8 Hz), 7.75 (1H, d, J=8 Hz), 8.07 (1H, d, J=8 Hz), 8.16 (2H, brs), 11.24 (1H, brs). MS(EI): 259(M+).

Example 5

3-Amino-4-(4-(dimethylamino)butyryl)-2H-isoquinolin-1-one oxalate (0.2 g) was obtained by the reaction in the same manner as in Example 1 using 3-amino-2H-isoquinolin-1-one (0.8 g) and 4-(dimethylamino)butanoic acid hydrochloride (1.1 g).

$^1$H-NMR (DMSO-$d_6$) δ: 1.90-2.05 (2H, m), 2.08 (6H, s), 2.90-3.04 (4H, m), 7.22 (1H, t, J=7 Hz), 7.59 (1H, t, J=8 Hz), 8.00-8.07 (3H, m), 11.16 (1H, brs). MS(EI): 273(M+).

Example 6

(R)-3-Amino-4-((1-methylpyrrolidin-2-yl)carbonyl)-2H-isoquinolin-1-one (82 mg) was obtained by the reaction in the same manner as in Example 1 using 3-amino-2H-isoquinolin-1-one (0.8 g) and N-methyl-D-proline hydrochloride (1.1 g).

$^1$H-NMR (DMSO-$d_6$) δ: 1.70-1.99 (3H, m), 2.05-2.16 (1H, m) 2.15 (3H, m), 2.32-2.43 (1H, m), 2.96-3.06 (1H, m), 3.71-3.77 (1H, m), 7.19 (1H, t, J=8 Hz), 7.54-7.64 (2H, m), 7.72 (2H, brs), 8.02 (1H, d, J=8 Hz), 11.02 (1H, brs). MS(EI): 271(M+).

Example 7

1-bromomethyl-3-methyl-5-methoxymethoxy-3H-pyrazolo[3,4-c]isoquinoline (3.0 g) obtained in Starting Material Synthetic Example 1 was dissolved in acetonitrile (20 mL), and potassium carbonate (2.0 g) and pyrrolidine (2.0 g) were added, and the mixture was stirred at room temperature for 2 hrs.

After the completion of the reaction, the solvent was evaporated. Water was added to the obtained residue, and the mixture was extracted with chloroform. The organic layer was dried over magnesium sulfate, and the solvent was evaporated. The obtained residue was dissolved in methanol (20 mL). Concentrated hydrochloric acid (4 mL) was added to the reaction mixture, and the mixture was heated under reflux. After the completion of the reaction, the solvent was evaporated, and aqueous potassium carbonate solution was added to the obtained residue. The mixture was extracted with chloroform, and the organic layer was dried over magnesium sulfate. The solvent was evaporated, and the obtained residue was purified by silica gel column chromatography (chloroform:methanol=20:1) to give 3-methyl-1-(pyrrolidin-1-yl)methyl-3H-pyrazolo[3,4-c]isoquinolin-5(4H)-one (0.85 g) as white crystals.

¹H-NMR (DMSO-d₆) δ: 1.65-1.75 (4H, m), 2.45-2.54 (4H, m), 3.80 (2H, s), 3.84 (3H, s), 7.39 (1H, t, J=8 Hz), 7.74 (1H, t, J=8 Hz), 8.14 (1H, d, J=8 Hz), 8.21 (1H, dd, J=1 Hz, 8 Hz), 12.31 (1H, brs). MS(EI): 282(M+).

Example 8

(S)-3-Amino-4-((1-methylpyrrolidin-2-yl)carbonyl)-2H-isoquinolin-1-one (0.39 g) was obtained by the reaction in the same manner as in Example 1 using 3-amino-2H-isoquinolin-1-one (0.8 g) and N-methyl-L-proline hydrochloride (1.1 g).

¹H-NMR (DMSO-d₆) δ: 1.70-1.99 (3H, m), 2.05-2.16 (1H, m), 2.15 (3H, m), 2.32-2.43 (1H, m), 2.96-3.06 (1H, m), 3.71-3.77 (1H, m), 7.19 (1H, t, J=8 Hz), 7.54-7.64 (2H, m), 7.72 (2H, brs), 8.02 (1H, d, J=8 Hz), 11.02 (1H, brs). MS(EI): 271(M+).

Example 9

3-Amino-4-(3-(pyrrolidin-1-yl)propionyl)-2H-isoquinolin-1-one hydrochloride (0.36 g) was obtained by the reaction in the same manner as in Example 1 using 3-amino-2H-isoquinolin-1-one (0.8 g) and 3-(pyrrolidin-1-yl)propionic acid hydrochloride (1.2 g).

¹H-NMR (DMSO-d₆) δ: 1.81-2.04 (4H, m), 2.92-3.06 (2H, m), 3.36-3.59 (6H, m), 7.25 (1H, t, J=7 Hz), 7.63 (1H, dt, J=1 Hz, 8 Hz), 7.74 (1H, d, J=8 Hz), 8.07 (1H, dd, J=1 Hz, 8 Hz), 8.17 (2H, brs), 10.27 (1H, brs), 11.30 (1H, brs). MS(EI): 285(M+).

Example 10

3-Amino-7-methyl-4-((dimethylamino)acetyl)-2H-isoquinolin-1-one hydrochloride (0.46 g) was obtained by the reaction in the same manner as in Example 1 using 3-amino-7-methyl-2H-isoquinolin-1-one (0.87 g) obtained in Starting Material Synthetic Example 2 and dimethylglycine hydrochloride (0.77 g)

¹H-NMR (DMSO-d₆) δ: 2.38 (3H, s), 2.79 (6H, s), 4.69 (2H, s), 7.43-7.52 (2H, m), 7.91 (1H, s), 8.68 (2H, brs), 9.73 (1H, brs), 11.61 (1H, brs). MS(EI): 259(M+).

Example 11

3-Amino-7-methyl-4-((pyrrolidin-1-yl)acetyl)-2H-isoquinolin-1-one (0.39 g) was obtained by the reaction in the same manner as in Example 1 using 3-amino-7-methyl-2H-isoquinolin-1-one (0.87 g) obtained in Starting Material Synthetic Example 2 and (pyrrolidin-1-yl)acetic acid hydrochloride (0.91 g).

¹H-NMR (DMSO-d₆) δ: 1.65-1.76 (4H, m), 2.34 (3H, s), 2.54-2.64 (4H, m), 3.48 (2H, s), 7.42 (1H, dd, J=2 Hz, 9 Hz), 7.83 (1H, d, J=1 Hz), 8.02 (2H, brs), 8.17 (1H, d, J=9 Hz), 11.02 (1H, brs). MS(EI): 285(M+).

Example 12

3-Amino-4-(3-(dimethylamino)propionyl)-7-methyl-2H-isoquinolin-1-one hydrochloride (0.41 g) was obtained by the reaction in the same manner as in Example 1 using 3-amino-7-methyl-2H-isoquinolin-1-one (0.87 g) obtained in Starting Material Synthetic Example 2 and 3-(dimethylamino)propionic acid hydrochloride (0.84 g).

¹H-NMR (DMSO-d₆) δ: 2.37 (3H, s), 2.77 (6H, s), 3.32-3.40 (4H, m), 7.46 (1H, dd, J=2 Hz, 8 Hz), 7.68 (1H, d, J=8 Hz), 7.88 (1H, s), 8.21 (2H, brs), 10.11 (1H, brs), 11.30 (1H, brs). MS(EI): 273(M+).

Example 13

3-Amino-4-((pyrrolidin-1-yl)acetyl)-2H-isoquinolin-1-one hydrochloride (3.2 g) was obtained by the reaction in the same manner as in Example 1 using 3-amino-2H-isoquinolin-1-one (3.2 g) and (pyrrolidin-1-yl)acetic acid hydrochloride (3.64 g).

¹H-NMR (DMSO-d₆) δ: 1.91-2.06 (4H, m), 2.50-2.70 (2H, m), 3.44-3.66 (2H, m), 4.80 (2H, s), 7.28 (1H, d, J=7 Hz), 7.59 (1H, d, J=8 Hz), 7.66 (1H, dt, J=2 Hz, 8 Hz), 8.68 (2H, brs), 10.05 (1H, brs), 11.63 (1H, brs). MS(EI): 271(M+).

Example 14

3-Amino-4-(2-(dimethylamino)acetyl)-7-fluoro-2H-isoquinolin-1-one hydrochloride (0.18 g) was obtained by the reaction in the same manner as in Example 1 using 3-amino-7-fluoro-2H-isoquinolin-1-one (1.0365 g) obtained in Starting Material Synthetic Example 34 and dimethylglycine hydrochloride (0.9082 g).

¹H-NMR (DMSO-d₆) δ: 2.79 (6H, s), 4.69 (2H, s), 7.58-7.64 (2H, m), 7.79 (1H, dd, J=2 Hz, J=9 Hz), 8.60 (2H, brs), 9.73 (1H, brs), 11.76 (1H, brs). MS(EI): 263(M+).

Example 15

3-Amino-7-fluoro-4-((pyrrolidin-1-yl)acetyl)-2H-isoquinolin-1-one hydrochloride (0.4156 g) was obtained in the same manner as in Example 1 using 3-amino-7-fluoro-2H-isoquinolin-1-one (0.9837 g) obtained in Starting Material Synthetic Example 34 and (pyrrolidin-1-yl)acetic acid hydrochloride (1.016 g).

¹H-NMR (DMSO-d₆) δ: 1.94 (4H, brs), 2.92-3.65 (4H, m), 4.79 (2H, s), 7.52-7.59 (1H, m), 7.66-7.71 (1H, m), 7.78 (1H, dd, J=3 Hz, J=9 Hz), 8.64 (2H, brs), 10.06 (1H, brs), 11.81 (1H, brs). MS(EI): 289(M+).

Example 16

3-Amino-4-(3-(dimethylamino)propionyl)-7-fluoro-2H-isoquinolin-1-one hydrochloride (0.0479 g) was obtained in the same manner as in Example 1 using 3-amino-7-fluoro-2H-isoquinolin-1-one (1.0528 g) obtained in Starting Material Synthetic Example 34 and (3-(dimethylamino)propionic acid hydrochloride (0.998 g).

¹H-NMR (DMSO-d₆) δ: 2.72 (6H, s), 2.92 (2H, t, J=14 Hz), 3.29-3.39 (2H, m), 6.62 (1H, s), 7.53-7.60 (1H, m), 7.69-7.78 (2H, m), 10.09 (1H, brs), 11.03 (1H, brs), 11.36 (1H, brs). MS(EI): 277(M+).

Example 17

3-Methyl-1-dimethylaminomethyl-3H-pyrazolo[3,4-c]isoquinolin-5(4H)-one (0.37 g) was obtained by the reaction in the same manner as in Example 7 using 1-bromomethyl-3-methyl-5-methoxymethoxy-3H-pyrazolo[3,4-c]isoquinoline (1.0 g) obtained in Starting Material Synthetic Example 1 and 50% aqueous dimethylamine solution (2 mL).

¹H-NMR (DMSO-d₆) δ: 2.21 (6H, s), 3.59 (2H, s), 3.84 (3H, s), 7.40 (1H, t, J=8 Hz), 7.74 (1H, dt, J=1 Hz, 8 Hz), 8.10 (1H, d, J=8 Hz), 8.22 (1H, d, J=8 Hz), 12.33 (1H, brs). MS(EI): 256(M+).

Example 18

3-Amino-4-(2-(dimethylamino)acetyl)-7-chloro-2H-isoquinolin-1-one hydrochloride (345 mg) was obtained by the reaction in the same manner as in Example 1 using 3-amino-7-chloro-2H-isoquinolin-1-one (1.0 g) obtained in Starting Material Synthetic Example 35 and dimethylglycine hydrochloride (789 mg).

$^1$H-NMR (DMSO-d$_6$) δ: 2.79 (6H, s), 4.69 (2H, s), 7.59 (1H, d, J=8.9 Hz), 7.71 (1H, d, J=8.9 Hz), 8.62 (1H, s), 8.62 (2H, brs), 9.72 (1H, brs), 11.74 (1H, brs). MS(EI): 279(M+).

Example 19

3-Amino-4-(3-(dimethylamino)propionyl)-7-chloro-2H-isoquinolin-1-one hydrochloride (312 mg) was obtained by the reaction in the same manner as in Example 1 using 3-amino-7-chloro-2H-isoquinolin-1-one (1.0 g) obtained in Starting Material Synthetic Example 35 and 3-dimethylaminopropionic acid hydrochloride (868 mg).

$^1$H-NMR (DMSO-d$_6$) δ: 2.77 (6H, m), 3.36 (4H, m), 7.63 (1H, d, J=8.9 Hz), 7.82 (1H, d, J=8.9 Hz), 7.99 (1H, s), 8.24 (2H, brs), 10.03 (1H, brs), 11.54 (1H, brs). MS (EI): 293(M+)

Example 20

3-Amino-4-(2-(pyrrolidin-1-yl)acetyl)-7-chloro-2H-isoquinolin-1-one hydrochloride (498 mg) was obtained by the reaction in the same manner as in Example 1 using 3-amino-7-chloro-2H-isoquinolin-1-one (1.0 g) obtained in Starting Material Synthetic Example 35 and (pyrrolidin-1-yl)acetic acid hydrochloride (930 mg).

$^1$H-NMR (DMSO-d$_6$) δ: 1.90-1.92 (4H, m), 3.06-3.08 (2H, m), 3.51-3.53 (2H, m), 4.77-4.79 (2H, m), 7.62-7.70 (2H, m), 8.02 (1H, s), 8.66 (2H, brs), 10.03 (1H, brs), 11.80 (1H, brs). MS(EI): 305(M+).

Example 21

3-Methyl-1-((4-methylpiperazin-1-yl)methyl)-3H-pyrazolo[3,4-c]isoquinolin-5(4H)-one (0.19 g) was obtained by the reaction in the same manner as in Example 7 using 1-bromomethyl-3-methyl-5-methoxymethoxy-3H-pyrazolo[3,4-c]isoquinoline (2.5 g) obtained in Starting Material Synthetic Example 1 and 1-methylpiperazine (2 mL).

$^1$H-NMR (DMSO-d$_6$) δ: 2.12 (3H, s), 2.13-2.57 (4H, m), 3.67 (2H, s), 3.84 (3H, s), 7.40 (1H, t, J=8 Hz), 7.74 (1H, t, J=8 Hz), 8.18 (1H, d, J=8 Hz), 8.22 (1H, dd, J=1 Hz, 8 Hz), 12.33 (1H, brs). MS(EI): 311(M+).

Example 22

3-Methyl-1-((morpholin-4-yl)methyl)-3H-pyrazolo[3,4-c]isoquinolin-5(4H)-one (0.70 g) was obtained by the reaction in the same manner as in Example 7 using 1-bromomethyl-3-methyl-5-methoxymethoxy-3H-pyrazolo[3,4-c]isoquinoline (2.5 g) obtained in Starting Material Synthetic Example 1 and morpholine (2 mL).

$^1$H-NMR (DMSO-d$_6$) δ: 2.40-2.44 (4H, m), 3.49-3.60 (4H, m), 3.69 (2H, s), 3.84 (3H, s), 7.40 (1H, t, J=8 Hz), 7.75 (1H, t, J=8 Hz), 8.18 (1H, d, J=8 Hz), 8.22 (1H, d, J=8 Hz), 12.33 (1H, brs). MS(EI): 298(M+).

Example 23

3-Methyl-1-((piperidin-1-yl)methyl)-3H-pyrazolo[3,4-c]isoquinolin-5(4H)-one hydrochloride (0.61 g) was obtained by the reaction in the same manner as in Example 7 using 1-bromomethyl-3-methyl-5-methoxymethoxy-3H-pyrazolo[3,4-c]isoquinoline (2.5 g) obtained in Starting Material Synthetic Example 1 and piperidine (2 mL).

$^1$H-NMR (DMSO-d$_6$) δ: 1.26-1.48 (1H, m), 1.63-1.84 (5H, m), 3.02-3.18 (2H, m), 3.51-3.64 (2H, m), 3.95 (3H, s), 4.68-4.74 (2H, m), 7.50 (1H, t, J=8 Hz), 7.81 (1H, t, J=8 Hz), 8.10 (1H, d, J=8 Hz), 8.29 (1H, dd, J=1 Hz, 8 Hz), 10.09 (1H, brs), 12.57 (1H, brs). MS (EI): 296(M+).

Example 24

1-Bromomethyl-3-methyl-5-methoxymethoxy-3H-pyrazolo[3,4-c]isoquinoline (11.3 g) obtained in Starting Material Synthetic Example 1 was dissolved in dimethylsulfoxide (50 mL), and sodium cyanide (1.66 g) was added at room temperature, and the mixture was stirred overnight. After the completion of the reaction, the reaction mixture was poured into ice-water and extracted with ethyl acetate. The organic layer was washed three times with saturated brine, and dried over magnesium sulfate. The solvent was evaporated, and the obtained residue was purified by silica gel column chromatography (hexane:ethyl acetate=2:1) to give 1-cyanomethyl-3-methyl-5-methoxymethoxy-3H-pyrazolo[3,4-c]isoquinoline (1.77 g).

$^1$H-NMR (CDCl$_3$) δ: 3.66 (3H, s), 4.07 (3H, s), 4.21 (2H, s), 5.85 (2H, s), 7.55 (1H, t, J=8 Hz), 7.85 (1H, t, J=8 Hz), 8.05 (1H, d, J=8 Hz), 8.43 (1H, d, J=8 Hz).

1-Cyanomethyl-3-methyl-5-methoxymethoxy-3H-pyrazolo[3,4-c]isoquinoline (1.77 g) and potassium hydroxide (1.06 g) were dissolved in water (5 mL) and ethanol (5 mL), and the mixture was heated under reflux for 6 hrs. After the completion of the reaction, the reaction mixture was poured into aqueous citric acid, and the precipitated crystals were collected by filtration to give (3-methyl-3H-5(4H)-oxo-pyrazolo[3,4-c]isoquinolin-1-yl)acetic acid (1.28 g).

$^1$H-NMR (DMSO-d$_6$) δ: 3.85 (3H, s), 3.92 (2H, s), 7.42 (1H, t, J=8 Hz), 7.71-7.80 (2H, m), 8.25 (1H, d, J=8 Hz), 12.38 (1H, brs).

(3-Methyl-3H-5(4H)-oxo-pyrazolo[3,4-c]isoquinolin-1-yl)acetic acid (1.28 g), pyrrolidine (0.43 g) and triethylamine (2.1 mL) were dissolved in dimethylformamide (10 mL), and diethyl cyanophosphate (1.0 mL) was added dropwise under ice-cooling. After the mixture was stirred overnight at room temperature, water and ethyl acetate was added to the reaction mixture, and the precipitated crystals were collected by filtration to give 1-(2-(pyrrolidin-1-yl)-2-oxoethyl)-3-methyl-3H-pyrazolo[3,4-c]isoquinolin-5(4H)-one (0.15 g).

1-(2-(Pyrrolidin-1-yl)-2-oxoethyl)-3-methyl-3H-pyrazolo[3,4-c]isoquinolin-5(4H)-one (0.15 g) was suspended in tetrahydrofuran (10 mL), and 1N borane-tetrahydrofuran complex (20 mL) was added, and the mixture was heated under reflux for 3 hrs.

After the completion of the reaction, diluted hydrochloric acid was added to acidify the reaction mixture, and the mixture was heated under reflux for 1 hr. After the completion of the reaction, aqueous potassium carbonate solution was added to alkalify the reaction mixture. The mixture was extracted with chloroform, and the organic layer was dried over magnesium sulfate. The solvent was evaporated, and the obtained residue was purified by silica gel column chromatography (chloroform:methanol=3:1) to give 1-(2-(pyrrolidin-1-yl)ethyl)-3-methyl-3H-pyrazolo[3,4-c]isoquinolin-5(4H)-one (60 mg).

$^1$H-NMR (DMSO-d$_6$) δ: 1.70-1.96 (4H, m), 2.62-2.70 (4H, m), 2.88 (2H, t, J=8 Hz), 3.14 (2H, t, J=8 Hz), 3.82 (3H, s), 7.42 (1H, t, J=8 Hz), 7.78 (1H, t, J=8 Hz), 7.86 (1H, d, J=8 Hz), 8.25 (1H, d, J=8 Hz).

Example 25

3-Methyl-4-(pyrrolidin-1-yl)methyl-2H-isoquinolin-1-one (3.74 g) was obtained by the reaction in the same manner as in Example 34 using 3-methyl-2H-isoquinolin-1-one (10.0 g) and pyrrolidine (35.0 mL).

$^1$H-NMR (CDCl$_3$) δ: 1.71-1.81 (4H, m), 2.47 (3H, s), 2.86 (4H, brs), 3.74 (2H, s), 7.44 (1H, t, J=8.4 Hz), 7.68 (1H, t, J=8.4 Hz), 7.97 (1H, d, J=8.4 Hz), 8.41 (1H, d, J=8.4 Hz), 10.2 (1H, brs). MS(EI): 242(M+).

Example 26

3-Amino-6-chloro-4-(2-(dimethylamino)acetyl)-2H-isoquinolin-1-one hydrochloride (572 mg) was obtained by the reaction in the same manner as in Example 1 using 3-amino-6-chloro-2H-isoquinolin-1-one (1.0 g) obtained in Starting Material Synthetic Example 36 and dimethylglycine hydrochloride (789 mg).

$^1$H-NMR (DMSO-d$_6$) δ: 2.79 (6H, s), 4.74 (2H, s), 7.34 (1H, d, J=8.4 Hz), 7.58 (1H, s), 8.08 (1H, d, J=8.4 Hz), 8.58 (2H, brs), 9.72 (1H, brs), 11.63 (1H, brs). MS(EI): 279(M+).

Example 27

Pyrrolidine (1.42 g) and 35% aqueous formalin solution (3.0 g) was dissolved in acetic acid (20 mL), and the mixture was stirred at 70° C. for 15 min. 7-Chloro-3-methyl-2H-isoquinolin-1-one (0.97 g) was added to the reaction mixture, and the mixture was heated under reflux for 7 hrs.

After the completion of the reaction, the reaction mixture was concentrated, and aqueous potassium carbonate solution was added. The mixture was extracted with chloroform, and the organic layer was dried over magnesium sulfate. The solvent was evaporated, and the obtained residue was purified by silica gel column chromatography (chloroform:methanol=20:1) to give 7-chloro-3-methyl-4-((pyrrolidin-1-yl)methyl)-2H-isoquinolin-1-one (0.75 g).

$^1$H-NMR (DMSO-d$_6$) δ: 1.63-1.70 (4H, m), 2.31 (3H, s), 2.44-2.53 (4H, m), 3.63 (2H, s), 7.71 (1H, dd, J=3 Hz, 9 Hz), 7.93 (1H, d, J=9 Hz), 8.08 (1H, d, J=3 Hz), 11.35 (1H, brs). MS(EI): 276(M+).

Example 28

7-Fluoro-3-methyl-4-((pyrrolidin-1-yl)methyl)-2H-isoquinolin-1-one (0.26 g) was obtained by the reaction in the same manner as in Example 27 using 7-fluoro-3-methyl-2H-isoquinolin-1-one (0.89 g).

$^1$H-NMR (DMSO-d$_6$) δ: 1.60-1.69 (4H, m), 2.30 (3H, s), 2.44-2.52 (4H, m), 3.63 (2H, s), 7.54-7.60 (1H, m), 7.18-7.84 (1H, m), 7.94-7.99 (1H, m), 11.29 (1H, brs). MS(EI): 260 (M+).

Example 30

3-Methyl-4-(dimethylaminomethyl)-2H-isoquinolin-1-one (3 mg) was obtained by the reaction in the same manner as in Example 27 using dimethylamine hydrochloride (0.82 g) and 3-methyl-2H-isoquinolin-1-one (0.8 g).

$^1$H-NMR (CDCl$_3$) δ: 2.31 (6H, s), 2.47 (3H, s), 3.53 (2H, s), 7.44 (1H, t, J=7 Hz), 7.69 (1H, dt, J=2 Hz, 8 Hz), 7.89 (1H, d, J=8 Hz), 8.42 (1H, dd, J=1 Hz, 8 Hz), 10.61 (1H, brs).

Example 31

4-(1-Benzoylpiperidin-4-yl)-2H-isoquinolin-1-one (2.5 g) obtained in Starting Material Synthetic Example 3 was dissolved in concentrated hydrochloric acid (30 mL) and acetic acid (30 mL), and the mixture was heated under reflux.

After the completion of the reaction, the solvent was evaporated, and the precipitated crystals were collected by filtration to give 4-(piperidin-4-yl)-2H-isoquinolin-1-one hydrochloride (1.4 g).

$^1$H-NMR (DMSO-d$_6$) δ: 1.76-2.05 (4H, m), 3.05-3.39 (5H, m), 6.88 (1H, d, J=5 Hz), 7.54 (1H, t, J=8 Hz), 7.78 (1H, t, J=8 Hz), 7.92 (1H, d, J=8 Hz), 8.27 (1H, d, J=8 Hz), 8.93-9.20 (2H, m), 11.26 (1H, d, J=5 Hz). MS(ESI): 229(M+1).

Example 32

4-(Piperidin-4-yl)-2H-isoquinolin-1-one hydrochloride (0.8 g) obtained in Example 31, potassium carbonate (2.0 g) and 2-bromoethanol (1.88 g) were dissolved in 2-butanone and water (1 mL), and the mixture was heated under reflux for 4 hrs. After the completion of the reaction, the solvent was evaporated, and water was added to the obtained residue. The mixture was extracted with chloroform, the organic layer dried over magnesium sulfate. The solvent was evaporated, and the obtained residue was purified by silica gel column chromatography (chloroform:methanol=4:1+triethylamine 2%) to give 4-(1-(2-hydroxyethyl)piperidin-4-yl)-2H-isoquinolin-1-one (0.46 g) as white crystals.

$^1$H-NMR (CDCl$_3$) δ: 1.63-1.89 (2H, m), 1.94-2.04 (2H, m), 2.23-2.36 (2H, m), 2.65 (2H, t, J=5 Hz), 2.88-3.00 (1H, m), 3.10-3.18 (2H, m), 3.71 (2H, t, J=5 Hz), 7.04 (1H, s), 7.51-7.57 (1H, m), 7.70-7.76 (2H, m), 8.50 (1H, d, J=8 Hz), 11.05 (1H, brs). MS(EI): 272(M+).

Example 33

4-(Piperidin-4-yl)-2H-isoquinolin-1-one hydrochloride (0.5 g) obtained in Example 31 and 35% aqueous formalin solution (0.33 g) were dissolved in acetonitrile (20 mL), and sodium triacetoxyborohydride (0.81 g) was added under ice-cooling, and the mixture was stirred at room temperature for 3 hrs. After the completion of the reaction, diluted hydrochloric acid was added to the reaction mixture. The mixture was once heated under reflux, and the solvent was evaporated. Aqueous potassium carbonate solution was added to the obtained residue, and the mixture was extracted with chloroform, and purified by silica gel column chromatography (chloroform:methanol=4:1+triethylamine 2%) to give 4-(1-methylpiperidin-4-yl)-2H-isoquinolin-1-one (88 mg) as white crystals.

$^1$H-NMR (CDCl$_3$) δ: 1.76-1.86 (2H, m), 1.96-2.04 (2H, m), 2.14-2.24 (2H, m), 2.38 (3H, s), 2.82-2.92 (1H, m), 3.04-3.12 (2H, m), 7.02 (1H, s), 7.50-7.55 (1H, m), 7.69-7.76(2H, m), 8.50 (1H, d, J=8 Hz), 10.99 (1H, brs). MS(EI): 242(M+).

Example 34

Piperidine (0.747 mL) and paraformaldehyde (271 mg) were dissolved in acetic acid (3 mL), and the mixture was stirred at 70° C. for 5 min. 3-Methyl-2H-isoquinolin-1-one (302 mg) was added to the reaction mixture, and the mixture was heated under reflux for 2.5 hrs. After the completion of the reaction, the reaction mixture was concentrated, aqueous potassium carbonate solution was added. The mixture was extracted with chloroform, and the organic layer was dried over magnesium sulfate. The solvent was evaporated, and the obtained residue was purified by silica gel column chromatography (chloroform:methanol=20:1) to give 3-methyl-4-(piperidin-1-yl)methyl-2H-isoquinolin-1-one (99.3 mg).

¹H-NMR (DMSO-d₆) δ: 1.30-1.50 (6H, m), 2.28 (3H, s), 2.39 (4H, brs), 3.46 (2H, s), 7.40 (1H, t, J=7.8 Hz), 7.68 (1H, t, J=7.8 Hz), 7.87 (1H, d, J=7.8 Hz), 8.15 (1H, d, J=7.8 Hz), 11.1 (1H, brs). MS(EI): 256(M+).

Example 35

While heating a mixture of dimethylamine hydrochloride (2.45 g) and 37% aqueous formalin solution (2.43 g) to 50° C., acetic anhydride (9.4 mL) was added dropwise thereto slowly. After the completion of the dropwise addition, the mixture was heated at 60° C. for 30 min. 3-Isopropyl-2H-isoquinolin-1-one (1.87 g) was added, and the mixture was stirred with heating at 80-100° C. for 1 day. After the completion of the reaction, the solvent was evaporated. The obtained residue was dissolved in 1N hydrochloric acid, and the mixture was washed with chloroform. Aqueous potassium carbonate solution was added to alkalify the aqueous layer, and the mixture was extracted with chloroform, and the organic layer was dried over magnesium sulfate. The solvent was evaporated, and the obtained residue was purified by silica gel column chromatography (chloroform:methanol=30:1) to give 4-dimethylaminomethyl-3-isopropyl-2H-isoquinolin-1-one (0.39 g).

¹H-NMR (CDCl₃) δ: 1.32 (6H, d, J=7 Hz), 2.30 (6H, s), 3.46-3.58 (1H, m), 3.55 (2H, s), 7.44 (1H, t, J=8 Hz), 7.68 (2H, dt, J=1 Hz, 8 Hz), 7.92 (1H, d, J=8 Hz), 8.40 (1H, d, J=8 Hz), 9.03 (1H, brs). MS(EI): 244(M+).

Example 36

N-(3-Isopropyl-2H-1-oxoisoquinolin-4-yl)methyl-trimethylammonium iodide (1.1 g) obtained in Starting Material Synthetic Example 6 and potassium carbonate (1.17 g) were dissolved in acetonitrile (5 mL) and water (1 mL), and pyrrolidine (0.4 g) was added, and the mixture was heated under reflux. After the completion of the reaction, the reaction mixture was concentrated. Water was added and the mixture was extracted with chloroform. The organic layer was dried over magnesium sulfate and the solvent was evaporated, and the obtained residue was purified by HPLC to give 4-(pyrrolidin-1-yl)methyl-3-isopropyl-2H-isoquinolin-1-one (62 mg).

¹H-NMR (CDCl₃) δ: 1.31 (6H, d, J=7 Hz), 1.70-1.80 (4H, m), 2.52-2.60 (4H, m), 3.52-3.64 (1H, m), 3.75 (2H, s), 7.44 (1H, t, J=8 Hz), 7.67 (2H, dt, J=1 Hz, 8 Hz), 7.99 (1H, d, J=8 Hz), 8.40 (1H, d, J=8 Hz), 8.92 (1H, brs). MS(EI): 270(M+).

Example 37

3-Methyl-4-((4-phenylpiperidin-1-yl)methyl)-2H-isoquinolin-1-one (45.2 mg) was obtained by the reaction in the same manner as in Example 40 using (3-methyl-2H-1-oxoisoquinolin-4-yl)methylpyrrolidinium iodide (210 mg) obtained in Starting Material Synthetic Example 33 and 4-phenylpiperidine (107 mg).

¹H-NMR (CDCl₃) δ: 1.65-1.82 (4H, m), 2.13-2.20 (2H, m), 2.49 (3H, s), 2.49-2.55 (1H, m), 3.05-3.09 (2H, m), 3.61 (2H, s), 7.15-7.30 (5H, m), 7.45 (1H, t, J=8.1 Hz), 7.69 (1H, t, J=8.1 Hz), 8.00 (1H,d, J=8.1 Hz), 8.43 (1H, d, J=8.1 Hz), 10.8 (1H, brs). MS(EI): 332(M+).

Example 38

(S)-3-Methyl-1-((3-hydroxypyrrolidin-1-yl)methyl)-3H-pyrazolo[3,4-c]isoquinolin-5(4H)-one (54 mg) was obtained by the reaction in the same manner as in Example 7 using 1-bromomethyl-3-methyl-5-methoxymethoxy-3H-pyrazolo[3,4-c]isoquinoline (6.0 g) obtained in Starting Material Synthetic Example 1 and (S)-3-pyrrolidinol (3.11 g).

¹H-NMR (DMSO-d₆) δ: 1.45-1.56 (1H, m), 1.82-2.00 (1H, m), 2.30-2.40 (1H, m), 2.45-2.55 (1H, m), 2.60-2.72 (1H, m), 2.72-2.83 (1H, m), 2.78-2.85 (1H, m), 3.10-3.15 (1H, m), 3.51 (2H, s), 3.79 (3H, brs), 4.58 (1H, J=4 Hz), 7.39 (1H, t, J=7 Hz), 7.73 (1H, t, J=7 Hz), 8.13 (1H, d, J=8 Hz), 8.21 (1H, d, J=8 Hz). MS(EI): 298(M+).

Example 39

(R)-3-Methyl-1-((3-hydroxypyrrolidin-1-yl)methyl)-3H-pyrazolo[3,4-c]isoquinolin-5(4H)-one (7 mg) was obtained by the reaction in the same manner as in Example 7 using 1-bromomethyl-3-methyl-5-methoxymethoxy-3H-pyrazolo[3,4-c]isoquinoline (6.0 g) obtained in Starting Material Synthetic Example 1 and (R)-3-pyrrolidinol hydrochloride (4.41 g).

¹H-NMR (DMSO-d₆) δ: 1.45-1.56 (1H, m), 1.82-2.00 (1H, m), 2.30-2.40 (1H, m), 2.45-2.55 (1H, m), 2.60-2.72 (1H, m), 2.72-2.83 (1H, m), 2.78-2.85 (1H, m), 3.10-3.15 (1H, m), 3.51 (2H, s), 3.79 (3H, brs), 4.72 (1H, J=4 Hz), 7.39 (1H, t, J=7 Hz), 7.73 (1H, t, J=7 Hz), 8.13 (1H, d, J=8 Hz), 8.21 (1H, d, J=8 Hz). MS(EI): 298(M+).

Example 40

(3-Methyl-2H-1-oxoisoquinolin-4-yl)methylpyrrolidinium iodide (203 mg) obtained in Starting Material Synthetic Example 33 was suspended in methanol (4 mL), and 1-phenylpiperazine (0.087 mL) was added, and the mixture was heated under reflux for 3 hrs. After the completion of the reaction, the solvent was evaporated under reduced pressure. The obtained residue was purified by silica gel column chromatography, and the fraction eluted with chloroform:methanol was concentrated, and the precipitated crystals were collected by filtration to give 3-methyl-4-((4-phenylpiperazin-1-yl)methyl)-2H-isoquinolin-1-one (114 mg).

¹H-NMR (DMSO-d₆) δ: 2.32 (3H, s), 2.55-2.61 (4H, m), 3.00-3.15 (4H, m), 3.59 (2H, s), 6.73-6.78 (1H, m), 6.89 (2H, d, J=8.1 Hz), 7.19 (2H, t, J=8.1 Hz), 7.42 (1H, t, J=8.1 Hz), 7.72 (1H, t, J=8.1 Hz), 7.93 (1H, d, J=8.1 Hz), 8.17 (1H, d, J=8.1 Hz), 11.2 (1H, brs). MS(EI): 333(M+).

Example 41

3-Methyl-4-diethylaminomethyl-2H-isoquinolin-1-one (79.1 mg) was obtained by the reaction in the same manner as in Example 40 using (3-methyl-2H-1-oxoisoquinolin-4-yl)methylpyrrolidinium iodide (301 mg) obtained in Starting Material Synthetic Example 33 and diethylamine (0.808 mL).

¹H-NMR (DMSO-d₆) δ: 0.98 (6H, t, J=7.2 Hz), 2.29 (3H, s), 2.45-2.52 (4H, m), 3.57 (2H, s), 7.40 (1H, t, J=8.1 Hz), 7.67 (1H, t, J=8.1 Hz), 7.95 (1H, d, J=8.1 Hz), 8.15 (1H, d, J=8.1 Hz), 11.2 (1H, brs). MS(EI): 244(M+).

Example 42

3-Methyl-4-(morpholin-4-yl)methyl-2H-isoquinolin-1-one (112 mg) was obtained by the reaction in the same manner as in Example 40 using (3-methyl-2H-1-oxoisoquinolin-4-yl)methylpyrrolidinium iodide (303 mg) obtained in Starting Material Synthetic Example 33 and morpholine (0.082 mL).

¹H-NMR (DMSO-d₆) δ: 2.29 (3H, s), 2.43 (4H, brs), 3.49-3.53 (6H, m), 7.41 (1H, t, J=7.8 Hz), 7.68 (1H, t, J=7.8 Hz), 7.89 (1H, d, J=7.8 Hz), 8.15 (1H, d, J=7.8 Hz), 11.2 (1H, brs). MS(EI): 258(M+).

Example 43

N-(3-Isopropyl-2H-1-oxoisoquinolin-4-yl)methyl-trimethylammonium iodide (0.3 g) obtained in Starting Material Synthetic Example 6 was dissolved in methanol (5 mL), and 1-phenylpiperazine (0.2 g) was added, and the mixture was heated under reflux. After the completion of the reaction, the reaction mixture was concentrated. Water was added and the mixture was extracted with chloroform. The aqueous layer was dried over magnesium sulfate and the solvent was evaporated. The obtained residue was purified by thin layer chromatography (chloroform:methanol=20:1) to give 4-(4-phenylpiperazin-1-yl)methyl-3-isopropyl-2H-isoquinolin-1-one (82 mg).

$^1$H-NMR (CDCl$_3$) δ: 1.30 (6H, d, J=8 Hz), 2.64-2.70 (4H, m), 3.12-3.19 (4H, m), 3.47-3.59 (1H, m), 3.68 (2H, s), 6.84 (1H, t, J=7 Hz), 6.91 (2H, d, J=9 Hz), 7.23-7.28 (2H, m), 7.45 (1H, t, J=8 Hz), 7.68 (1H, dt, J=1 Hz, 8 Hz), 8.00 (1H, d, J=8 Hz), 8.40 (1H, d, J=8 Hz), 8.49 (1H, brs).

Example 44

7-Chloro-4-(piperidin-4-yl)-2H-isoquinolin-1-one hydrochloride (0.47 g) was obtained by the reaction in the same manner as in Example 31 using 4-(1-benzoylpiperidin-4-yl)-7-chloro-2H-isoquinolin-1-one (0.66 g) obtained in Starting Material Synthetic Example 4.

$^1$H-NMR (DMSO-d$_6$) δ: 1.72-2.02 (4H, m), 3.07-3.38 (5H, m), 6.92 (1H, d, J=6 Hz), 7.81 (1H, dd, J=2 Hz, 9 Hz), 7.97 (1H, d, J=9 Hz), 8.19 (1H, d, J=2 Hz), 8.88-9.10 (2H, m), 11.46 (1H, d, J=6 Hz). MS(EI): 262(M+).

Example 45

7-Fluoro-4-(piperidin-4-yl)-2H-isoquinolin-1-one hydrochloride (1.6 g) was obtained by the reaction in the same manner as in Example 31 using 4-(1-benzoylpiperidin-4-yl)-7-fluoro-2H-isoquinolin-1-one (1.9 g) obtained in Starting Material Synthetic Example 5.

$^1$H-NMR (DMSO-d$_6$) δ: 1.76-2.05 (4H, m), 3.02-3.39 (5H, m), 6.86 (1H, d, J=6 Hz), 7.64-7.71 (1H, m), 7.92 (1H, dd, J=3 Hz, 9 Hz), 8.02 (1H, dd, J=5 Hz, 9 Hz), 8.86-9.14 (2H, m), 11.41 (1H, d, J=5 Hz). MS(EI): 246(M+).

Example 46

7-Chloro-4-(1-methylpiperidin-4-yl)-2H-isoquinolin-1-one (0.22 g) as white crystals was obtained by the reaction in the same manner as in Example 33 using 7-chloro-4-(piperidin-4-yl)-2H-isoquinolin-1-one hydrochloride (0.3 g) obtained in Example 44.

$^1$H-NMR (CDCl$_3$) δ: 1.70-1.82 (2H, m), 1.90-2.00 (2H, m), 2.10-2.21 (2H, m), 2.36 (3H, s), 2.73-2.86 (1H, m), 3.02-3.10 (2H, m), 7.01 (1H, s), 7.64-7.71 (2H, m), 8.47 (1H, d, J=2 Hz), 11.11 (1H, brs). MS(EI): 276(M+).

Example 47

7-Fluoro-4-(1-methylpiperidin-4-yl)-2H-isoquinolin-1-one hydrochloride (0.37 g) as white crystals was obtained by the reaction in the same manner as in Example 33 using 7-fluoro-4-(piperidin-4-yl)-2H-isoquinolin-1-one hydrochloride (0.5 g) obtained in Example 45.

$^1$H-NMR (DMSO-d$_6$) δ: 1.80-2.07 (4H, m), 2.78 (3H, s), 3.07-3.54 (5H, m), 6.87 (1H, d, J=6 Hz), 7.65-7.72 (1H, m), 7.90-8.00 (2H, m), 10.36 (1H, brs), 11.41 (1H, d, J=6 Hz). MS(EI): 260(M+).

Example 48

7-Fluoro-4-(1-(2-hydroxyethyl)piperidin-4-yl)-2H-isoquinolin-1-one hydrochloride (0.41 g) as white crystals was obtained by the reaction in the same manner as in Example 32 using 7-fluoro-4-(piperidin-4-yl)-2H-isoquinolin-1-one hydrochloride (0.5 g) obtained in Example 45.

$^1$H-NMR (DMSO-d$_6$) δ: 1.80-2.04 (4H, m), 2.78 (3H, s), 3.11-3.50 (5H, m), 3.57-3.66 (2H, m), 3.80-3.88 (2H, m), 5.34-5.38 (1H, m), 6.86 (1H, d, J=6 Hz), 7.65-7.72 (1H, m), 7.90-8.02 (2H, m), 10.16 (1H, brs), 11.40 (1H, d, J=6 Hz). MS(EI): 290(M+).

Example 49

3-Ethyl-2H-isoquinolin-1-one (5.7 g) and N,N-dimethylmethyleneammonium iodide (12.1 g) were dissolved in dimethylformamide (100 mL), and the mixture was stirred with heating at 100° C. During stirring, N,N-dimethylmethyleneammonium iodide (4.0 g) was added, and the mixture was further stirred with heating for 2 hr.

After the completion of the reaction, the solvent was evaporated. The obtained residue was dissolved in 1N hydrochloric acid, and the mixture was washed with chloroform. Aqueous potassium carbonate solution was added to alkalify the aqueous layer, and the mixture was extracted with chloroform, and the organic layer was dried over magnesium sulfate. The solvent was evaporated, and the obtained residue was purified by silica gel column chromatography (chloroform:methanol=30:1) to give 4-dimethylaminomethyl-3-ethyl-2H-isoquinolin-1-one (3.3 g).

$^1$H-NMR (CDCl$_3$) δ: 1.33 (3H, t, J=8 Hz), 2.30 (6H, s), 2.81 (2H, q, J=8 Hz), 3.53 (2H, s), 7.44 (1H, t, J=8 Hz), 7.68 (2H, dt, J=1 Hz, 8 Hz), 7.93 (1H, d, J=8 Hz), 8.42 (1H, d, J=8 Hz), 10.57 (1H, brs). MS(EI): 230(M+).

Example 50

4-(Pyrrolidin-1-yl)methyl-3-ethyl-2H-isoquinolin-1-one (220 mg) was obtained by the reaction in the same manner as in Example 43 using N-(3-ethyl-2H-1-oxoisoquinolin-4-yl)methyl-trimethylammonium iodide (1.0 g) obtained in Starting Material Synthetic Example 7.

$^1$H-NMR (CDCl$_3$) δ: 1.32 (3H, t, J=8 Hz), 1.66-1.79 (4H, m), 2.52-2.62 (4H, m), 2.82 (2H, q, J=8 Hz), 3.73 (2H, s), 7.44 (1H, t, J=8 Hz), 7.67 (2H, dt, J=1 Hz, 8 Hz), 8.02 (1H, d, J=8 Hz), 8.42 (1H, dd, J=1 Hz, 8 Hz), 10.37 (1H, brs). MS(EI): 256(M+).

Example 51

7-Chloro-3-methyl-1-(pyrrolidin-1-yl)methyl-3H-pyrazolo[3,4-c]isoquinolin-5(4H)-one is obtained by the reaction in the same manner as in Example 7 using 1-bromomethyl-7-chloro-3-methyl-5-methoxymethoxy-3H-pyrazolo[3,4-c]isoquinoline obtained in Starting Material Synthetic Example 8 and pyrrolidine.

Example 52

7-Chloro-3-methyl-1-dimethylaminomethyl-3H-pyrazole[3,4-c]isoquinolin-5(4H)-one is obtained by the reaction in the same manner as in Example 7 using 1-bromomethyl-7-chloro-3-methyl-5-methoxymethoxy-3H-pyrazolo[3,4-c]isoquinoline obtained in Starting Material Synthetic Example 8 and 50% aqueous dimethylamine solution.

Example 53

A solution of 3-dimethyl-7-fluoro-5-methoxymethoxy-3H-pyrazolo[3,4-c]isoquinoline (0.62 g) obtained in Starting Material Synthetic Example 91, N-bromosuccinimide (0.48 g) and 2,2'-azobis(isobutyronitrile) (0.037 g) in carbon tetrachloride (25 mL) was heated under reflux for 3 hrs.

After the completion of the reaction, the reaction solution was allowed to cool to room temperature, and the precipitated solid was removed by filtration. The filtrate was concentrated, and the residue was filtrated using silica gel (hexane:ethyl acetate=2:1). The filtrate was concentrated to give 1-bromomethyl-7-fluoro-5-methoxymethoxy-3-methyl-3H-pyrazolo[3,4-c]isoquinoline (0.50 g) as crude crystals. The crude crystals (0.50 g) of 1-bromomethyl-7-fluoro-5-methoxymethoxy-3-methyl-3H-pyrazolo[3,4-c]isoquinoline, piperidine (0.30 g) and potassium carbonate (0.39 g) were dissolved in acetonitrile (20 mL), and the reaction solution was stirred at room temperature for 2 days. After the completion of the reaction, the reaction solution was poured into water and extracted with chloroform. The organic layer was dried over magnesium sulfate, and the solvent was evaporated. The residue was purified by silica gel chromatography (hexane:ethyl acetate=10:1) to give 7-fluoro-3-methyl-1-(pyrrolidin-1-ylmethyl)-3H-pyrazolo[3,4-c]isoquinolin-5(4H)-one (0.079 g).

$^1$H-NMR (CDCl$_3$) δ: 1.79 (4H, s), 2.63 (4H, s), 3.93 (2H, s), 4.13 (3H, s), 7.45-7.52 (1H, m), 8.06-8.10 (1H, m), 8.32-8.37 (1H, m).

7-fluoro-3-methyl-1-(pyrrolidin-1-ylmethyl)-3H-pyrazolo[3,4-c]isoquinolin-5(4H)-one hydrochloride $^1$H-NMR (DMSO-d$_6$) δ: 1.93 (2H, brs), 2.02 (2H, brs), 3.23 (2H, brs), 3.62 (2H, brs), 3.94 (3H, s), 4.82 (2H, s), 7.67-7.73 (1H, m), 7.92-7.96 (1H, m), 8.05-8.10 (1H, m), 10.66 (1H, s), 12.72 (1H, s).

Example 54

7-Fluoro-3-methyl-1-dimethylaminomethyl-3H-pyrazolo[3,4-c]isoquinolin-5(4H)-one is obtained by the reaction in the same manner as in Example 53 using 1-bromomethyl-7-fluoro-3-methyl-5-methoxymethoxy-3H-pyrazolo[3,4-c]isoquinoline obtained in Example 53 and 50% aqueous dimethylamine solution.

Example 55

7-Methoxy-3-methyl-1-(pyrrolidin-1-yl)methyl-3H-pyrazolo[3,4-c]isoquinolin-5(4H)-one is obtained by the reaction in the same manner as in Example 7 using 1-bromomethyl-7-methoxy-3-methyl-5-methoxymethoxy-3H-pyrazolo[3,4-c]isoquinoline obtained in Starting Material Synthetic Example 10 and pyrrolidine.

Example 56

7-Methoxy-3-methyl-1-dimethylaminomethyl-3H-pyrazolo[3,4-c]isoquinolin-5(4H)-one is obtained by the reaction in the same manner as in Example 7 using 1-bromomethyl-7-methoxy-3-methyl-5-methoxymethoxy-3H-pyrazolo[3,4-c]isoquinoline obtained in Starting Material Synthetic Example 10 and 50% aqueous dimethylamine solution.

Example 57

3-Methyl-1-(4-phenylpiperidin-1-yl)methyl-3H-pyrazolo[3,4-c]isoquinolin-5(4H)-one is obtained by the reaction in the same manner as in Example 7 using 1-bromomethyl-3-methyl-5-methoxymethoxy-3H-pyrazolo[3,4-c]isoquinoline obtained in Starting Material Synthetic Example 1 and 4-phenylpiperidine.

Example 58

3-Methyl-1-(4-phenylpiperazin-1-yl)methyl-3H-pyrazolo[3,4-c]isoquinolin-5(4H)-one hydrochloride (0.64 g) was obtained by the reaction in the same manner as in Example 7 using 1-bromomethyl-3-methyl-5-methoxymethoxy-3H-pyrazolo[3,4-c]isoquinoline (1.0 g) obtained in Starting Material Synthetic Example 1 and 1-phenylpiperazine (0.53 g).

$^1$H-NMR (DMSO-d$_6$) δ: 3.03-3.13 (2H, m), 3.25-3.36 (2H, m), 3.66-3.78 (2H, m), 3.80-3.90 (2H, m), 3.96 (3H, s), 4.86 (2H, s), 6.86 (1H, t, J=8 Hz), 6.99 (2H, d, J=8 Hz), 7.26 (2H, t, J=8 Hz), 7.51 (1H, t, J=8 Hz), 7.82 (1H, t, J=8 Hz), 8.16 (1H, d, J=8 Hz), 8.30 (1H, d, J=8 Hz), 10.72 (1H, brs), 12.60 (1H, brs). MS(EI): 373(M+).

Example 59

3-Methyl-1-(4-phenyl-1,2,3,6-tetrahydropyridin-1-yl)methyl-3H-pyrazolo[3,4-c]isoquinolin-5(4H)-one hydrochloride (0.49 g) was obtained by the reaction in the same manner as in Example 7 using 1-bromomethyl-3-methyl-5-methoxymethoxy-3H-pyrazolo[3,4-c]isoquinoline (1.0 g) obtained in Starting Material Synthetic Example 1 and 4-phenyl-1,2,3,6-tetrahydropyridine hydrochloride (0.65 g).

$^1$H-NMR (DMSO-d$_6$) δ: 2.77-2.87 (2H, m), 3.96-4.12 (4H, m), 3.96 (3H, s), 4.87 (2H, s), 6.21 (1H, s), 7.32-7.54 (6H, m), 7.81 (2H, t, J=8 Hz), 8.13 (1H, d, J=8 Hz), 8.30 (1H, d, J=8 Hz), 10.74 (1H, brs), 12.60 (1H, brs). MS(EI): 370(M+).

Example 60

(R)-3-Methyl-1-(2-hydroxymethylpyrrolidin-1-yl)methyl-3H-pyrazolo[3,4-c]isoquinolin-5(4H)-one hydrochloride (0.97 g) was obtained by the reaction in the same manner as in Example 7 using 1-bromomethyl-3-methyl-5-methoxymethoxy-3H-pyrazolo[3,4-c]isoquinoline (1.0 g) obtained in Starting Material Synthetic Example 1 and D-prolinol (0.33 g).

$^1$H-NMR (DMSO-d$_6$) δ: 1.61-2.10 (4H, m), 3.30-3.55 (2H, m), 3.76-3.90 (3H, m), 3.94 (3H, s), 4.67 (1H, dd, J=8 Hz, 14 Hz), 5.09 (1H, d, J=14 Hz), 7.50 (1H, t, J=8 Hz), 7.78 (2H, t, J=8 Hz), 8.11 (1H, d, J=8 Hz), 8.28 (1H, d, J=8 Hz), 10.03 (1H, brs), 12.56 (1H, brs). MS(EI): 312(M+).

Example 61

(S)-3-Methyl-1-(2-hydroxymethylpyrrolidin-1-yl)methyl-3H-pyrazolo[3,4-c]isoquinolin-5(4H)-one hydrochloride (0.88 g) was obtained by the reaction in the same manner as in Example 7 using 1-bromomethyl-3-methyl-5-methoxymethoxy-3H-pyrazolo[3,4-c]isoquinoline (1.0 g) obtained in Starting Material Synthetic Example 1 and L-prolinol (1.0 g).

$^1$H-NMR (DMSO-d$_6$) δ: 1.61-2.10 (4H, m), 3.30-3.55 (2H, m), 3.76-3.90 (3H, m), 3.94 (3H, s), 4.67 (1H, dd, J=8 Hz, 14 Hz), 5.09 (1H, d, J=14 Hz), 7.50 (1H, t, J=8 Hz), 7.78 (2H, t, J=8 Hz), 8.11 (1H, d, J=8 Hz), 8.28 (1H, d, J=8 Hz), 10.03 (1H, brs), 12.56 (1H, brs). MS(EI): 312(M+).

Example 62

1-(Pyrrolidin-1-yl)methylisoxazolo[5,4-c]isoquinolin-5(4H)-one is obtained by the reaction in the same manner as in Example 7 using 1-bromomethyl-5-methoxymethoxyisoxazolo[5,4-c]isoquinoline obtained in Starting Material Synthetic Example 11 and pyrrolidine.

Example 63

1-Dimethylaminomethylisoxazolo[5,4-c]isoquinolin-5(4H)-one is obtained by the reaction in the same manner as in Example 7 using 1-bromomethyl-5-methoxymethoxyisoxazolo[5,4-c]isoquinoline obtained in Starting Material Synthetic Example 11 and 50% aqueous dimethylamine solution.

Example 64

7-Chloro-1-dimethylaminomethylisoxazolo[5,4-c]isoquinolin-5(4H)-one is obtained by the reaction in the same manner as in Example 7 using 7-chloro-1-bromomethyl-5-methoxymethoxyisoxazolo[5,4-c]isoquinoline obtained in Starting Material Synthetic Example 12 and 50% aqueous dimethylamine solution.

Example 65

7-Chloro-1-(pyrrolidin-1-yl)methylisoxazolo[5,4-c]isoquinolin-5(4H)-one is obtained by the reaction in the same manner as in Example 7 using 7-chloro-1-bromomethyl-5-methoxymethoxyisoxazolo[5,4-c]isoquinoline obtained in Starting Material Synthetic Example 12 and pyrrolidine.

Example 66

7-Fluoro-1-dimethylaminomethylisoxazolo[5,4-c]isoquinolin-5(4H)-one is obtained by the reaction in the same manner as in Example 7 using 7-fluoro-1-bromomethyl-5-methoxymethoxyisoxazolo[5,4-c]isoquinoline obtained in Starting Material Synthetic Example 13 and 50% aqueous dimethylamine solution.

Example 67

7-Fluoro-1-(pyrrolidin-1-yl)methylisoxazolo[5,4-c]isoquinolin-5(4H)-one is obtained by the reaction in the same manner as in Example 7 using 7-fluoro-1-bromomethyl-5-methoxymethoxyisoxazolo[5,4-c]isoquinoline obtained in Starting Material Synthetic Example 13 and pyrrolidine.

Example 68

1-(Pyrrolidin-1-yl)methylisothiazolo[5,4-c]isoquinolin-5(4H)-one is obtained by the reaction in the same manner as in Example 7 using 1-bromomethyl-5-methoxymethoxyisothiazolo[5,4-c]isoquinoline obtained in Starting Material Synthetic Example 14 and pyrrolidine.

Example 69

1-Dimethylaminomethylisothiazolo[5,4-c]isoquinolin-5(4H)-one is obtained by the reaction in the same manner as in Example 7 using 1-bromomethyl-5-methoxymethoxyisothiazolo[5,4-c]isoquinoline obtained in Starting Material Synthetic Example 14 and 50% aqueous dimethylamine solution.

Example 70

7-Chloro-1-dimethylaminomethylisothiazolo[5,4-c]isoquinolin-5(4H)-one is obtained by the reaction in the same manner as in Example 7 using 7-chloro-1-bromomethyl-5-methoxymethoxyisothiazolo[5,4-c]isoquinoline obtained in Starting Material Synthetic Example 15 and 50% aqueous dimethylamine solution.

Example 71

7-Chloro-1-(pyrrolidin-1-yl)methylisothiazolo[5,4-c]isoquinolin-5(4H)-one is obtained by the reaction in the same manner as in Example 7 using 7-chloro-1-bromomethyl-5-methoxymethoxyisothiazolo[5,4-c]isoquinoline obtained in Starting Material Synthetic Example 15 and pyrrolidine.

Example 72

7-Fluoro-1-dimethylaminomethylisothiazolo[5,4-c]isoquinolin-5(4H)-one is obtained by the reaction in the same manner as in Example 7 using 7-fluoro-1-bromomethyl-5-methoxymethoxyisothiazolo[5,4-c]isoquinoline obtained in Starting Material Synthetic Example 16 and 50% aqueous dimethylamine solution.

Example 73

7-Fluoro-1-(pyrrolidin-1-yl)methylisothiazolo[5,4-c]isoquinolin-5(4H)-one is obtained by the reaction in the same manner as in Example 7 using 7-fluoro-1-bromomethyl-5-methoxymethoxyisothiazolo[5,4-c]isoquinoline obtained in Starting Material Synthetic Example 16 and pyrrolidine.

Example 74

4-(1-Ethylpiperidin-4-yl)-2H-isoquinolin-1-one is obtained by the reaction in the same manner as in Example 33 using 4-(piperidin-4-yl)-2H-isoquinolin-1-one hydrochloride obtained in Example 31 and acetaldehyde.

Example 91

4-(Pyrrolidin-3-yl)-2H-isoquinolin-1-one hydrochloride is obtained by the reaction in the same manner as in Example 31 using 4-(1-benzoylpyrrolidin-3-yl)-2H-isoquinolin-1-one obtained in Starting Material Synthetic Example 21.

Example 92

4-(1-Methylpyrrolidin-3-yl)-2H-isoquinolin-1-one is obtained by the reaction in the same manner as in Example 33 using 4-(pyrrolidin-3-yl)-2H-isoquinolin-1-one hydrochloride obtained in Example 91.

Example 93

4-(1-Ethylpyrrolidin-3-yl)-2H-isoquinolin-1-one is obtained by the reaction in the same manner as in Example 33 using 4-(pyrrolidin-3-yl)-2H-isoquinolin-1-one hydrochloride obtained in Example 91 and acetaldehyde.

Example 94

4-(1-(2-Hydroxyethyl)pyrrolidin-3-yl)-2H-isoquinolin-1-one is obtained by the reaction in the same manner as in Example 32 using 4-(pyrrolidin-3-yl)-2H-isoquinolin-1-one hydrochloride obtained in Example 91.

Example 95

4-(Pyrrolidin-3-yl)-7-chloro-2H-isoquinolin-1-one hydrochloride is obtained by the reaction in the same manner

Example 96

4-(1-Methylpyrrolidin-3-yl)-7-chloro-2H-isoquinolin-1-one is obtained by the reaction in the same manner as in Example 33 using 4-(pyrrolidin-3-yl)-7-chloro-2H-isoquinolin-1-one hydrochloride obtained in Example 95.

Example 97

4-(1-Ethylpyrrolidin-3-yl)-7-chloro-2H-isoquinolin-1-one is obtained by the reaction in the same manner as in Example 33 using 4-(pyrrolidin-3-yl)-7-chloro-2H-isoquinolin-1-one hydrochloride obtained in Example 95 and acetaldehyde.

Example 98

4-(1-(2-Hydroxyethyl)pyrrolidin-3-yl)-7-chloro-2H-isoquinolin-1-one is obtained by the reaction in the same manner as in Example 32 using 4-(pyrrolidin-3-yl)-7-chloro-2H-isoquinolin-1-one hydrochloride obtained in Example 95.

Example 99

4-(Pyrrolidin-3-yl)-7-fluoro-2H-isoquinolin-1-one hydrochloride is obtained by the reaction in the same manner as in Example 31 using 4-(1-benzoylpyrrolidin-3-yl)-7-fluoro-2H-isoquinolin-1-one obtained in Starting Material Synthetic Example 23.

Example 100

4-(1-Methylpyrrolidin-3-yl)-7-fluoro-2H-isoquinolin-1-one is obtained by the reaction in the same manner as in Example 33 using 4-(pyrrolidin-3-yl)-7-fluoro-2H-isoquinolin-1-one hydrochloride obtained in Example 99.

Example 101

4-(1-Ethylpyrrolidin-3-yl)-7-fluoro-2H-isoquinolin-1-one is obtained by the reaction in the same manner as in Example 33 using 4-(pyrrolidin-3-yl)-7-fluoro-2H-isoquinolin-1-one hydrochloride obtained in Example 99 and acetaldehyde.

Example 102

4-(1-(2-Hydroxyethyl)pyrrolidin-3-yl)-7-fluoro-2H-isoquinolin-1-one is obtained by the reaction in the same manner as in Example 32 using 4-(pyrrolidin-3-yl)-7-fluoro-2H-isoquinolin-1-one hydrochloride obtained in Example 99.

Example 122

3-Methyl-4-[(4-methylpiperazin-1-yl)methyl]-2H-isoquinolin-1-one hydroiodide (172 mg) was obtained by the reaction in the same manner as in Example 40 using (3-methyl-2H-1-oxoisoquinolin-4-yl)methylpyrrolidinium iodide (301 mg) obtained in Starting Material Synthetic Example 33 and 1-methylpiperazine (0.104 mL).

$^1$H-NMR (DMSO-d$_6$) δ: 2.30 (3H, s), 2.30-2.42 (2H, m), 2.77 (3H, s), 2.85-3.10 (4H, m), 3.25-3.45 (2H, m), 3.62 (2H, s), 7.42 (1H, t, J=8.1 Hz), 7.69 (1H, t, J=8.1 Hz), 7.86 (1H, d, J=8.1 Hz), 8.17 (1H, d, J=8.1 Hz), 9.24 (1H, brs), 11.3 (1H, brs). MS (EI): 271(M+).

Example 123

3-Methyl-4-[4-(2-Hydroxyethyl)piperazin-1-yl]methyl-2H-isoquinolin-1-one hydroiodide (142 mg) was obtained by the reaction in the same manner as in Example 40 using (3-methyl-2H-1-oxoisoquinolin-4-yl)methylpyrrolidinium iodide (302 mg) obtained in Starting Material Synthetic Example 33 and 1-piperazineethanol (124 mg).

$^1$H-NMR (DMSO-d$_6$) δ: 2.30 (3H, s), 2.42-2.51 (2H, m), 2.85-3.10 (4H, m), 3.10-3.20 (2H, m), 3.35-3.50 (2H, m), 3.62 (2H, s), 3.65-3.75 (2H, m), 5.30 (1H, brs), 7.43 (1H, t, J=7.5 Hz), 7.69 (1H, t, J=7.5 Hz), 7.87 (1H, d, J=7.5 Hz), 8.17 (1H, d, J=7.5 Hz), 9.24 (1H, brs), 11.3 (1H, brs). MS(EI): 301(M+).

Example 124

3-Methyl-4-(4-benzylpiperidin-1-yl)methyl-2H-isoquinolin-1-one (141 mg) was obtained by the reaction in the same manner as in Example 40 using (3-methyl-2H-1-oxoisoquinolin-4-yl)methylpyrrolidinium iodide (302 mg) obtained in Starting Material Synthetic Example 33 and 4-benzylpiperidine (0.166 mL).

$^1$H-NMR (DMSO-d$_6$) δ: 1.06-1.15 (2H, m), 1.49-1.52 (3H, m), 1.90-1.97 (2H, m), 2.26 (3H, s), 2.45-2.47 (2H, m), 2.83-2.86 (2H, m), 3.46 (2H, s), 7.12-7.18 (3H, m), 7.23-7.28 (2H, m), 7.40 (1H, t, J=8.1 Hz), 7.62 (1H, t, J=8.1 Hz), 7.85 (1H, d, J=8.1 Hz), 8.15 (1H, d, J=8.1 Hz), 11.2 (1H, brs). MS(EI): 346(M+).

Example 125

3-Methyl-4-(1,2,3,4-tetrahydroisoquinolin-2-yl)methyl-2H-isoquinolin-1-one (94.9 mg) was obtained by the reaction in the same manner as in Example 40 using (3-methyl-2H-1-oxoisoquinolin-4-yl)methylpyrrolidinium iodide (303 mg) obtained in Starting Material Synthetic Example 33 and 1,2,3,4-tetrahydroisoquinoline (0.12 mL).

$^1$H-NMR (DMSO-d$_6$) δ: 2.34 (3H, s), 2.74 (4H, s), 3.64 (2H, s), 3.70 (2H, s), 7.02-7.08 (4H, m), 7.40 (1H, t, J=7.8 Hz), 7.65 (1H, t, J=7.8 Hz), 7.93 (1H, d, J=7.8 Hz), 8.16 (1H, d, J=7.8 Hz), 11.2 (1H, brs). MS (EI): 304(M+).

Example 126

3-Methyl-4-(indolin-1-yl)methyl-2H-isoquinolin-1-one (143 mg) was obtained by the reaction in the same manner as in Example 40 using (3-methyl-2H-1-oxoisoquinolin-4-yl) methylpyrrolidinium iodide (303 mg) obtained in Starting Material Synthetic Example 33 and indoline (0.106 mL).

$^1$H-NMR (DMSO-d$_6$) δ: 2.35 (3H, s), 2.75 (2H, t, J=8.4 Hz), 3.09 (2H, t, J=8.4 Hz), 4.29 (2H, s), 6.63 (1H, t, J=7.8 Hz), 6.88 (1H, d, J=7.8 Hz), 7.04-7.06 (2H, m), 7.43 (1H, t, J=8.1 Hz), 7.69 (1H, t, J=8.1 Hz), 7.75 (1H, d, J=8.1 Hz), 8.20 (1H, d, J=8.1 Hz), 11.3 (1H, brs). MS(EI): 290(M+).

Example 127

3-Methyl-4-(diisopropylamino)methyl-2H-isoquinolin-1-one (84.6 mg) was obtained by the reaction in the same manner as in Example 40 using (3-methyl-2H-1-oxoisoquinolin-4-yl)methylpyrrolidinium iodide (304 mg) obtained in Starting Material Synthetic Example 33 and diisopropylamine (0.549 mL).

$^1$H-NMR (DMSO-d$_6$) δ: 1.03 (12H, d, J=6.6 Hz), 2.31 (3H, s), 2.92-2.98 (2H, m), 3.71 (2H, s), 7.39 (1H, t, J=7.8 Hz), 7.65 (1H, t, J=7.8 Hz), 8.11-8.18 (2H, m), 11.2 (1H, brs). MS(EI): 272(M+).

Example 128

3-Methyl-4-((S)-3-hydroxypyrrolidin-1-yl)methyl-2H-isoquinolin-1-one (71.8 mg) was obtained by the reaction in the same manner as in Example 40 using N-(3-methyl-2H-1-oxoisoquinolin-4-yl)methyl-trimethylammonium iodide (504 mg) obtained in Starting Material Synthetic Example 49 and (S)-3-pyrrolidinol (147 mg).

$^1$H-NMR (DMSO-d$_6$) δ: 1.45-1.55 (1H, m), 1.90-2.00 (1H, m), 2.31-2.36 (4H, m), 2.45-2.65 (2H, m), 2.75-2.80 (1H, m), 3.55-3.70 (2H, m), 4.10-4.20 (1H, m), 4.65 (1H, d, J=4.2 Hz), 7.41 (1H, t, J=6.9 Hz), 7.68 (1H, t, J=6.9 Hz), 7.88 (1H, d, J=8.1Hz), 8.16 (1H, d, J=8.1 Hz), 11.2 (1H, brs). MS(ESI): 259(M+1).

Example 129

(R)-3-Pyrrolidine hydrochloride (210 mg) and potassium carbonate (258 mg) were suspended in methanol (4 mL), and the mixture was stirred at room temperature for 30 min. After the insoluble material was removed by filtration, N-(3-methyl-2H-1-oxoisoquinolin-4-yl)methyl-trimethylammonium iodide (502 mg) obtained in Starting Material Synthetic Example 49 was added, and by the reaction in the same manner as in Example 40, 3-methyl-4-((R)-3-hydroxypyrrolidin-1-yl)methyl-2H-isoquinolin-1-one (85.4 mg) was obtained.

$^1$H-NMR (DMSO-d$_6$) δ: 1.45-1.55 (1H, m), 1.90-2.00 (1H, m), 2.29-2.36 (4H, m), 2.45-2.65 (2H, m), 2.74-2.80 (1H, m), 3.55-3.70 (2H, m), 4.10-4.20 (1H, m), 4.66 (1H, d, J=4.2 Hz), 7.41 (1H, t, J=7.2 Hz), 7.68 (1H, t, J=7.2 Hz), 7.88 (1H, d, J=8.4 Hz), 8.16 (1H, d, J=8.4 Hz), 11.2 (1H, brs). MS(ESI): 259(M+1).

Example 130

3-Methyl-4-((R)-2-hydroxymethylpyrrolidin-1-yl)methyl-2H-isoquinolin-1-one (48.7 mg) was obtained by the reaction in the same manner as in Example 40 using N-(3-methyl-2H-1-oxoisoquinolin-4-yl)methyl-trimethylammonium iodide (251 mg) obtained in Starting Material Synthetic Example 49 and (D)-prolinol (82.7 μL).

$^1$H-NMR (DMSO-d$_6$) δ: 1.50-1.57 (3H, m), 1.80-1.95 (1H, m), 2.26-2.32 (4H, m), 2.54-2.59 (1H, m), 2.69-2.71 (1H, m), 3.30-3.35 (1H, m), 3.46-3.53 (2H, m), 4.10 (1H, d, J=13 Hz), 4.53-4.56 (1H, m), 7.40 (1H, t, J=7.5 Hz), 7.66 (1H, t, J=7.5 Hz), 8.04 (1H, d, J=8.4 Hz), 8.15 (1H, m, J=8.4 Hz), 11.1 (1H, brs). MS(ESI): 273(M+1).

Example 131

3-Methyl-4-((S)-2-hydroxymethylpyrrolidin-1-yl)methyl-2H-isoquinolin-1-one (83.8 mg) was obtained by the reaction in the same manner as in Example 40 using N-(3-methyl-2H-1-oxoisoquinolin-4-yl)methyl-trimethylammonium iodide (250 mg) obtained in Starting Material Synthetic Example 49 and (L)-prolinol (82.7 μL).

$^1$H-NMR (DMSO-d$_6$) δ: 1.49-1.57 (3H, m), 1.80-1.95 (1H, m), 2.24-2.32 (4H, m), 2.54-2.59 (1H,m), 2.69-2.71 (1H, m), 3.30-3.35 (1H, m), 3.46-3.53 (2H, m), 4.10 (1H, d, J=13 Hz), 4.53-4.56 (1H, m), 7.40 (1H, t, J=7.5 Hz), 7.68 (1H, t, J=7.5 Hz), 8.04 (1H, d, J=8.1 Hz), 8.15 (8.1 Hz), 11.2 (1H, brs). MS(ESI): 273(M+1).

Example 132

3-Methyl-4-(4-hydroxypiperidin-1-yl)methyl-2H-isoquinolin-1-one is obtained by the reaction in the same manner as in Example 40 using (3-methyl-2H-1-oxoisoquinolin-4-yl)methylpyrrolidinium iodide obtained in Starting Material Synthetic Example 33 and 4-hydroxypiperidine.

Example 133

3-Methyl-4-(4-phenyl-1,2,3,6-tetrahydropyridin-1-yl)methyl-2H-isoquinolin-1-one is obtained by the reaction in the same manner as in Example 40 using (3-methyl-2H-1-oxoisoquinolin-4-yl)methylpyrrolidinium iodide obtained in Starting Material Synthetic Example 33 and 4-phenyl-1,2,3,6-tetrahydropyridine.

Example 134

7-Chloro-4-dimethylaminomethyl-3-methyl-2H-isoquinolin-1-one (1.59 g) was obtained by the reaction in the same manner as in Example 49 using 7-chloro-3-methyl-2H-isoquinolin-1-one (3.92 g) obtained in Starting Material Synthetic Example 29.

$^1$H-NMR (DMSO-d$_6$) δ: 2.16 (6H, s), 2.29 (3H, s), 3.42 (2H, s), 7.70 (1H, dd, J=9.0 Hz, 2.1 Hz), 7.89 (1H, d, J=9.0 Hz), 8.08 (1H, d, J=2.1 Hz), 11.4 (1H, brs).

Example 135

7-Chloro-4-diethylaminomethyl-3-methyl-2H-isoquinolin-1-one is obtained by the reaction in the same manner as in Example 43 using N-(7-chloro-3-methyl-2H-1-oxoisoquinolin-4-yl)methyl-trimethylammonium iodide obtained in Starting Material Synthetic Example 29 and diethylamine.

Example 136

7-Chloro-4-(4-phenylpiperidin-1-yl)methyl-3-methyl-2H-isoquinolin-1-one is obtained by the reaction in the same manner as in Example 43 using N-(7-chloro-3-methyl-2H-1-oxoisoquinolin-4-yl)methyl-trimethylammonium iodide obtained in Starting Material Synthetic Example 29 and 4-phenylpiperidine.

Example 137

7-Chloro-4-(4-phenylpiperazin-1-yl)methyl-3-methyl-2H-isoquinolin-1-one is obtained by the reaction in the same manner as in Example 43 using N-(7-chloro-3-methyl-2H-1-oxoisoquinolin-4-yl)methyl-trimethylammonium iodide obtained in Starting Material Synthetic Example 29 and 1-phenylpiperazine.

Example 138

7-Chloro-4-(morpholin-4-yl)methyl-3-methyl-2H-isoquinolin-1-one is obtained by the reaction in the same manner as in Example 43 using N-(7-chloro-3-methyl-2H-1-oxoisoquinolin-4-yl)methyl-trimethylammonium iodide obtained in Starting Material Synthetic Example 29 and morpholine.

Example 139

7-Chloro-4-(4-methylpiperazin-1-yl)methyl-3-methyl-2H-isoquinolin-1-one is obtained by the reaction in the same manner as in Example 43 using N-(7-chloro-3-methyl-2H-1-oxoisoquinolin-4-yl)methyl-trimethylammonium iodide obtained in Starting Material Synthetic Example 29 and 1-methylpiperazine.

Example 140

7-Chloro-4-(4-(2-hydroxyethyl)piperazin-1-yl)methyl-3-methyl-2H-isoquinolin-1-one is obtained by the reaction in the same manner as in Example 43 using N-(7-chloro-3-methyl-2H-1-oxoisoquinolin-4-yl)methyl-trimethylammonium iodide obtained in Starting Material Synthetic Example 29 and 1-(2-hydroxyethyl)piperazine.

Example 141

7-Chloro-4-(4-benzylpiperidin-1-yl)methyl-3-methyl-2H-isoquinolin-1-one is obtained by the reaction in the same manner as in Example 43 using N-(7-chloro-3-methyl-2H-1-oxoisoquinolin-4-yl)methyl-trimethylammonium iodide obtained in Starting Material Synthetic Example 29 and 4-benzylpiperidine.

Example 142

7-Chloro-4-(1,2,3,4-tetrahydroisoquinolin-2-yl)methyl-3-methyl-2H-isoquinolin-1-one is obtained by the reaction in the same manner as in Example 43 using N-(7-chloro-3-methyl-2H-1-oxoisoquinolin-4-yl)methyl-trimethylammonium iodide obtained in Starting Material Synthetic Example 29 and 1,2,3,4-tetrahydroisoquinoline.

Example 143

7-Chloro-4-(indolin-1-yl)methyl-3-methyl-2H-isoquinolin-1-one is obtained by the reaction in the same manner as in Example 43 using N-(7-chloro-3-methyl-2H-1-oxoisoquinolin-4-yl)methyl-trimethylammonium iodide obtained in Starting Material Synthetic Example 29 and indoline.

Example 144

7-Chloro-4-diisopropylaminomethyl-3-methyl-2H-isoquinolin-1-one is obtained by the reaction in the same manner as in Example 43 using N-(7-chloro-3-methyl-2H-1-oxoisoquinolin-4-yl)methyl-trimethylammonium iodide obtained in Starting Material Synthetic Example 29 and diisopropylamine.

Example 145

(S)-7-Chloro-4-(3-hydroxypyrrolidin-1-yl)methyl-3-methyl-2H-isoquinolin-1-one (67.9 mg) was obtained by the reaction in the same manner as in Example 43 using N-(7-chloro-3-methyl-2H-1-oxoisoquinolin-4-yl)methyl-trimethylammonium iodide (204 mg) obtained in Starting Material Synthetic Example 29 and (S)-3-hydroxypyrrolidine (90.6 mg).
$^1$H-NMR (DMSO-d$_6$) δ: 1.45-1.60 (1H, m), 1.85-2.05 (1H, m), 2.30-2.34 (4H, m), 2.46-2.61 (2H, m), 2.73-2.79 (1H, m), 3.60-3.67 (2H, m), 4.10-4.20 (1H, m), 4.65 (1H, d, J=4.2 Hz), 7.71 (1H, dd, J=9.0 Hz, 2.4 Hz), 7.92 (1H, d, J=9.0 Hz), 8.08 (1H, d, J=2.4 Hz), 11.4 (1H, brs). MS(ESI): 293(M+1).

Example 146

(R)-7-Chloro-4-(3-hydroxypyrrolidin-1-yl)methyl-3-methyl-2H-isoquinolin-1-one (79.8 mg) was obtained by the reaction in the same manner as in Example 129 using N-(7-chloro-3-methyl-2H-1-oxoisoquinolin-4-yl)methyl-trimethylammonium iodide (204 mg) obtained in Starting Material Synthetic Example 29 and (R)-3-hydroxypyrrolidine (132 mg).
$^1$H-NMR (DMSO-d$_6$) δ: 1.40-1.60 (1H, m), 1.85-2.00 (1H, m), 2.29-2.34 (4H, m), 2.46-2.60 (2H, m), 2.73-2.78 (1H, m), 3.60-3.67 (2H, m), 4.13-4.15 (1H, m), 4.65 (1H, d, J=4.2 Hz), 7.71 (1H, dd, J=9.0 Hz, 2.7 Hz), 7.92 (1H, d, J=9.0 Hz), 8.08 (1H, d, J=2.7 Hz), 11.4 (1H, brs). MS(ESI): 293(M+1).

Example 147

(R)-7-Chloro-4-(2-hydroxymethylpyrrolidin-1-yl)methyl-3-methyl-2H-isoquinolin-1-one (59.3 mg) was obtained by the reaction in the same manner as in Example 43 using N-(7-chloro-3-methyl-2H-1-oxoisoquinolin-4-yl)methyl-trimethylammonium iodide (204 mg) obtained in Starting Material Synthetic Example 29 and D-prolinol (101 μL).
$^1$H-NMR (DMSO-d$_6$) δ: 1.50-1.60 (3H, m), 1.75-1.90 (1H, m), 2.16-2.32 (4H, m), 2.55-2.80 (2H, m), 3.40-3.50 (3H, m), 4.08 (1H, d, J=13 Hz), 4.57 (1H, brs), 7.66-7.72 (1H, m), 8.02-8.15 (2H, m), 11.3 (1H, brs). MS(ESI): 307(M+1).

Example 148

(S)-7-Chloro-4-(2-hydroxymethylpyrrolidin-1-yl)methyl-3-methyl-2H-isoquinolin-1-one (51.5 mg) was obtained by the reaction in the same manner as in Example 43 using N-(7-chloro-3-methyl-2H-1-oxois.oquinolin-4-yl)methyl-trimethylammonium iodide (204 mg) obtained in Starting Material Synthetic Example 29 and L-prolinol (101 μL).
$^1$H-NMR (DMSO-d$_6$) δ: 1.50-1.60 (3H, m), 1.75-1.90 (1H, m), 2.16-2.32 (4H, m), 2.55-2.80 (2H, m), 3.40-3.50 (3H, m), 4.08 (1H, d, J=14 Hz), 4.56-4.59 (1H, m), 7.66-7.70 (1H, m), 8.08-8.15 (2H, m), 11.3 (1H, brs). MS(ESI): 307(M+1).

Example 149

7-Chloro-4-(4-hydroxypiperidin-1-yl)methyl-3-methyl-2H-isoquinolin-1-one is obtained by the reaction in the same manner as in Example 43 using N-(7-chloro-3-methyl-2H-1-oxoisoquinolin-4-yl)methyl-trimethylammonium iodide obtained in Starting Material Synthetic Example 29 and 4-hydroxypiperidine.

Example 150

7-Chloro-4-(4-phenyl-1,2,3,6-tetrahydropyridin-1-yl)methyl-3-methyl-2H-isoquinolin-1-one is obtained by the reaction in the same manner as in Example 43 using N-(7-chloro-3-methyl-2H-1-oxoisoquinolin-4-yl)methyl-trimethylammonium iodide obtained in Starting Material Synthetic Example 29 and 4-phenyl-1,2,3,6-tetrahydropyridine.

Example 151

7-Fluoro-4-dimethylaminomethyl-3-methyl-2H-isoquinolin-1-one (616 mg) was is obtained by the reaction in the same manner as in Example 49 using 7-fluoro-3-methyl-2H-isoquinolin-1-one (3.20 g).
$^1$H-NMR (DMSO-d$_6$) δ: 2.17 (6H, s), 2.28 (3H, s), 3.43 (2H, s), 7.54-7.60 (1H, m), 7.78-7.83 (1H, m), 7.91-7.95 (1H, m), 11.3 (1H, brs).

Example 152

7-Fluoro-4-diethylaminomethyl-3-methyl-2H-isoquinolin-1-one is obtained by the reaction in the same manner as in Example 43 using N-(7-fluoro-3-methyl-2H-1-oxoisoquinolin-4-yl)methyl-trimethylammonium iodide obtained in Starting Material Synthetic Example 30 and diethylamine.

Example 153

7-Fluoro-4-(4-phenylpiperidin-1-yl)methyl-3-methyl-2H-isoquinolin-1-one is obtained by the reaction in the same manner as in Example 43 using N-(7-fluoro-3-methyl-2H-1-oxoisoquinolin-4-yl)methyl-trimethylammonium iodide obtained in Starting Material Synthetic Example 30 and 4-phenylpiperidine.

Example 154

7-Fluoro-4-(4-phenylpiperazin-1-yl)methyl-3-methyl-2H-isoquinolin-1-one is obtained by the reaction in the same manner as in Example 43 using N-(7-fluoro-3-methyl-2H-1-oxoisoquinolin-4-yl)methyl-trimethylammonium iodide obtained in Starting Material Synthetic Example 30 and 1-phenylpiperazine.

Example 155

7-Fluoro-4-(morpholin-4-yl)methyl-3-methyl-2H-isoquinolin-1-one is obtained by the reaction in the same manner as in Example 43 using N-(7-fluoro-3-methyl-2H-1-oxoisoquinolin-4-yl)methyl-trimethylammonium iodide obtained in Starting Material Synthetic Example 30 and morpholine.

Example 156

7-Fluoro-4-(4-methylpiperazin-1-yl)methyl-3-methyl-2H-isoquinolin-1-one is obtained by the reaction in the same manner as in Example 43 using N-(7-fluoro-3-methyl-2H-1-oxoisoquinolin-4-yl)methyl-trimethylammonium iodide obtained in Starting Material Synthetic Example 30 and 1-methylpiperazine.

Example 157

7-Fluoro-4-(4-(2-hydroxyethyl)piperazin-1-yl)methyl-3-methyl-2H-isoquinolin-1-one is obtained by the reaction in the same manner as in Example 43 using N-(7-fluoro-3-methyl-2H-1-oxoisoquinolin-4-yl)methyl-trimethylammonium iodide obtained in Starting Material Synthetic Example 30 and 1-(2-hydroxyethyl)piperazine.

Example 158

7-Fluoro-4-(4-benzylpiperidin-1-yl)methyl-3-methyl-2H-isoquinolin-1-one is obtained by the reaction in the same manner as in Example 43 using N-(7-fluoro-3-methyl-2H-1-oxoisoquinolin-4-yl)methyl-trimethylammonium iodide obtained in Starting Material Synthetic Example 30 and 4-benzylpiperidine.

Example 159

7-Fluoro-4-(1,2,3,4-tetrahydroisoquinolin-2-yl)methyl-3-methyl-2H-isoquinolin-1-one is obtained by the reaction in the same manner as in Example 43 using N-(7-fluoro-3-methyl-2H-1-oxoisoquinolin-4-yl)methyl-trimethylammonium iodide obtained in Starting Material Synthetic Example 30 and 1,2,3,4-tetrahydroisoquinoline.

Example 160

7-Fluoro-4-(indolin-1-yl)methyl-3-methyl-2H-isoquinolin-1-one is obtained by the reaction in the same manner as in Example 43 using N-(7-fluoro-3-methyl-2H-1-oxoisoquinolin-4-yl)methyl-trimethylammonium iodide obtained in Starting Material Synthetic Example 30 and indoline.

Example 161

7-Fluoro-4-diisopropylaminomethyl-3-methyl-2H-isoquinolin-1-one is obtained by the reaction in the same manner as in Example 43 using N-(7-fluoro-3-methyl-2H-1-oxoisoquinolin-4-yl)methyl-trimethylammonium iodide obtained in Starting Material Synthetic Example 30 and diisopropylamine.

Example 162

(S)-7-Fluoro-4-(3-hydroxypyrrolidin-1-yl)methyl-3-methyl-2H-isoquinolin-1-one (21.4 mg) was obtained by the reaction in the same manner as in Example 43 using N-(7-fluoro-3-methyl-2H-1-oxoisoquinolin-4-yl)methyl-trimethylammonium iodide (204 mg) obtained in Starting Material Synthetic Example 30 and (S)-3-hydroxypyrrolidine (92.9 mg).
$^1$H-NMR (DMSO-$d_6$) δ: 1.40-1.60 (1H, m), 1.85-2.00 (1H, m), 2.30-2.40 (4H, m), 2.46-2.61 (2H, m), 2.74-2.79 (1H, m), 3.58-3.67 (2H, m), 4.16 (1H, brs), 4.65 (1H, d, J=3.9 Hz), 7.55-7.61 (1H, m), 7.78-7.81 (1H, m), 7.94-7.99 (1H, m), 11.3 (1H, brs). MS(ESI): 277(M+1).

Example 163

(R)-7-Fluoro-4-(3-hydroxypyrrolidin-1-yl)methyl-3-methyl-2H-isoquinolin-1-one (26.4 mg) was obtained by the reaction in the same manner as in Example 129 using N-(7-fluoro-3-methyl-2H-1-oxoisoquinolin-4-yl)methyl-trimethylammonium iodide (203 mg) obtained in Starting Material Synthetic Example 30 and (R)-3-hydroxypyrrolidine hydrochloride (138 mg).
$^1$H-NMR (DMSO-$d_6$) δ: 1.40-1.60 (1H, m), 1.85-2.00 (1H, m), 2.30-2.40 (4H, m), 2.46-2.61 (2H, m), 2.74-2.79 (1H, m), 3.58-3.67 (2H, m), 4.16 (1H, brs), 4.65 (1H, d, J=3.6 Hz), 7.55-7.70 (1H, m), 7.78-7.81 (1H, m), 7.94-7.99 (1H, m), 11.3 (1H, brs). MS(ESI): 277(M+1).

Example 164

(R)-7-Fluoro-4-(2-hydroxymethylpyrrolidin-1-yl)methyl-3-methyl-2H-isoquinolin-1-one (33.4 mg) was obtained by the reaction in the same manner as in Example 43 using N-(7-fluoro-3-methyl-2H-1-oxoisoquinolin-4-yl)methyl-trimethylammonium iodide (201 mg) obtained in Starting Material Synthetic Example 30 and D-prolinol (105 μL).
$^1$H-NMR (DMSO-$d_6$) δ: 1.50-1.60 (3H, m), 1.75-1.90 (1H, m), 2.17-2.31 (4H, m), 2.55-2.75 (2H, m), 3.35-3.60 (3H, m), 4.10 (1H, d, J=13 Hz), 4.58 (1H, brs), 7.52-7.61 (1H, m), 7.77-7.81 (1H, m), 8.12-8.17 (1H, m), 11.3 (1H, brs). MS(ESI): 291(M+1).

Example 165

(S)-7-Fluoro-4-(2-hydroxymethylpyrrolidin-1-yl)methyl-3-methyl-2H-isoquinolin-1-one (25.0 mg) was obtained by the reaction in the same manner as in Example 43 using N-(7-fluoro-3-methyl-2H-1-oxoisoquinolin-4-yl)methyl-trimethylammonium iodide (201 mg) obtained in Starting Material Synthetic Example 30 and L-prolinol (105 μL).
$^1$H-NMR (DMSO-$d_6$) δ: 1.50-1.60 (3H, m), 1.75-1.90 (1H, m), 2.17-2.31 (4H, m), 2.55-2.73 (2H, m), 3.40-3.60 (3H, m), 4.10 (1H, d, J=13 Hz), 4.58 (1H, brs), 7.52-7.58 (1H, m), 7.77-7.81 (1H, m), 8.12-8.17 (1H, m), 11.3 (1H, brs). MS(ESI): 291(M+1).

Example 166

7-Fluoro-4-(4-hydroxypiperidin-1-yl)methyl-3-methyl-2H-isoquinolin-1-one is obtained by the reaction in the same manner as in Example 43 using N-(7-fluoro-3-methyl-2H-1-oxoisoquinolin-4-yl)methyl-trimethylammonium iodide obtained in Starting Material Synthetic Example 30 and 4-hydroxypiperidine.

Example 167

7-Fluoro-4-(4-phenyl-1,2,3,6-tetrahydropyridin-1-yl)methyl-3-methyl-2H-isoquinolin-1-one is obtained by the reaction in the same manner as in Example 43 using N-(7-fluoro-3-methyl-2H-1-oxoisoquinolin-4-yl)methyl-trimethylammonium iodide obtained in Starting Material Synthetic Example 30 and 4-phenyl-1,2,3,6-tetrahydropyridine.

Example 168

(S)-4-(3-Hydroxypyrrolidin-1-yl)methyl-3-ethyl-2H-isoquinolin-1-one is obtained by the reaction in the same manner as in Example 43 using N-(3-ethyl-2H-1-oxoisoquinolin-4-yl)methyl-trimethylammonium iodide obtained in Starting Material Synthetic Example 7 and (S)-3-hydroxypyrrolidine.

Example 169

(R)-4-(3-Hydroxypyrrolidin-1-yl)methyl-3-ethyl-2H-isoquinolin-1-one is obtained by the reaction in the same manner as in Example 43 using N-(3-ethyl-2H-1-oxoisoquinolin-4-yl)methyl-trimethylammonium iodide obtained in Starting Material Synthetic Example 7 and (R)-3-hydroxypyrrolidine.

Example 170

(R)-4-(2-Hydroxymethylpyrrolidin-1-yl)methyl-3-ethyl-2H-isoquinolin-1-one is obtained by the reaction in the same manner as in Example 43 using N-(3-ethyl-2H-1-oxoisoquinolin-4-yl)methyl-trimethylammonium iodide obtained in Starting Material Synthetic Example 7 and D-prolinol.

Example 171

(S)-4-(2-Hydroxymethylpyrrolidin-1-yl)methyl-3-ethyl-2H-isoquinolin-1-one is obtained by the reaction in the same manner as in Example 43 using N-(3-ethyl-2H-1-oxoisoquinolin-4-yl)methyl-trimethylammonium iodide obtained in Starting Material Synthetic Example 7 and L-prolinol.

Example 172

4-(4-Hydroxypiperidin-1-yl)methyl-3-ethyl-2H-isoquinolin-1-one is obtained by the reaction in the same manner as in Example 43 using N-(3-ethyl-2H-1-oxoisoquinolin-4-yl)methyl-trimethylammonium iodide obtained in Starting Material Synthetic Example 7 and 4-hydroxypiperidine.

Example 173

(S)-4-(3-Hydroxypyrrolidin-1-yl)methyl-3-isopropyl-2H-isoquinolin-1-one is obtained by the reaction in the same manner as in Example 43 using N-(3-isopropyl-2H-1-oxoisoquinolin-4-yl)methyl-trimethylammonium iodide obtained in Starting Material Synthetic Example 6 and (S)-3-hydroxypyrrolidine.

Example 174

(R)-4-(3-Hydroxypyrrolidin-1-yl)methyl-3-isopropyl-2H-isoquinolin-1-one is obtained by the reaction in the same manner as in Example 43 using N-(3-isopropyl-2H-1-oxoisoquinolin-4-yl)methyl-trimethylammonium iodide obtained in Starting Material Synthetic Example 6 and (R)-3-hydroxypyrrolidine.

Example 175

(R)-4-(2-Hydroxymethylpyrrolidin-1-yl)methyl-3-isopropyl-2H-isoquinolin-1-one is obtained by the reaction in the same manner as in Example 43 using N-(3-isopropyl-2H-1-oxoisoquinolin-4-yl)methyl-trimethylammonium iodide obtained in Starting Material Synthetic Example 6 and D-prolinol.

Example 176

(S)-4-(2-Hydroxymethylpyrrolidin-1-yl)methyl-3-isopropyl-2H-isoquinolin-1-one is obtained by the reaction in the same manner as in Example 43 using N-(3-isopropyl-2H-1-oxoisoquinolin-4-yl)methyl-trimethylammonium iodide obtained in Starting Material Synthetic Example 6 and L-prolinol.

Example 177

4-(4-Hydroxypiperidin-1-yl)methyl-3-isopropyl-2H-isoquinolin-1-one is obtained by the reaction in the same manner as in Example 43 using N-(3-isopropyl-2H-1-oxoisoquinolin-4-yl)methyl-trimethylammonium iodide obtained in Starting Material Synthetic Example 6 and 4-hydroxypiperidine.

Example 178

7-Chloro-4-dimethylaminomethyl-3-ethyl-2H-isoquinolin-1-one is obtained by the reaction in the same manner as in Example 49 using 7-chloro-3-ethyl-2H-isoquinolin-1-one.

Example 179

7-Chloro-4-(pyrrolidin-1-yl)methyl-3-ethyl-2H-isoquinolin-1-one is obtained by the reaction in the same manner as in Example 43 using N-(7-chloro-3-ethyl-2H-1-oxoisoquinolin-4-yl)methyl-trimethylammonium iodide obtained in Starting Material Synthetic Example 31 and pyrrolidine.

Example 180

(S)-7-Chloro-4-(3-hydroxypyrrolidin-1-yl)methyl-3-ethyl-2H-isoquinolin-1-one is obtained by the reaction in the same manner as in Example 43 using N-(7-chloro-3-ethyl-2H-1-oxoisoquinolin-4-yl)methyl-trimethylammonium iodide obtained in Starting Material Synthetic Example 31 and (S)-3-hydroxypyrrolidine.

Example 181

(R)-7-Chloro-4-(3-hydroxypyrrolidin-1-yl)methyl-3-ethyl-2H-isoquinolin-1-one is obtained by the reaction in the same manner as in Example 43 using N-(7-chloro-3-ethyl-2H-1-oxoisoquinolin-4-yl)methyl-trimethylammonium iodide obtained in Starting Material Synthetic Example 31 and (R)-3-hydroxypyrrolidine.

Example 182

(R)-7-Chloro-4-(2-hydroxymethylpyrrolidin-1-yl)methyl-3-ethyl-2H-isoquinolin-1-one is obtained by the reaction in the same manner as in Example 43 using N-(7-chloro-3-ethyl-2H-1-oxoisoquinolin-4-yl)methyl-trimethylammonium iodide obtained in Starting Material Synthetic Example 31 and D-prolinol.

Example 183

(S)-7-Chloro-4-(2-hydroxymethylpyrrolidin-1-yl)methyl-3-ethyl-2H-isoquinolin-1-one is obtained by the reaction in the same manner as in Example 43 using N-(7-chloro-3-ethyl-2H-1-oxoisoquinolin-4-yl)methyl-trimethylammonium iodide obtained in Starting Material Synthetic Example 31 and L-prolinol.

Example 184

7-Chloro-3-ethyl-4-(4-hydroxypiperidin-1-yl)methyl-2H-isoquinolin-1-one is obtained by the reaction in the same manner as in Example 43 using N-(7-chloro-3-ethyl-2H-1-oxoisoquinolin-4-yl)methyl-trimethylammonium iodide obtained in Starting Material Synthetic Example 31 and 4-hydroxypiperidine.

Example 185

7-Fluoro-4-dimethylaminomethyl-3-ethyl-2H-isoquinolin-1-one is obtained by the reaction in the same manner as in Example 49 using 7-fluoro-3-ethyl-2H-isoquinolin-1-one;

Example 186

7-Fluoro-4-(pyrrolidin-1-yl)methyl-3-ethyl-2H-isoquinolin-1-one is obtained by the reaction in the same manner as in Example 43 using N-(7-fluoro-3-ethyl-2H-1-oxoisoquinolin-4-yl)methyl-trimethylammonium iodide obtained in Starting Material Synthetic Example 32 and pyrrolidine.

Example 187

(S)-7-Fluoro-4-(3-hydroxypyrrolidin-1-yl)methyl-3-ethyl-2H-isoquinolin-1-one is obtained by the reaction in the same manner as in Example 43 using N-(7-fluoro-3-ethyl-2H-1-oxoisoquinolin-4-yl)methyl-trimethylammonium iodide obtained in Starting Material Synthetic Example 32 and (S)-3-hydroxypyrrolidine.

Example 188

(R)-7-Fluoro-4-(3-hydroxypyrrolidin-1-yl)methyl-3-ethyl-2H-isoquinolin-1-one is obtained by the reaction in the same manner as in Example 43 using N-(7-fluoro-3-ethyl-2H-1-oxoisoquinolin-4-yl)methyl-trimethylammonium iodide obtained in Starting Material Synthetic Example 32 and (R)-3-hydroxypyrrolidine.

Example 189

(R)-7-Fluoro-4-(2-hydroxymethylpyrrolidin-1-yl)methyl-3-ethyl-2H-isoquinolin-1-one is obtained by the reaction in the same manner as in Example 43 using N-(7-fluoro-3-ethyl-2H-1-oxoisoquinolin-4-yl)methyl-trimethylammonium iodide obtained in Starting Material Synthetic Example 32 and D-prolinol.

Example 190

(S)-7-Fluoro-4-(2-hydroxymethylpyrrolidin-1-yl)methyl-3-ethyl-2H-isoquinolin-1-one is obtained by the reaction in the same manner as in Example 43 using N-(7-fluoro-3-ethyl-2H-1-oxoisoquinolin-4-yl)methyl-trimethylammonium iodide obtained in Starting Material Synthetic Example 32 and L-prolinol.

Example 191

7-Fluoro-3-ethyl-4-(4-hydroxypiperidin-1-yl)methyl-2H-isoquinolin-1-one is obtained by the reaction in the same manner as in Example 43 using N-(7-fluoro-3-ethyl-2H-1-oxoisoquinolin-4-yl)methyl-trimethylammonium iodide obtained in Starting Material Synthetic Example 32 and 4-hydroxypiperidine.

Example 192

7-Chloro-4-(1-(2-hydroxyethyl)piperidin-4-yl)-2H-isoquinolin-1-one is obtained by the reaction in the same manner as in Example 32 using 7-chloro-4-(piperidin-4-yl)-2H-isoquinolin-1-one hydrochloride obtained in Example 44.

Example 193

3-(2-Chloroethyl)-1-methylpyrazolo[3,4-c]isoquinolin-5(4H)-one (0.25 g) obtained in Starting Material Synthetic Example 40 was suspended in pyrrolidine (2 mL), and the mixture was stirred under heating at 100° C. for 10 min. After the completion of the reaction, pyrrolidine was evaporated. Aqueous potassium carbonate solution was added to the obtained residue, and the mixture was extracted with chloroform. The organic layer was dried over magnesium sulfate and concentrated. The obtained residue was subjected to silica gel chromatography, and the fraction eluted with chloroform:methanol=30:1 was concentrated, and the precipitated crystals were collected by filtration to give 1-methyl-3-[2-(pyrrolidin-1-yl)ethyl]pyrazolo[3,4-c]isoquinolin-5(4H)-one (0.13 g).
$^1$H-NMR (DMSO-$d_6$) δ: 1.62-1.80 (4H, m), 2.43-2.58 (7H, m), 2.84 (2H, t, J=6 Hz), 4.30 (2H, t, J=6 Hz), 7.40 (1H, t, J=8 Hz), 7.75 (1H, t, J=8 Hz), 7.88 (1H, d, J=8 Hz), 8.22 (1H, d, J=8 Hz).

Example 194

1-Methyl-3-[2-(4-methylpiperazin-1-yl)ethyl]pyrazolo[3,4-c]isoquinolin-5(4H)-one (0.38 g) was obtained by the reaction in the same manner as in Example 193 using 3-(2-chloroethyl)-1-methylpyrazolo[3,4-c]isoquinolin-5(4H)-one (0.6 g) obtained in Starting Material Synthetic Example 40 and 1-methylpiperazine (2 mL).
$^1$H-NMR (DMSO-$d_6$) δ: 2.13 (3H, s), 2.19-2.40 (4H, m), 2.52 (3H, s), 2.70 (2H, t, J=6 Hz), 3.25-3.45 (4H, m), 4.29 (2H, t, J=6 Hz), 7.40 (1H, t, J=8 Hz), 7.75 (1H, t, J=8 Hz), 7.88 (1H, d, J=8 Hz), 8.23 (1H, d, J=8 Hz), 12.59 (1H, brs).

Example 195

1-Methyl-3-[2-(morpholin-4-yl)ethyl]pyrazolo[3,4-c]isoquinolin-5(4H)-one (0.56 g) was obtained in the reaction in the same manner as in Example 193 using 3-(2-chloroethyl)-1-methylpyrazolo[3,4-c]isoquinolin-5(4H)-one (0.6 g) obtained in Starting Material Synthetic Example 40 and morpholine (2 mL).

¹H-NMR (DMSO-d₆) δ: 2.45-2.51 (4H, m), 2.52 (3H, s), 2.70 (2H, t, J=6 Hz), 3.53-3.57 (4H, m), 4.30 (2H, t, J=6 Hz), 7.40 (1H, t, J=8 Hz), 7.75 (1H, t, J=8 Hz), 7.88 (1H, d, J=8 Hz), 8.23 (1H, d, J=8 Hz), 12.39 (1H, brs).

Example 196 and Example 197

A mixture of 6-fluoro-4-(1-methylpiperidin-4-yl)-2H-isoquinolin-1-one and 8-fluoro-4-(1-methylpiperidin-4-yl)-2H-isoquinolin-1-one was obtained by the reaction in the same manner as in Example 198 using 1-benzoyl-4-(3-fluorobenzoyl)piperidine as a starting material. This mixture was purified by HPLC to give both isomers.

8-fluoro-4-(1-methylpiperidin-4-yl)-2H-isoquinolin-1-one.

melting point: 227.6-229.3° C.

¹H-NMR (300 MHz, CDCl₃) δ: 1.63-1.82 (2H, m), 1.96 (2H, d, J=13 Hz), 2.07-2.20 (2H, m), 2.35 (3H, s), 2.69-2.84 (1H, m), 3.03 (2H, d, J=12 Hz), 7.06 (1H, s), 7.07-7.17 (1H, m), 7.51 (1H, d, J=8 Hz), 7.58-7.69 (1H, m), 11.21 (1H, brs).

6-fluoro-4-(1-methylpiperidin-4-yl)-2H-isoquinolin-1-one.

melting point: 228.9-230.6° C.

¹H-NMR (300 MHz, CDCl₃) δ: 1.64-1.83 (2H, m), 1.96 (2H, d, J=13 Hz), 2.10-2.21 (2H, m), 2.36 (3H, s), 2.66-2.79 (1H, m), 3.03 (2H, d, J=12 Hz), 7.04 (1H, s), 7.19-7.39 (2H, m), 8.46-8.55 (1H, m), 11.20 (1H, brs).

Example 198

(E)- and (Z)-β-(1-Benzoylpiperidin-4-yl)-4-trifluoromethylcinnamic acid (12.72 g) was obtained by the reaction in the same manner as in Starting Material Synthetic Example 3 using 1-benzoyl-4-(4-trifluoromethylbenzoyl)piperidine (14.64 g).

4-(1-Benzoylpiperidin-4-yl)-7-trifluoromethyl-2H-isoquinolin-1-one (0.21 g) was obtained by the reaction in the same manner as in Starting Material Synthetic Example 3 using (E)- and (Z)-β-(1-benzoylpiperidin-4-yl)-4-trifluoromethylcinnamic acid (3.173 g).

4-(Piperidin-4-yl)-7-trifluoromethyl-2H-isoquinolin-1-one hydrochloride (33.4 mg) was obtained by the reaction in the same manner as in Example 31 using 4-(1-benzoylpiperidin-4-yl)-7-trifluoromethyl-2H-isoquinolin-1-one (0.21 g).

4-(1-Methylpiperidin-4-yl)-7-trifluoromethyl-2H-isoquinolin-1-one (12.2 mg) was obtained by the reaction in the same manner as in Example 33 using 4-(piperidin-4-yl)-7-trifluoromethyl-2H-isoquinolin-1-one hydrochloride (33.4 mg).

melting point: 231.8-234.6° C.

¹H-NMR (300 MHz, CDCl₃) δ: 1.70-2.01 (4H, m), 2.14-2.29 (2H, m), 2.40 (3H, s), 2.79-2.92 (1H, m), 3.08 (2H, d, J=12 Hz), 7.12 (1H, s), 7.82-7.95(2H, m), 8.79 (1H, s), 10.99 (1H, brs).

Example 199

(R)-7-Fluoro-3-methyl-1-[(3-hydroxypyrrolidin-1-yl)methyl]-3H-pyrazolo[3,4-c]isoquinolin-5(4H)-one was obtained by the reaction in the same manner as in Example 53 using (R)-3-pyrrolidine hydrochloride instead of pyrrolidine.

¹H-NMR(MeOD) δ: 1.66-1.76 (1H, m), 2.08-2.20 (1H, m), 2.58-2.66 (2H, m), 2.79-2.93 (2H, m), 3.89 (3H, s), 3.94 (2H, s), 4.32-4.38 (1H, m), 7.49-7.56 (1H, m), 7.89-7.96 (1H, m), 8.26-8.30 (1H, m).

Example 200

(S)-7-Fluoro-3-methyl-1-[(3-hydroxypyrrolidin-1-yl)methyl]-3H-pyrazolo[3,4-c]isoquinolin-5(4H)-one was obtained by the reaction in the same manner as in Example 53 using (S)-3-pyrrolidine hydrochloride instead of pyrrolidine.

¹H-NMR(MeOD) δ: 1.66-1.75 (1H, m), 2.08-2.20 (1H, m), 2.58-2.66 (2H, m), 2.79-2.93 (2H, m), 3.89 (3H, s), 3.94 (2H, s), 4.32-4.38 (1H, m), 7.50-7.56 (1H, m), 7.92-7.96 (1H, m), 8.26-8.30 (1H, m).

Example 201

7-Methoxy-4-(1-methylpiperidin-4-yl)-2H-isoquinolin-1-one was obtained by the reaction in the same manner as in Example 198 using 1-benzoyl-4-(4-methoxybenzoyl)piperidine as a starting material.

melting point: 224.9-226.2° C.

¹H-NMR (300 MHz, CDCl₃) δ: 1.65-1.82 (2H, m), 1.97 (2H, d, J=13 Hz), 2.06-2.20 (2H, m), 2.36 (3H, s), 2.73-2.88 (1H, m), 3.03 (2H, d, J=11 Hz), 3.96 (3H, s), 6.93 (1H,s), 7.30-7.39 (1H, m), 7.69 (1H, d, J=9 Hz), 7.90 (1H, d, J=3 Hz), 11.14 (1H, brs). MS(EI)272(M+).

Example 202

4-(1,2,3,6-Tetrahydropyridin-4-yl)-2H-isoquinolin-1-one (0.8 g) was dissolved in a mixed solvent of acetonitrile and water, and 35% aqueous formalin solution (0.5 mL) was added, and sodium triacetoxyborohydride (1.0 g) was added with stirring at room temperature. After the completion of the reaction, the solvent was evaporated. Aqueous potassium carbonate solution was added to the obtained residue, and the mixture was extracted with chloroform.

The organic layer was dried over magnesium sulfate, and the solvent was evaporated. The obtained residue was subjected to silica gel column chromatography, and the fraction eluted with chloroform:methanol=10:1+triethylamine 2% was concentrated. The precipitated crystals were collected by filtration to give 4-(1-methyl-1,2,3,6-tetrahydropyridin-4-yl)-2H-isoquinolin-1-one (0.15 g).

¹H-NMR (CDCl₃) δ: 2.48 (3H, s), 2.49-2.55 (2H, m), 2.70-2.78 (2H, m), 3.16-3.19 (2H, m), 5.79 (1H, m), 7.00 (1H, s), 7.48-7.55 (1H, m), 7.61-7.70 (2H, m), 8.45 (1H, d, J=8 Hz), 10.71 (1H, brs).

Example 203

7-Methyl-4-(1-methylpiperidin-4-yl)-2H-isoquinolin-1-one was obtained by the reaction in the same manner as in Example 198 using 1-benzoyl-4-(4-methylbenzoyl)piperidine as a starting material.

melting point: 212.8-214.8° C.

¹H-NMR (300 MHz, CDCl₃) δ: 1.66-1.82 (2H, m), 1.97 (2H, d, J=13 Hz), 2.07-2.21 (2H, m), 2.36 (3H, s), 2.51 (3H, s), 2.75-2.89 (1H, m), 3.02 (2H, d, J=12 Hz), 6.99 (1H, s), 7.50-7.58 (1H, m), 7.65 (1H, d, J=8 Hz), 8.31 (1H,s), 11.45 (1H, brs). MS(EI)256(M+).

Example 204

7-Dimethylamino-4-(1-methylpiperidin-4-yl)-2H-isoquinolin-1-one was obtained by the reaction in the same manner as in Example 198 using 1-benzoyl-4-(4-dimethylaminobenzoyl)piperidine as a starting material.

$^1$H-NMR (300 MHz, CDCl$_3$) δ: 1.63-2.01 (4H, m), 2.08-2.20 (2H, m), 2.35 (3H, s), 2.71-2.86 (1H, m), 2.98-3.11 (8H, m), 6.79 (1H, s), 7.19-7.26 (1H, m), 7.61-7.70 (2H, m), 10.60 (1H, brs). MS(EI)285(M+).

Example 205

4-(1-Benzyl-1,2,3,6-tetrahydropyridin-4-yl)-2H-isoquinolin-1-one (4.2 g) obtained in Example 206 was dissolved in dichloroethane (50 mL), and molecular sieve 4A (5.0 g) was added, and then 1-chloroethyl chloroformate (2.15 mL) was added under ice-cooling. The mixture was stirred at room temperature for 1 hr and then refluxed for 1 hr, and the solvent was evaporated.

The reaction mixture was dissolved in methanol, and the mixture was heated under reflux for 1 hr. After the molecular sieve 4A was removed by filtration, the solvent was evaporated, and the obtained residue was dissolved in 1N hydrochloric acid. The mixture was washed with hexane, and potassium carbonate was added to the aqueous layer. The mixture was extracted with chloroform, and the organic layer was dried over magnesium sulfate. The solvent was evaporated, and the obtained residue was subjected to silica gel column chromatography (NH silica gel, Fuji Silysia Chemical Ltd.). The fraction eluted with chloroform:methanol=20:1 was concentrated, and the precipitated crystals were collected by filtration to give 4-(1,2,3,6-tetrahydropyridin-4-yl)-2H-isoquinolin-1-one (1.6 g).

$^1$H-NMR (CDCl$_3$) δ: 2.30-2.40 (2H, m), 3.10-3.20 (2H, m), 3.50-3.60 (2H, m), 5.84 (1H, m), 7.00 (1H,s), 7.49-7.54 (1H, m), 7.64-7.71 (2H, m), 8.46 (1H, d, J=8 Hz).

Example 206

4-(Pyridin-4-yl)-2H-isoquinolin-1-one (5.2 g) obtained in Starting Material Synthetic Example 41 was dissolved in a mixed solvent (200 mL, chloroform:methanol=10:1), and benzyl bromide (4.4 g) was added, and the mixture was allowed to leave at room temperature for 48 hr. After the completion of the reaction, the solvent was evaporated. Acetone was added to the obtained residue, and the precipitated crystals were collected by filtration to give 1-benzyl-4-(1-oxo-2H-isoquinolin-4-yl)pyridinium bromide (9.0 g).

1-Benzyl-4-(1-oxo-2H-isoquinolin-4-yl)pyridinium bromide (9.0 g) was dissolved in methanol (100 mL), and sodium borohydride (3.7 g) was added in small portions with stirring at room temperature. After the completion of the reaction, the solvent was evaporated. Water was added to the obtained residue, and the mixture was extracted with chloroform. The organic layer was dried over magnesium sulfate, and the solvent was evaporated. Ethyl acetate was added to the obtained residue, and the precipitated crystals were collected by filtration to give 4-(1-benzyl-1,2,3,6-tetrahydropyridin-4-yl)-2H-isoquinolin-1-one (6.5 g).

$^1$H-NMR (CDCl$_3$) δ: 2.40-2.50 (2H, m), 2.71-2.78 (2H, m), 3.17-3.30 (2H, m), 3.69 (2H, s), 5.77 (1H, m), 6.99 (1H,s), 7.26-7.73 (8H, m), 8.45 (1H, d, J=8 Hz), 10.50(1H, brs).

Example 207

4-(1,2,3,6-Tetrahydropyridin-4-yl)-2H-isoquinolin-1-one (0.4 g) obtained in Example 205 and potassium carbonate (1 g) were suspended in acetonitrile (10 mL) and water (1 mL), and isopropyl iodide (0.35 mL) was added at room temperature. The mixture was stirred under heating overnight at 40° C. After the completion of the reaction, the solvent was evaporated. Aqueous potassium carbonate solution was added to the obtained residue, and the mixture was extracted with chloroform. The organic layer was dried over magnesium sulfate, and the solvent was evaporated. The obtained residue was subjected to silica gel column chromatography (NH silica gel, Fuji Silysia Chemical Ltd.). The fraction eluted with chloroform:methanol=25:1 was concentrated, and the precipitated crystals were collected by filtration to give 4-(1-isopropyl-1,2,3,6-tetrahydropyridin-4-yl)-2H-isoquinolin-1-one.

$^1$H-NMR (CDCl$_3$) δ: 1.16 (6H, d, J=6 Hz), 2.42-2.48 (2H, m), 2.77-2.91 (3H, m), 3.26-3.30 (2H, m), 5.80 (1H, m), 6.99 (1H, s), 7.47-7.53 (1H, m), 7.63-7.70 (2H, m), 8.45 (1H, d, J=8 Hz), 10.36 (1H, brs).

Example 208

4-(1-Ethyl-1,2,3,6-tetrahydropyridin-4-yl)-2H-isoquinolin-1-one was obtained by the reaction in the same manner as in Example 207 using 4-(1,2,3,6-tetrahydropyridin-4-yl)-2H-isoquinolin-1-one (0.37 g) obtained in Example 205 and ethyl iodide (0.14 mL).

$^1$H-NMR (CDCl$_3$) δ: 1.22 (3H, t, J=7 Hz), 2.45-2.54 (2H, m), 2.63 (2H, q, J=7 Hz), 2.76-2.81 (2H, m), 3.20-3.24 (2H, m), 5.80 (1H, m), 6.99 (1H, s), 7.48-7.53 (1H, m), 7.63-7.70 (2H, m)8.45 (1H, d, J=8 Hz), 10.41 (1H, brs).

Example 209

1-(Piperidin-4-yl)-3-methyl-pyrazolo[3,4-c]isoquinolin-5(4H)-one hydrochloride (1.0 g) obtained in Example 227 and 35% aqueous formalin solution (0.53 g) were suspended in water (20 mL), and sodium triacetoxyborohydride (1.3 g) was added at room temperature, and the mixture was stirred for 1 hr. After the completion of the reaction, the solvent was evaporated, and aqueous potassium carbonate solution was added to the obtained residue. The mixture was extracted with a mixed solvent (chloroform:methanol=10:1), and the organic layer was dried over magnesium sulfate. The solvent was evaporated, and ethanol was added to the precipitated crystals. The precipitated crystals was collected by filtration and washed with ethyl acetate to give 1-(1-methylpiperidin-4-yl)-3-methyl-pyrazolo[3,4-c]isoquinolin-5(4H)-one (0.51 g) as pale-brown crystals.

$^1$H-NMR (CDCl$_3$) δ: 2.01-2.23 (6H, m), 2.37 (3H, s), 3.03-3.12 (3H, m), 4.10 (3H, s), 7.42 (1H, t, J=8 Hz), 7.75 (1H, dt, J=1 Hz, 8 Hz), 7.83 (1H, d, J=8 Hz), 8.49 (1H, d, J=8 Hz). MS(EI): 296(M+).

Example 210

1-(1-Ethylpiperidin-4-yl)-3-methyl-pyrazolo[3,4-c]isoquinolin-5(4H)-one (0.17 g) was obtained by the reaction in the same manner as in Example 207 using 1-(piperidin-4-yl)-3-methyl-pyrazolo[3,4-c]isoquinolin-5(4H)-one hydrochloride (0.5 g) obtained in Example 227 and ethyl iodide (0.15 mL).

$^1$H-NMR (CDCl$_3$) δ: 1.15 (3H, t, J=7 Hz), 1.98-2.20 (6H, m), 2.52 (2H, q, J=7 Hz), 3.12-3.17 (3H, m), 4.09 (3H, s), 7.42 (1H, t, J=8 Hz), 7.75 (1H, dt, J=1 Hz, 8 Hz), 7.84 (1H, d, J=8 Hz), 8.49 (1H, dd, J=1 Hz, 8 Hz). MS (EI): 310(M+).

Example 211

1-(1-Isopropylpiperidin-4-yl)-3-methyl-pyrazolo[3,4-c]isoquinolin-5(4H)-one (0.17 g) was obtained by the reaction in the same manner as in Example 207 using 1-(piperidin-4-yl)-3-methyl-pyrazolo[3,4-c]isoquinolin-5(4H)-one hydrochloride (0.5 g) obtained in Example 227 and isopropyl iodide (0.5 mL).

$^1$H-NMR (CDCl$_3$) δ: 1.11 (6H, d, J=7 Hz), 1.97-2.15 (4H, m), 2.35-2.43 (2H, m), 2.75-2.85 (1H, m), 3.00-3.12 (3H, m), 4.09 (3H, s), 7.42 (1H, t, J=8 Hz), 7.75 (1H, dt, J=1 Hz, 8Hz), 7.85 (1H, d, J=8 Hz), 8.48 (1H, dd, J=1 Hz, 8 Hz). MS(EI): 324(M+).

Example 212

7-Fluoro-4-(1-ethylpiperidin-4-yl)-2H-isoquinolin-1-one (94.7 mg) was obtained by the reaction in the same manner as in Example 207 using 7-fluoro-4-(piperidin-4-yl)-2H-isoquinolin-1-one hydrochloride (300 mg) obtained in Example 45 and ethyl iodide (93.4 μL).

$^1$H-NMR (DMSO-d$_6$) δ: 1.02 (3H, t, J=7 Hz), 1.50-1.66 (2H, m), 1.75-1.87 (2H, m), 2.00-2.10 (2H, m), 2.37 (2H, q, J=7 Hz), 2.73-2.83 (1H, m), 2.93-3.00 (2H, m), 6.88 (1H, s), 7.63 (1H, dt, J=3 Hz, 9 Hz), 7.86-7.92 (2H, m), 11.28 (1H, brs). MS(ESI): 275(M+1).

Example 213

7-Fluoro-4-(1-isopropylpiperidin-4-yl)-2H-isoquinolin-1-one (79.2 mg) was obtained by the reaction in the same manner as in Example 207 using 7-fluoro-4-(piperidin-4-yl)-2H-isoquinolin-1-one hydrochloride (200 mg) obtained in Example 45 and isopropyl iodide (77.7 μL).

$^1$H-NMR (DMSO-d6) δ: 1.00 (6H, d, J=7 Hz), 1.45-1.63 (2H, m), 1.76-1.85 (2H, m), 2.25-2.35 (2H, m), 2.63-2.90 (4H, m), 2.73-2.83 (1H, m), 2.93-3.00 (2H, m), 6.87 (1H, d, J=4 Hz), 7.63 (1H, dt, J=3 Hz, 9 Hz), 7.87-7.92 (2H, m), 11.27 (1H, brs). MS(ESI): 289(M+1).

Example 214

3-(4-Bromophenyl)-5-methoxymethoxy-1-methyl-3H-pyrazolo[3,4-c]isoquinoline (0.5 g) obtained in Starting Material Synthetic Example 46, 2-(di-t-butylphosphono)biphenyl (0.04 g), sodium t-butoxide (0.19 g) and pyrrolidine (0.18 g) were dissolved in toluene (10 mL), and purged with nitrogen. Palladium acetate (II, 0.02 g) was added to reaction solution, and the mixture was heated under reflux for 1 hr to allow to reaction.

After the completion of the reaction, the mixture was purified by silica gel column chromatography (hexane:ethyl acetate=4:1) to give crude crystals. The crude crystals were dissolved in a mixed solution of concentrated hydrochloric acid (1 mL) and methanol (20 mL), and the mixture was stirred at room temperature for 3 hrs. After the completion of the reaction, the solvent was evaporated, and the obtained solid was washed with acetone to give 1-methyl-3-[4-(pyrrolidin-1-yl)phenyl]-3,4-dihydropyrazolo[3,4-c]isoquinolin-5-one hydrochloride (0.36 g).

$^1$H-NMR (DMSO-d$_6$) δ: 1.98-2.02 (4H, m), 2.62 (3H, s), 3.27-3.32 (4H, m), 6.66 (2H, d, J=9 Hz), 7.38 (2H, d, J=9 Hz), 7.44 (1H, t, J=8 Hz), 7.79 (1H, t, J=8 Hz), 7.98 (1H, d, J=8 Hz), 8.24 (1H, d, J=7 Hz).

Example 215

1-Methyl-3-[4-(piperidin-1-yl)phenyl]-3,4-dihydropyrazolo[3,4-c]isoquinolin-5-one hydrochloride was obtained by the reaction in the same manner as in Example 214 using 3-(4-bromophenyl)-5-methoxymethoxy-1-methyl-3H-pyrazolo[3,4-c]isoquinoline obtained in Starting Material Synthetic Example 46 and piperidine.

$^1$H-NMR (DMSO-d$_6$) δ: 1.64 (2H, brs), 1.81 (4H, brs), 2.66 (3H, s), 3.42 (4H, brs), 7.46-7.86 (6H, m), 8.03-8.05 (1H, m), 8.27 (1H, d, J=8 Hz), 12.12 (1H, brs).

Example 216

1-Methyl-3-[4-(morpholin-4-yl)phenyl]-3,4-dihydropyrazolo[3,4-c]isoquinolin-5-one hydrochloride was obtained by the reaction in the same manner as in Example 214 using 3-(4-bromophenyl)-5-methoxymethoxy-1-methyl-3H-pyrazolo[3,4-c]isoquinoline obtained in Starting Material Synthetic Example 46 and morpholine.

$^1$H-NMR (DMSO-d$_6$) δ: 2.63 (3H, s), 3.17-3.22 (4H, m), 3.77-3.80 (4H, m), 7.10 (2H, d, J=9 Hz), 7.46 (1H, t, J=8 Hz), 7.51 (2H, brd), 7.81 (1H, t, J=8 Hz), 7.91 (1H, d, J=8 Hz), 8.25 (1H, d, J=8 Hz).

Example 217

1-Methyl-3-[4-(4-methylpiperazin-1-yl)phenyl]-3,4-dihydropyrazolo[3,4-c]isoquinolin-5-one dihydrochloride was obtained by the reaction in the same manner as in Example 214 using 3-(4-bromophenyl)-5-methoxymethoxy-1-methyl-3H-pyrazolo[3,4-c]isoquinoline obtained in Starting Material Synthetic Example 46 and 1-methylpiperazine.

$^1$H-NMR (DMSO-d$_6$) δ: 2.64 (3H, s), 2.85 (3H, s), 3.16 (4H, brs), 3.51 (2H, brs), 3.90 (2H, brs), 7.15 (2H, d, J=9 Hz), 7.47 (1H, t, J=8 Hz), 7.55 (2H, brs), 7.81 (1H, t, J=8 Hz), 8.01 (1H, d, J=8 Hz), 8.26 (1H, d, J=8 Hz), 10.57 (1H, s), 12.03 (2H, brs).

Example 218

1-Methyl-3-[4-(4-phenylpiperazin-1-yl)phenyl]-3,4-dihydropyrazolo[3,4-c]isoquinolin-5-one hydrochloride was obtained by the reaction in the same manner as in Example 214 using 3-(4-bromophenyl)-5-methoxymethoxy-1-methyl-3H-pyrazolo[3,4-c]isoquinoline obtained in Starting Material Synthetic Example 46 and 1-phenylpiperazine.

$^1$H-NMR (DMSO-d$_6$) δ: 2.64 (3H, s), 3.41 (4H, brs), 3.44 (4H, brs), 6.91 (1H, t, J=7 Hz), 7.12-7.33 (6H, m), 7.46 (1H, t, J=7 Hz), 7.54 (2H, brs), 7.81 (1H, t, J=8 Hz), 8.01 (1H, d, J=8 Hz), 8.26 (1H, d, J=8 Hz).

Example 219

1-Methyl-3-[4-(3-dimethylaminopyrrolidin-1-yl)phenyl]-3,4-dihydropyrazolo[3,4-c]isoquinolin-5-one dihydrochloride was obtained by the reaction in t-butanol in the same manner as in Example 214 using 3-(4-bromophenyl)-5-methoxymethoxy-1-methyl-3H-pyrazolo[3,4-c]isoquinoline obtained in Starting Material Synthetic Example 46 and 3-dimethylaminopyrrolidine hydrochloride.

$^1$H-NMR (DMSO-d$_6$) δ: 2.25-2.34 (1H, m), 2.42-2.54 (1H, m), 2.62 (3H, s), 2.86 (6H, t, J=5 Hz), 3.26-3.34 (1H, m), 3.54-3.59 (2H, m), 3.66-3.75 (1H, m), 3.99-4.04 (1H, m), 6.74 (2H, d, 9 Hz), 7.43-7.49 (3H, m), 7.80 (1H, t, J=7 Hz), 7.99 (1H, d, J=7 Hz), 8.25 (1H, d, J=8 Hz), 10.62 (1H, s), 11.93 (2H, brs).

Example 220

1-Methyl-3-[4-(4-dimethylaminopiperidin-1-yl)phenyl]-3,4-dihydropyrazolo[3,4-c]isoquinolin-5-one dihydrochloride was obtained by the reaction in t-butanol in the same manner as in Example 214 using 3-(4-bromophenyl)-5-methoxymethoxy-1-methyl-3H-pyrazolo[3,4-c]isoquinoline obtained in Starting Material Synthetic Example 46 and 4-dimethylaminopiperidine hydrochloride.

$^1$H-NMR (DMSO-d$_6$) δ: 1.70-1.81 (2H, m), 2.11-2.15 (2H, m), 2.63 (3H, s), 2.76 (3H, s), 2.77 (3H, s), 2.72-2.83 (2H, m), 3.34-3.39 (2H, m), 3.92-3.96 (1H, m), 7.13 (2H, d, 9 Hz), 7.46 (1H, t, 8 Hz), 7.44-7.54 (2H, m), 7.81 (1H, t, J=7 Hz), 8.00 (1H, d, J=7 Hz), 8.25 (1H, d, J=8 Hz), 10.25 (1H, s), 12.00 (2H, brs).

Example 221

7-Fluoro-1-(piperidin-4-yl)-3-methyl-pyrazolo[3,4-c]isoquinolin-5(4H)-one hydrochloride (5.4 g) was obtained by the reaction in the same manner as in Example 227 using a mixture (1:1, 21.6 g) obtained in Starting Material Synthetic Example 45 of 5-amino-1-methyl-3-(1-ethoxycarbonylpiperidin-4-yl)-4-(4-fluorophenyl)pyrazole and 5-amino-1-methyl-3-(1-methoxycarbonylpiperidin-4-yl)-4-(4-fluorophenyl)pyrazole.

$^1$H-NMR (DMSO-d$_6$) δ: 1.91-2.18 (4H, m), 3.10-3.55 (5H, m), 3.85 (3H, s), 7.64 (1H, dt, J=3 Hz, 9 Hz), 7.93 (1H, dd, J=3 Hz, 10 Hz), 8.00 (1H, dd, J=5 Hz, 9 Hz), 8.77 (1H, brs), 9.00 (1H, brs), 12.52 (1H, brs).

Example 222

7-Fluoro-1-(1-methylpiperidin-4-yl)-3-methyl-pyrazolo[3,4-c]isoquinolin-5(4H)-one (0.70 g) was obtained by the reaction in the same manner as in Example 209 using 7-fluoro-1-(piperidin-4-yl)-3-methyl-pyrazolo[3,4-c]isoquinolin-5(4H)-one hydrochloride (1.0 g) obtained in Example 221.

$^1$H-NMR (CDCl$_3$) δ: 2.01-2.23 (6H, m), 2.37 (3H, s), 2.99-3.07 (3H, m), 4.10 (3H, s), 7.49 (1H, dt, J=3 Hz, 9 Hz), 7.81 (1H, dd, J=3 Hz, 9 Hz), 8.11 (1H, dd, J=3 Hz, 9 Hz). MS(EI): 314(M+).

Example 223

1-(1-Ethylpiperidin-4-yl)-7-fluoro-3-methyl-pyrazolo[3,4-c]isoquinolin-5(4H)-one (0.57 g) was obtained by the reaction in the same manner as in Example 207 using 7-fluoro-1-(piperidin-4-yl)-3-methyl-pyrazolo[3,4-c]isoquinolin-5(4H)-one hydrochloride (1.0 g) obtained in Example 221 and ethyl iodide (0.29 mL).

$^1$H-NMR (CDCl$_3$) δ: 1.14 (3H, t, J=7 Hz), 1.99-2.18 (6H, m), 2.50 (2H, q, J=7 Hz), 3.06-3.18 (3H, m), 4.05 (3H, s), 7.49 (1H, t, J=8 Hz), 7.82 (1H, dd, J=3 Hz, 9 Hz), 8.12 (1H, dd, J=3 Hz, 9 Hz). MS(EI): 328(M+).

Example 224

7-Fluoro-1-(l-isopropylpiperidin-4-yl)-3-methyl-pyrazolo[3,4-c]isoquinolin-5(4H)-one (0.15 g) was obtained by the reaction in the same manner as in Example 207 using 7-fluoro-1-(piperidin-4-yl)-3-methyl-pyrazolo[3,4-c]isoquinolin-5(4H)-one hydrochloride (0.5 g) obtained in Example 221 and isopropyl iodide (0.3 mL).

$^1$H-NMR (CDCl$_3$) δ: 1.11 (6H, d, J=7 Hz), 1.95-2.12 (4H, m), 2.34-2.53 (2H, m), 2.80-2.85 (1H, m), 3.00-3.10 (3H, m), 4.08 (3H, s), 7.50 (1H, dt, J=3 Hz, 8 Hz), 7.84 (1H, dd, J=2 Hz, 9 Hz), 8.12 (1H, dd, J=3 Hz, 6 Hz). MS (EI): 342(M+).

Example 225

7-Fluoro-1-(1-propylpiperidin-4-yl)-3-methyl-pyrazolo[3,4-c]isoquinolin-5(4H)-one (0.71 g) was obtained by the reaction in the same manner as in Example 207 using 7-fluoro-1-(piperidin-4-yl)-3-methyl-pyrazolo[3,4-c]isoquinolin-5(4H)-one hydrochloride (1.0 g) obtained in Example 221 and propyl iodide (0.35 mL).

$^1$H-NMR (DMSO-d$_6$) δ: 0.89 (3H, t, J=7Hz), 1.42-1.58 (2H, m), 1.76-2.01 (4H, m), 2.25-2.50 (3H, m), 2.73-3.20 (4H, m), 3.83 (3H, s), 7.67 (1H, dt, J=3 Hz, 9 Hz), 7.86-7.95 (2H, m), 12.33 (1H, brs). MS(EI): 342(M+).

Example 226

1-(1-Propylpiperidin-4-yl)-3-methyl-pyrazolo[3,4-c]isoquinolin-5(4H)-one (0.58 g) was obtained by the reaction in the same manner as in Example 207 using 1-(piperidin-4-yl)-3-methyl-pyrazolo[3,4-c]isoquinolin-5(4H)-one hydrochloride (1.0 g) obtained in Example 227 and propyl iodide (0.37 mL).

$^1$H-NMR (DMSO-d$_6$) δ: 0.89 (3H, t, J=7 Hz), 1.42-1.58 (2H, m), 1.75-2.02 (4H, m), 2.09-2.5 0(3H, m), 2.70-3.20 (4H, m), 3.83 (3H, s), 7.39 (1H, t, J=8 Hz), 7.74-7.83 (2H, m), 8.25 (1H, d, J=8 Hz), 12.27 (1H,brs). MS(EI): 342(M+).

Example 227

Triphosgene (1.33 g) was dissolved in methylene chloride (10 mL), a solution (20 mL) of 5-amino-1-methyl-3-(1-ethoxycarbonylpiperidin-4-yl)-4-phenylpyrazole (4.2 g) obtained in Starting Material Synthetic Example 43 and pyridine (2.53 g) in methylene chloride was added dropwise under ice-cooling.

After the completion of the dropwise addition, the mixture was stirred at room temperature for 4 hrs and ice-cooled. Aluminum chloride (13.6 g) was added to the reaction mixture, and the mixture was stirred overnight at room temperature. After the completion of the reaction, the reaction mixture was poured into ice-water, and potassium carbonate was added to alkalify the reaction mixture. An excess amount of ethyl chloroformate was added to the reaction mixture, and the mixture was stirred at room temperature. The insoluble material was remove by filtration, and the aqueous layer was extracted with chloroform. The organic layer was dried over magnesium sulfate, and the solvent was evaporated to give a mixture of 1-(1-ethoxycarbonylpiperidin-4-yl)-3-methyl-pyrazolo[3,4-c]isoquinolin-5(4H)-one and 4-ethoxycarbonyl-1-(1-ethoxycarbonylpiperidin-4-yl)-3-methyl-pyrazolo[3,4-c]isoquinolin-5-one as solid. Further purification was not performed and the mixture was used in the next reaction. The total amount of the above-mentioned mixture was dissolved in acetic acid (100 mL) and concentrated hydrochloric acid (100 mL), and the mixture was heated under reflux for 24 hrs. After the completion of the reaction, the solvent was evaporated, and the precipitated crystals were collected by filtration to give 1-(piperidin-4-yl)-3-methyl-pyrazolo[3,4-c] isoquinolin-5(4H)-one hydrochloride (3.7 g).

$^1$H-NMR (DMSO-d$_6$) δ: 1.90-2.18 (4H, m), 3.10-3.58 (5H, m), 3.85 (3H, s), 7.43 (1H, t, J=7 Hz), 7.77 (1H, t, J=8 Hz), 7.94 (1H, d, J=8 Hz), 8.26 (1H, d, J=7 Hz), 8.94-9.02 (1H, m), 9.20-9.24 (1H, m), 12.34 (1H, brs).

Example 228

7-Fluoro-3-methyl-1-[(piperidin-4-yl)methyl]-3,4-dihydropyrazolo[3,4-c]isoquinolin-5-one hydrochloride (0.33 g) was obtained by the reaction in the same manner as in Example 227 using 5-amino-3-[(1-ethoxycarbonylpiperidin-4-yl)methyl]-4-(4-fluorophenyl)-1-methylpyrazole (12.36 g) obtained in Starting Material Synthetic Example 48.

¹H-NMR (DMSO-d₆) δ: 1.41-1.53 (2H, m), 1.85-1.91 (2H, m), 2.02 (1H, m), 2.73-2.89 (4H, m), 3.21-3.25 (2H, m), 3.83 (3H, s), 7.65 (1H, m), 7.90-7.96 (2H, m), 8.60 (1H, brs), 8.84 (1H, brs), 12.51 (1H, brs).

Example 229

7-Fluoro-3-methyl-1-[(1-methylpiperidin-4-yl)methyl]-3,4-dihydropyrazolo[3,4-c]isoquinolin-5-one (0.013 g) was obtained by the reaction in the same manner as in Example 209 using 7-fluoro-3-methyl-1-[(piperidin-4-yl)methyl]-3,4-dihydro-pyrazolo[3,4-c]isoquinolin-5-one hydrochloride (0.33 g) obtained in Example 228.
¹H-NMR (DMSO-d₆) δ: 1.33 (2H, m), 1.69 (3H, m), 1.89 (2H, m), 2.17 (3H, s), 2.81 (4H, m), 3.82 (3H, s), 7.62-7.69 (1H, m), 7.87-7.93 (2H, m).

Example 230

3-Methyl-1-(1-methylpyrrolidin-3-yl)-3,4-dihydropyrazolo[3,4-c]isoquinolin-5-one was obtained by the reaction in the same manner as in Starting Material Synthetic Example 42, Starting Material Synthetic Example 43, Example 227 and Example 209 using methyl 1-ethoxycarbonylpyrrolidine-3-carboxylate as a starting material.
¹H-NMR (300 MHz, CDCl₃) δ: 2.30-2.51 (2H, m), 2.48 (3H, s), 2.69-2.80 (1H, m), 2.85-2.98 (2H, m), 3.18 (1H, t, J=9 Hz), 3.89-4.02 (1H, m), 4.10 (3H, s), 7.36-7.45 (1H, m), 7.68-7.77 (1H, m), 7.94 (1H, d, J=8 Hz), 8.44 (1H, d, J=8 Hz).

Example 231

A mixture (1:1, 17.5 g) of α-(1-ethoxycarbonylpiperidin-4-yl)carbonylphenylacetonitrile and α-(1-methoxycarbonylpiperidin-4-yl)carbonylphenylacetonitrile was obtained as an oil by the reaction in the same manner as in Starting Material Synthetic Example 42 Example 207 using phenylacetonitrile (15.0 g), methyl 1-ethoxycarbonylisonipecotate (23.0 g).
¹H-NMR (CDCl₃) δ: 1.23 (1.5H, t, J=6.9 Hz), 1.45-1.69 (4H, m), 2.72-2.87 (3H, m), 3.67 (1.5H, s), 4.07-4.14 (3H, m), 4.80 (1H, s), 7.16-7.28 (2H, m), 7.37-7.46 (3H, m). MS(ESI): 287(M+1), 301(M+1).

A mixture (1:1, 17.5 g) of α-(1-ethoxycarbonylpiperidin-4-yl)carbonylphenylacetonitrile and α-(1-methoxycarbonylpiperidin-4-yl)carbonylphenylacetonitrile, hydroxylamine hydrochloride (5.63 g) and sodium acetate (13.1 g) were suspended in water (20 mL) and ethanol (160 mL), and the suspension was heated under reflux for 6 hrs. After the completion of the reaction, the mixture was cooled to room temperature. The insoluble material was filtered off using ethanol, and the filtrate was concentrated under reduced pressure. The residue was dissolved in chloroform, and washed with water and saturated brine. The chloroform layer was concentrated under reduced pressure, and the obtained crystals were purified by column chromatography (n-hexane:ethyl acetate=3:1→1:1) to give a mixture (1:1, 7.02 g) of 5-amino-3-(1-ethoxycarbonylpiperidin-4-yl)-4-phenylisoxazole and 5-amino-3-(1-methoxycarbonylpiperidin-4-yl)-4-phenylisoxazole as pale-yellow crystals.
¹H-NMR (CDCl₃) δ: 1.24 (1.5H, t, J=7.1 Hz), 1.66-1.86 (4H, m), 2.77-2.88 (3H, m), 3.67 (1.5H,s), 4.07-4.14 (3H, m), 4.48 (1H, brs), 7.26-7.35 (3H, m), 7.41-7.46 (2H, m). MS(ESI): 302(M+1), 316(M+1).

Triphosgene (1.83 g) was dissolved in methylene chloride (20 mL), a solution (30 mL) of a mixture (1:1, 5.57 g) of 5-amino-3-(1-ethoxycarbonylpiperidin-4-yl)-4-phenylisoxazole and 5-amino-3-(1-methoxycarbonylpiperidin-4-yl)-4-phenylisoxazole, and pyridine (3.50 g) in methylene chloride was added dropwise under ice-cooling. After the completion of the dropwise addition, the mixture was stirred under ice-cooling for 20 min, and then at room temperature for 6.5 hrs. The reaction mixture was ice-cooled, aluminum chloride (16.7 g) was added, and the mixture was stirred overnight at room temperature. After the completion of the reaction, the reaction mixture was poured into ice-water, and potassium carbonate was added to alkalify the reaction mixture. An excess amount of ethyl chloroformate was added to the reaction mixture, and the mixture was stirred at room temperature. The insoluble material was filtered off through celite, and the aqueous layer was extracted with chloroform. The organic layer was dried over magnesium sulfate, and the solvent was evaporated under reduced pressure. The precipitated crystals were collected by filtration with diethyl ether and a small amount of methanol to give a mixture (1:1, 2.74 g) of 1-(1-ethoxycarbonylpiperidin-4-yl)-isoxazolo[5,4-c]isoquinolin-5(4H)-one and 1-(1-methoxycarbonylpiperidin-4-yl)-isoxazolo[5,4-c]isoquinolin-5(4H)-one as colorless crystals.
¹H-NMR (DMSO-d₆) δ: 1.20 (1.5H, t, J=6.9 Hz), 1.59-1.70 (2H, m), 2.05-2.09 (2H, m), 3.00-3.25 (2H, m), 3.50-3.62 (1H, m), 3.62 (1.5H, s), 4.03-4.10 (3H, m), 7.51 (1H, t, J=7.2 Hz), 7.79-7.91 (2H, m), 8.28-8.31 (1H, m). MS (ESI): 328(M+1), 342(M+1).

A mixture (1:1, 2.74 g) of 1-(1-ethoxycarbonylpiperidin-4-yl)-isoxazolo[5,4-c]isoquinolin-5(4H)-one and 1-(1-methoxycarbonylpiperidin-4-yl)-isoxazolo[5,4-c]isoquinolin-5(4H)-one was suspended in acetic acid (15 mL) and concentrated hydrochloric acid (15 mL), and the suspension was heated under reflux for 18 hrs. After the completion of the reaction, the solvent was evaporated. Water and a small amount of methanol were added to the precipitated crystals, and the obtained solution was washed with ethyl acetate, and the aqueous phase was concentrated under reduced pressure. The precipitated crystals were washed with isopropyl alcohol and collected by filtration to give 1-(piperidin-4-yl)-isoxazolo[5,4-c]isoquinolin-5(4H)-one hydrochloride (2.39 g).
¹H-NMR (DMSO-d₆) δ: 1.95-2.10 (2H, m), 2.20-2.24 (2H, m), 3.18-3.40 (4H, m), 3.69-3.78 (1H, m), 7.55 (1H, t, J=7.8 Hz), 7.82-7.87 (1H, m), 7.99 (1H, d, J=7.8 Hz), 8.29 (1H, d, J=7.8 Hz), 9.30 (2H, brs). MS (ESI): 270(M+1).

Example 232

1-(1-Methylpiperidin-4-yl)-isoxazolo[5,4-c]isoquinolin-5(4H)-one (390 mg) was obtained by the reaction in the same manner as in Example 209 using 1-(piperidin-4-yl)-isoxazolo[5,4-c]isoquinolin-5(4H)-one hydrochloride (904 mg).
¹H-NMR (DMSO-d₆) δ: 1.80-1.99 (2H, m), 2.11-2.15 (2H, m), 2.46 (3H, s), 2.50-2.63 (2H, m), 3.11-3.17 (2H, m), 3.25-3.45 (1H, m), 7.50 (1H, t, J=7.8 Hz), 7.79-7.90 (2H, m), 8.28 (1H, d, J=7.8 Hz). MS(ESI): 284(M+1).

Example 233

1-(1-Ethylpiperidin-4-yl)-isoxazolo[5,4-c]isoquinolin-5(4H)-one (240 mg) was obtained by the reaction in the same manner as in Example 207 using 1-(piperidin-4-yl)-isoxazolo[5,4-c]isoquinolin-5(4H)-one hydrochloride (903 mg).
¹H-NMR (DMSO-d₆) δ: 1.15 (3H, t, J=7.2 Hz), 1.80-2.00 (2H, m), 2.15-2.20 (2H, m), 2.65-2.78 (4H, m), 3.24-3.49 (3H, m), 7.52 (1H, t, J=7.8 Hz), 7.60-7.89 (2H, m), 8.28 (1H, d, J=7.8 Hz). MS(ESI): 298(M+1).

The structural formulas of the respective Example compounds are shown in the following. The following numbers correspond to the above-mentioned Example numbers.

87
1 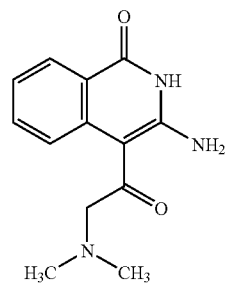
2 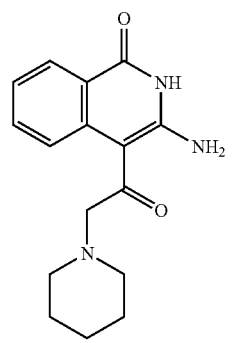
3 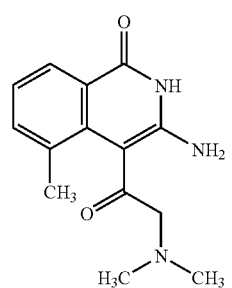
4 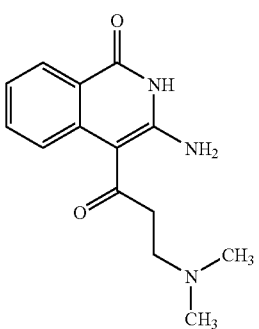
5 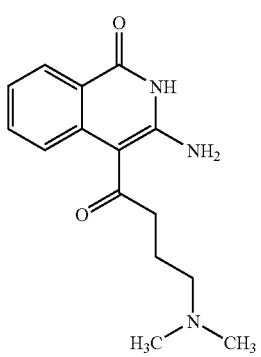
88
-continued
6 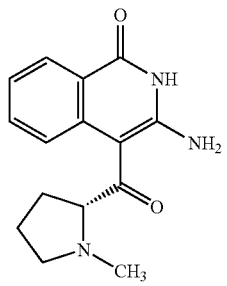
7 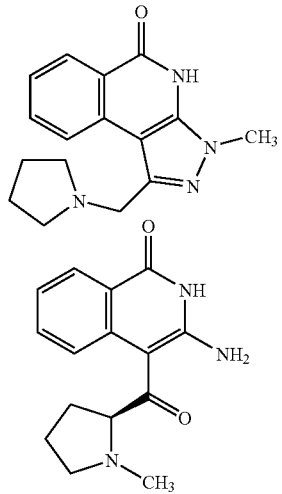
8 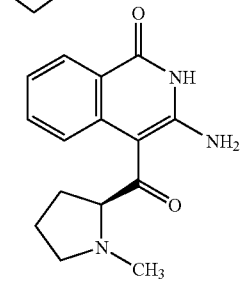
9 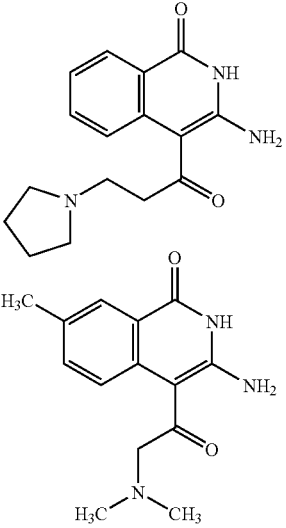
10 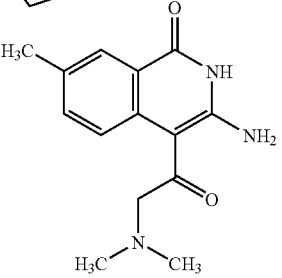
11 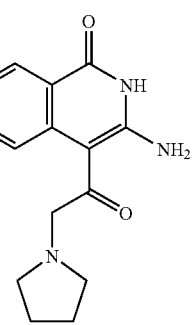

-continued
12
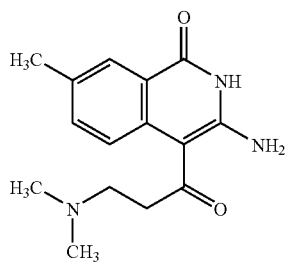
13
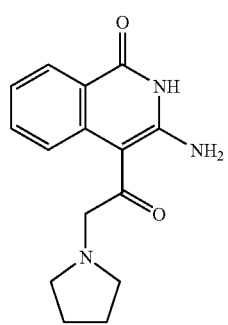
14
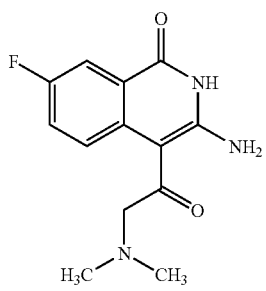
15
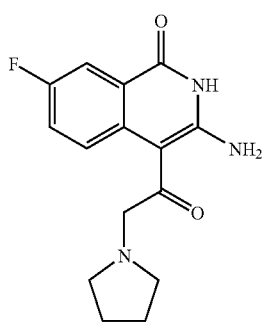
16
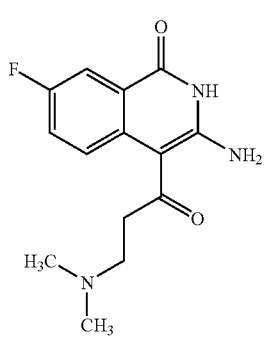
-continued
17
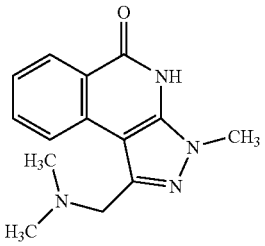
18
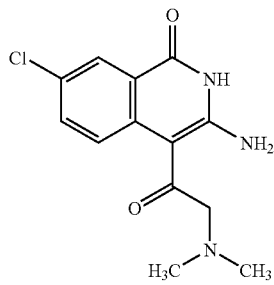
19
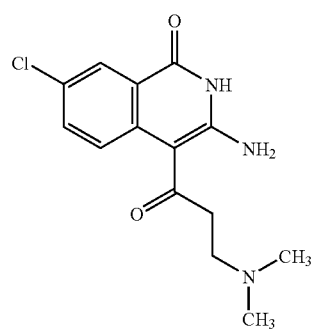
20
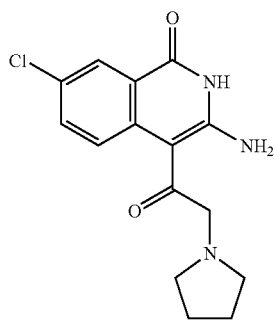
21
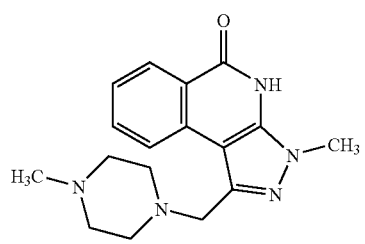

-continued
22
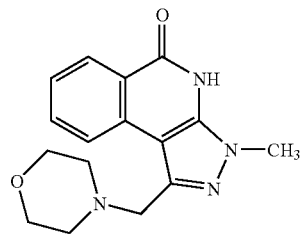
23
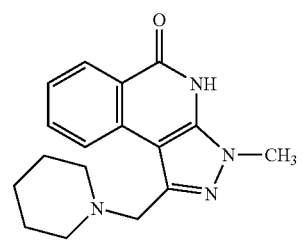
24
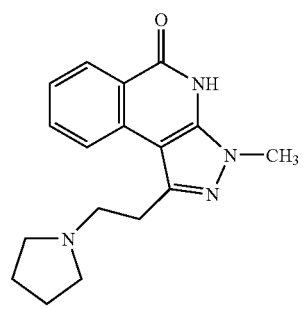
25
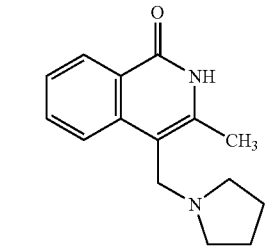
26
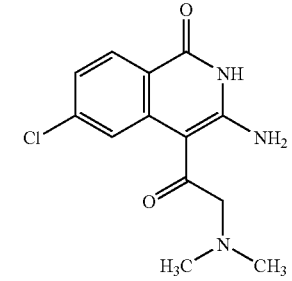
27
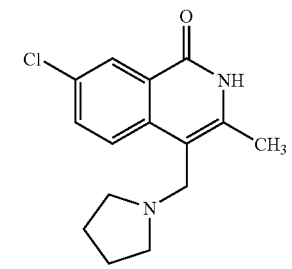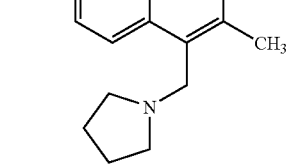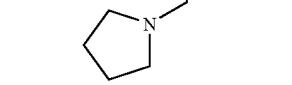
-continued
28
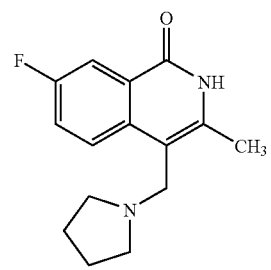
29
missing number
30
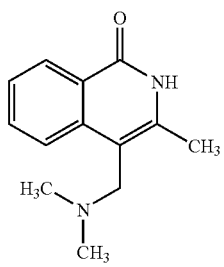
31
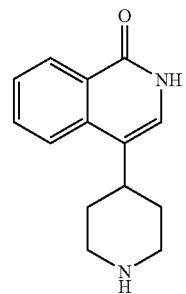
32
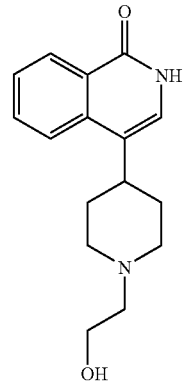
33
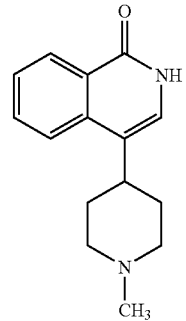

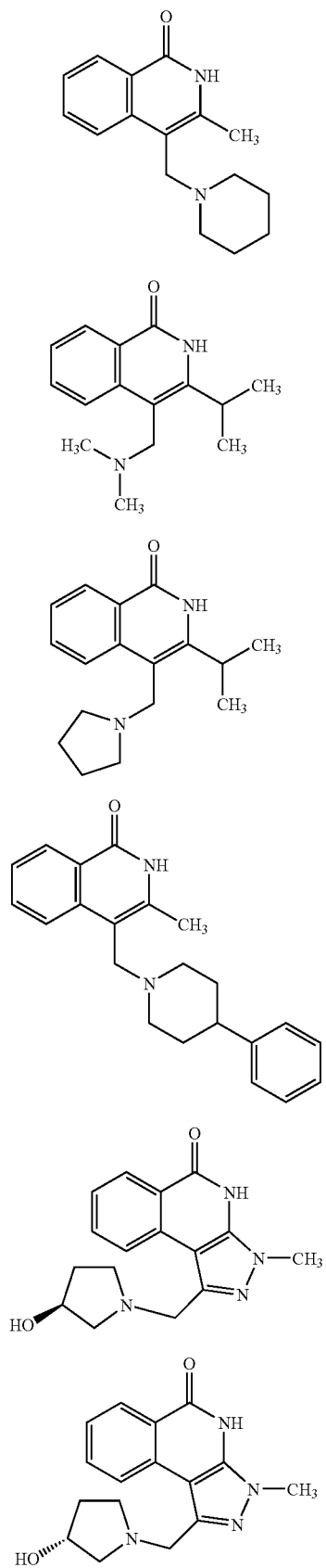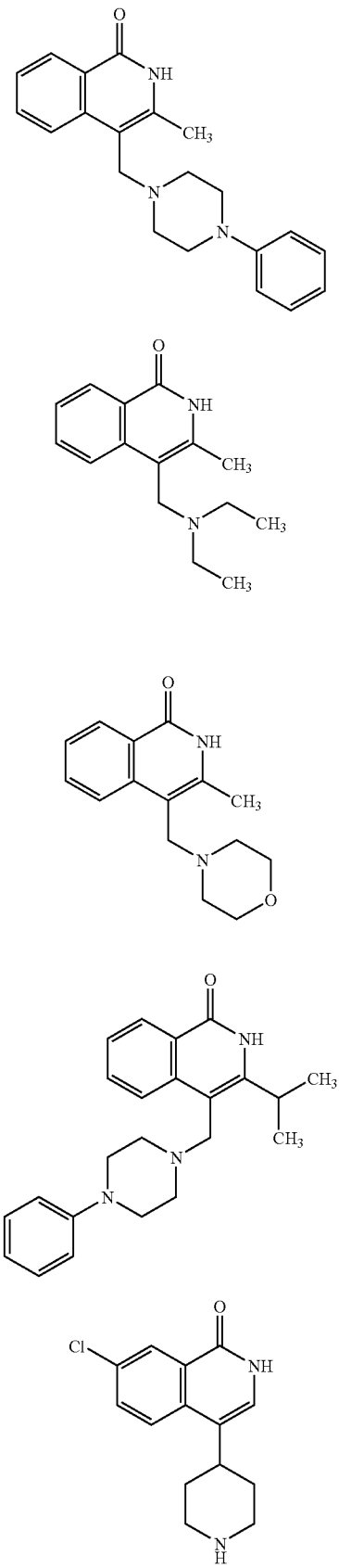

| 45 | 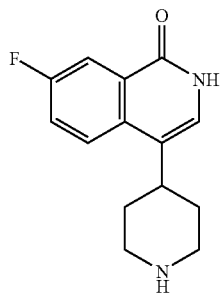 | 46 |
|---|---|---|
| | 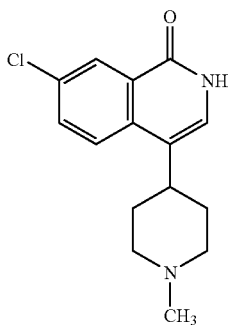 | 47 |
| | 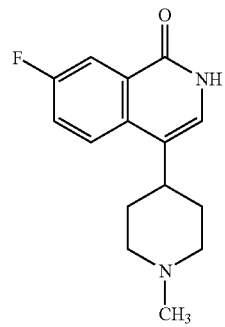 | 48 |
| | 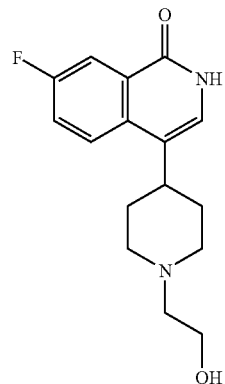 | 49 |
| | 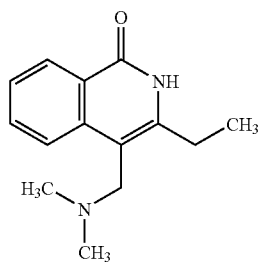 | |
| 50 | 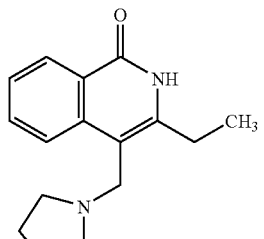 |
|---|---|
| 51 | 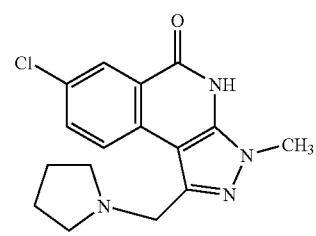 |
| 52 | 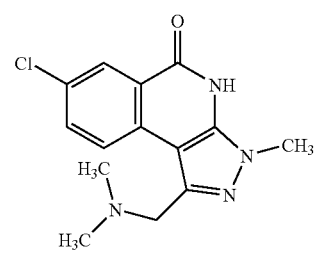 |
| 53 | 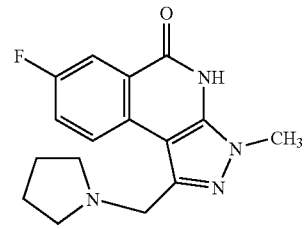 |
| 54 | 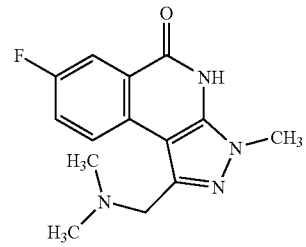 |
| 55 | 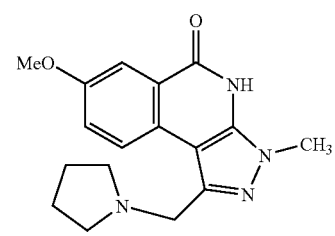 |

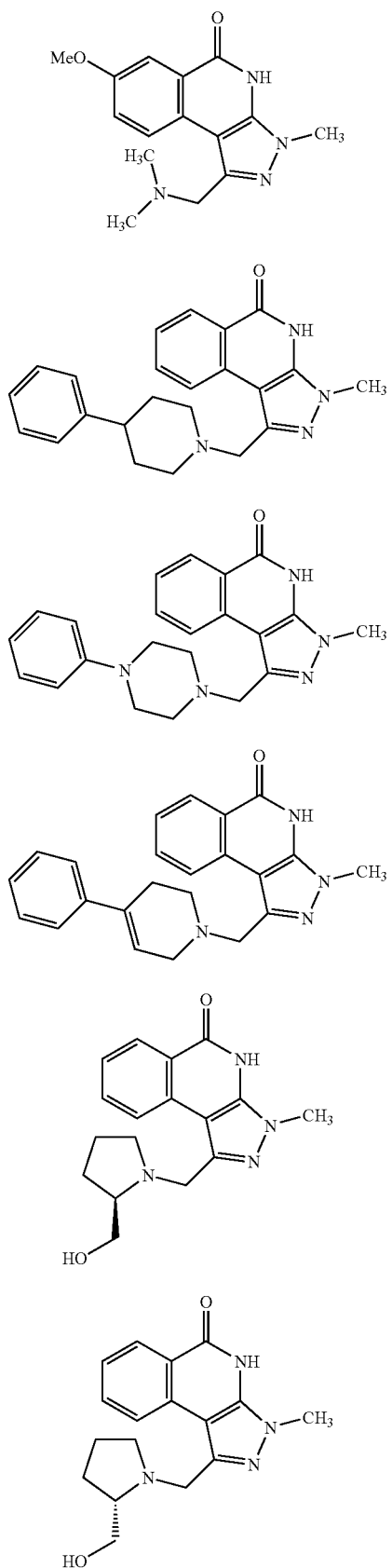
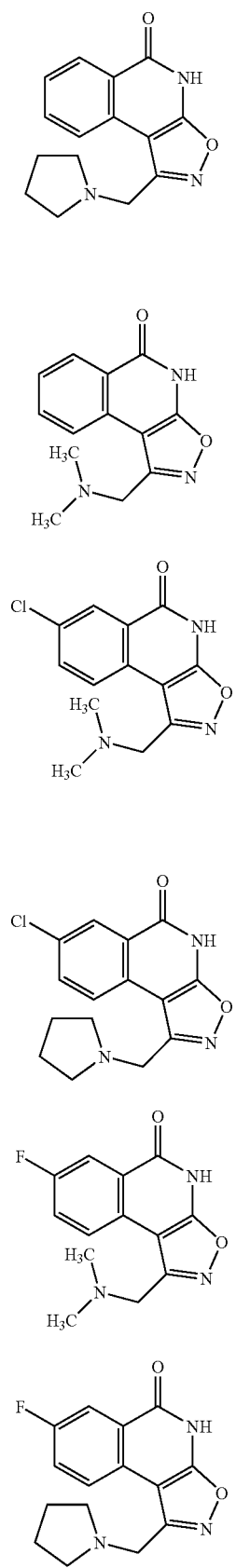

68 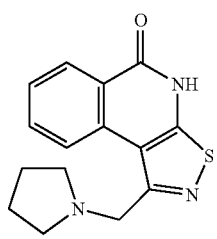
69 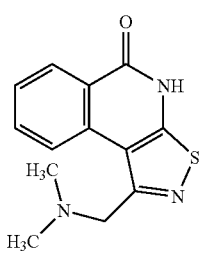
70 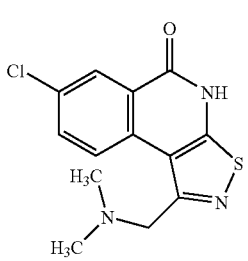
71 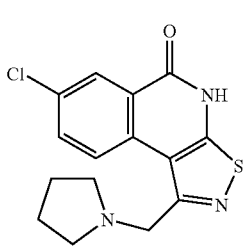
72 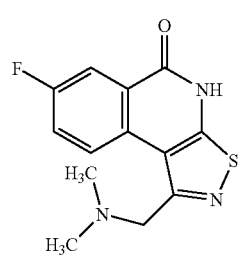
73 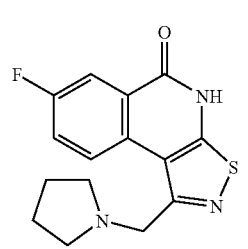
74 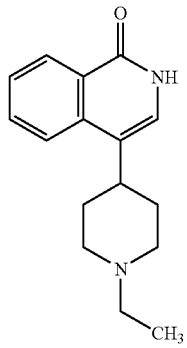
Examples 75-90 are missing numbers.
91 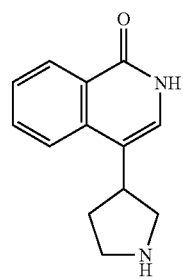
92 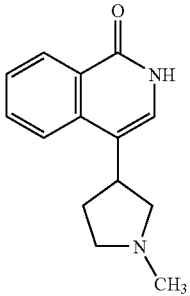
93 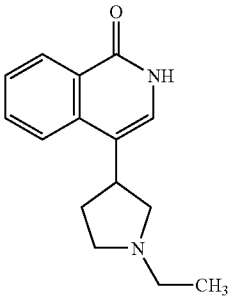
94 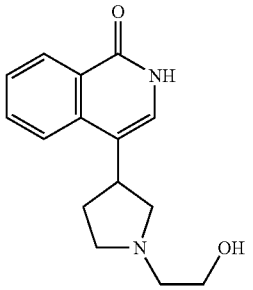

-continued
95
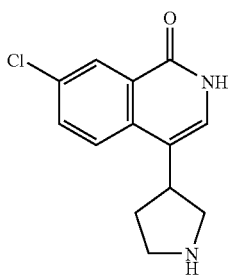
96
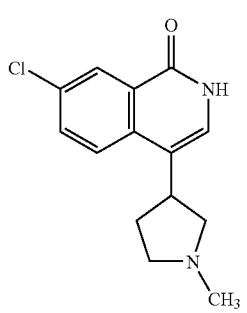
97
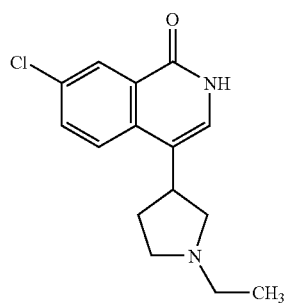
98
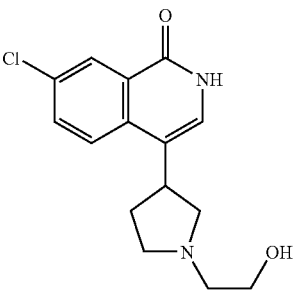
99
-continued
100
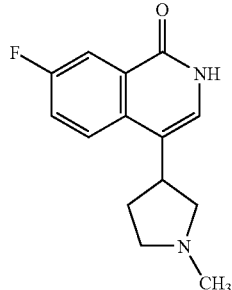
101
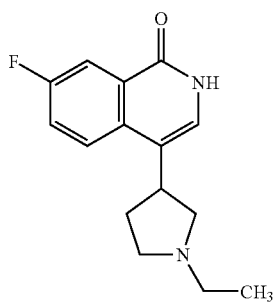
102
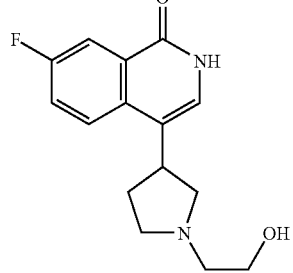
Examples 103-121 are missing numbers.
121 missing number
122
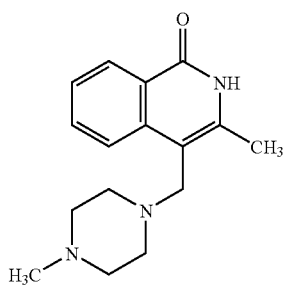
123
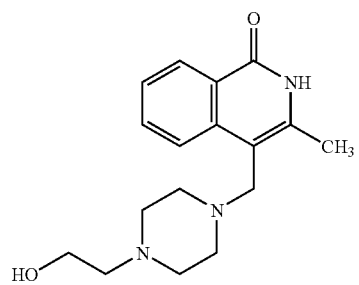

-continued
124
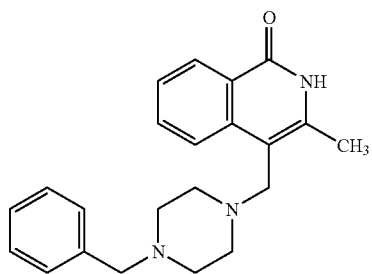
125
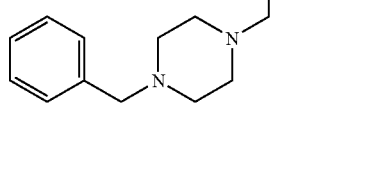
126
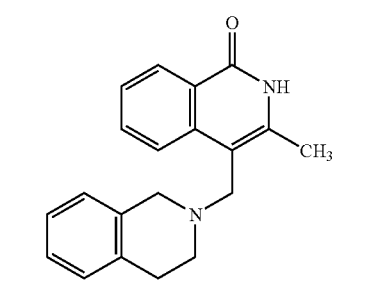
127
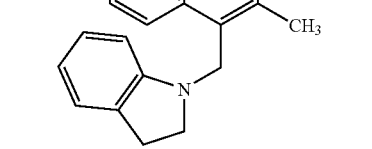
128
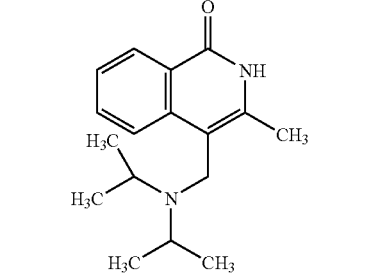
-continued
129
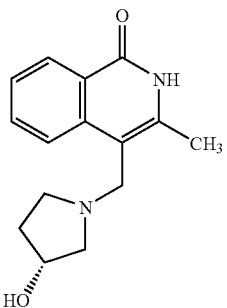
130
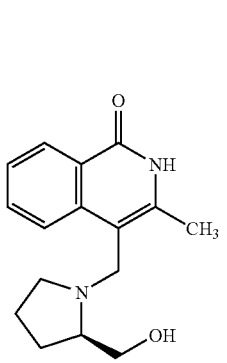
131
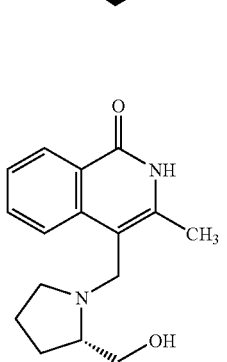
132
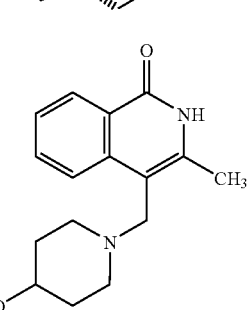
133
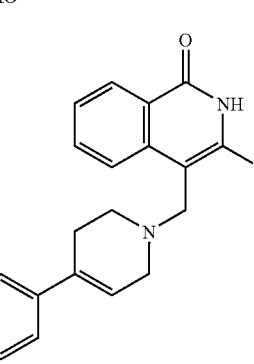

-continued
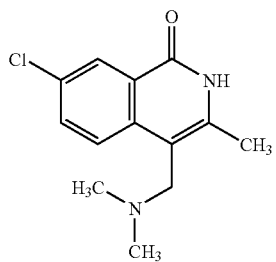
134
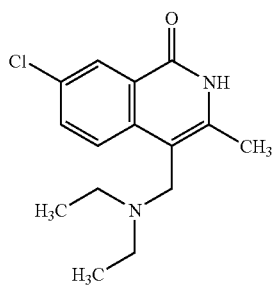
135
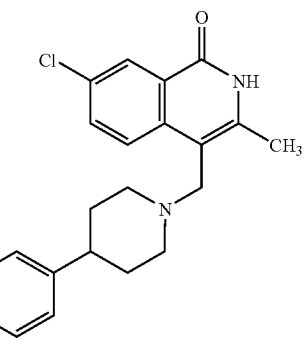
136
137
138
-continued
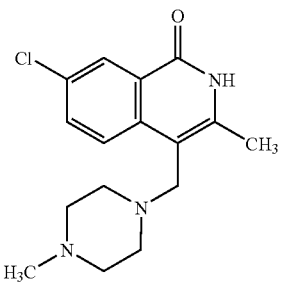
139
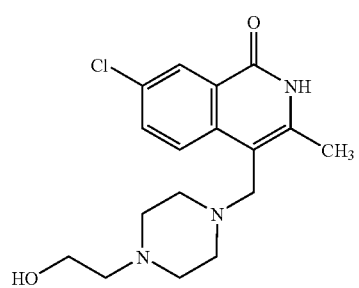
140
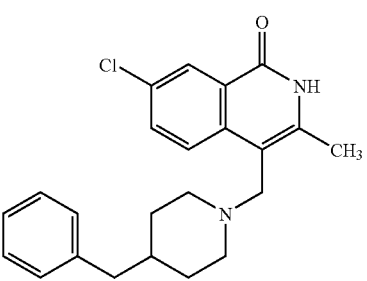
141
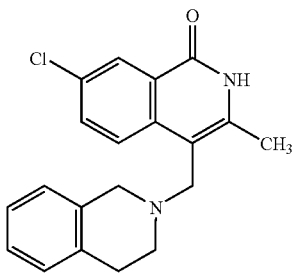
142
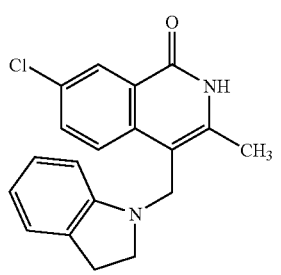
143

144 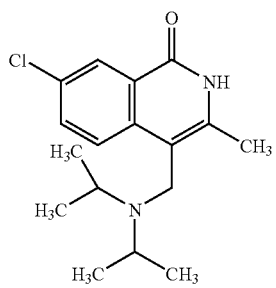
145 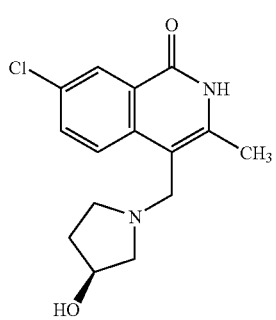
146 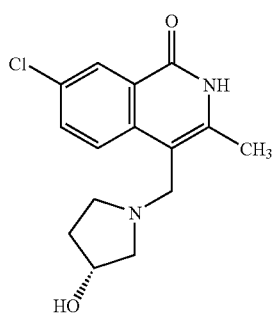
147 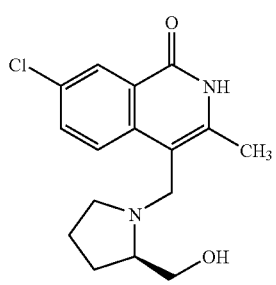
148 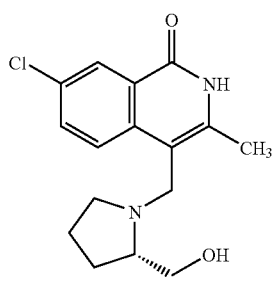
149 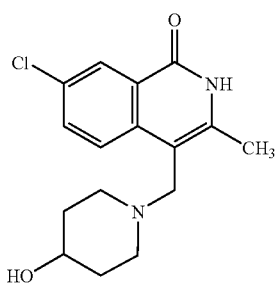
150 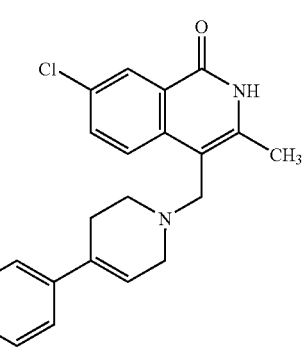
151 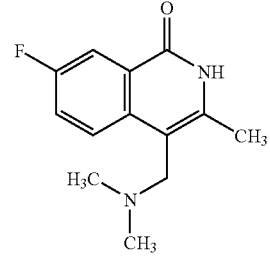
152 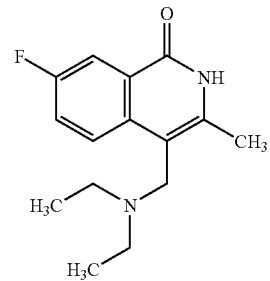
153 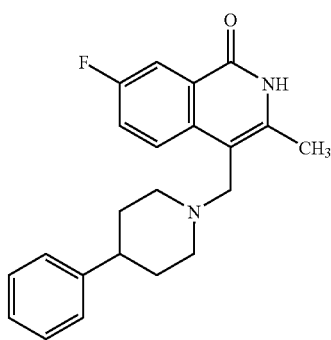

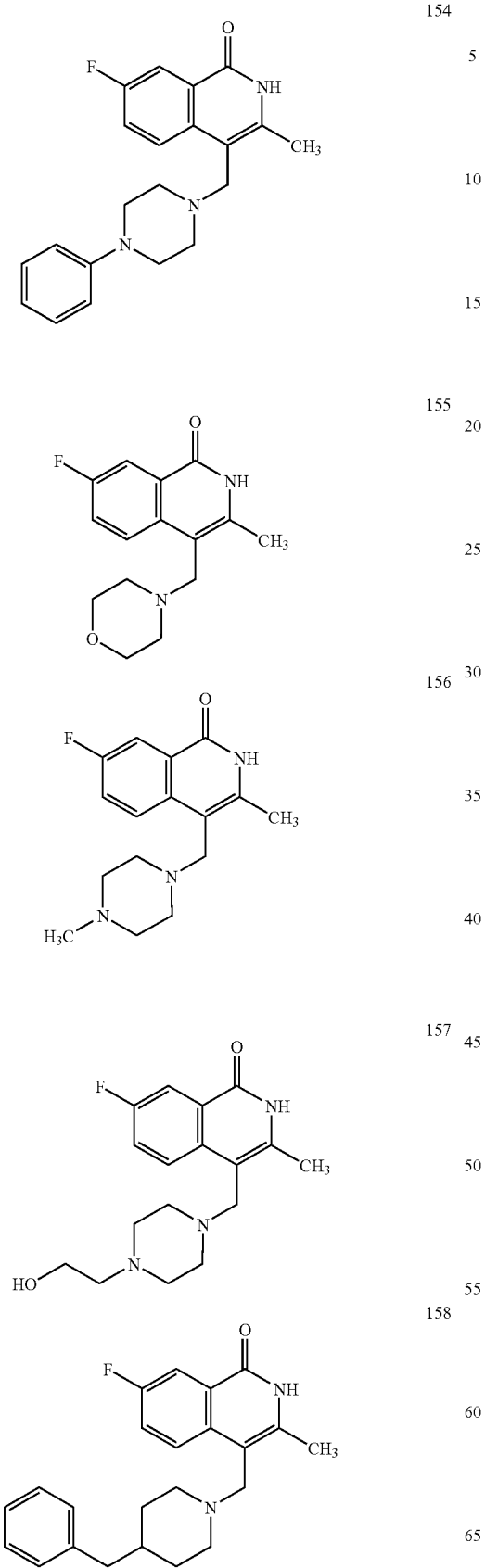
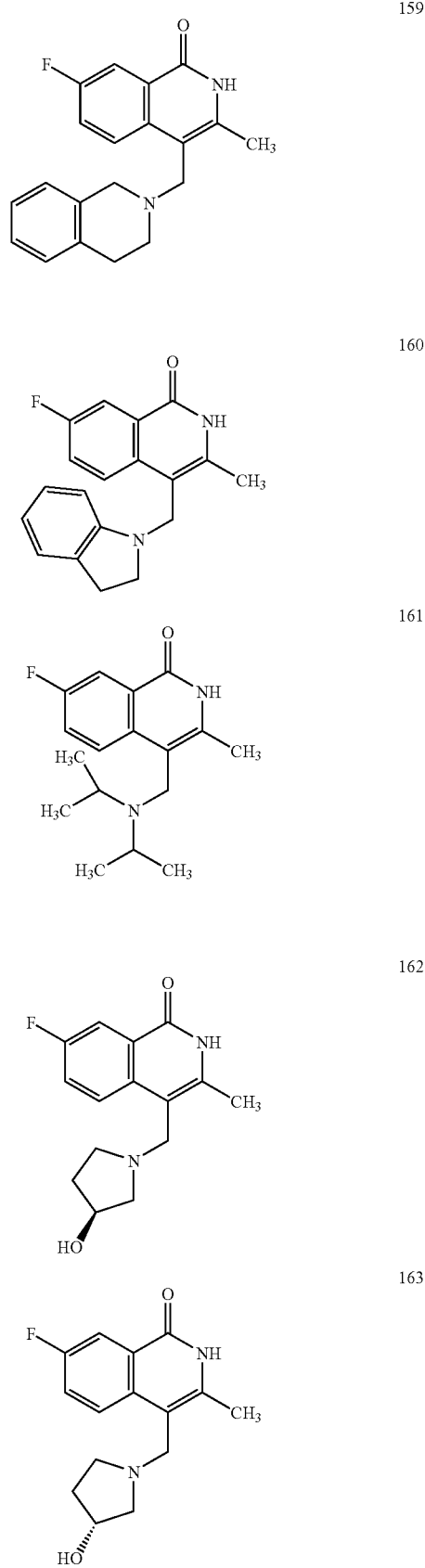

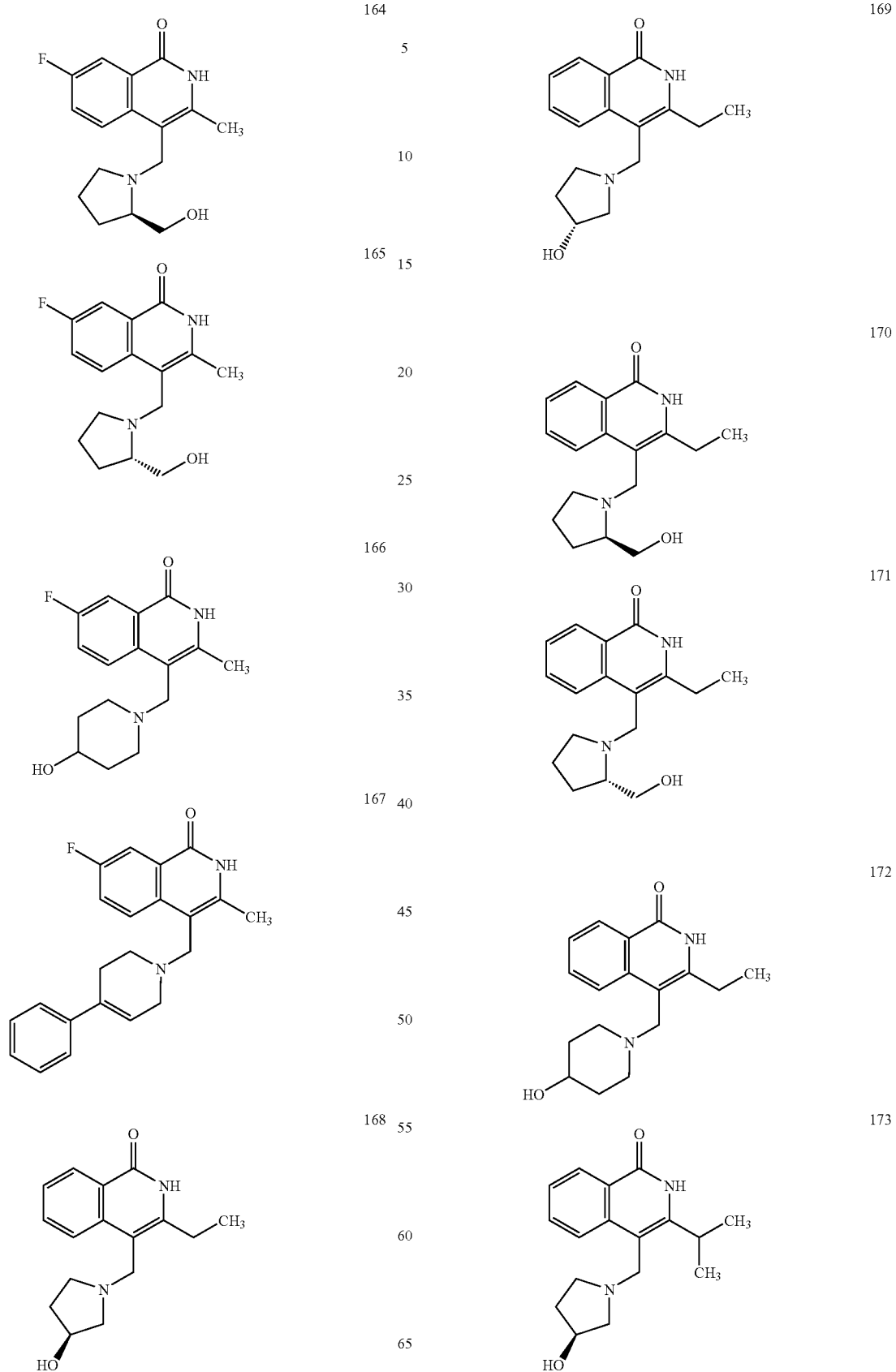

113                                              114
-continued                                       -continued
174                                              179
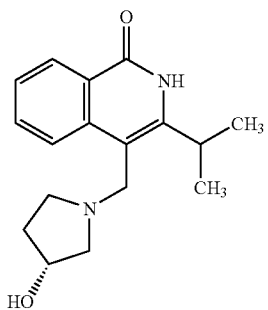                             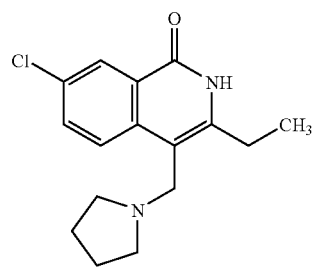
175                                              180
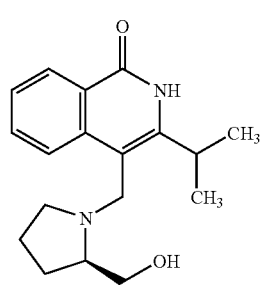                             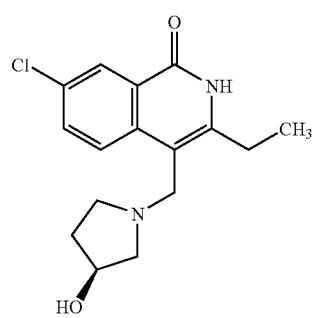
176                                              181
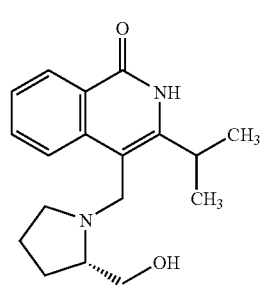                             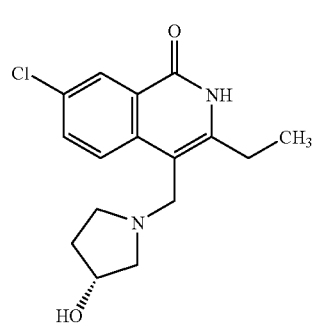
177                                              182
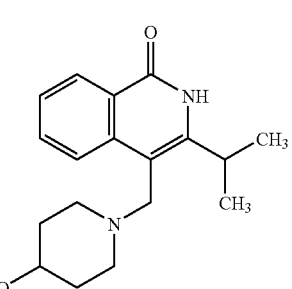                             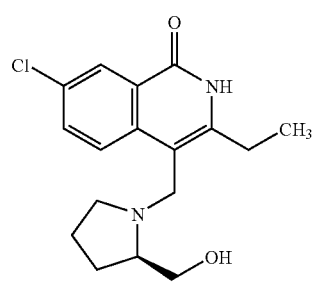
178                                              183
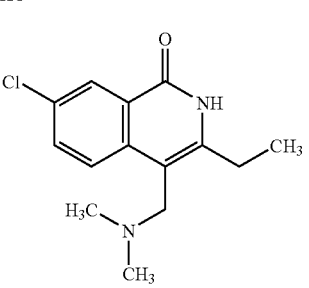                             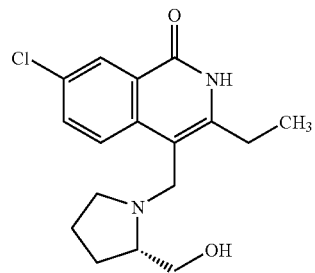

| 115 | 116 |
|---|---|
| -continued | -continued |
184
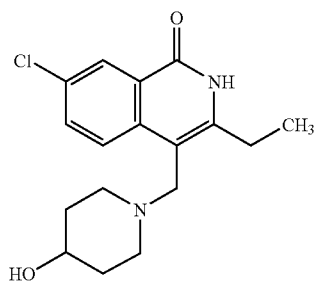
189
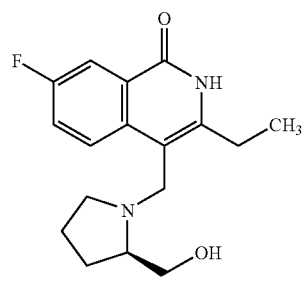
185
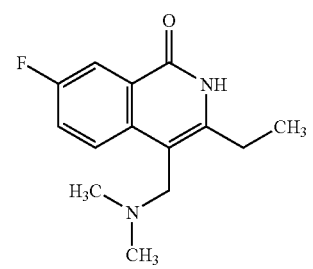
190
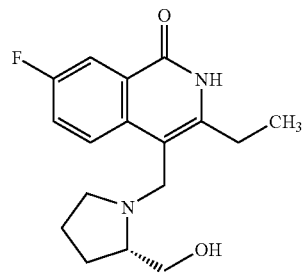
186
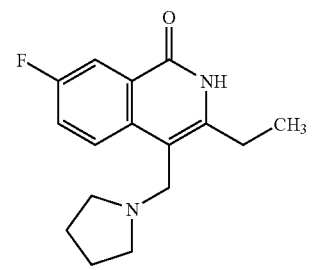
191
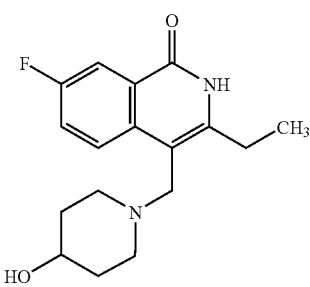
187
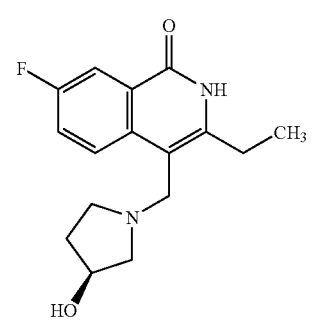
192
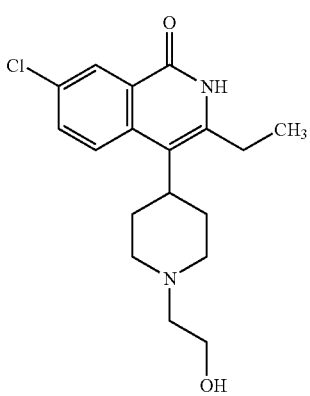
188
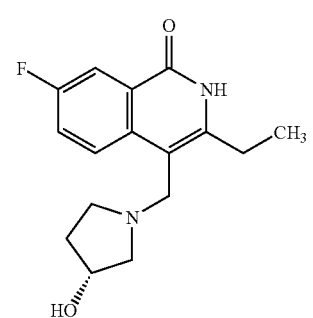
193
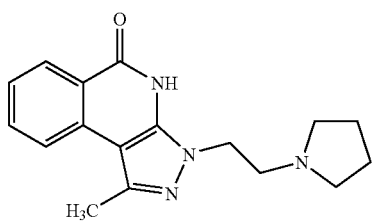

-continued
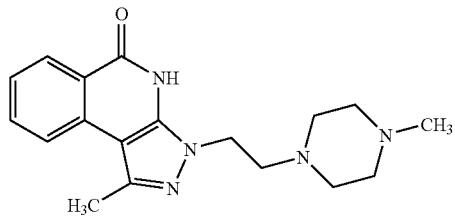
194
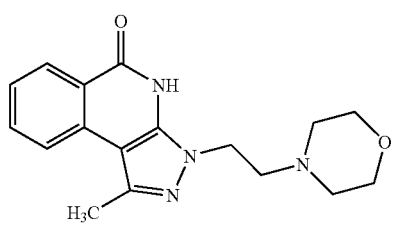
195
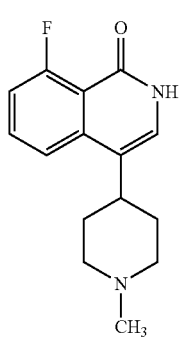
196
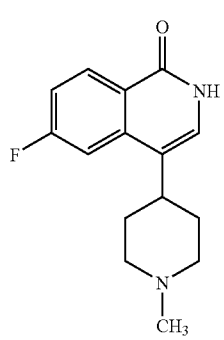
197
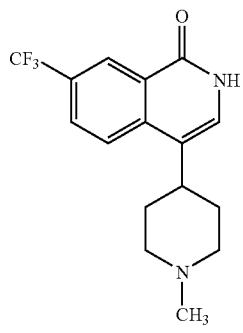
198
-continued
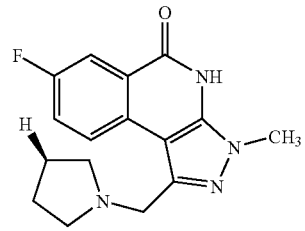
199
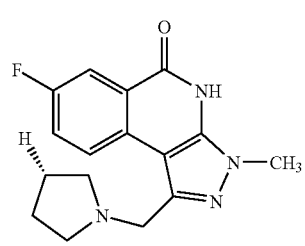
200
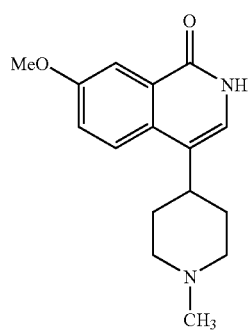
201
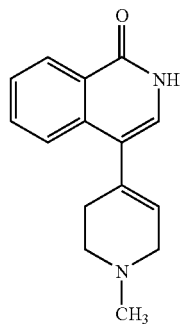
202
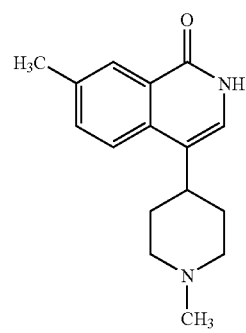
203

-continued
204
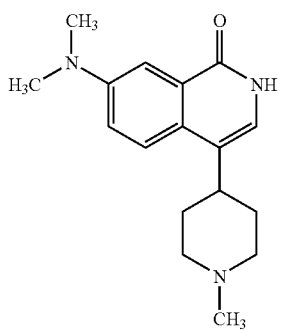
205
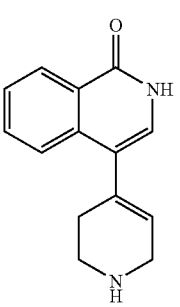
206
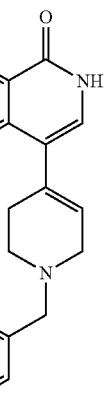
207
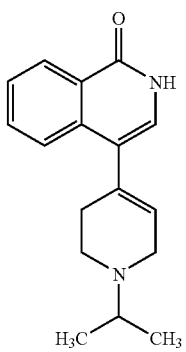
-continued
208
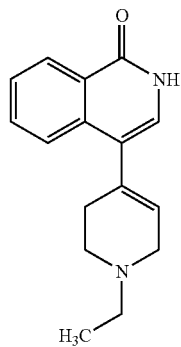
209
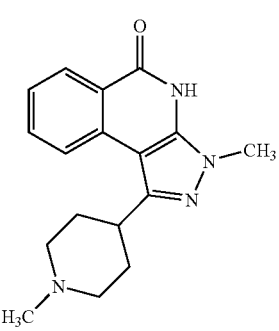
210
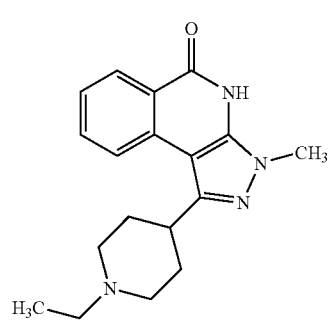
211
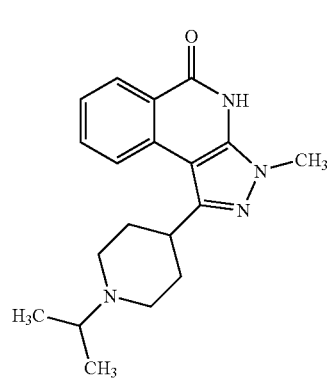

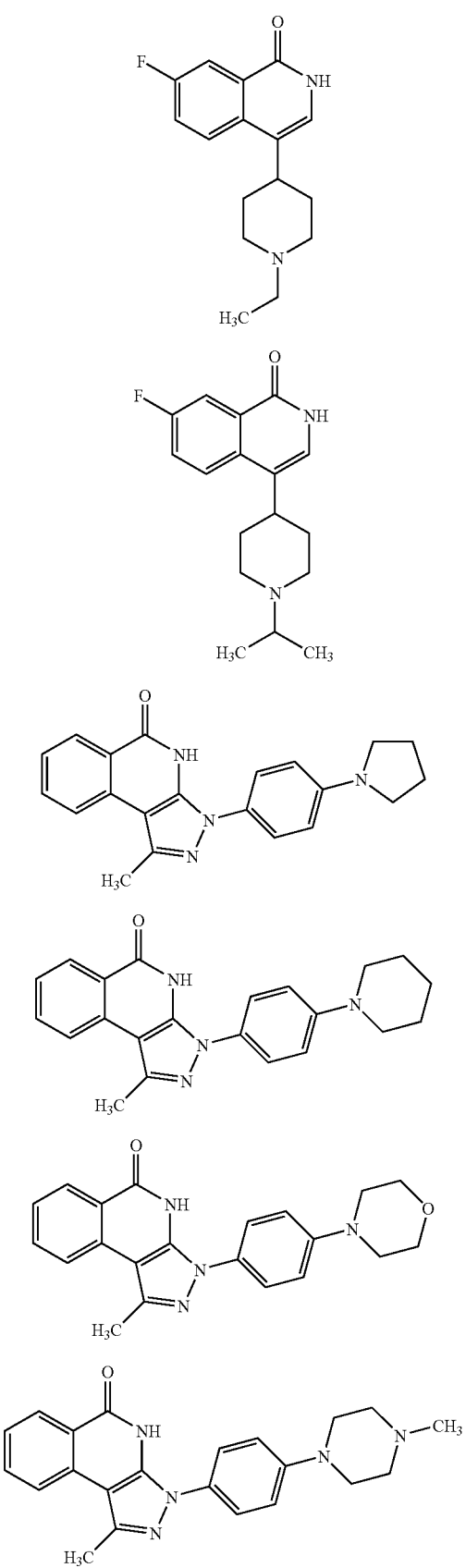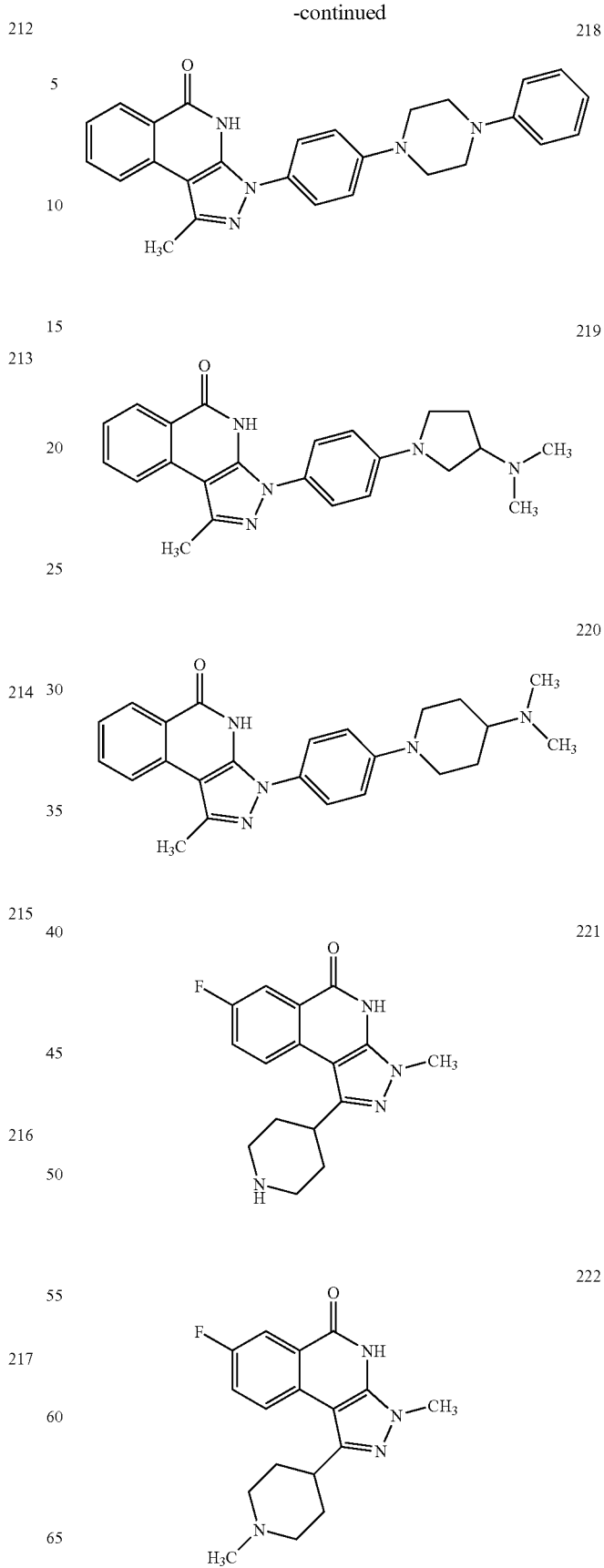

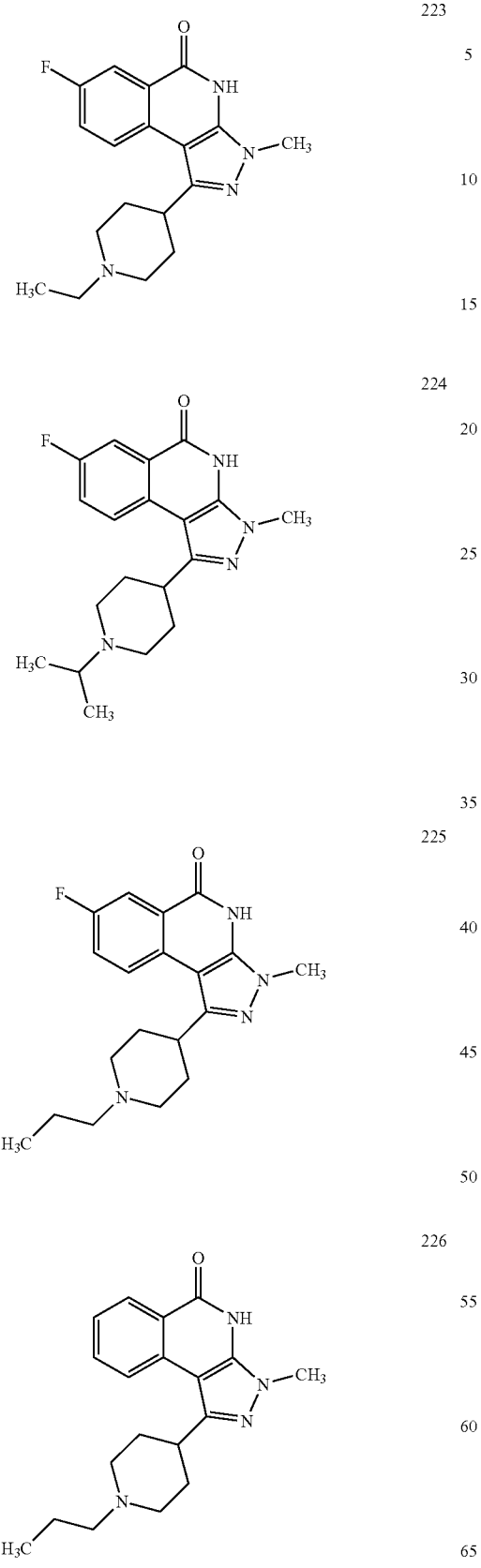
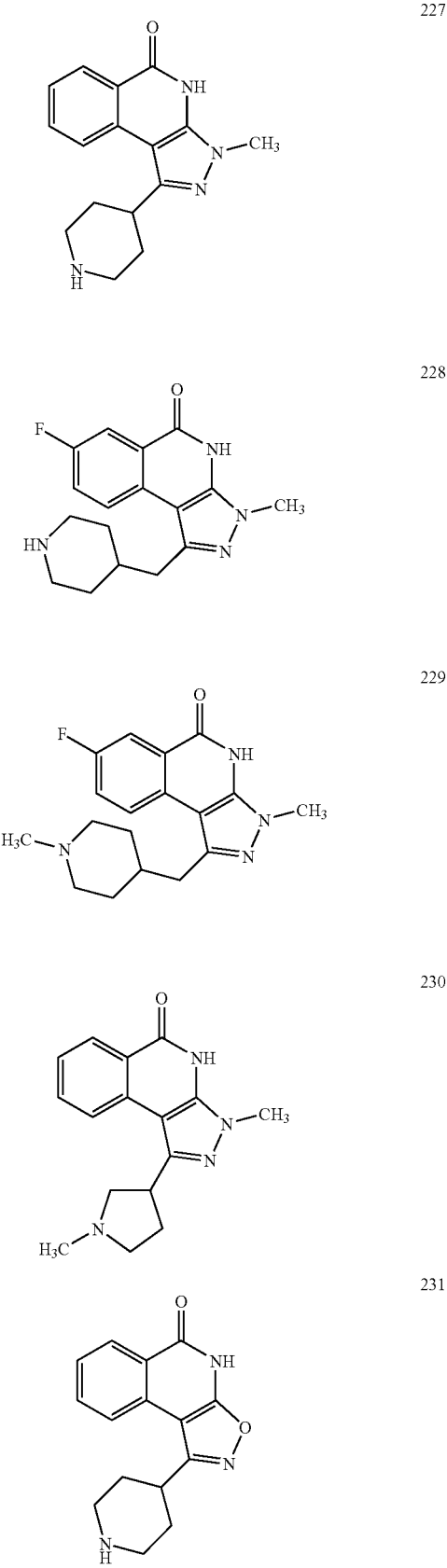

-continued

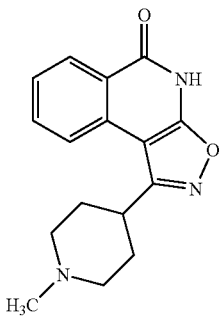

232

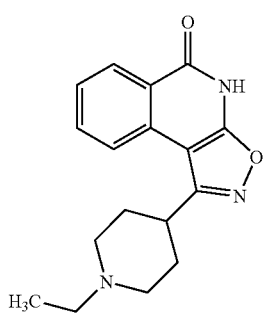

233

Experimental Example

PARP Enzyme Activity Inhibitory Action

As an enzyme source, recombinant human PARP (4667-02X, Trevigen) was used. A poly ADP-ribosilation reaction was started by adding $^3$H-NAD (1.85 kBq, NAD [adenine-2,8-$^3$H], Daiichi Chemicals Co., Ltd.) and activated DNA (0.02 mg/mL, 4667-03X, Trevigen) and then the enzyme source to an enzyme reaction buffer (10 mM Tris/HCl (pH 8.0), 1 mM MgCl$_2$, 28 mM KCl, 28 mM NaCl). After incubation at 25° C. for 15 min., the reaction was stopped by adding 20% trichloroacetic acid, and the resulting acid insoluble fraction was adsorbed to a GF/B filter. Then, the filter was washed several times with 5% trichloroacetic acid, and the radioactivity on the filter was measured with a liquid scintillation counter.

The results are shown in Table 1. The PARP activity was determined by subtracting the radioactivity of an enzyme source non-addition sample as a blank value, and a 50% enzyme inhibitory value (IC$_{50}$ value) of each test compound was calculated with the radioactivity of a compound non-addition sample as 100%.

TABLE 1

| Test compound | PARP enzyme inhibitory activity IC$_{50}$ (nM) |
| --- | --- |
| Ex. 1 | 43 |
| Ex. 7 | 32 |
| Ex. 14 | 40 |
| Ex. 21 | 143 |
| Ex. 25 | 67 |
| Ex. 27 | 39 |
| Ex. 28 | 45 |
| Ex. 31 | 31 |
| Ex. 32 | 34 |
| Ex. 33 | 40 |
| Ex. 44 | 22 |
| Ex. 45 | 22 |
| Ex. 46 | 37 |

TABLE 1-continued

| Test compound | PARP enzyme inhibitory activity IC$_{50}$ (nM) |
| --- | --- |
| Ex. 47 | 23 |
| Ex. 48 | 24 |
| Ex. 209 | 43 |
| Ex. 210 | 25 |
| Ex. 212 | 47 |
| Ex. 221 | 30 |
| Ex. 222 | 44 |
| Ex. 223 | 30 |
| Ex. 225 | 42 |
| Ex. 226 | 47 |
| Control drug (DPQ) | 1000 |

DPQ=3,4-dihydro-5-[4-(1-piperidinyl)-butoxy]-1(2H)-isoquinolinone (PARP inhibitor described in each of WO99/08680 and WO99/11649)

From above-mentioned results, it has recognized that the compounds shown in Examples of the present invention have superior PARP inhibitory activity as compared to known compounds.

INDUSTRIAL APPLICABILITY

The compound of the above-mentioned formula (I) or (II), an optical isomer thereof, a pharmaceutically acceptable salt thereof, a hydrate thereof, a water adduct thereof and a solvate thereof are stable in aqueous solutions, have a potent PARP inhibitory activity as compared to known compounds, and are useful as a therapeutic drug of cerebral infarction, particularly acute cerebral infarction.

This application is based on a patent application No. 340174/2002 filed in Japan, the contents of which are hereby incorporated by reference.

The invention claimed is:

1. An isoquinoline compound represented by the following formula (I)

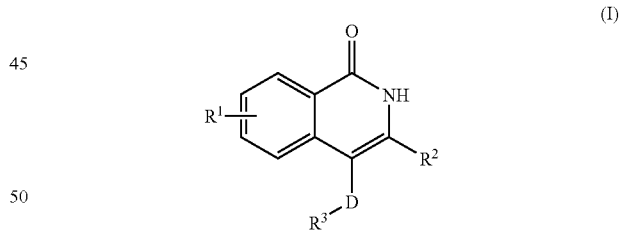

(I)

wherein $R^1$ is a hydrogen atom, a halogen atom, alkyl, alkoxy, haloalkyl, a hydroxyl group, amino, alkylamino, dialkylamino, nitro, cyano, acyl, carboxyl, alkoxycarbonyl, carbamoyl, N-alkylcarbamoyl, N,N-dialkylcarbamoyl, acylamino, diacylamino, thiol, alkylthio, alkoxycarbonylamino, sulfamoyl, N-alkylsulfamoyl, N,N-dialkylsulfamoyl or alkoxyalkyloxy;

$R^2$ is a hydrogen atom, alkyl or amino;

D is void, —C(O)—(CH$_2$)$_n$— wherein n is an integer of 0 to 7, or straight chain or branched chain alkylene having 1 to 8 carbon atoms, provided that when D is methylene, then $R^2$ is alkyl and when D is void, then $R^2$ is a hydrogen atom; and R³ is amino, monoalkylamino, dialkylamino, or a group selected from the following formulas (a), (b), (c) and (d), provided that when D is void, then R³ is (a) or (d) and when n is 0, then R³ is (a),

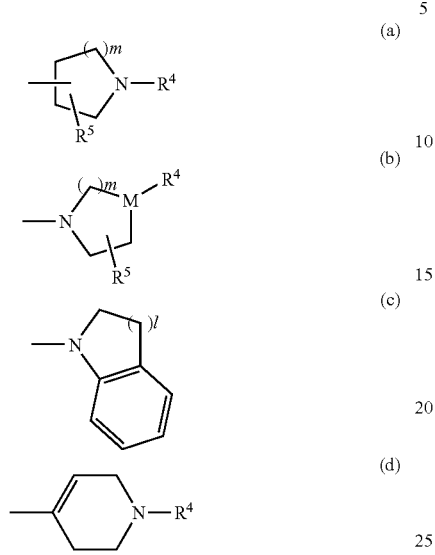

wherein
m is an integer of 1 to 3,
l is an integer of 1 to 3,
R⁴ is void, a hydrogen atom, alkyl, hydroxyalkyl, amino, monoalkylamino, dialkylamino, alkoxycarbonyl, alkylsulfonyl, acyl, acylamino, aryl optionally having substituent(s), heteroaryl optionally having substituent(s), arylalkyl optionally having substituent(s), heteroarylalkyl optionally having substituent(s), sulfamoyl or alkylsulfonylamino,
R⁵ is a hydrogen atom, a hydroxyl group, alkyl, hydroxyalkyl or ketone, and
M is —CH—, —C═C—, a nitrogen atom, an oxygen atom or a sulfur atom;
an optically active form thereof, a pharmaceutically acceptable salt thereof, a hydrate thereof, a water adduct thereof or a solvate thereof.

2. The isoquinoline compound of claim 1, wherein, in the formula (I),
R¹ is a hydrogen atom, a halogen atom, alkyl having 1 to 4 carbon atoms, alkoxy having 1 to 4 carbon atoms, haloalkyl having 1 to 4 carbon atoms, a hydroxyl group, amino, dialkylamino having 1 to 4 carbon atoms, nitro, cyano, acyl having 1 to 4 total carbon atoms, carboxyl, alkoxycarbonyl having 1 to 4 carbon atoms, carbamoyl, N-alkylcarbamoyl, N,N-dialkylcarbamoyl, acylamino, diacylamino, thiol, alkylthio, alkoxycarbonylamino, sulfamoyl, N-alkylsulfamoyl, N,N-dialkylsulfamoyl or alkoxyalkyloxy;
R² is a hydrogen atom, alkyl having 1 to 4 carbon atoms or amino;
D is void, —C(O)—(CH₂)ₙ— wherein n is an integer of 0 to 7, or straight chain or branched chain alkylene having 1 to 8 carbon atoms, provided that when D is methylene, then R² is alkyl having 1 to 4 carbon atoms and when D is void, then R² is a hydrogen atom; and
R³ is amino, monoalkylamino having 1 to 4 carbon atoms, dialkylamino having 1 to 4 carbon atoms, or a group selected from the formulas (a), (b), (c) and (d), provided that when D is void, then R³ is (a) or (d) and when n is 0, then R³ is (a),
wherein
m is an integer of 1 to 3,
l is an integer of 1 to 3,
R⁴ is a hydrogen atom, alkyl having 1 to 4 carbon atoms, hydroxyalkyl having 1 to 4 carbon atoms, amino, monoalkylamino having 1 to 4 carbon atoms, dialkylamino having 1 to 4 carbon atoms, alkoxycarbonyl having 1 to 4 carbon atoms, alkylsulfonyl having 1 to 4 carbon atoms, acyl, acylamino, aryl optionally having substituent(s), heteroaryl optionally having substituent(s), arylalkyl optionally having substituent(s), heteroarylalkyl optionally having substituent(s), sulfamoyl or alkylsulfonylamino,
R⁵ is a hydrogen atom, a hydroxyl group, alkyl having 1 to 4 carbon atoms, hydroxyalkyl or ketone, and
M is —CH—, —C═C—, a nitrogen atom, an oxygen atom or a sulfur atom;
an optically active form thereof, a pharmaceutically acceptable salt thereof, a hydrate thereof, a water adduct thereof or a solvate thereof.

3. The isoquinoline compound of claim 1, wherein, in the formula (I),
R¹ is a hydrogen atom, a halogen atom, alkyl having 1 to 4 carbon atoms or alkoxy having 1 to 4 carbon atoms;
R² is a hydrogen atom or alkyl having 1 to 4 carbon atoms;
D is void or straight chain or branched chain alkylene having 1 to 5 carbon atoms, provided that when D is methylene, then R² is alkyl having 1 to 4 carbon atoms and when D is void, then R² is a hydrogen atom; and
R³ is dialkylamino having 1 to 4 carbon atoms or a group selected from the formulas (a), (b) and (d), provided that when D is void, then R³ is (a) or (d),
wherein
m is an integer of 1 to 3,
R⁴ is a hydrogen atom, alkyl having 1 to 4 carbon atoms, hydroxyalkyl having 1 to 4 carbon atoms, aryl optionally having substituent(s), heteroaryl optionally having substituent(s), arylalkyl optionally having substituent(s), heteroarylalkyl optionally having substituent(s),
R⁵ is a hydrogen atom, a hydroxyl group, alkyl having 1 to 4 carbon atoms or hydroxyalkyl, and
M is —CH—, a nitrogen atom or oxygen atom;
an optically active form thereof, a pharmaceutically acceptable salt thereof, a hydrate thereof, a water adduct thereof or a solvate thereof.

4. The isoquinoline compound of claim 1, wherein, in the formula (I),
R¹ is a hydrogen atom, a halogen atom, alkyl having 1 to 4 carbon atoms or alkoxy having 1 to 4 carbon atoms;
R² is a hydrogen atom;
D is void; and
R³ is the formula (a) or (d),
wherein
m is an integer of 1 to 3,
l is an integer of 1 to 3,
R⁴ is a hydrogen atom, alkyl having 1 to 4 carbon atoms, hydroxyalkyl having 1 to 4 carbon atoms, aryl optionally having substituent(s), heteroaryl optionally having substituent(s), arylalkyl optionally having substituent(s), heteroarylalkyl optionally having substituent(s), and $R^5$ is a hydrogen atom, a hydroxyl group, alkyl having 1 to 4 carbon atoms or hydroxyalkyl having 1 to 4 carbon atoms;
an optically active form thereof, a pharmaceutically acceptable salt thereof, a hydrate thereof, a water adduct thereof or a solvate thereof.

5. The isoquinoline compound of claim 1, wherein, in the formula (I),
$R^1$ is a hydrogen atom, a halogen atom, alkyl having 1 to 4 carbon atoms or alkoxy having 1 to 4 carbon atoms;
$R^2$ is a hydrogen atom;
D is void; and
$R^3$ is a group represented by the formula (a),
wherein
m is an integer of 1 to 3,
$R^4$ is a hydrogen atom, alkyl having 1 to 4 carbon atoms or hydroxyalkyl having 1 to 4 carbon atoms, and
$R^5$ is a hydrogen atom, a hydroxyl group, alkyl having 1 to 4 carbon atoms or hydroxyalkyl having 1 to 4 carbon atoms;
an optically active form thereof, a pharmaceutically acceptable salt thereof, a hydrate thereof, a water adduct thereof or a solvate thereof.

6. The isoquinoline compound of claim 1, wherein, in the formula (I),
$R^1$ is a hydrogen atom, a fluorine atom, a chlorine atom, methyl or methoxy;
$R^2$ is a hydrogen atom;
D is void; and
$R^3$ is a group represented by the formula (a),
wherein
m is 2,
$R^4$ is a hydrogen atom, methyl, ethyl or 2-hydroxyethyl, and
$R^5$ is a hydrogen atom;
an optically active form thereof, a pharmaceutically acceptable salt thereof, a hydrate thereof, a water adduct thereof or a solvate thereof.

7. The isoquinoline compound of claim 1, which is selected from
(196) 8-fluoro-4-(1-methylpiperidin-4-yl)-2H-isoquinolin-1-one,
(197) 6-fluoro-4-(1-methylpiperidin-4-yl)-2H-isoquinolin-1-one,
(198) 4-(1-methylpiperidin-4-yl)-7-trifluoromethyl-2H-isoquinolin-1-one,
(201) 7-methoxy-4-(1-methylpiperidin-4-yl)-2H-isoquinolin-1-one,
(202) 4-(1-methyl-1,2,3,6-tetrahydropyridin-4-yl)-2H-isoquinolin-1-one,
(203) 7-methyl-4-(1-methylpiperidin-4-yl)-2H-isoquinolin-1-one,
(204) 7-dimethylamino-4-(1-methylpiperidin-4-yl)-2H-isoquinolin-1-one,
(205) 4-(1,2,3,6-tetrahydropyridin-4-yl)-2H-isoquinolin-1-one,
(206) 4-(1-benzyl-1,2,3,6-tetrahydropyridin-4-yl)-2H-isoquinolin-1-one,
(207) 4-(1-isopropyl-1,2,3,6-tetrahydropyridin-4-yl)-2H-isoquinolin-1-one,
(208) 4-(1-ethyl-1,2,3,6-tetrahydropyridin-4-yl)-2H-isoquinolin-1-one,
(212) 7-fluoro-4-(1-ethylpiperidin-4-yl)-2H-isoquinolin-1-one, and
(213) 7-fluoro-4-(1-isopropylpiperidin-4-yl)-2H-isoquinolin-1-one,
an optically active form thereof, a pharmaceutically acceptable salt thereof, a hydrate thereof, a water adduct thereof or a solvate thereof.

8. The isoquinoline compound of claim 1, wherein, in the formula (I),
$R^1$ is a hydrogen atom, a fluorine atom or a chlorine atom;
$R^2$ is a hydrogen atom;
D is void; and
$R^3$ is a group represented by the formula (a),
wherein
m is 2,
$R^4$ is a hydrogen atom, methyl, ethyl or 2-hydroxyethyl, and
$R^5$ is a hydrogen atom;
an optically active form thereof, a pharmaceutically acceptable salt thereof, a hydrate thereof, a water adduct thereof or a solvate thereof.

9. The isoquinoline compound of claim 1, which is selected from
(31) 4-(piperidin-4-yl)-2H-isoquinolin-1-one,
(32) 4-(1-(2-hydroxyethyl)piperidin-4-yl)-2H-isoquinolin-1-one,
(33) 4-(1-methylpiperidin-4-yl)-2H-isoquinolin-1-one,
(44) 7-chloro-4-(piperidin-4-yl)-2H-isoquinolin-1-one,
(45) 7-fluoro-4-(piperidin-4-yl)-2H-isoquinolin-1-one,
(46) 7-chloro-4-(1-methylpiperidin-4-yl)-2H-isoquinolin-1-one,
(47) 7-fluoro-4-(1-methylpiperidin-4-yl)-2H-isoquinolin-1-one,
(48) 7-fluoro-4-(1-(2-hydroxyethyl)piperidin-4-yl)-2H-isoquinolin-1-one,
(74) 4-(1-ethylpiperidin-4-yl)-2H-isoquinolin-1-one,
(192) 7-chloro-4-(1-(2-hydroxyethyl)piperidin-4-yl)-2H-isoquinolin-1-one, and
(212) 7-fluoro-4-(1-ethylpiperidin-4-yl)-2H-isoquinolin-1-one,
an optically active form thereof, a pharmaceutically acceptable salt thereof, a hydrate thereof, a water adduct thereof or a solvate thereof.

10. The isoquinoline compound of claim 1, wherein, in the formula (I),
$R^1$ is a hydrogen atom, a halogen atom, alkyl, alkoxy, haloalkyl, a hydroxyl group, amino, dialkylamino, nitro, cyano, acyl, carboxyl, alkoxycarbonyl, carbamoyl, N-alkylcarbamoyl, N,N-dialkylcarbamoyl, acylamino, diacylamino, thiol, alkylthio, alkoxycarbonylamino, sulfamoyl, N-alkylsulfamoyl, N,N-dialkylsulfamoyl or alkoxyalkyloxy;
$R^2$ is a hydrogen atom, alkyl or amino;
D is void, —C(O)—(CH$_2$)$_n$— wherein n is an integer of 0 to 7, or straight chain or branched chain alkylene chain having 1 to 8 carbon atoms, provided that when D is methylene, then $R^2$ is alkyl and when D is void, then $R^2$ is a hydrogen atom; and
$R^3$ is amino, monoalkylamino, dialkylamino, or a group selected from the above-mentioned formulas (a), (b) and (c), provided that when D is void, then $R^3$ is (a) and when n is 0, then $R^3$ is (a),
wherein
m is an integer of 1 to 3,
l is an integer of 1 to 3,
$R^4$ is a hydrogen atom, alkyl, hydroxyalkyl, amino, monoalkylamino, dialkylamino, alkoxycarbonyl, alkylsulfonyl, acyl, acylamino, aryl optionally having substituent(s), heteroaryl optionally having substituent(s), arylalkyl optionally having substituent(s), heteroarylalkyl optionally having substituent(s), sulfamoyl or alkylsulfonylamino, $R^5$ is a hydrogen atom, a hydroxyl group, alkyl, hydroxyalkyl or ketone, and M is —CH—, —C≡C—, a nitrogen atom, an oxygen atom or a sulfur atom;

an optically active form thereof, a pharmaceutically acceptable salt thereof, a hydrate thereof, a water adduct thereof or a solvate thereof.

11. The isoquinoline compound of claim 10, wherein, in the formula (I), $R^1$ is a hydrogen atom, a halogen atom, alkyl having 1 to 4 carbon atoms, alkoxy having 1 to 4 carbon atoms, haloalkyl having 1 to 4 carbon atoms, a hydroxyl group, amino, dialkylamino having 1 to 4 carbon atoms, nitro, cyano, acyl having 1 to 4 carbon atoms, carboxyl, alkoxycarbonyl having 1 to 4 carbon atoms, carbamoyl, N-alkylcarbamoyl having 1 to 4 carbon atoms, N,N-dialkylcarbamoyl having 1 to 4 carbon atoms, acylamino having 1 to 4 carbon atoms, diacylamino having 1 to 4 carbon atoms, thiol, alkylthio having 1 to 4 carbon atoms, alkoxycarbonylamino having 1 to 4 carbon atoms, sulfamoyl, N-alkylsulfamoyl having 1 to 4 carbon atoms, N,N-dialkylsulfamoyl having 1 to 4 carbon atoms or alkoxyalkyloxy having 1 to 4 carbon atoms;

$R^2$ is a hydrogen atom, alkyl having 1 to 4 carbon atoms or amino;

D is void, —C(O)—(CH$_2$)$_n$— wherein n is an integer of 0 to 7, or alkylene chain having 1 to 5 carbon atoms, provided that when D is methylene, then $R^2$ is alkyl having 1 to 4 carbon atoms and when D is void, then $R^2$ is a hydrogen atom; and $R^3$ is amino, monoalkylamino having 1 to 4 carbon atoms, dialkylamino having 1 to 4 carbon atoms, or a group selected from the formulas (a), (b) and (c), provided that when D is void, then $R^3$ is a group represented by the formula (a) and when n is 0, then $R^3$ is a group represented by the formula (a), wherein m is an integer of 1 to 3, l is an integer of 1 to 3, $R^4$ is a hydrogen atom, alkyl having 1 to 4 carbon atoms, hydroxyalkyl having 1 to 4 carbon atoms, arylalkyl optionally having substituent(s) or aryl optionally having substituent(s), $R^5$ is a hydrogen atom, a hydroxyl group, alkyl having 1 to 4 carbon atoms, hydroxyalkyl having 1 to 4 carbon atoms, and M is —CH—, —C≡C—, a nitrogen atom or oxygen atom;

an optically active form thereof, a pharmaceutically acceptable salt thereof, a hydrate thereof, a water adduct thereof or a solvate thereof.

12. The isoquinoline compound of claim 10, wherein, in the formula (I), $R^1$ is a hydrogen atom, a halogen atom, alkyl having 1 to 4 carbon atoms or alkoxy having 1 to 4 carbon atoms;

$R^2$ is a hydrogen atom, alkyl having 1 to 4 carbon atoms or amino;

D is void, —C(O)—(CH$_2$)$_n$— wherein n is an integer of 0 to 5, or alkylene chain having 1 to 5 carbon atoms, provided that when D is methylene, then $R^2$ is alkyl having 1 to 4 carbon atoms and when D is void, then $R^2$ is a hydrogen atom; and $R^3$ is amino, monoalkylamino having 1 to 4 carbon atoms, dialkylamino having 1 to 4 carbon atoms, or a group selected from the formulas (a), (b) and (c), provided that when D is void, then $R^3$ is a group represented by the formula (a) and when n is 0, then $R^3$ is a group represented by the formula (a), wherein m is an integer of 1 to 3, l is an integer of 1 to 3, $R^4$ is a hydrogen atom, alkyl having 1 to 4 carbon atoms, hydroxyalkyl having 1 to 4 carbon atoms, arylalkyl optionally having substituent(s) or aryl optionally having substituent(s), $R^5$ is a hydrogen atom, a hydroxyl group, alkyl having 1 to 4 carbon atoms or hydroxyalkyl having 1 to 4 carbon atoms, and M is —CH—, —C≡C— or a nitrogen atom or an oxygen atom;

an optically active form thereof, a pharmaceutically acceptable salt thereof, a hydrate thereof, a water adduct thereof or a solvate thereof.

13. The isoquinoline compound of claim 10, wherein, in the formula (I), $R^1$ is a hydrogen atom, a fluorine atom, a chlorine atom, methyl, or methoxy;

$R^2$ is a hydrogen atom, methyl, ethyl, isopropyl or amino;

D is void, —C(O)—(CH$_2$)$_n$— wherein n is an integer of 0 to 3, or methylene, provided that when D is methylene, then $R^2$ is methyl, ethyl or isopropyl and when D is void, then $R^2$ is a hydrogen atom; and $R^3$ is dimethylamino, diethylamino, diisopropylamino or a group selected from the following formulas (a), (b) and (c), provided that when D is void, then $R^3$ is (a) and when n is 0, then $R^3$ is (a), wherein m is an integer of 1 to 2, l is an integer of 1 to 2, $R^4$ is a hydrogen atom, methyl, ethyl, 2-hydroxyethyl, phenyl or benzyl, $R^5$ is a hydrogen atom, a hydroxyl group or hydroxymethyl, and M is —CH—, —C≡C—, a nitrogen atom or an oxygen atom;

an optically active form thereof, a pharmaceutically acceptable salt thereof, a hydrate thereof, a water adduct thereof or a solvate thereof.

14. The isoquinoline compound of claim 10, which is selected from (1) 3-amino-4-(2-(dimethylamino)acetyl)-2H-isoquinolin-1-one, (2) 3-amino-4-(2-(piperidin-1-yl)acetyl)-2H-isoquinolin-1-one, (3) 3-amino-4-(2-(dimethylamino)acetyl)-5-methyl-2H-isoquinolin-1-one, (4) 3-amino-4-(3-(dimethylamino)propionyl)-2H-isoquinolin-1-one, (5) 3-amino-4-(4-(dimethylamino)butyryl)-2H-isoquinolin-1-one, (6) (R)-3-amino-4-((1-methylpyrrolidin-2-yl)carbonyl)-2H-isoquinolin-1-one, (8) (S)-3-amino-4-((1-methylpyrrolidin-2-yl)carbonyl)-2H-isoquinolin-1-one, (9) 3-amino-4-(3-(pyrrolidin-1-yl)propionyl)-2H-isoquinolin-1-one,

(10) 3-amino-7-methyl-4-((dimethylamino)acetyl)-2H-isoquinolin-1-one,

(11) 3-amino-7-methyl-4-((pyrrolidin-1-yl)acetyl)-2H-isoquinolin-1-one,

(12) 3-amino-4-(3-(dimethylamino)propionyl)-7-methyl-2H-isoquinolin-1-one,

(13) 3-amino-4-((pyrrolidin-1-yl)acetyl)-2H-isoquinolin-1-one,
(14) 3-amino-4-(2-(dimethylamino)acetyl)-7-fluoro-2H-isoquinolin-1-one,
(15) 3-amino-7-fluoro-4-((pyrrolidin-1-yl)acetyl)-2H-isoquinolin-1-one,
(16) 3-amino-4-(3-(dimethylamino)propionyl)-7-fluoro-2H-isoquinolin-1-one,
(18) 3-amino-4-(2-(dimethylamino)acetyl)-7-chloro-2H-isoquinolin-1-one,
(19) 3-amino-4-(3-(dimethylamino)propionyl)-7-chloro-2H-isoquinolin-1-one,
(20) 3-amino-4-(2-(pyrrolidin-1-yl)acetyl)-7-chloro-2H-isoquinolin-1-one,
(25) 3-methyl-4-(pyrrolidin-1-yl)methyl-2H-isoquinolin-1-one,
(26) 3-amino-6-chloro-4-(2-(dimethylamino)acetyl)-2H-isoquinolin-1-one,
(27) 7-chloro-3-methyl-4-((pyrrolidin-1-yl)methyl)-2H-isoquinolin-1-one,
(28) 7-fluoro-3-methyl-4-((pyrrolidin-1-yl)methyl)-2H-isoquinolin-1-one,
(29) 4-((pyrrolidin-1-yl)methyl)-2H-isoquinolin-1-one,
(30) 3-methyl-4-(dimethylaminomethyl)-2H-isoquinolin-1-one,
(31) 4-(piperidin-4-yl)-2H-isoquinolin-1-one,
(32) 4-(1-(2-hydroxyethyl)piperidin-4-yl)-2H-isoquinolin-1-one,
(33) 4-(1-methylpiperidin-4-yl)-2H-isoquinolin-1-one,
(34) 3-methyl-4-(piperidin-1-yl)methyl-2H-isoquinolin-1-one,
(35) 4-dimethylaminomethyl-3-isopropyl-2H-isoquinolin-1-one,
(36) 4-(pyrrolidin-1-yl)methyl-3-isopropyl-2H-isoquinolin-1-one,
(37) 3-methyl-4-((4-phenylpiperidin-1-yl)methyl)-2H-isoquinolin-1-one,
(40) 3-methyl-4-((4-phenylpiperazin-1-yl)methyl)-2H-isoquinolin-1-one,
(41) 3-methyl-4-diethylaminomethyl-2H-isoquinolin-1-one,
(42) 3-methyl-4-(morpholin-4-yl)methyl-2H-isoquinolin-1-one,
(43) 4-(4-phenylpiperazin-1-yl)methyl-3-isopropyl-2H-isoquinolin-1-one,
(44) 7-chloro-4-(piperidin-4-yl)-2H-isoquinolin-1-one,
(45) 7-fluoro-4-(piperidin-4-yl)-2H-isoquinolin-1-one,
(46) 7-chloro-4-(1-methylpiperidin-4-yl)-2H-isoquinolin-1-one,
(47) 7-fluoro-4-(1-methylpiperidin-4-yl)-2H-isoquinolin-1-one,
(48) 7-fluoro-4-(1-(2-hydroxyethyl)piperidin-4-yl)-2H-isoquinolin-1-one,
(49) 4-dimethylaminomethyl-3-ethyl-2H-isoquinolin-1-one,
(50) 4-(pyrrolidin-1-yl)methyl-3-ethyl-2H-isoquinolin-1-one,
(74) 4-(1-ethylpiperidin-4-yl)-2H-isoquinolin-1-one,
(75) 4-(piperidin-4-yl)-3-methyl-2H-isoquinolin-1-one,
(76) 4-(1-methylpiperidin-4-yl)-3-methyl-2H-isoquinolin-1-one,
(77) 4-(1-(2-hydroxyethyl)piperidin-4-yl)-3-methyl-2H-isoquinolin-1-one,
(78) 4-(1-ethylpiperidin-4-yl)-3-methyl-2H-isoquinolin-1-one,
(79) 4-(piperidin-4-yl)-7-chloro-3-methyl-2H-isoquinolin-1-one,
(80) 4-(1-methylpiperidin-4-yl)-7-chloro-3-methyl-2H-isoquinolin-1-one,
(81) 4-(1-(2-hydroxyethyl)piperidin-4-yl)-7-chloro-3-methyl-2H-isoquinolin-1-one,
(82) 4-(1-ethylpiperidin-4-yl)-7-chloro-3-methyl-2H-isoquinolin-1-one,
(83) 4-(piperidin-4-yl)-7-fluoro-3-methyl-2H-isoquinolin-1-one,
(84) 4-(1-methylpiperidin-4-yl)-7-fluoro-3-methyl-2H-isoquinolin-1-one,
(85) 4-(1-(2-hydroxyethyl)piperidin-4-yl)-7-fluoro-3-methyl-2H-isoquinolin-1-one,
(86) 4-(1-ethylpiperidin-4-yl)-7-fluoro-3-methyl-2H-isoquinolin-1-one,
(87) 4-(piperidin-4-yl)-3,7-dimethyl-2H-isoquinolin-1-one,
(88) 4-(1-methylpiperidin-4-yl)-3,7-dimethyl-2H-isoquinolin-1-one,
(89) 4-(1-(2-hydroxyethyl)piperidin-4-yl)-3,7-dimethyl-2H-isoquinolin-1-one,
(90) 4-(1-ethylpiperidin-4-yl)-3,7-dimethyl-2H-isoquinolin-1-one,
(91) 4-(pyrrolidin-3-yl)-2H-isoquinolin-1-one,
(92) 4-(1-methylpyrrolidin-3-yl)-2H-isoquinolin-1-one,
(93) 4-(1-ethylpyrrolidin-3-yl)-2H-isoquinolin-1-one,
(94) 4-(1-(2-hydroxyethyl)pyrrolidin-3-yl)-2H-isoquinolin-1-one,
(95) 4-(pyrrolidin-3-yl)-7-chloro-2H-isoquinolin-1-one,
(96) 4-(1-methylpyrrolidin-3-yl)-7-chloro-2H-isoquinolin-1-one,
(97) 4-(1-ethylpyrrolidin-3-yl)-7-chloro-2H-isoquinolin-1-one,
(98) 4-(1-(2-hydroxyethyl)pyrrolidin-3-yl)-7-chloro-2H-isoquinolin-1-one,
(99) 4-(pyrrolidin-3-yl)-7-fluoro-2H-isoquinolin-1-one,
(100) 4-(1-methylpyrrolidin-3-yl)-7-fluoro-2H-isoquinolin-1-one,
(101) 4-(1-ethylpyrrolidin-3-yl)-7-fluoro-2H-isoquinolin-1-one,
(102) 4-(1-(2-hydroxyethyl)pyrrolidin-3-yl)-7-fluoro-2H-isoquinolin-1-one,
(103) 4-(pyrrolidin-3-yl)-3-methyl-2H-isoquinolin-1-one,
(104) 4-(1-methylpyrrolidin-3-yl)-3-methyl-2H-isoquinolin-1-one,
(105) 4-(1-ethylpyrrolidin-3-yl)-3-methyl-2H-isoquinolin-1-one,
(106) 4-(1-(2-hydroxyethyl)pyrrolidin-3-yl)-3-methyl-2H-isoquinolin-1-one,
(107) 4-(pyrrolidin-3-yl)-7-chloro-3-methyl-2H-isoquinolin-1-one,
(108) 4-(1-methylpyrrolidin-3-yl)-7-chloro-3-methyl-2H-isoquinolin-1-one,
(109) 4-(1-ethylpyrrolidin-3-yl)-7-chloro-3-methyl-2H-isoquinolin-1-one,
(110) 4-(1-(2-hydroxyethyl)pyrrolidin-3-yl)-7-chloro-3-methyl-2H-isoquinolin-1-one,
(111) 4-(pyrrolidin-3-yl)-7-fluoro-3-methyl-2H-isoquinolin-1-one,
(112) 4-(1-methylpyrrolidin-3-yl)-7-fluoro-3-methyl-2H-isoquinolin-1-one,
(113) 4-(1-ethylpyrrolidin-3-yl)-7-fluoro-3-methyl-2H-isoquinolin-1-one,
(114) 4-(1-(2-hydroxyethyl)pyrrolidin-3-yl)-7-fluoro-3-methyl-2H-isoquinolin-1-one,
(115) 4-(pyrrolidin-2-yl)-3-methyl-2H-isoquinolin-1-one,
(116) 4-(1-methylpyrrolidin-2-yl)-3-methyl-2H-isoquinolin-1-one, (117) 4-(1-(2-hydroxyethyl)pyrrolidin-2-yl)-3-methyl-2H-isoquinolin-1-one,
(118) 4-(pyrrolidin-2-yl)-7-chloro-3-methyl-2H-isoquinolin-1-one,
(119) 4-(1-methylpyrrolidin-2-yl)-7-chloro-3-methyl-2H-isoquinolin-1-one,
(120) 4-(pyrrolidin-2-yl)-7-fluoro-3-methyl-2H-isoquinolin-1-one,
(121) 4-(1-methylpyrrolidin-2-yl)-7-fluoro-3-methyl-2H-isoquinolin-1-one,
(122) 3-methyl-4-[(4-methylpiperazin-1-yl)methyl]-2H-isoquinolin-1-one,
(123) 3-methyl-4-[4-(2-hydroxyethyl)piperazin-1-yl]methyl-2H-isoquinolin-1-one,
(124) 3-methyl-4-(4-benzylpiperidin-1-yl)methyl-2H-isoquinolin-1-one,
(125) 3-methyl-4-(1,2,3,4-tetrahydroisoquinolin-2-yl)methyl-2H-isoquinolin-1-one,
(126) 3-methyl-4-(indolin-1-yl)methyl-2H-isoquinolin-1-one,
(127) 3-methyl-4-(diisopropylamino)methyl-2H-isoquinolin-1-one,
(128) (S)-3-methyl-4-(3-hydroxypyrrolidin-1-yl)methyl-2H-isoquinolin-1-one,
(129) (R)-3-methyl-4-(3-hydroxypyrrolidin-1-yl)methyl-2H-isoquinolin-1-one,
(130) (R)-3-methyl-4-(2-hydroxymethylpyrrolidin-1-yl)methyl-2H-isoquinolin-1-one,
(131) (S)-3-methyl-4-(2-hydroxymethylpyrrolidin-1-yl)methyl-2H-isoquinolin-1-one,
(132) 3-methyl-4-(4-hydroxypiperidin-1-yl)methyl-2H-isoquinolin-1-one,
(133) 3-methyl-4-(4-phenyl-1,2,3,6-tetrahydropyridin-1-yl)methyl-2H-isoquinolin-1-one,
(134) 7-chloro-4-dimethylaminomethyl-3-methyl-2H-isoquinolin-1-one,
(135) 7-chloro-4-diethylaminomethyl-3-methyl-2H-isoquinolin-1-one,
(136) 7-chloro-4-(4-phenylpiperidin-1-yl)methyl-3-methyl-2H-isoquinolin-1-one,
(137) 7-chloro-4-(4-phenylpiperazin-1-yl)methyl-3-methyl-2H-isoquinolin-1-one,
(138) 7-chloro-4-(morpholin-4-yl)methyl-3-methyl-2H-isoquinolin-1-one,
(139) 7-chloro-4-(4-methylpiperazin-1-yl)methyl-3-methyl-2H-isoquinolin-1-one,
(140) 7-chloro-4-(4-(2-hydroxyethyl)piperazin-1-yl)methyl-3-methyl-2H-isoquinolin-1-one,
(141) 7-chloro-4-(4-benzylpiperidin-1-yl)methyl-3-methyl-2H-isoquinolin-1-one,
(142) 7-chloro-4-(1,2,3,4-tetrahydroisoquinolin-2-yl)methyl-3-methyl-2H-isoquinolin-1-one,
(143) 7-chloro-4-(indolin-1-yl)methyl-3-methyl-2H-isoquinolin-1-one,
(144) 7-chloro-4-diisopropylaminomethyl-3-methyl-2H-isoquinolin-1-one,
(145) (S)-7-chloro-4-(3-hydroxypyrrolidin-1-yl)methyl-3-methyl-2H-isoquinolin-1-one,
(146) (R)-7-chloro-4-(3-hydroxypyrrolidin-1-yl)methyl-3-methyl-2H-isoquinolin-1-one,
(147) (R)-7-chloro-4-(2-hydroxymethylpyrrolidin-1-yl)methyl-3-methyl-2H-isoquinolin-1-one,
(148) (S)-7-chloro-4-(2-hydroxymethylpyrrolidin-1-yl)methyl-3-methyl-2H-isoquinolin-1-one,
(149) 7-chloro-4-(4-hydroxypiperidin-1-yl)methyl-3-methyl-2H-isoquinolin-1-one,
(150) 7-chloro-4-(4-phenyl-1,2,3,6-tetrahydropyridin-1-yl)methyl-3-methyl-2H-isoquinolin-1-one,
(151) 7-fluoro-4-dimethylaminomethyl-3-methyl-2H-isoquinolin-1-one,
(152) 7-fluoro-4-diethylaminomethyl-3-methyl-2H-isoquinolin-1-one,
(153) 7-fluoro-4-(4-phenylpiperidin-1-yl)methyl-3-methyl-2H-isoquinolin-1-one,
(154) 7-fluoro-4-(4-phenylpiperazin-1-yl)methyl-3-methyl-2H-isoquinolin-1-one,
(155) 7-fluoro-4-(morpholin-4-yl)methyl-3-methyl-2H-isoquinolin-1-one,
(156) 7-fluoro-4-(4-methylpiperazin-1-yl)methyl-3-methyl-2H-isoquinolin-1-one,
(157) 7-fluoro-4-(4-(2-hydroxyethyl)piperazin-1-yl)methyl-3-methyl-2H-isoquinolin-1-one,
(158) 7-fluoro-4-(4-benzylpiperidin-1-yl)methyl-3-methyl-2H-isoquinolin-1-one,
(159) 7-fluoro-4-(1,2,3,4-tetrahydroisoquinolin-2-yl)methyl-3-methyl-2H-isoquinolin-1-one,
(160) 7-fluoro-4-(indolin-1-yl)methyl-3-methyl-2H-isoquinolin-1-one,
(161) 7-fluoro-4-diisopropylaminomethyl-3-methyl-2H-isoquinolin-1-one,
(162) (S)-7-fluoro-4-(3-hydroxypyrrolidin-1-yl)methyl-3-methyl-2H-isoquinolin-1-one,
(163) (R)-7-fluoro-4-(3-hydroxypyrrolidin-1-yl)methyl-3-methyl-2H-isoquinolin-1-one,
(164) (R)-7-fluoro-4-(2-hydroxymethylpyrrolidin-1-yl)methyl-3-methyl-2H-isoquinolin-1-one,
(165) (S)-7-fluoro-4-(2-hydroxymethylpyrrolidin-1-yl)methyl-3-methyl-2H-isoquinolin-1-one,
(166) 7-fluoro-4-(4-hydroxypiperidin-1-yl)methyl-3-methyl-2H-isoquinolin-1-one,
(167) 7-fluoro-4-(4-phenyl-1,2,3,6-tetrahydropyridin-1-yl)methyl-3-methyl-2H-isoquinolin-1-one,
(168) (S)-4-(3-hydroxypyrrolidin-1-yl)methyl-3-ethyl-2H-isoquinolin-1-one,
(169) (R)-4-(3-hydroxypyrrolidin-1-yl)methyl-3-ethyl-2H-isoquinolin-1-one,
(170) (R)-4-(2-hydroxymethylpyrrolidin-1-yl)methyl-3-ethyl-2H-isoquinolin-1-one,
(171) (S)-4-(2-hydroxymethylpyrrolidin-1-yl)methyl-3-ethyl-2H-isoquinolin-1-one,
(172) 4-(4-hydroxypiperidin-1-yl)methyl-3-ethyl-2H-isoquinolin-1-one,
(173) (S)-4-(3-hydroxypyrrolidin-1-yl)methyl-3-isopropyl-2H-isoquinolin-1-one,
(174) (R)-4-(3-hydroxypyrrolidin-1-yl)methyl-3-isopropyl-2H-isoquinolin-1-one,
(175) (R)-4-(2-hydroxymethylpyrrolidin-1-yl)methyl-3-isopropyl-2H-isoquinolin-1-one,
(176) (S)-4-(2-hydroxymethylpyrrolidin-1-yl)methyl-3-isopropyl-2H-isoquinolin-1-one,
(177) 4-(4-hydroxypiperidin-1-yl)methyl-3-isopropyl-2H-isoquinolin-1-one,
(178) 7-chloro-4-dimethylaminomethyl-3-ethyl-2H-isoquinolin-1-one,
(179) 7-chloro-4-(pyrrolidin-1-yl)methyl-3-ethyl-2H-isoquinolin-1-one,
(180) (S)-7-chloro-4-(3-hydroxypyrrolidin-1-yl)methyl-3-ethyl-2H-isoquinolin-1-one,
(181) (R)-7-chloro-4-(3-hydroxypyrrolidin-1-yl)methyl-3-ethyl-2H-isoquinolin-1-one,
(182) (R)-7-chloro-4-(2-hydroxymethylpyrrolidin-1-yl)methyl-3-ethyl-2H-isoquinolin-1-one, (183) (S)-7-chloro-4-(2-hydroxymethylpyrrolidin-1-yl)methyl-3-ethyl-2H-isoquinolin-1-one,
(184) 7-chloro-3-ethyl-4-(4-hydroxypiperidin-1-yl)methyl-2H-isoquinolin-1-one,
(185) 7-fluoro-4-dimethylaminomethyl-3-ethyl-2H-isoquinolin-1-one,
(186) 7-fluoro-4-(pyrrolidin-1-yl)methyl-3-ethyl-2H-isoquinolin-1-one,
(187) (S)-7-fluoro-4-(3-hydroxypyrrolidin-1-yl)methyl-3-ethyl-2H-isoquinolin-1-one,
(188) (R)-7-fluoro-4-(3-hydroxypyrrolidin-1-yl)methyl-3-ethyl-2H-isoquinolin-1-one,
(189) (R)-7-fluoro-4-(2-hydroxymethylpyrrolidin-1-yl)methyl-3-ethyl-2H-isoquinolin-1-one,
(190) (S)-7-fluoro-4-(2-hydroxymethylpyrrolidin-1-yl)methyl-3-ethyl-2H-isoquinolin-1-one,
(191) 7-fluoro-3-ethyl-4-(4-hydroxypiperidin-1-yl)methyl-2H-isoquinolin-1-one, and
(192) 7-chloro-4-(1-(2-hydroxyethyl)piperidin-4-yl)-2H-isoquinolin-1-one,
an optically active form thereof, a pharmaceutically acceptable salt thereof, a hydrate thereof, a water adduct thereof or a solvate thereof.

15. The isoquinoline compound of claim 10, which is selected from
(1) 3-amino-4-(2-(dimethylamino)acetyl)-2H-isoquinolin-1-one,
(2) 3-amino-4-(2-(piperidin-1-yl)acetyl)-2H-isoquinolin-1-one,
(3) 3-amino-4-(2-(dimethylamino)acetyl)-5-methyl-2H-isoquinolin-1-one,
(4) 3-amnino-4-(3-(dimethylamino)propionyl)-2H-isoquinolin-1-one,
(5) 3-amino-4-(4-(dimethylamino)butyryl)-2H-isoquinolin-1-one,
(6) (R)-3-amino-4-((1-methylpyrrolidin-2-yl)carbonyl)-2H-isoquinolin-1-one,
(8) (S)-3-amino-4-((1-methylpyrrolidin-2-yl)carbonyl)-2H-isoquinolin-1-one,
(9) 3-amino-4-(3-(pyrrolidin-1-yl)propionyl)-2H-isoquinolin-1-one,
(10) 3-amino-7-methyl-4-((dimethylamino)acetyl)-2H-isoquinolin-1-one,
(11) 3-amino-7-methyl-4-((pyrrolidin-1-yl)acetyl)-2H-isoquinolin-1-one,
(12) 3-amino-4-(3-(dimethylamino)propionyl)-7-methyl-2H-isoquinolin-1-one,
(13) 3-amino-4-((pyrrolidin-1-yl)acetyl)-2H-isoquinolin-1-one,
(14) 3-amino-4-(2-(dimethylamino)acetyl)-7-fluoro-2H-isoquinolin-1-one,
(15) 3-amino-7-fluoro-4-((pyrrolidin-1-yl)acetyl)-2H-isoquinolin-1-one,
(16) 3-amino-4-(3-(dimethylamino)propionyl)-7-fluoro-2H-isoquinolin-1-one,
(18) 3-amino-4-(2-(dimethylamino)acetyl)-7-chloro-2H-isoquinolin-1-one,
(19) 3-amino-4-(3-(dimethylamino)propionyl)-7-chloro-2H-isoquinolin-1-one,
(20) 3-amino-4-(2-(pyrrolidin-1-yl)acetyl)-7-chloro-2H-isoquinolin-1-one,
(25) 3-methyl-4-(pyrrolidin-1-yl)methyl-2H-isoquinolin-1-one,
(26) 3-amino-6-chloro-4-(2-(dimethylamino)acetyl)-2H-isoquinolin-1-one,
(27) 7-chloro-3-methyl-4-((pyrrolidin-1-yl)methyl)-2H-isoquinolin-1-one,
(28) 7-fluoro-3-methyl-4-((pyrrolidin-1-yl)methyl)-2H-isoquinolin-1-one,
(29) 4-((pyrrolidin-1-yl)methyl)-2H-isoquinolin-1-one,
(30) 3-methyl-4-(dimethylaminomethyl)-2H-isoquinolin-1-one,
(31) 4-(piperidin-4-yl)-2H-isoquinolin-1-one,
(32) 4-(1-(2-hydroxyethyl)piperidin-4-yl)-2H-isoquinolin-1-one,
(33) 4-(1-methylpiperidin-4-yl)-2H-isoquinolin-1-one,
(34) 3-methyl-4-(piperidin-1-yl)methyl-2H-isoquinolin-1-one,
(35) 4-dimethylaminomethyl-3-isopropyl-2H-isoquinolin-1-one,
(36) 4-(pyrrolidin-1-yl)methyl-3-isopropyl-2H-isoquinolin-1-one,
(37) 3-methyl-4-((4-phenylpiperidin-1-yl)methyl)-2H-isoquinolin-1-one,
(40) 3-methyl-4-((4-phenylpiperazin-1-yl)methyl)-2H-isoquinolin-1-one,
(41) 3-methyl-4-diethylaminomethyl-2H-isoquinolin-1-one,
(42) 3-methyl-4-(morpholin-4-yl)methyl-2H-isoquinolin-1-one,
(43) 4-(4-phenylpiperazin-1-yl)methyl-3-isopropyl-2H-isoquinolin-1-one,
(44) 7-chloro-4-(piperidin-4-yl)-2H-isoquinolin-1-one,
(45) 7-fluoro-4-(piperidin-4-yl)-2H-isoquinolin-1-one,
(46) 7-chloro-4-(1-methylpiperidin-4-yl)-2H-isoquinolin-1-one,
(47) 7-fluoro-4-(1-methylpiperidin-4-yl)-2H-isoquinolin-1-one,
(48) 7-fluoro-4-(1-(2-hydroxyethyl)piperidin-4-yl)-2H-isoquinolin-1-one,
(49) 4-dimethylaminomethyl-3-ethyl-2H-isoquinolin-1-one,
(50) 4-(pyrrolidin-1-yl)methyl-3-ethyl-2H-isoquinolin-1-one,
(122) 3-methyl-4-[(4-methylpiperazin-1-yl)methyl]-2H-isoquinolin-1-one,
(123) 3-methyl-4-[4-(2-hydroxyethyl)piperazin-1-yl]methyl-2H-isoquinolin-1-one,
(124) 3-methyl-4-(4-benzylpiperidin-1-yl)methyl-2H-isoquinolin-1-one,
(125) 3-methyl-4-(1,2,3,4-tetrahydroisoquinolin-2-yl)methyl-2H-isoquinolin-1-one
(126) 3-methyl-4-(indolin-1-yl)methyl-2H-isoquinolin-1-one, and
(127) 3-methyl-4-(diisopropylamino)methyl-2H-isoquinolin-1-one,
an optically active form thereof, a pharmaceutically acceptable salt thereof, a hydrate thereof, a water adduct thereof or a solvate thereof.

16. The isoquinoline compound of claim 10, wherein, in the formula (I),
$R^1$ is a hydrogen atom, a fluorine atom or a chlorine atom;
$R^2$ is a hydrogen atom;
D is void; and
$R^3$ is a group selected from the formula (a),
wherein m is 2,
$R^4$ is a hydrogen atom, methyl or hydroxyethyl, and
$R^5$ is hydrogen;
an optically active form thereof, a pharmaceutically acceptable salt thereof, a hydrate thereof, a water adduct thereof or a solvate thereof.

17. The isoquinoline compound of claim 10, which is selected from
(31) 4-(piperidin-4-yl)-2H-isoquinolin-1-one,

(32) 4-(1-(2-hydroxyethyl)piperidin-4-yl)-2H-isoquinolin-1-one,
(33) 4-(1-methylpiperidin-4-yl)-2H-isoquinolin-1-one,
(44) 7-chloro-4-(piperidin-4-yl)-2H-isoquinolin-1-one,
(45) 7-fluoro-4-(piperidin-4-yl)-2H-isoquinolin-1-one,
(46) 7-chloro-4-(1-methylpiperidin-4-yl)-2H-isoquinolin-1-one,
(47) 7-fluoro-4-(1-methylpiperidin-4-yl)-2H-isoquinolin-1-one,
(48) 7-fluoro-4-(1-(2-hydroxyethyl)piperidin-4-yl)-2H-isoquinolin-1-one,
(74) 4-(1-ethylpiperidin-4-yl)-2H-isoquinolin-1-one, and
(192) 7-chloro-4-(1-(2-hydroxyethyl)piperidin-4-yl)-2H-isoquinolin-1-one,
an optically active form thereof, a pharmaceutically acceptable salt thereof, a hydrate thereof, a water adduct thereof or a solvate thereof.

18. An agent for the prophylaxis and/or treatment of a disease caused by hyperactivity of poly(ADP-ribose)polymerase, which comprises the isoquinoline compound of claim 1, an optically active form thereof, a pharmaceutically acceptable salt thereof, a hydrate thereof, a water adduct thereof or a solvate thereof.

19. The agent for the prophylaxis and/or treatment of claim 18, wherein the disease caused by hyperactivity of poly(ADP-ribose)polymerase is cerebral infarction.

20. The agent for the prophylaxis and/or treatment of claim 19, wherein the disease caused by hyperactivity of poly(ADP-ribose)polymerase is acute cerebral infarction.

21. A poly(ADP-ribose)polymerase inhibitor comprising the isoquinoline compound of claim 1, an optically active form thereof, a pharmaceutically acceptable salt thereof, a hydrate thereof, a water adduct thereof or a solvate thereof.

22. A pharmaceutical composition which comprises the isoquinoline compound of claim 1, an optically active form thereof, a pharmaceutically acceptable salt thereof, a hydrate thereof, a water adduct thereof or a solvate thereof, and a pharmaceutically acceptable carrier.

23. A method for treating cerebral infraction in a mammal in need thereof, which comprises administering an effective amount of the isoquinoline compound of claim 1, an optically active form thereof, a pharmaceutically acceptable salt thereof, a hydrate thereof, a water adduct thereof or a solvate thereof to the mammal.

24. The method of claim 23, wherein the cerebral infarction is acute cerebral infarction.

* * * * *